(12) United States Patent
Amari et al.

(10) Patent No.: US 9,133,185 B2
(45) Date of Patent: Sep. 15, 2015

(54) HETEROARYL DERIVATIVES

(71) Applicant: CHIESI FARMACEUTICI S.P.A., Parma (IT)

(72) Inventors: Gabriele Amari, Parma (IT); Elisabetta Armani, Parma (IT); Eleonora Ghidini, Parma (IT); Charles Baker-Glenn, Saffron Walden (GB); Hervé Van De Poël, Saffron Walden (GB); Ben Whittaker, Saffron Walden (GB)

(73) Assignee: Chiesi Farmaceutici S.p.A, Parma (IT)

( * ) Notice: Subject to any disclaimer, the term of this patent is extended or adjusted under 35 U.S.C. 154(b) by 0 days.

(21) Appl. No.: 14/560,140

(22) Filed: Dec. 4, 2014

(65) Prior Publication Data
US 2015/0158858 A1　Jun. 11, 2015

(30) Foreign Application Priority Data
Dec. 5, 2013　(EP) .................................. 13195930

(51) Int. Cl.
| | | |
|---|---|---|
| *C07D 453/02* | (2006.01) | |
| *C07D 409/14* | (2006.01) | |
| *A61K 31/444* | (2006.01) | |
| *A61K 31/4439* | (2006.01) | |
| *A61K 31/4545* | (2006.01) | |
| *A61K 31/4436* | (2006.01) | |
| *A61K 31/44* | (2006.01) | |
| *A61M 16/14* | (2006.01) | |
| *A61M 15/00* | (2006.01) | |

(52) U.S. Cl.
CPC .............. *C07D 453/02* (2013.01); *A61K 31/44* (2013.01); *A61K 31/4436* (2013.01); *A61K 31/4439* (2013.01); *A61K 31/4545* (2013.01); *A61M 15/0065* (2013.01); *A61M 16/14* (2013.01); *C07D 409/14* (2013.01); *A61M 2202/064* (2013.01)

(58) Field of Classification Search
None
See application file for complete search history.

(56) References Cited

U.S. PATENT DOCUMENTS

| | | |
|---|---|---|
| 2014/0155373 A1 | 6/2014 | Armani et al. |
| 2014/0155427 A1 | 6/2014 | Armani et al. |
| 2014/0155428 A1 | 6/2014 | Armani et al. |

FOREIGN PATENT DOCUMENTS

| | | |
|---|---|---|
| EP | 2 386 555 | 11/2011 |
| WO | 2013/057013 | 4/2013 |

OTHER PUBLICATIONS

Extended European Search Report in Application No. 13195930.6 issued Feb. 4, 2014.

*Primary Examiner* — Timothy R Rozof
(74) *Attorney, Agent, or Firm* — Oblon, McClelland, Maier & Neustadt, L.L.P.

(57) ABSTRACT

Compounds of formula (I) described herein are both phosphodiesterase 4 (PDE4) enzyme inhibitors and muscarinic M3 receptor antagonists and are useful for the prevention and/or treatment of diseases of the respiratory tract characterized by airway obstruction.

15 Claims, No Drawings

HETEROARYL DERIVATIVES

CROSS REFERENCES TO RELATED APPLICATIONS

This application claims priority to European Patent Application No. 13195930.6, filed on Dec. 5, 2013, which is incorporated herein by reference in its entirety.

BACKGROUND OF THE INVENTION

1. Field of the Invention

The present invention relates to novel compounds which are both phosphodiesterase 4 (PDE4) enzyme inhibitors and muscarinic M3 receptor antagonists. More particularly, the present invention relates to compounds of formula (I) as below described, methods of preparing such compounds, compositions containing them and therapeutic uses thereof.

2. Discussion of the Background

Chronic obstructive pulmonary disease (COPD) is a respiratory disorder characterized by progressive, not fully reversible, airflow limitation associated with an abnormal pulmonary inflammatory response to noxious particles or gases. For this reason, bronchial relaxation and inflammatory response suppression represent a mechanistic approach to the treatment of COPD that might improve symptoms such as dyspnea, wheezing, chest tightness, cough and mucus secretion, improve health status and reduce exacerbations.

Nowadays, the drug therapy options for COPD fall into 2 general classes: bronchodilators, (β2-adrenoceptor agonists, antimuscarinic agents and methylxanthines) and antiinflammatory agents (glucocorticosteroids and selective phosphodiesterase-4 (PDE4) inhibitors). Bronchodilator drugs are the current mainstay of treatment for symptoms' relief.

As anticholinergic bronchodilators, the efficacy of muscarinic M3 antagonists is based on the fact that the major reversible component of airflow narrowing in COPD patients is the increase of acetylcholine (ACh) released to airway smooth muscle, by the bronchial postganglionic vagal efferent in some pathological conditions. Therefore, compounds that antagonize the action of ACh at muscarinic receptors are able to counteract the bronchoconstriction and thus improve lung function in these patients.

Muscarinic antagonists block the effects of ACh at muscarinic receptors. Currently, there are five known muscarinic receptor subtypes (M1-M5); human airway smooth muscle contains M1, M2 and M3 receptors. M1 receptors facilitate neurotransmission through parasympathetic ganglia and are weakly expressed on submucosal glands in human airways. The M2 receptors are located on the smooth-muscle fibers. Some studies have suggested a small role of M2 mediating the inhibition of airway smooth-muscle relaxation caused by adenylyl cyclase activation by compounds such as beta agonists. In addition, presynaptic M2 receptors are found on postganglionic parasympathetic nerves that project to airway smooth muscle and mucus-producing cells. These presynaptic M2 autoreceptors provide a negative feedback mechanism, which, when stimulated, inhibit further release of ACh. Postsynaptic M3 receptors are known to mediate both contraction of smooth muscle in the respiratory tract and mucus secretion, making them a major target for symptomatic relief of COPD. Consequently, in the airways, the major effects of muscarinic antagonists are bronchodilation and reduction of mucus secretion via blockage of ACh-induced effects in the parasympathetic nervous system.

Given the distribution of muscarinic receptors, systemically available agents that bind to muscarinic receptors outside of the respiratory tract have the potential to produce unwanted side effects such as tachycardia, dry mouth, urinary retention and constipation. Whereas dry mouth is the most common systemic anticholinergic side effect associated with the use of antimuscarinic antagonists as a result of the systemic blockade of M1 and M3 receptors the most potentially serious systemic effect is tachycardia, which results from the blockade of cardiac M2 receptors.

Inhaled anticholinergic antimuscarinic drugs approved for the treatment of COPD include ipratropium bromide (Atrovent®), oxitropium bromide (Oxivent®) and tiotropium bromide (Spiriva®). Both ipratropium and oxitropium are short-acting agents. In contrast, tiotropium bromide is the only long-acting antimuscarinic agent (LAMA) currently marketed for COPD, proved to be suitable for once-daily administration as a dry powder. Several others newer LAMAs are newly registered for the treatment of COPD, including aclidinium bromide and glycopyrrolate bromide, or are currently in phase III development, including umeclidinium.

Although bronchodilators are quite effective to improve symptoms, they do not address the underlying chronic inflammation or the changes in airway structure.

Standard treatment with glucocorticosteroids as antiinflammatory agents has demonstrated limited efficacy. However, among the antiinflammatory agents currently being developed, PDE4 inhibitors proved to be effective in attenuating the responses of various inflammatory cells, through their ability to elevate cAMP levels.

PDE4 is the predominant PDE expressed in neutrophils and T cells, suggesting that PDE4 inhibitors would be effective in controlling inflammation in COPD. Inhibition of PDE4 in inflammatory cells influences various specific responses, such as the production and/or release of pro-inflammatory mediators including cytokines and reactive oxygen species, with a well-documented efficacy in animal models mimicking certain aspects of asthma and COPD, as well as inflammatory bowel disease, atopic dermatitis, psoriasis and rheumatoid arthritis.

The selective PDE4 inhibitor, roflumilast (Daxas®) is an approved phosphodiesterase-4 inhibitor for the treatment of COPD associated with chronic bronchitis and a history of exacerbations. Roflumilast inhibits lung inflammation and emphysema in a smoking model of COPD in mice. In COPD patients, oral roflumilast given over 4 weeks significantly reduces the numbers of neutrophils (by 36%) and CXCL8 concentrations in sputum. In clinical trials roflumilast (500 mg once daily) given over 12 months improved lung function in COPD patients to a small extent but had little effect in reducing exacerbations or improving quality of life. More recently roflumilast has been shown to significantly improve FEV 1 (by approximately 50 mL) and reduce exacerbation (by about 15%) in patients with severe disease who have frequent exacerbations and mucus hypersecretion. Roflumilast provides clinical benefit when added to salmeterol or tiotropium and so may be used as an additional treatment in patients with severe disease.

However, the clinical utility of PDE4 inhibitors has so far been compromised by the occurrence of mechanism-associated side effects, including headache, nausea and emesis, which often limited the maximally tolerated dose. This problem could be overcome by inhaled delivery and designing compounds with a potentially more advantageous therapeutic window.

Since bronchial relaxation and inflammatory response suppression represent a mechanistic approach to the treatment of COPD, the combination of muscarinic M3 antagonism with selective PDE4 inhibition may lead to a new class of drugs, combining both bronchodilating and antiinflammatory properties in one molecule, which may open new perspectives in the management of COPD.

Thus, there remains

SUMMARY OF THE INVENTION

Accordingly, it is one object of the present invention to provide novel compounds which are both phosphodiesterase 4 (PDE4) enzyme inhibitors and muscarinic M3 receptor antagonists.

It is another object of the present invention to provide methods of preparing such compounds.

It is another object of the present invention to provide novel compositions which contain such a compound.

It is another object of the present invention to provide novel methods of preventing and/or treating certain diseases and conditions by administering such a compound.

These and other objects, which will become apparent during the following detailed description, have been achieved by the inventors' discovery of the compounds of the invention.

Thus, the present invention provides compounds which act both as inhibitors of the phosphodiesterase 4 (PDE4) enzyme and as muscarinic M3 receptor antagonists, methods of preparing said compounds, compositions containing them and therapeutic use thereof.

In particular the invention provides compounds of formula (I),

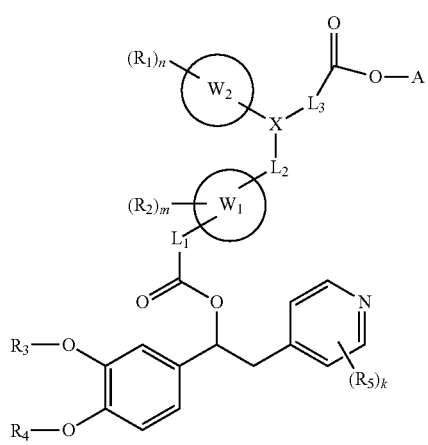

wherein each $R_1$ is hydrogen or is independently selected in the group consisting of: halogen, $(C_1-C_4)$ alkyl, $(C_1-C_4)$ alkoxy, $(C_1-C_4)$ haloalkyl, hydroxy, $—SO_2NR_6R_7$, $—CN$, $—NR_8SO_2R_9$, $—NR_6R_7$, $—CONR_6R_7$ and $—NR_8COR_9$ and wherein said $(C_1-C_4)$ alkyl is optionally substituted by one or more groups selected from $(C_3-C_7)$ cycloalkyl, hydroxy and $—NR_6R_7$ and wherein said $(C_1-C_4)$ alkoxy is optionally substituted by one or more halogens or groups $(C_3-C_7)$ cycloalkyl wherein, $R_6$ is hydrogen or $(C_1-C_6)$ alkyl;
$R_7$ is hydrogen or $(C_1-C_6)$ alkyl;
$R_8$ is hydrogen or $(C_1-C_6)$ alkyl;
$R_9$ is hydrogen or $(C_1-C_6)$ alkyl;
n is an integer ranging from 1 to 3;

each $R_2$ is hydrogen or is selected in the group consisting of: halogen, $(C_1-C_4)$ alkyl, $(C_1-C_4)$ alkoxy, $(C_1-C_4)$haloalkyl, hydroxy, $—SO_2NR_{10}R_{11}$, $—CN$ and $—NR_{12}SO_2R_{13}$ and wherein said $(C_1-C_4)$ alkyl and said $(C_1-C_4)$ alkoxy are optionally substituted by one or more group $(C_3-C_7)$ cycloalkyl wherein $R_{10}$ is hydrogen or $(C_1-C_6)$ alkyl;
$R_{11}$ is hydrogen or $(C_1-C_6)$ alkyl;
$R_{12}$ is hydrogen or $(C_1-C_6)$ alkyl;
$R_{13}$ is hydrogen or $(C_1-C_6)$ alkyl;
m is an integer ranging from 1 to 3;

$R_3$ and $R_4$ are different or the same and are independently selected from the group consisting of:
H;
$(C_3-C_7)$ cycloalkylcarbonyl;
$(C_1-C_6)$ alkyl, optionally substituted by one or more substituents selected from $(C_3-C_7)$ cycloalkyl or $(C_5-C_7)$ cycloalkenyl;
$(C_1-C_6)$ haloalkyl;
$(C_3-C_7)$ cycloalkyl;
$(C_5-C_7)$ cycloalkenyl;
$(C_2-C_6)$ alkenyl; and
$(C_2-C_6)$ alkynyl;

or $R_3$ and $R_4$, together with the interconnecting atoms, form a 2,2-difluoro-1,3-dioxolane ring of formula (r) fused to the phenyl moiety which bears groups $—OR_3$ and $—OR_4$, wherein asterisks indicate carbon atoms shared with such phenyl ring:

each $R_5$, whenever present, is independently selected from the group consisting of: CN, $NO_2$, $CF_3$ and halogen atoms;

k is 0 or an integer ranging from 1 to 3;

$L_1$ is selected from the list consisting of:
a bond,
$—(CH_2)_p—$,
$[3]-(CH_2)_p—O-[4]$
$[3]-(CH_2)_p—NR_{10}—(CH_2)_t-[4]$
$[3]-(CH_2)_p—OC(O)-[4]$
$[3]-(CH_2)_p—NR_{10}C(O)-[4]$
$[3]-(CH_2)_p—NR_{10}S(O_2)-[4]$ and
$[3]-(CH_2)_p—S(O_2)—N(R_{10})-[4]$ wherein [3] and [4] represent, respectively the point of attachment of group $L_1$ to the carbonyl group and to the ring $W_1$ and wherein
$R_{10}$ is as described above,
p is an integer ranging from 1 to 4 and
t is an integer ranging from 1 to 4

$W_1$ is selected from a divalent $(C_5-C_6)$ heteroarylene group;

$W_2$ is selected from an aryl and a heteroaryl;

$L_2$ is a group selected from $—(CH_2)_q—$ wherein q is 1 or 2

$L_3$ is a bond or a group selected from $—(CH_2)_s—$ wherein s is 1 or 2

X is selected from N and $[1]-N(R_{19})—CH<[2]$ wherein [1] represents the point of attachment of group X to $L_2$ and [2] represents the point of attachment of group X to the group $W_2$ and to the group $L_3-C(O)OA$ and wherein $R_{19}$ is selected from hydrogen, $(C_1-C_6)$ alkyl and benzyl or, when $W_2$ is a phenyl ring, $R_{19}$ is optionally a $(C_1-C_6)$ alkylene connected to $W_2$ in ortho position with respect to X, so as to form with $W_2$ and together with the interconnecting atoms a condensed ring as per formula (t) wherein "  " indicate a point of attachment to the rest of the molecule:

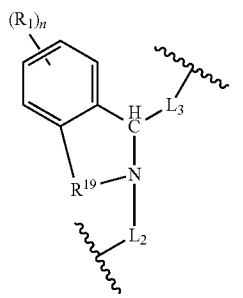

(t)

A is selected from:
a group —(CH$_2$)$_s$—NR$_{16}$R$_{17}$ wherein s is an integer ranging from 1 to 4 and R$_{16}$ and R$_{17}$ are independently selected from hydrogen or (C$_1$-C$_4$) alkyl; and
a saturated monocyclic, bicyclic or tricyclic heterocyclic ring system containing one N heteroatom or NR$_{18}$ group wherein R$_{18}$ is selected from (C$_1$-C$_4$) alkyl and benzyl;
their N-oxides on the pyridine ring, deuterated derivatives;
and pharmaceutically acceptable salts, or solvates thereof.

The present invention further provides the corresponding N-oxides on the pyridine ring of compounds of formula (I) which are represented by formula (IA):

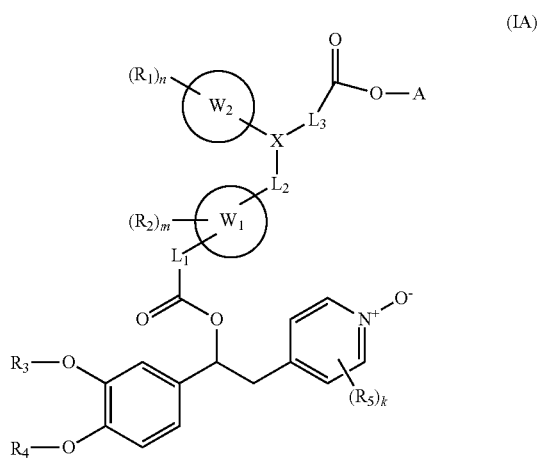

(IA)

wherein R$_1$, R$_2$, R$_3$, R$_4$, R$_5$, L$_1$, W$_1$, L$_2$, W$_2$, X, L$_3$, A, m, n, and k are as described above.

The present invention further provides the corresponding deuterated derivatives of compounds of formula (I) wherein at least one hydrogen atom is substituted by corresponding atoms of deuterium.

The present invention also encompasses the pharmaceutically acceptable salts and/or solvates thereof.

The term "pharmaceutically acceptable salts" refers to derivatives of compounds of formula (I) or of their corresponding N-oxides on the pyridine ring wherein the parent compound is suitably modified by converting any of the free acid or basic group, if present, into the corresponding addition salt with any base or acid conventionally intended as being pharmaceutically acceptable. Suitable examples of said salts may thus include mineral or organic acid addition salts of basic residues such as amino groups, as well as mineral or organic acid residues such as carboxylic groups.

Cations of inorganic bases which can be suitably used to prepare salts within the invention comprise ions of alkali or alkaline earth metals such as potassium, sodium, calcium or magnesium.

Those obtained by reacting the main compound, functioning as a base, with an inorganic or organic acid to form a salt comprise, for example, salts of hydrochloric acid, hydrobromic acid, sulfuric acid, phosphoric acid, acetic acid, methane sulfonic acid, camphor sulfonic acid, oxalic acid, maleic acid, fumaric acid, succinic acid and citric acid.

The skilled person will appreciate that many organic compounds can form complexes with solvents in which they are reacted or from which they are precipitated or crystallized. These complexes are known as "solvates". Pharmaceutically acceptable solvates of compound of the invention are within the scope of the present invention.

Included within the scope of the present invention are also polymorphs and crystalline forms of compounds of formula (I), of their N-oxides on the pyridine ring, or of pharmaceutically acceptable salts, or solvates thereof.

Hereinafter, compounds of formula (I), (IA), (IB), (IC), (ID), (Ia), (Ib), (Ic), (Id) and (I)', corresponding N-oxides on the pyridine ring, enantiomers, diastereoisomers thereof, their pharmaceutically acceptable salts and solvates, and polymorphs or crystalline forms thereof defined in any aspect of the invention (except intermediate compounds described in the chemical processes) are referred to as "compounds of the present invention".

The present invention further comprises a process for the preparation of compounds of the present invention.

The present invention also provides pharmaceutical compositions of compounds of the present invention either alone or in combination, in admixture with one or more pharmaceutically acceptable carriers.

In a further aspect, the present invention provides the use of the compounds of the present invention as a medicament.

In one aspect, the present invention provides the use of the compounds of the present invention for the manufacture of a medicament.

In particular, the present invention provides the use of the compounds of the present invention for the prevention and/or treatment of any disease wherein an inhibition of PDE4 activity along with muscarinic M3 receptor antagonism is desirable.

In particular, the compounds of the present invention alone or combined with other active ingredients may be administered for the prevention and/or treatment of a disease the respiratory tract characterized by airway obstruction such as asthma and COPD. In one embodiment, the compounds of the invention may be administered for the prevention and/or treatment of COPD.

In a further aspect, the present invention provides the use of compounds of the present invention for the preparation of a medicament for the prevention and/or treatment of any disease wherein an inhibition of PDE4 activity along with muscarinic M3 receptor antagonism is desirable.

Moreover, the present invention provides a method for prevention and/or treatment of any disease wherein an inhibition of PDE4 activity along with muscarinic M3 receptor antagonism is desirable, said method comprises administering to a patient in need of such treatment a therapeutically effective amount of a compound of the present invention.

A further aspect of the invention provides a suitable inhalation device, comprising a pharmaceutical composition of a compound of the present invention, which may be respectively selected from a single- or multi-dose dry powder inhaler, a pressurized metered dosed inhaler or a nebulizer and in particular a soft mist nebulizer.

A further aspect of the present invention provides a kit comprising a pharmaceutical composition of a compound of the present invention either alone or in combination with one or more active ingredient and a device which may be a single- or multi-dose dry powder inhaler, a metered dose inhaler or a nebulizer.

DETAILED DESCRIPTION OF THE PREFERRED EMBODIMENTS

The term "halogen atoms" includes fluorine, chlorine, bromine, and iodine, preferably chlorine.

The term "$(C_1-C_x)$ alkyl" where x is an integer greater than 1, refers to straight-chained and branched alkyl groups wherein the number of constituent carbon atoms is in the range 1 to x. Particular alkyl groups are methyl, ethyl, n-propyl, i-propyl, n-butyl, sec-butyl, i-butyl, and t-butyl.

By analogy, the term "$(C_1-C_x)$alkylene" refers to a divalent $(C_1-C_x)$alkyl radical, wherein $(C_1-C_x)$alkyl is as above defined.

The term "$(C_1-C_x)$ alkoxy" where x is an integer greater than 1 refers to straight-chained and branched alkoxy groups wherein the number of constituent carbon atoms is in the range 1 to x. Particular alkoxy groups are methoxy, ethoxy, n-propoxy, i-propoxy, n-butoxy, sec-butoxy, i-butoxy, and t-butoxy.

The expression "$(C_1-C_x)$haloalkyl" refers to the above defined "$(C_1-C_x)$alkyl" groups wherein one or more hydrogen atoms are replaced by one or more halogen atoms, which can be the same or different from each other. Examples of said $(C_1-C_6)$haloalkyl groups may thus include halogenated, polyhalogenated and fully halogenated alkyl groups wherein all of the hydrogen atoms are replaced by halogen atoms, e.g. trifluoromethyl or difluoro methyl groups.

The term "$(C_3-C_y)$cycloalkyl", where y is an integer greater than or equal to 3, refers to saturated cyclic hydrocarbon groups containing from 3 to y ring carbon atoms. Examples include cyclopropyl, cyclobutyl, cyclopentyl, cyclohexyl and cycloheptyl.

The expression "$(C_3-C_y)$cycloalkylcarbonyl" refers to $(C_3-C_y)$cycloalkylCO-groups wherein the group "$(C_3-C_y)$cycloalkyl" has the meaning above defined.

The term "$(C_2-C_6)$alkenyl" refers to straight or branched, conjugated or not conjugated, carbon chains with one or more double bonds, in cis or trans configuration, wherein the number of atoms is in the range 2 to 6.

The term "$(C_5-C_z)$ cycloalkenyl", where z is an integer greater than or equal to 5, refers to cyclic hydrocarbon groups containing from 5 to z ring carbon atoms and one or more double bonds.

The term "$(C_2-C_6)$alkynyl" refers to straight or branched carbon chains with one or more triple bonds wherein the number of atoms is in the range 2 to 6.

The expression "$(C_5-C_6)$ heteroarylene" refers to divalent monocyclic ring systems with 5 to 6 ring atoms, and in which at least one ring atom is a heteroatom (e.g. N, NH, S, or O). Non-limiting examples of suitable $(C_5-C_6)$ heteroarylene systems include, for instance, thiophenediyl, furanediyl, pyrrolediyl, pyrazolediyl, imidazolediyl, triazolediyl, tetrazolediyl, isoxazolediyl, oxazolediyl, isothiazolediyl, thiazolediyl, pyridinediyl radicals at any suitable position and the like.

The term "aryl" refers to mono or bi-cyclic systems which have 6 to 10 ring carbon atoms, wherein at least one ring is aromatic.

The expression "heteroaryl" refers to mono or bi-cyclic systems with 5 to 11 ring atoms, in which at least one ring is aromatic and in which at least one ring atom is a heteroatom (e.g. N, NH, S, or O).

Examples of suitable aryl or heteroaryl monocyclic systems with 5 to 6 ring atoms include, for instance, benzene, thiophene, pyrrole, pyrazole, imidazole, triazole, tetrazole, isoxazole, oxazole, isothiazole, thiazole, pyridine, furan derived radicals and the like.

Examples of suitable aryl or heteroaryl bicyclic systems with more than 6 ring atoms include naphthalene, biphenylene, tetrahydronaphthalene, purine, pteridine, benzimidazole, benzotriazole, quinoline, isoquinoline, indole, isoindole, indazole, benzothiophene, benzofuran, benxoxazole, dihydrobenzo dioxin, dihydrobenzo dioxepin, benzo-oxazin radicals and the like.

The expression "heterocyclic ring system" refers to optionally substituted mono-, bi- or tri-cyclic ring systems which may be saturated, partially unsaturated or unsaturated, such as $(C_3-C_7)$ heterocycloalkyl or heteroaryl having 5 to 11 ring atoms in which at least one ring atom is a heteroatom (e.g. N, S, or O), included in the definition are bridged mono-, bi- or tri-cyclic ring systems.

Examples of "heterocyclic ring system" are represented by: pyrrolidinyl, imidazolidinyl, piperazinyl, piperidinyl, quinuclidinyl, 8-azabicyclo[3.2.1]octanyl or dehydroxy scopine radical all optionally substituted by $(C_1-C_x)$ alkyl or benzyl on a nitrogen atom.

The present invention is directed to a class of compounds which act both as inhibitors of the phosphodiesterase 4 (PDE4) enzyme and as muscarinic M3 receptor antagonists.

The present invention provides compounds of general formula (I), N-oxides on the pyridine ring, deuterated derivatives and pharmaceutically acceptable salts or solvates thereof:

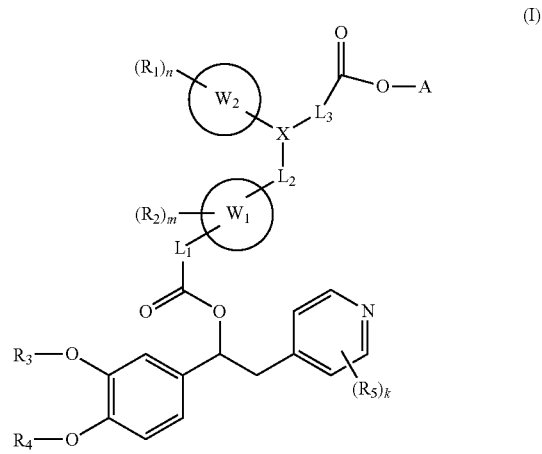

(I)

wherein $R_1$, $R_2$, $R_3$, $R_4$, $R_5$, $L_1$, $W_1$, $L_2$, $W_2$, $X$, $L_3$, $A$, $n$, $m$ and $k$ are as above defined.

It will be apparent to those skilled in the art that compounds of general formula (I) at least contain one stereogenic center, namely represented by the carbon atom (1), and therefore exist as optical stereoisomers.

It will be apparent to the skilled person that compounds according to the invention may have at least two stereogenic centers, thus they may accordingly exist at least as four diastereoisomers. Where the compounds according to the invention possess more than two stereogenic centers, they will exist as $2^n$ diastereoisomers (wherein n here refers to the number of stereogenic centers). It is to be understood that all such isomers and mixtures thereof in any proportion are encompassed within the scope of the present invention.

In a preferred embodiment, the present invention is directed to compounds of formula (I)', which are compounds of formula (I) as above defined where the absolute configuration of carbon (1) is that shown herebelow:

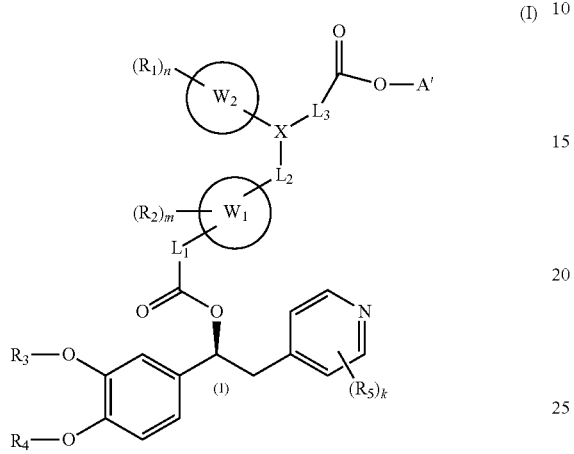

The absolute configuration for carbon (1) is assigned on the basis of Cahn-Ingold-Prelog nomenclature based on groups' priorities.

In one preferred embodiment, for compounds of formula (I), the absolute configuration at carbon (1) is (S). Compounds having such configuration generally show better PDE4 activity vs the corresponding compounds having (R) configuration at carbon (1).

In one embodiment, when A is a group of formula (I) as below defined, compounds of formula (I) may exist as at least four diastereoisomers couples (Ia), (Ib), (Ic) and (Id) herebelow reported, which are comprised within the scope of the present invention; when X is [1]-N($R_{19}$)—CH<[2] and [1] represents the point of attachment of group X to $L_2$ and [2] represents the point of attachment of group X to $W_2$ and to the carbonyl group, each couple of diastereoisomers (Ia), (Ib), (Ic), (Id) is constituted by a mixture of corresponding epimers at stereogenic center at the carbon atom of group X.

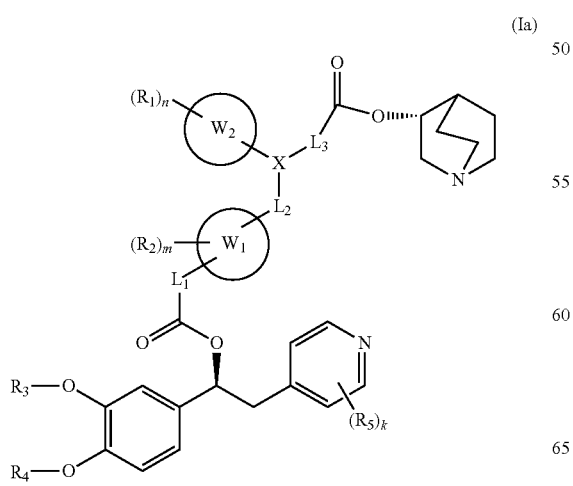

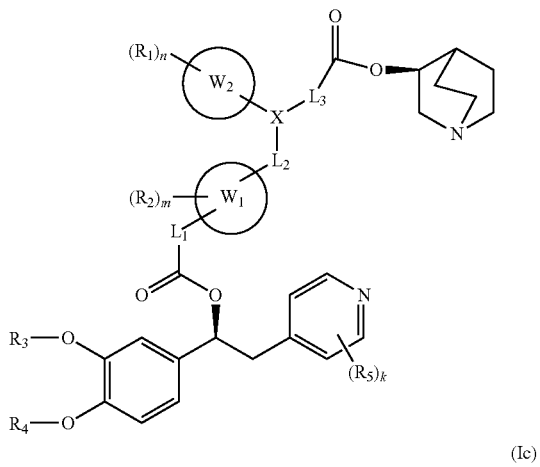

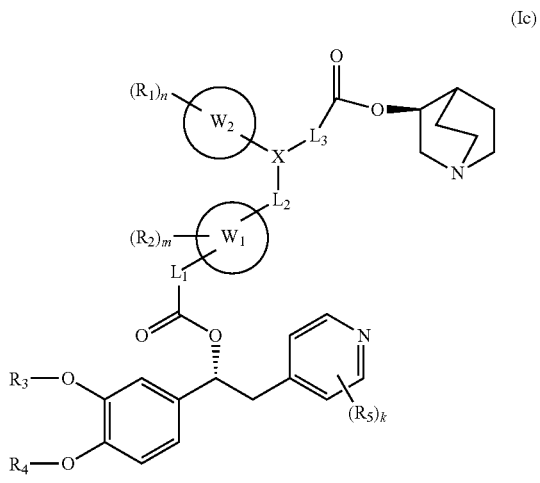

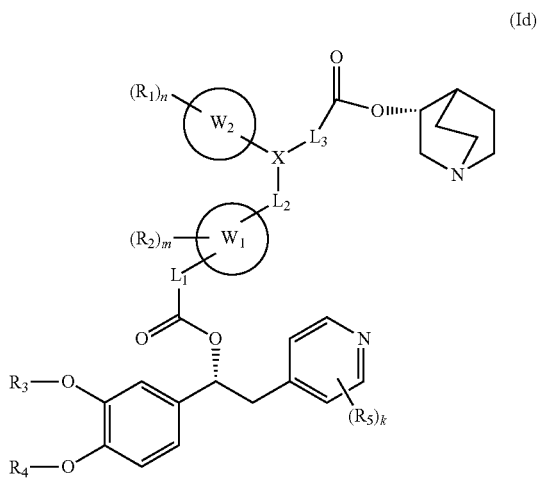

It will be apparent to the skilled person that compounds of formula (Ia), (Ib), (Ic), (Id) may be also obtained as single diastereoisomers wherein, when X is [1]-N($R_{19}$)—CH<[2] and [1] represents the point of attachment of group X to $L_2$ and [2] represents the point of attachment of group X to $W_2$ and to the carbonyl group, the stereogenic centre at carbon atom of X is defined as R or S.

In one embodiment, compounds of formula (Ia) are provided as above reported, or single diastereoisomers thereof.

It is to be understood that all preferred groups or embodiments described herebelow and hereabove for compounds of formula (I) may be combined among each other and apply to compounds of formula (IA), (IB), (IC), (ID), (Ia), (Ib), (Ic), (Id) and (I)' as well mutatis mutandis.

In a preferred embodiment, the present invention provides compounds of formula (IA), which are N-oxides on the pyridine ring of compounds of formula (I), deuterated derivatives and pharmaceutically acceptable salts and solvates thereof:

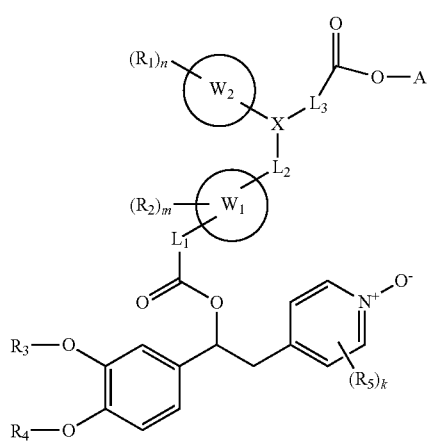

(IA)

wherein $R_1$, $R_2$, $R_3$, $R_4$, $R_5$, $L_1$, $W_1$, $L_2$, $W_2$, A, X, $L_3$, m, n, and k are as described above.

In a preferred embodiment, k is 2 and $R_5$ are halogen atoms. In a further preferred embodiment, $R_5$ are two chlorine atoms at positions 3 and 5 of the pyridine ring.

In one preferred embodiment, $R_4$ is selected from $(C_1-C_6)$ haloalkyl and $(C_1-C_6)$ alkyl and $R_3$ is selected from $(C_3-C_7)$ cycloalkyl or $(C_1-C_6)$ alkyl which is optionally substituted by $(C_3-C_7)$ cycloalkyl.

In another preferred embodiment, $R_3$ and $R_4$, together with the interconnecting atoms, form a 2,2-difluoro-1,3-dioxolane ring of formula (r) fused to the phenyl moiety which bears groups —$OR_3$ and —$OR_4$, wherein asterisks indicate carbon atoms shared with such phenyl ring:

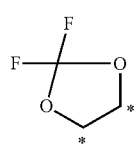

(r)

In a further preferred embodiment, $R_4$ is $(C_1-C_6)$ haloalkyl and $R_3$ is $(C_1-C_6)$ alkyl which is substituted by $(C_3-C_7)$ cycloalkyl.

In another preferred embodiment, $R_3$ is $(C_1-C_6)$ alkyl and $R_4$ is $(C_1-C_6)$ alkyl.

In another preferred embodiment, X is [1]-N($R_{19}$)—CH< [2] wherein [1] represents the point of attachment of group X to $L_2$ and [2] represents the point of attachment of group X to the group $W_2$ and to the group $L_3$-C(O)OA, $W_2$ is a phenyl ring, $R_{19}$ is a $(C_1-C_6)$ alkylene connected to $W_2$ in ortho position with respect to X, so as to form with $W_2$ a condensed ring as per formula (t):

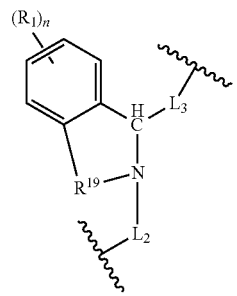

(t)

In a further preferred embodiment, the above said condensed ring as per formula (t) is 1,2,3,4-tetrahydroisoquinoline-1yl-2yl.

A preferred group of compounds is that wherein the 4-pyridinyl ring is substituted in 3 and 5 with two atoms of chlorine, according to the general formula (IB)

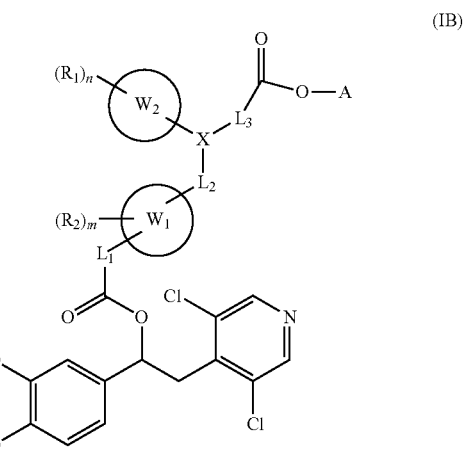

(IB)

wherein $R_1$, $R_2$, $R_3$, $R_4$, A, $L_1$, $W_1$, $L_2$, $W_2$, X, $L_3$, m and n are as defined above for compounds of formula (I); and the corresponding N-oxide on the pyridine ring, deuterated derivatives and pharmaceutically acceptable salts and solvates thereof.

Another preferred group of compounds is that shown below according to general formula (IC):

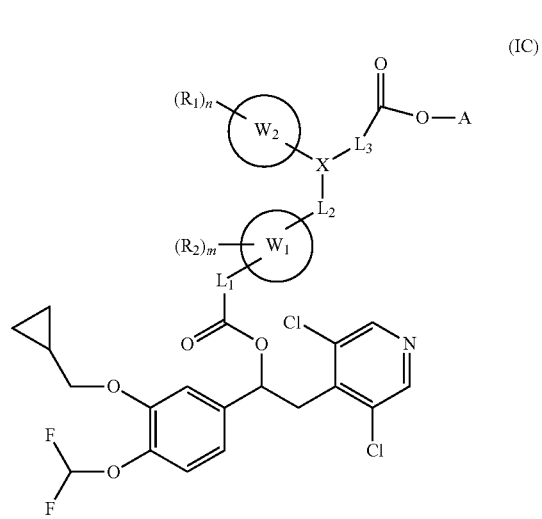

(IC)

wherein R₁, R₂, A, L₁, W₁, L₂, W₂, X, L₃, m and n are as defined above for compounds of formula (I); and the corresponding N-oxide on the pyridine ring, or pharmaceutically acceptable salts thereof.

A more preferred group of compounds is that shown below according to general formula (ID):

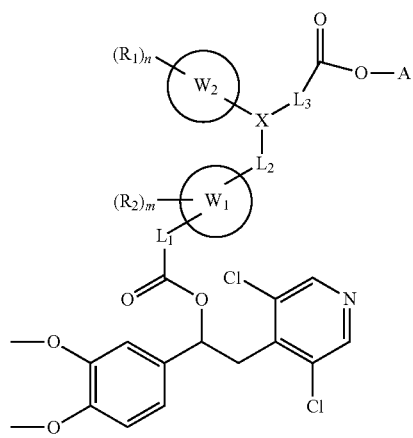

(ID)

wherein R₁, R₂, A, L₁, W₁, L₂, W₂, X, L₃, m and n are as defined above for compounds of formula (I), the corresponding N-oxide on the pyridine ring, and pharmaceutically acceptable salts and solvates thereof.

In one embodiment, A is a group (b) represented by a group of formula (I), (ii), (iii) or (iv):

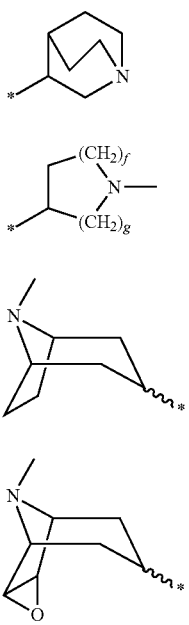

(i)

(ii)

(iii)

(iv)

wherein
f=1, 2 or 3;
g=1, 2 or 3.

In another embodiment, A is a group (b) represented by a group of formula (i):

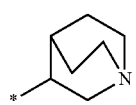

(i)

According to a preferred embodiment, the present invention provides the compounds reported below:

[(1S)-2-(3,5-dichloro-1-oxido-pyridin-1-ium-4-yl)-1-(3,4-dimethoxyphenyl)ethyl]5-[(2-fluoro-N-[(3R)-quinuclidin-3-yl]oxycarbonyl-anilino)methyl]thiophene-2-carboxylate;

[(1S)-2-(3,5-dichloro-1-oxido-pyridin-1-ium-4-yl)-1-(3,4-dimethoxyphenyl)ethyl]5-[(2-fluoro-N-[(3S)-quinuclidin-3-yl]oxycarbonyl-anilino)methyl]thiophene-2-carboxylate;

[(1S)-2-(3,5-dichloro-1-oxido-pyridin-1-ium-4-yl)-1-(3,4-dimethoxyphenyl)ethyl]5-[[2-fluoro-N-[[(1R,5S)-8-methyl-8-azabicyclo[3.2.1]octan-3-yl]oxycarbonyl]anilino]methyl]thiophene-2-carboxylate;

[(1S)-2-(3,5-dichloro-1-oxido-pyridin-1-ium-4-yl)-1-(3,4-dimethoxyphenyl)ethyl]5-[[2-fluoro-N-[(1-methyl-4-piperidyl)oxycarbonyl]anilino]methyl]thiophene-2-carboxylate;

[(1S)-2-(3,5-dichloro-1-oxido-pyridin-1-ium-4-yl)-1-(3,4-dimethoxyphenyl)ethyl]5-[(2-hydroxy-N-[(3R)-quinuclidin-3-yl]oxycarbonyl-anilino)methyl]thiophene-2-carboxylate;

[(1S)-2-(3,5-dichloro-1-oxido-pyridin-1-ium-4-yl)-1-[4-(difluoromethoxy)-3-(trideuteriomethoxy)phenyl]ethyl]5-[(2-fluoro-N-[(3R)-quinuclidin-3-yl]oxycarbonyl-anilino)methyl]thiophene-2-carboxylate;

[(1S)-2-(3,5-dichloro-1-oxido-pyridin-1-ium-4-yl)-1-[4-(difluoromethoxy)-3-ethoxy-phenyl]ethyl]5-[(2-fluoro-N-[(3R)-quinuclidin-3-yl]oxycarbonyl-anilino)methyl]thiophene-2-carboxylate;

[(1S)-2-(3,5-dichloro-1-oxido-pyridin-1-ium-4-yl)-1-[4-(difluoromethoxy)-3-methoxy-phenyl]ethyl]5-[(2-fluoro-N-[(3R)-quinuclidin-3-yl]oxycarbonyl-anilino)methyl]thiophene-2-carboxylate;

[(1S)-2-(3,5-dichloro-1-oxido-pyridin-1-ium-4-yl)-1-(3,4-dimethoxyphenyl)ethyl]5-[[3-pyridyl-[(3R)-quinuclidin-3-yl]oxycarbonyl-amino]methyl]thiophene-2-carboxylate;

[(1S)-2-(3,5-dichloro-1-oxido-pyridin-1-ium-4-yl)-1-(3,4-dimethoxyphenyl)ethyl]5-[[2-pyridyl-[(3R)-quinuclidin-3-yl]oxycarbonyl-amino]methyl]thiophene-2-carboxylate;

[1-[3-(cyclopropylmethoxy)-4-methoxy-phenyl]-2-(3,5-dichloro-1-oxido-pyridin-1-ium-4-yl)ethyl]5-[(2-fluoro-N-[(3R)-quinuclidin-3-yl]oxycarbonyl-anilino)methyl]thiophene-2-carboxylate;

[(1S)-1-[3-(cyclopropylmethoxy)-4-(difluoromethoxy)phenyl]-2-(3,5-dichloro-1-oxido-pyridin-1-ium-4-yl)ethyl]5-[[2-pyridyl-[(3R)-quinuclidin-3-yl]oxycarbonyl-amino]methyl]thiophene-2-carboxylate;

[(1S)-1-[3-(cyclopropylmethoxy)-4-(difluoromethoxy)phenyl]-2-(3,5-dichloro-1-oxido-pyridin-1-ium-4-yl)ethyl]5-[[3-pyridyl-[(3R)-quinuclidin-3-yl]oxycarbonyl-amino]methyl]thiophene-2-carboxylate;

[(1S)-1-[3-(cyclopropylmethoxy)-4-(difluoromethoxy)phenyl]-2-(3,5-dichloro-1-oxido-pyridin-1-ium-4-yl)ethyl]5-

- [(2-fluoro-N-[(3R)-quinuclidin-3-yl]oxycarbonyl-anilino)methyl]thiophene-2-carboxylate;
- [(1S)-2-(3,5-dichloro-1-oxido-pyridin-1-ium-4-yl)-1-(3,4-dimethoxyphenyl)ethyl]5-[(2-methoxy-N-[(3R)-quinuclidin-3-yl]oxycarbonyl-anilino)methyl]thiophene-2-carboxylate;
- [(1S)-2-(3,5-dichloro-1-oxido-pyridin-1-ium-4-yl)-1-(3,4-dimethoxyphenyl)ethyl]5-[[[(3R)-quinuclidin-3-yl]oxycarbonyl-thiazol-2-yl-amino]methyl]thiophene-2-carboxylate;
- [(1S)-2-(3,5-dichloro-1-oxido-pyridin-1-ium-4-yl)-1-[4-(difluoromethoxy)-3-isopropoxy-phenyl]ethyl]5-[(2-fluoro-N-[(3R)-quinuclidin-3-yl]oxycarbonyl-anilino)methyl]thiophene-2-carboxylate;
- [(1S)-1-[3-(cyclopropylmethoxy)-4-(difluoromethoxy)phenyl]-2-(3,5-dichloro-1-oxido-pyridin-1-ium-4-yl)ethyl]5-[[[(3R)-quinuclidin-3-yl]oxycarbonyl-thiazol-2-yl-amino]methyl]thiophene-2-carboxylate;
- [(1S)-2-(3,5-dichloro-1-oxido-pyridin-1-ium-4-yl)-1-(3,4-dimethoxyphenyl)ethyl]5-[[(2-methoxy-3-pyridyl)-[(3R)-quinuclidin-3-yl]oxycarbonyl-amino]methyl]thiophene-2-carboxylate;
- [(1S)-2-(3,5-dichloro-1-oxido-pyridin-1-ium-4-yl)-1-(3,4-dimethoxyphenyl)ethyl]5-[(3-cyano-N-[(3R)-quinuclidin-3-yl]oxycarbonyl-anilino)methyl]thiophene-2-carboxylate;
- [(1S)-2-(3,5-dichloro-1-oxido-pyridin-1-ium-4-yl)-1-(3,4-dimethoxyphenyl)ethyl]5-[(3-fluoro-N-[(3R)-quinuclidin-3-yl]oxycarbonyl-anilino)methyl]thiophene-2-carboxylate;
- [(1S)-2-(3,5-dichloro-1-oxido-pyridin-1-ium-4-yl)-1-(3,4-dimethoxyphenyl)ethyl]5-[(N-[(3R)-quinuclidin-3-yl]oxycarbonylanilino)methyl]thiophene-2-carboxylate;
- [(1S)-2-(3,5-dichloro-1-oxido-pyridin-1-ium-4-yl)-1-(3,4-dimethoxyphenyl)ethyl]5-[[3-(difluoromethyl)-N-[(3R)-quinuclidin-3-yl]oxycarbonyl-anilino]methyl]thiophene-2-carboxylate;
- [(1S)-2-(3,5-dichloro-1-oxido-pyridin-1-ium-4-yl)-1-(3,4-dimethoxyphenyl)ethyl]5-[(3-hydroxy-N-[(3R)-quinuclidin-3-yl]oxycarbonyl-anilino)methyl]thiophene-2-carboxylate;
- [(1S)-1-[3-(cyclopropylmethoxy)-4-(difluoromethoxy)phenyl]-2-(3,5-dichloro-1-oxido-pyridin-1-ium-4-yl)ethyl]5-[(3-hydroxy-N-[(3R)-quinuclidin-3-yl]oxycarbonyl-anilino)methyl]thiophene-2-carboxylate;
- [(1S)-2-(3,5-dichloro-1-oxido-pyridin-1-ium-4-yl)-1-(3,4-dimethoxyphenyl)ethyl]5-[(2-fluoro-N-[(3R)-1-methylpyrrolidin-3-yl]oxycarbonyl-anilino)methyl]thiophene-2-carboxylate;
- [(1S)-2-(3,5-dichloro-1-oxido-pyridin-1-ium-4-yl)-1-(3,4-dimethoxyphenyl)ethyl]-4-[(2-fluoro-N-[(3R)-quinuclidin-3-yl]oxycarbonyl-anilino)methyl]thiophene-2-carboxylate;
- [(1S)-2-(3,5-dichloro-1-oxido-pyridin-1-ium-4-yl)-1-[4-(difluoromethoxy)-3-methoxy-phenyl]ethyl]5-[[2-pyridyl-[(3R)-quinuclidin-3-yl]oxycarbonyl-amino]methyl]thiophene-2-carboxylate;
- [(1S)-2-(3,5-dichloro-1-oxido-pyridin-1-ium-4-yl)-1-[4-(difluoromethoxy)-3-isopropoxy-phenyl]ethyl]5-[[2-pyridyl-[(3R)-quinuclidin-3-yl]oxycarbonyl-amino]methyl]thiophene-2-carboxylate;
- [(1S)-2-(3,5-dichloro-1-oxido-pyridin-1-ium-4-yl)-1-[4-(difluoromethoxy)-3-isopropoxy-phenyl]ethyl]5-[(2-fluoro-N-[(3R)-quinuclidin-3-yl]oxycarbonyl-anilino)methyl]-thiophene-3-carboxylate;
- [(1S)-2-(3,5-dichloro-1-oxido-pyridin-1-ium-4-yl)-1-[4-(difluoromethoxy)-3-isopropoxy-phenyl]ethyl]-4-[(2-fluoro-N-[(3R)-quinuclidin-3-yl]oxycarbonyl-anilino)methyl]thiophene-2-carboxylate;
- [(1S)-2-(3,5-dichloro-1-oxido-pyridin-1-ium-4-yl)-1-(3,4-dimethoxyphenyl)ethyl]5-[(2-fluoro-N-[(3R)-quinuclidin-3-yl]oxycarbonyl-anilino)methyl]thiophene-3-carboxylate;
- [(1S)-2-(3,5-dichloro-1-oxido-pyridin-1-ium-4-yl)-1-(3,4-dimethoxyphenyl)ethyl]6-[(N-[(3R)-quinuclidin-3-yl]oxycarbonylanilino) methyl]pyridine-3-carboxylate;
- [(1S)-2-(3,5-dichloro-1-oxido-pyridin-1-ium-4-yl)-1-(3,4-dimethoxyphenyl)ethyl]5-[(N-[(3R)-quinuclidin-3-yl]oxycarbonylanilino)methyl]-furan-2-carboxylate;
- [(1S)-2-(3,5-dichloro-1-oxido-pyridin-1-ium-4-yl)-1-(3,4-dimethoxyphenyl)ethyl]6-[(N-[(3R)-quinuclidin-3-yl]oxycarbonylanilino)methyl]pyridine-2-carboxylate;
- [(1S)-2-(3,5-dichloro-1-oxido-pyridin-1-ium-4-yl)-1-(3,4-dimethoxyphenyl)ethyl]2-[(N-[(3R)-quinuclidin-3-yl]oxycarbonylanilino)methyl]oxazole-4-carboxylate;
- [(1S)-2-(3,5-dichloro-1-oxido-pyridin-1-ium-4-yl)-1-(3,4-dimethoxyphenyl)ethyl]5-[[[1-(3-fluorophenyl)-2-oxo-2-[(3R)-quinuclidin-3-yl]oxy-ethyl]amino]methyl]thiophene-2-carboxylate;
- [(1S)-2-(3,5-dichloro-1-oxido-pyridin-1-ium-4-yl)-1-(3,4-dimethoxyphenyl)ethyl]5-[[[1-(2-fluorophenyl)-2-oxo-2-[(3R)-quinuclidin-3-yl]oxy-ethyl]amino]methyl]thiophene-2-carboxylate;
- [(1S)-1-[3-(cyclopropylmethoxy)-4-(difluoromethoxy)phenyl]-2-(3,5-dichloro-1-oxido-pyridin-1-ium-4-yl)ethyl]5-[[[1-(2-methoxyphenyl)-2-oxo-2-[(3R)-quinuclidin-3-yl]oxy-ethyl]amino]methyl]thiophene-2-carboxylate;
- [(1S)-1-[3-(cyclopropylmethoxy)-4-(difluoromethoxy)phenyl]-2-(3,5-dichloro-1-oxido-pyridin-1-ium-4-yl)ethyl]5-[[[1-(2-fluorophenyl)-2-oxo-2-[(3R)-quinuclidin-3-yl]oxy-ethyl]amino]methyl]thiophene-2-carboxylate;
- [(1S)-1-[3-(cyclopropylmethoxy)-4-(difluoromethoxy)phenyl]-2-(3,5-dichloro-1-oxido-pyridin-1-ium-4-yl)ethyl]5-[[[2-oxo-1-phenyl-2-[(3R)-quinuclidin-3-yl]oxy-ethyl]amino]methyl]thiophene-2-carboxylate;
- [(1S)-2-(3,5-dichloro-1-oxido-pyridin-1-ium-4-yl)-1-(3,4-dimethoxyphenyl)ethyl]5-[[[2-oxo-1-phenyl-2-[(3R)-quinuclidin-3-yl]oxy-ethyl]amino]methyl]thiophene-2-carboxylate;
- [(1S)-1-[3-(cyclopropylmethoxy)-4-(difluoromethoxy)phenyl]-2-(3,5-dichloro-1-oxido-pyridin-1-ium-4-yl)ethyl]5-[[[1-(3-fluorophenyl)-2-oxo-2-[(3R)-quinuclidin-3-yl]oxy-ethyl]amino]methyl]thiophene-2-carboxylate;
- [(1S)-1-[3-(cyclopropylmethoxy)-4-(difluoromethoxy)phenyl]-2-(3,5-dichloro-1-oxido-pyridin-1-ium-4-yl)ethyl]5-[[[2-oxo-1-(3-pyridyl)-2-[(3R)-quinuclidin-3-yl]oxy-ethyl]amino]methyl]thiophene-2-carboxylate;
- [(1S)-2-(3,5-dichloro-1-oxido-pyridin-1-ium-4-yl)-1-(3,4-dimethoxyphenyl)ethyl]5-[[[1-(2-fluorophenyl)-2-[(1-methyl-4-piperidyl)oxy]-2-oxo-ethyl]amino]methyl]thiophene-2-carboxylate;
- [(1S)-2-(3,5-dichloro-1-oxido-pyridin-1-ium-4-yl)-1-(3,4-dimethoxyphenyl)ethyl]5-[[[2-[(1-benzyl-4-piperidyl)oxy]-1-(2-fluorophenyl)-2-oxo-ethyl]amino]methyl]thiophene-2-carboxylate;
- [(1S)-2-(3,5-dichloro-1-oxido-pyridin-1-ium-4-yl)-1-(3,4-dimethoxyphenyl)ethyl]5-[[[1-(3-fluorophenyl)-2-oxo-2-[(3R)-quinuclidin-3-yl]oxy-ethyl]amino]methyl]thiophene-2-carboxylate single diastereoisomer 1;
- [(1S)-2-(3,5-dichloro-1-oxido-pyridin-1-ium-4-yl)-1-(3,4-dimethoxyphenyl)ethyl]5-[[[1-(3-fluorophenyl)-2-oxo-2-[(3R)-quinuclidin-3-yl]oxy-ethyl]amino]methyl]thiophene-2-carboxylate single diastereoisomer 2;

[(1S)-2-(3,5-dichloro-1-oxido-pyridin-1-ium-4-yl)-1-(3,4-dimethoxyphenyl)ethyl]5-[[[2-oxo-1-phenyl-2-[(3R)-quinuclidin-3-yl]oxy-ethyl]amino]methyl]thiophene-2-carboxylate single diastereoisomer 1;

[(1S)-2-(3,5-dichloro-1-oxido-pyridin-1-ium-4-yl)-1-(3,4-dimethoxyphenyl)ethyl]5-[[[2-oxo-1-phenyl-2-[(3R)-quinuclidin-3-yl]oxy-ethyl]amino]methyl]thiophene-2-carboxylate single diastereoisomer 2;

[(1S)-2-(3,5-dichloro-1-oxido-pyridin-1-ium-4-yl)-1-(3,4-dimethoxyphenyl)ethyl]5-[[[1-(2-fluorophenyl)-2-oxo-2-[(3R)-quinuclidin-3-yl]oxy-ethyl]amino]methyl]thiophene-2-carboxylate single diastereoisomer 1;

[(1S)-2-(3,5-dichloro-1-oxido-pyridin-1-ium-4-yl)-1-(3,4-dimethoxyphenyl)ethyl]5-[[[1-(2-fluorophenyl)-2-oxo-2-[(3)-quinuclidin-3-yl]oxy-ethyl]amino]methyl]thiophene-2-carboxylate single diastereoisomer 2;

[(1S)-1-[3-(cyclopropylmethoxy)-4-(difluoromethoxy)phenyl]-2-(3,5-dichloro-1-oxido-pyridin-1-ium-4-yl)ethyl]5-[[[1-(2-fluorophenyl)-2-oxo-2-[(3R)-quinuclidin-3-yl]oxy-ethyl]amino]methyl]thiophene-2-carboxylate single diastereoisomer 1;

[(1S)-1-[3-(cyclopropylmethoxy)-4-(difluoromethoxy)phenyl]-2-(3,5-dichloro-1-oxido-pyridin-1-ium-4-yl)ethyl]5-[[[1-(2-fluorophenyl)-2-oxo-2-[(3R)-quinuclidin-3-yl]oxy-ethyl]amino]methyl]thiophene-2-carboxylate single diastereoisomer 2;

[(1S)-1-[3-(cyclopropylmethoxy)-4-(difluoromethoxy)phenyl]-2-(3,5-dichloro-1-oxido-pyridin-1-ium-4-yl)ethyl]5-[[[2-oxo-1-phenyl-2-[(3R)-quinuclidin-3-yl]oxy-ethyl]amino]methyl]thiophene-2-carboxylate single diastereoisomer 1;

[(1S)-1-[3-(cyclopropylmethoxy)-4-(difluoromethoxy)phenyl]-2-(3,5-dichloro-1-oxido-pyridin-1-ium-4-yl)ethyl]5-[[[2-oxo-1-phenyl-2-[(3R)-quinuclidin-3-yl]oxy-ethyl]amino]methyl]thiophene-2-carboxylate single diastereoisomer 2;

[(1S)-1-[3-(cyclopropylmethoxy)-4-(difluoromethoxy)phenyl]-2-(3,5-dichloro-1-oxido-pyridin-1-ium-4-yl)ethyl]5-[[[1-(2-methoxyphenyl)-2-oxo-2-[(3R)-quinuclidin-3-yl]oxy-ethyl]amino]methyl]thiophene-2-carboxylate single diastereoisomer 1;

[(1S)-1-[3-(cyclopropylmethoxy)-4-(difluoromethoxy)phenyl]-2-(3,5-dichloro-1-oxido-pyridin-1-ium-4-yl)ethyl]5-[[[1-(3-fluorophenyl)-2-oxo-2-[(3R)-quinuclidin-3-yl]oxy-ethyl]amino]methyl]thiophene-2-carboxylate single diastereoisomer 1

[(1S)-2-(3,5-dichloro-1-oxido-pyridin-1-ium-4-yl)-1-(3,4-dimethoxyphenyl)ethyl]5-[(2-fluoro-3-hydroxy-N-[(3R)-quinuclidin-3-yl]oxycarbonyl-anilino)methyl]thiophene-2-carboxylate;

[(1S)-2-(3,5-dichloro-1-oxido-pyridin-1-ium-4-yl)-1-(3,4-dimethoxyphenyl)ethyl]5-[(3-fluoro-5-hydroxy-N-[(3R)-quinuclidin-3-yl]oxycarbonyl-anilino)methyl]thiophene-2-carboxylate;

[(1S)-2-(3,5-dichloro-1-oxido-pyridin-1-ium-4-yl)-1-(3,4-dimethoxyphenyl)ethyl]5-[(3-hydroxy-2-methyl-N-[(3R)-quinuclidin-3-yl]oxycarbonyl-anilino)methyl]thiophene-2-carboxylate;

[(1S)-2-(3,5-dichloro-1-oxido-pyridin-1-ium-4-yl)-1-(3,4-dimethoxyphenyl)ethyl]5-[[2-(hydroxymethyl)-N-[(3R)-quinuclidin-3-yl]oxycarbonyl-anilino]methyl]thiophene-2-carboxylate;

[(1S)-2-(3,5-dichloro-1-oxido-pyridin-1-ium-4-yl)-1-(3,4-dimethoxyphenyl)ethyl]2-[4-[(2-fluoro-N-[(3R)-quinuclidin-3-yl]oxycarbonyl-anilino)methyl]pyrazol-1-yl]acetate;

diastereoisomer 1 of [1-[3-(cyclopropylmethoxy)-4-methoxy-phenyl]-2-(3,5-dichloro-1-oxido-pyridin-1-ium-4-yl)ethyl]5-[(2-fluoro-N-[(3R)-quinuclidin-3-yl]oxycarbonyl-anilino)methyl]thiophene-2-carboxylate;

diastereoisomer 2 of [1-[3-(cyclopropylmethoxy)-4-methoxy-phenyl]-2-(3,5-dichloro-1-oxido-pyridin-1-ium-4-yl)ethyl]5-[(2-fluoro-N-[(3R)-quinuclidin-3-yl]oxycarbonyl-anilino)methyl]thiophene-2-carboxylate;

[(1S)-2-(3,5-dichloro-1-oxido-pyridin-1-ium-4-yl)-1-(3,4-dimethoxyphenyl)ethyl]5-[(2,6-dihydroxyphenyl)-N-[(3R)-quinuclidin-3-yl]oxycarbonyl-anilino)methyl]thiophene-2-carboxylate formate salt;

[(1S)-2-(3,5-dichloro-1-oxido-pyridin-1-ium-4-yl)-1-(3,4-dimethoxyphenyl)ethyl]5-[(2-hydroxy-5-methoxyphenyl)-N-[(3R)-quinuclidin-3-yl]oxycarbonyl-anilino)methyl]thiophene-2-carboxylate;

[(1S)-2-(3,5-dichloro-1-oxido-pyridin-1-ium-4-yl)-1-(3,4-dimethoxyphenyl)ethyl]5-[(2-hydroxy-5-(trifluoromethoxy)phenyl)-N-[(3R)-quinuclidin-3-yl]oxycarbonyl-anilino)methyl]thiophene-2-carboxylate formate salt;

[(1S)-2-(3,5-dichloro-1-oxido-pyridin-1-ium-4-yl)-1-(3,4-dimethoxyphenyl)ethyl]5-[(2,3-dihydroxyphenyl)-N-[(3R)-quinuclidin-3-yl]oxycarbonyl-anilino)methyl]thiophene-2-carboxylate formate salt;

[(1R)-2-(3,5-dichloro-1-oxido-pyridin-1-ium-4-yl)-1-(3,4-dimethoxyphenyl)ethyl]5-[[[2-oxo-1-phenyl-2-[(3R)-quinuclidin-3-yl]oxy-ethyl]amino]methyl]thiophene-2-carboxylate;

Epimeric mixture 1 of [1-[3-(cyclopentoxy)-4-methoxy-phenyl]-2-(3,5-dichloro-1-oxido-pyridin-1-ium-4-yl)ethyl]5-[[[2-oxo-1-phenyl-2-[(3R)-quinuclidin-3-yl]oxy-ethyl]amino]methyl]thiophene-2-carboxylate dihydrochloride;

Epimeric mixture 2 of [1-[3-(cyclopentoxy)-4-methoxy-phenyl]-2-(3,5-dichloro-1-oxido-pyridin-1-ium-4-yl)ethyl]5-[[[2-oxo-1-phenyl-2-[(3R)-quinuclidin-3-yl]oxy-ethyl]amino]methyl]thiophene-2-carboxylate dihydrochloride;

Epimeric mixture 1 of [1-[3-(cyclopropylmethoxy)-4-methoxy-phenyl]-2-(3,5-dichloro-1-oxido-pyridin-1-ium-4-yl)ethyl]5-[[[2-oxo-1-phenyl-2-[(3R)-quinuclidin-3-yl]oxy-ethyl]amino]methyl]thiophene-2-carboxylate;

Epimeric mixture 2 of [1-[3-(cyclopropylmethoxy)-4-methoxy-phenyl]-2-(3,5-dichloro-1-oxido-pyridin-1-ium-4-yl)ethyl]5-[[[2-oxo-1-phenyl-2-[(3R)-quinuclidin-3-yl]oxy-ethyl]amino]methyl]thiophene-2-carboxylate;

[(1S)-2-(3,5-dichloro-1-oxido-pyridin-1-ium-4-yl)-1-[4-(difluoromethoxy)-3-isopropoxy-phenyl]ethyl]5-[[[2-oxo-1-phenyl-2-[(3R)-quinuclidin-3-yl]oxy-ethyl]amino]methyl]thiophene-2-carboxylate; formate salt;

[(1S)-2-(3,5-dichloro-1-oxido-pyridin-1-ium-4-yl)-1-(3,4-dimethoxyphenyl)ethyl]5-[[[2-oxo-1-phenyl-2-[(3R)-quinuclidin-3-yl]oxy-ethyl]amino]methyl]thiophene-3-carboxylate;

[(1S)-2-(3,5-dichloro-1-oxido-pyridin-1-ium-4-yl)-1-(3,4-dimethoxyphenyl)ethyl]5-[[[1-(2-fluorophenyl)-2-oxo-2-[(3R)-quinuclidin-3-yl]oxy-ethyl]amino]methyl]thiophene-3-carboxylate;

[(1S)-2-(3,5-dichloro-1-oxido-pyridin-1-ium-4-yl)-1-(3,4-dimethoxyphenyl)ethyl]-4-[[[2-oxo-1-phenyl-2-[(3R)-quinuclidin-3-yl]oxy-ethyl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[[2-[2-(dimethylamino)ethoxy]-2-oxo-1-phenyl-ethyl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[[1-[3-(difluoromethyl)phenyl]-2-oxo-2-[(3R)-quinuclidin-3-yl]oxy-ethyl]amino]
methyl]thiophene-2-carboxylate;

[(1S)-2-(3,5-dichloro-1-oxido-pyridin-1-ium-4-yl)-1-(3,4-dimethoxyphenyl)ethyl]5-[[methyl-[2-oxo-1-phenyl-2-[(3R)-quinuclidin-3-yl]oxy-ethyl]amino]methyl]
thiophene-2-carboxylate;

[(1S)-2-(3,5-dichloro-1-oxido-pyridin-1-ium-4-yl)-1-(3,4-dimethoxyphenyl)ethyl]5-[[[2-[(3S)-1-methylpyrrolidin-3-yl]oxy-2-oxo-1-phenyl-ethyl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[[1-(3-hydroxyphenyl)-2-oxo-2-[(3R)-quinuclidin-3-yl]oxy-ethyl]amino]methyl]
thiophene-2-carboxylate;

[(3R)-quinuclidin-3-yl]2-[[5-[2-[(1S)-2-(3,5-dichloro-1-oxido-pyridin-1-ium-4-yl)-1-(3,4-dimethoxyphenyl)
ethoxy]-2-oxo-ethyl]-2-thienyl]methylamino]-2-phenyl-acetate;

[(1S)-2-(3,5-dichloro-1-oxido-pyridin-1-ium-4-yl)-1-(3,4-dimethoxyphenyl)ethyl]5-[[[1-(thiophen-2-yl)-2-oxo-2-(R)-quinuclidin-3-yloxy-ethyl]amino]methyl]thiophene-2-carboxylate;

[(1S)-2-(3,5-dichloro-1-oxido-pyridin-1-ium-4-yl)-1-[4-(difluoromethoxy)-3-methoxy-phenyl]ethyl]5-[[[2-oxo-1-phenyl-2-[(3R)-quinuclidin-3-yl]oxy-ethyl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[[2-[(3R)-1-methylpyrrolidin-3-yl]oxy-2-oxo-1-phenyl-ethyl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[[2-(1-methylazetidin-3-yl)oxy-2-oxo-1-phenyl-ethyl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[[2-[[(3R)-1-methyl-3-piperidyl]oxy]-2-oxo-1-phenyl-ethyl]amino]methyl]
thiophene-2-carboxylate; formate salt;

[(1S)-2-(3,5-dichloro-1-oxido-pyridin-1-ium-4-yl)-1-(3,4-dimethoxyphenyl)ethyl]5-[[[2-[3-(dimethylamino)propoxy]-2-oxo-1-phenyl-ethyl]amino]methyl]thiophene-2-carboxylate;

Epimeric mixture 2 of [2-(3,5-dichloro-1-oxido-pyridin-1-ium-4-yl)-1-(3-ethoxy-4-methoxy-phenyl)ethyl]5-[[[2-oxo-1-phenyl-2-[(3R)-quinuclidin-3-yl]oxy-ethyl]amino]methyl]thiophene-2-carboxylate;

Epimeric mixture 1 of [2-(3,5-dichloro-1-oxido-pyridin-1-ium-4-yl)-1-(3-ethoxy-4-methoxy-phenyl)ethyl]5-[[[2-oxo-1-phenyl-2-[(3R)-quinuclidin-3-yl]oxy-ethyl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[[2-[(8-methyl-8-azabicyclo[3.2.1]octan-3-yl)oxy]-2-oxo-1-phenyl-ethyl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[[1-(2-fluorophenyl)-2-[(3R)-1-methylpyrrolidin-3-yl]oxy-2-oxo-ethyl]amino]methyl]
thiophene-2-carboxylate;

[(1S)-2-(3,5-dichloro-1-oxido-pyridin-1-ium-4-yl)-1-(3,4-dimethoxyphenyl)ethyl]5-[[[2-[(8-benzyl-8-azabicyclo[3.2.1]octan-3-yl)oxy]-2-oxo-1-phenyl-ethyl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[[2-[[(1R,5R)-8-benzyl-8-azabicyclo[3.2.1]octan-3-yl]oxy]-2-oxo-1-phenyl-ethyl]
amino]methyl]thiophene-2-carboxylate;

[(1S)-2-(3,5-dichloro-1-oxido-pyridin-1-ium-4-yl)-1-(3,4-dimethoxyphenyl)ethyl]5-[[[2-[[(1R,5R)-8-methyl-8-azabicyclo[3.2.1]octan-3-yl]oxy]-2-oxo-1-phenyl-ethyl]
amino]methyl]thiophene-2-carboxylate;

[(1S)-2-(3,5-dichloro-1-oxido-pyridin-1-ium-4-yl)-1-(3,4-dimethoxyphenyl)ethyl]5-[[[2-[(1-benzyl-4-piperidyl)oxy]-2-oxo-1-phenyl-ethyl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[[2-[(1-methyl-4-piperidyl)oxy]-2-oxo-1-phenyl-ethyl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[[1-(o-tolyl)-2-oxo-2-[(3R)-quinuclidin-3-yl]oxy-ethyl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[[3-oxo-1-phenyl-3-[(3R)-quinuclidin-3-yl]oxy-propyl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[[1-(2-fluorophenyl)-3-oxo-3-[(3R)-quinuclidin-3-yl]oxy-propyl]amino]methyl]
thiophene-2-carboxylate;

[(1S)-2-(3,5-dichloro-1-oxido-pyridin-1-ium-4-yl)-1-(3,4-dimethoxyphenyl)ethyl]5-[[[3-[(1-methyl-4-piperidyl)oxy]-3-oxo-1-phenyl-propyl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[[3-[(3R)-1-methylpyrrolidin-3-yl]oxy-3-oxo-1-phenyl-propyl]amino]methyl]
thiophene-2-carboxylate;

[(1S)-2-(3,5-dichloro-1-oxido-pyridin-1-ium-4-yl)-1-(3,4-dimethoxyphenyl)ethyl]5-[[ethyl-[2-oxo-1-phenyl-2-[(3R)-quinuclidin-3-yl]oxy-ethyl]amino]methyl]
thiophene-2-carboxylate;

[(3R)-quinuclidin-3-yl]2-[[5-[(1S)-2-(3,5-dichloro-1-oxido-pyridin-1-ium-4-yl)-1-(3,4-dimethoxyphenyl)ethoxy]carbonyl-2-thienyl]methyl]-3,4-dihydro-1H-isoquinoline-1-carboxylate;

[(3R)-quinuclidin-3-yl]2-[2-[5-[2-[(1S)-2-(3,5-dichloro-1-oxido-pyridin-1-ium-4-yl)-1-(3,4-dimethoxyphenyl)
ethoxy]-2-oxo-ethyl]-2-thienyl]ethylamino]-2-phenyl-acetate;

[(1S)-2-(3,5-dichloro-1-oxido-pyridin-1-ium-4-yl)-1-(3,4-dimethoxyphenyl)ethyl]5-[2-[[2-oxo-1-phenyl-2-[(3R)-quinuclidin-3-yl]oxy-ethyl]amino]ethyl]thiophene-2-carboxylate;

[(1S)-2-(3,5-dichloro-1-oxido-pyridin-1-ium-4-yl)-1-(3,4-dimethoxyphenyl)ethyl]5-[[[1-(2-fluorophenyl)-2-[(1-methyl-4-piperidyl)oxy]-2-oxo-ethyl]amino]methyl]
thiophene-2-carboxylate single diastereoisomer 1;

[(1S)-2-(3,5-dichloro-1-oxido-pyridin-1-ium-4-yl)-1-(3,4-dimethoxyphenyl)ethyl]5-[[[1-(2-fluorophenyl)-2-[(1-methyl-4-piperidyl)oxy]-2-oxo-ethyl]amino]methyl]
thiophene-2-carboxylate single diastereoisomer 2;

[(1S)-2-(3,5-dichloro-1-oxido-pyridin-1-ium-4-yl)-1-(3,4-dimethoxyphenyl)ethyl]5-[[[2-[(3R)-1-methylpyrrolidin-3-yl]oxy-2-oxo-1-phenyl-ethyl]amino]methyl]thiophene-2-carboxylate single diastereoisomer 1;

[(1S)-2-(3,5-dichloro-1-oxido-pyridin-1-ium-4-yl)-1-(3,4-dimethoxyphenyl)ethyl]5-[[[2-[(3R)-1-methylpyrrolidin-3-yl]oxy-2-oxo-1-phenyl-ethyl]amino]methyl]thiophene-2-carboxylate single diastereoisomer 2;

single diastereoisomer 1 of epimeric mixture 1 of [1-[3-(cyclopentoxy)-4-methoxy-phenyl]-2-(3,5-dichloro-1- oxido-pyridin-1-ium-4-yl)ethyl]5-[[[2-oxo-1-phenyl-2-[(3R)-quinuclidin-3-yl]oxy-ethyl]amino]methyl]thiophene-2-carboxylate;

single diastereoisomer 2 of epimeric mixture 1 of [1-[3-(cyclopentoxy)-4-methoxy-phenyl]-2-(3,5-dichloro-1-oxido-pyridin-1-ium-4-yl)ethyl]5-[[[2-oxo-1-phenyl-2-[(3R)-quinuclidin-3-yl]oxy-ethyl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[methyl-[2-oxo-1-phenyl-2-[(3R)-quinuclidin-3-yl]oxy-ethyl]amino]methyl]thiophene-2-carboxylate single diastereoisomer 1;

[(1S)-2-(3,5-dichloro-1-oxido-pyridin-1-ium-4-yl)-1-(3,4-dimethoxyphenyl)ethyl]5-[[methyl-[2-oxo-1-phenyl-2-[(3R)-quinuclidin-3-yl]oxy-ethyl]amino]methyl]thiophene-2-carboxylate single diastereoisomer 2;

single diastereoisomer 1 of epimeric mixture 2 of [1-[3-(cyclopentoxy)-4-methoxy-phenyl]-2-(3,5-dichloro-1-oxido-pyridin-1-ium-4-yl)ethyl]5-[[[2-oxo-1-phenyl-2-[(3R)-quinuclidin-3-yl]oxy-ethyl]amino]methyl]thiophene-2-carboxylate;

single diastereoisomer 2 of epimeric mixture 2 of [1-[3-(cyclopentoxy)-4-methoxy-phenyl]-2-(3,5-dichloro-1-oxido-pyridin-1-ium-4-yl)ethyl]5-[[[2-oxo-1-phenyl-2-[(3R)-quinuclidin-3-yl]oxy-ethyl]amino]methyl]thiophene-2-carboxylate;

[(3R)-quinuclidin-3-yl]2-[[5-[(1S)-2-(3,5-dichloro-1-oxido-pyridin-1-ium-4-yl)-1-(3,4-dimethoxyphenyl)ethoxy]carbonyl-2-thienyl]methyl]-3,4-dihydro-1H-isoquinoline-1-carboxylate single diastereoisomer 1;

[(3R)-quinuclidin-3-yl]2-[[5-[(1S)-2-(3,5-dichloro-1-oxido-pyridin-1-ium-4-yl)-1-(3,4-dimethoxyphenyl)ethoxy]carbonyl-2-thienyl]methyl]-3,4-dihydro-1H-isoquinoline-1-carboxylate single diastereoisomer 2;

[(1S)-2-(3,5-dichloro-1-oxido-pyridin-1-ium-4-yl)-1-(3,4-dimethoxyphenyl)ethyl]5-[[[2-[[(1R,5R)-8-methyl-8-azabicyclo[3.2.1]octan-3-yl]oxy]-2-oxo-1-phenyl-ethyl]amino]methyl]thiophene-2-carboxylate single diastereoisomer 1;

[(1S)-2-(3,5-dichloro-1-oxido-pyridin-1-ium-4-yl)-1-(3,4-dimethoxyphenyl)ethyl]5-[[[2-[[(1R,5R)-8-methyl-8-azabicyclo[3.2.1]octan-3-yl]oxy]-2-oxo-1-phenyl-ethyl]amino]methyl]thiophene-2-carboxylate single diastereoisomer 2;

[(1S)-2-(3,5-dichloro-1-oxido-pyridin-1-ium-4-yl)-1-[4-(difluoromethoxy)-3-isopropoxy-phenyl]ethyl]5-[[[2-oxo-1-phenyl-2-[(3R)-quinuclidin-3-yl]oxy-ethyl]amino]methyl]thiophene-2-carboxylate single diastereoisomer 1;

[(1S)-2-(3,5-dichloro-1-oxido-pyridin-1-ium-4-yl)-1-[4-(difluoromethoxy)-3-isopropoxy-phenyl]ethyl]5-[[[2-oxo-1-phenyl-2-[(3R)-quinuclidin-3-yl]oxy-ethyl]amino]methyl]thiophene-2-carboxylate single diastereoisomer 2;

[(1S)-2-(3,5-dichloro-1-oxido-pyridin-1-ium-4-yl)-1-(3,4-dimethoxyphenyl)ethyl]5-[[ethyl-[2-oxo-1-phenyl-2-[(3R)-quinuclidin-3-yl]oxy-ethyl]amino]methyl]thiophene-2-carboxylate; formic acid single diastereoisomer 1;

[(1S)-2-(3,5-dichloro-1-oxido-pyridin-1-ium-4-yl)-1-(3,4-dimethoxyphenyl)ethyl]5-[[ethyl-[2-oxo-1-phenyl-2-[(3R)-quinuclidin-3-yl]oxy-ethyl]amino]methyl]thiophene-2-carboxylate single diastereoisomer 2;

[(1S)-2-(3,5-dichloro-1-oxido-pyridin-1-ium-4-yl)-1-(3,4-dimethoxyphenyl)ethyl]5-[[[2-[2-(dimethylamino)ethoxy]-2-oxo-1-phenyl-ethyl]amino]methyl]thiophene-2-carboxylate single diastereoisomer 1;

[(1S)-2-(3,5-dichloro-1-oxido-pyridin-1-ium-4-yl)-1-(3,4-dimethoxyphenyl)ethyl]5-[[[2-[2-(dimethylamino)ethoxy]-2-oxo-1-phenyl-ethyl]amino]methyl]thiophene-2-carboxylate single diastereoisomer 2;

[(1S)-2-(3,5-dichloro-1-oxido-pyridin-1-ium-4-yl)-1-(3,4-dimethoxyphenyl)ethyl]5-[[[1-(2-fluorophenyl)-2-[(3R)-1-methylpyrrolidin-3-yl]oxy-2-oxo-ethyl]amino]methyl]thiophene-2-carboxylate single diastereoisomer 1;

[(1S)-2-(3,5-dichloro-1-oxido-pyridin-1-ium-4-yl)-1-(3,4-dimethoxyphenyl)ethyl]5-[[[1-(2-fluorophenyl)-2-[(3R)-1-methylpyrrolidin-3-yl]oxy-2-oxo-ethyl]amino]methyl]thiophene-2-carboxylate single diastereoisomer 2;

[(1S)-2-(3,5-dichloro-1-oxido-pyridin-1-ium-4-yl)-1-(3,4-dimethoxyphenyl)ethyl]5-[[[2-[[(3R)-1-methyl-3-piperidyl]oxy]-2-oxo-1-phenyl-ethyl]amino]methyl]thiophene-2-carboxylate single diastereoisomer 1;

[(1S)-2-(3,5-dichloro-1-oxido-pyridin-1-ium-4-yl)-1-(3,4-dimethoxyphenyl)ethyl]5-[[[2-[[(3R)-1-methyl-3-piperidyl]oxy]-2-oxo-1-phenyl-ethyl]amino]methyl]thiophene-2-carboxylate single diastereoisomer 2;

[(1S)-2-(3,5-dichloro-1-oxido-pyridin-1-ium-4-yl)-1-(3,4-dimethoxyphenyl)ethyl]5-[[[2-[3-(dimethylamino)propoxy]-2-oxo-1-phenyl-ethyl]amino]methyl]thiophene-2-carboxylate single diastereoisomer 1;

[(1S)-2-(3,5-dichloro-1-oxido-pyridin-1-ium-4-yl)-1-(3,4-dimethoxyphenyl)ethyl]5-[[[2-[3-(dimethylamino)propoxy]-2-oxo-1-phenyl-ethyl]amino]methyl]thiophene-2-carboxylate single diastereoisomer 2;

[(1S)-2-(3,5-dichloro-1-oxido-pyridin-1-ium-4-yl)-1-(3,4-dimethoxyphenyl)ethyl]5-[[[2-oxo-1-phenyl-2-[(3R)-quinuclidin-3-yl]oxy-ethyl]amino]methyl]thiophene-3-carboxylate single diastereoisomer 1;

[(1S)-2-(3,5-dichloro-1-oxido-pyridin-1-ium-4-yl)-1-(3,4-dimethoxyphenyl)ethyl]5-[[[2-oxo-1-phenyl-2-[(3R)-quinuclidin-3-yl]oxy-ethyl]amino]methyl]thiophene-3-carboxylate single diastereoisomer 2;

[(1S)-2-(3,5-dichloro-1-oxido-pyridin-1-ium-4-yl)-1-(3,4-dimethoxyphenyl)ethyl]-4-[[[2-oxo-1-phenyl-2-[(3R)-quinuclidin-3-yl]oxy-ethyl]amino]methyl]thiophene-2-carboxylate single diastereoisomer 1;

[(1S)-2-(3,5-dichloro-1-oxido-pyridin-1-ium-4-yl)-1-(3,4-dimethoxyphenyl)ethyl]-4-[[[2-oxo-1-phenyl-2-[(3R)-quinuclidin-3-yl]oxy-ethyl]amino]methyl]thiophene-2-carboxylate single diastereoisomer 2;

[(1S)-2-(3,5-dichloro-1-oxido-pyridin-1-ium-4-yl)-1-(3,4-dimethoxyphenyl)ethyl]5-[[[1-(2-fluorophenyl)-2-oxo-2-[(3R)-quinuclidin-3-yl]oxy-ethyl]amino]methyl]thiophene-3-carboxylate single diastereoisomer 1;

[(1S)-2-(3,5-dichloro-1-oxido-pyridin-1-ium-4-yl)-1-(3,4-dimethoxyphenyl)ethyl]5-[[[1-(2-fluorophenyl)-2-oxo-2-[(3R)-quinuclidin-3-yl]oxy-ethyl]amino]methyl]thiophene-3-carboxylate single diastereoisomer 2;

[(1S)-2-(3,5-dichloro-1-oxido-pyridin-1-ium-4-yl)-1-(3,4-dimethoxyphenyl)ethyl]5-[[[2-[(3S)-1-methylpyrrolidin-3-yl]oxy-2-oxo-1-phenyl-ethyl]amino]methyl]thiophene-2-carboxylate single diastereoisomer 1;

[(1S)-2-(3,5-dichloro-1-oxido-pyridin-1-ium-4-yl)-1-(3,4-dimethoxyphenyl)ethyl]5-[[[2-[(3S)-1-methylpyrrolidin-3-yl]oxy-2-oxo-1-phenyl-ethyl]amino]methyl]thiophene-2-carboxylate single diastereoisomer 2;

[(1S)-2-(3,5-dichloro-1-oxido-pyridin-1-ium-4-yl)-1-(3,4-dimethoxyphenyl)ethyl]5-[[[1-(3-hydroxyphenyl)-2-oxo-2-[(3R)-quinuclidin-3-yl]oxy-ethyl]amino]methyl]thiophene-2-carboxylate single diastereoisomer 1;

[(1S)-2-(3,5-dichloro-1-oxido-pyridin-1-ium-4-yl)-1-(3,4-dimethoxyphenyl)ethyl]5-[[[1-(3-hydroxyphenyl)-2-oxo-2-[(3R)-quinuclidin-3-yl]oxy-ethyl]amino]methyl]thiophene-2-carboxylate single diastereoisomer 2;

[(1S)-2-(3,5-dichloro-1-oxido-pyridin-1-ium-4-yl)-1-(3,4-dimethoxyphenyl)ethyl]5-[[[2-[(1-methyl-4-piperidyl)oxy]-2-oxo-1-phenyl-ethyl]amino]methyl]thiophene-2-carboxylate single diastereomer 1;

[(1S)-2-(3,5-dichloro-1-oxido-pyridin-1-ium-4-yl)-1-(3,4-dimethoxyphenyl)ethyl]5-[[[2-[(1-methyl-4-piperidyl)oxy]-2-oxo-1-phenyl-ethyl]amino]methyl]thiophene-2-carboxylate single diastereomer 2;

[(1R)-2-(3,5-dichloro-1-oxido-pyridin-1-ium-4-yl)-1-(3,4-dimethoxyphenyl)ethyl]5-[[[2-oxo-1-phenyl-2-[(3R)-quinuclidin-3-yl]oxy-ethyl]amino]methyl]thiophene-2-carboxylate single diastereomer 1;

[(1R)-2-(3,5-dichloro-1-oxido-pyridin-1-ium-4-yl)-1-(3,4-dimethoxyphenyl)ethyl]5-[[[2-oxo-1-phenyl-2-[(3R)-quinuclidin-3-yl]oxy-ethyl]amino]methyl]thiophene-2-carboxylate single diastereomer 2;

[(1S)-2-(3,5-dichloro-1-oxido-pyridin-1-ium-4-yl)-1-(3,4-dimethoxyphenyl)ethyl]5-[2-[[2-oxo-1-phenyl-2-[(3R)-quinuclidin-3-yl]oxy-ethyl]amino]ethyl]thiophene-2-carboxylate single diastereomer 1;

[(1S)-2-(3,5-dichloro-1-oxido-pyridin-1-ium-4-yl)-1-(3,4-dimethoxyphenyl)ethyl]5-[2-[[2-oxo-1-phenyl-2-[(3R)-quinuclidin-3-yl]oxy-ethyl]amino]ethyl]thiophene-2-carboxylate single diastereomer 2;

[(1S)-2-(3,5-dichloro-1-oxido-pyridin-1-ium-4-yl)-1-(3,4-dimethoxyphenyl)ethyl]5-[[[1-(o-tolyl)-2-oxo-2-[(3R)-quinuclidin-3-yl]oxy-ethyl]amino]methyl]thiophene-2-carboxylate single diastereomer 1;

[(1S)-2-(3,5-dichloro-1-oxido-pyridin-1-ium-4-yl)-1-(3,4-dimethoxyphenyl)ethyl]5-[[[1-(o-tolyl)-2-oxo-2-[(3R)-quinuclidin-3-yl]oxy-ethyl]amino]methyl]thiophene-2-carboxylate single diastereomer 2;

[(3R)-quinuclidin-3-yl]2-[2-[5-[2-[(1S)-2-(3,5-dichloro-1-oxido-pyridin-1-ium-4-yl)-1-(3,4-dimethoxyphenyl)ethoxy]-2-oxo-ethyl]-2-thienyl]ethylamino]-2-phenyl-acetate single diastereomer 1;

[(3R)-quinuclidin-3-yl]2-[2-[5-[2-[(1S)-2-(3,5-dichloro-1-oxido-pyridin-1-ium-4-yl)-1-(3,4-dimethoxyphenyl)ethoxy]-2-oxo-ethyl]-2-thienyl]ethylamino]-2-phenyl-acetate single diastereomer 2;

[(3R)-quinuclidin-3-yl]2-[[5-[2-[(1S)-2-(3,5-dichloro-1-oxido-pyridin-1-ium-4-yl)-1-(3,4-dimethoxyphenyl)ethoxy]-2-oxo-ethyl]-2-thienyl]methylamino]-2-phenyl-acetate single diastereomer 1;

[(1S)-2-(3,5-dichloro-1-oxido-pyridin-1-ium-4-yl)-1-(3,4-dimethoxyphenyl)ethyl]5-[[[3-oxo-1-phenyl-3-[(3R)-quinuclidin-3-yl]oxy-propyl]amino]methyl]thiophene-2-carboxylate single diastereomer 1;

[(1S)-2-(3,5-dichloro-1-oxido-pyridin-1-ium-4-yl)-1-(3,4-dimethoxyphenyl)ethyl]5-[[[3-oxo-1-phenyl-3-[(3R)-quinuclidin-3-yl]oxy-propyl]amino]methyl]thiophene-2-carboxylate single diastereomer 2;

[(1S)-2-(3,5-dichloro-1-oxido-pyridin-1-ium-4-yl)-1-(3,4-dimethoxyphenyl)ethyl]5-[[[1-(2-fluorophenyl)-3-oxo-3-[(3R)-quinuclidin-3-yl]oxy-propyl]amino]methyl]thiophene-2-carboxylate single diastereomer 1;

[(1S)-2-(3,5-dichloro-1-oxido-pyridin-1-ium-4-yl)-1-(3,4-dimethoxyphenyl)ethyl]5-[[[1-(2-fluorophenyl)-3-oxo-3-[(3R)-quinuclidin-3-yl]oxy-propyl]amino]methyl]thiophene-2-carboxylate single diastereomer 2;

[(1S)-2-(3,5-dichloro-1-oxido-pyridin-1-ium-4-yl)-1-(3,4-dimethoxyphenyl)ethyl]5-[[[3-[(3R)-1-methylpyrrolidin-3-yl]oxy-3-oxo-1-phenyl-propyl]amino]methyl]thiophene-2-carboxylate single diastereomer 1;

[(1S)-2-(3,5-dichloro-1-oxido-pyridin-1-ium-4-yl)-1-(3,4-dimethoxyphenyl)ethyl]5-[[[3-[(3R)-1-methylpyrrolidin-3-yl]oxy-3-oxo-1-phenyl-propyl]amino]methyl]thiophene-2-carboxylate single diastereomer 2;

[(1S)-2-(3,5-dichloro-1-oxido-pyridin-1-ium-4-yl)-1-(3,4-dimethoxyphenyl)ethyl]5-[[[3-[(1-methyl-4-piperidyl)oxy]-3-oxo-1-phenyl-propyl]amino]methyl]thiophene-2-carboxylate single diastereomer 1;

[(1S)-2-(3,5-dichloro-1-oxido-pyridin-1-ium-4-yl)-1-(3,4-dimethoxyphenyl)ethyl]5-[[[3-[(1-methyl-4-piperidyl)oxy]-3-oxo-1-phenyl-propyl]amino]methyl]thiophene-2-carboxylate single diastereomer 2;

[(1S)-2-(3,5-dichloro-1-oxido-pyridin-1-ium-4-yl)-1-(3,4-dimethoxyphenyl)ethyl]5-[(2,6-dihydroxyphenyl)-N-[(3R)-quinuclidin-3-yl]oxycarbonyl-anilino)methyl]thiophene-2-carboxylate;

[(1S)-2-(3,5-dichloro-1-oxido-pyridin-1-ium-4-yl)-1-(3,4-dimethoxyphenyl)ethyl]5-[(2-hydroxy-5-(trifluoromethoxy)phenyl)-N-[(3R)-quinuclidin-3-yl]oxycarbonyl-anilino)methyl]thiophene-2-carboxylate;

[(1S)-2-(3,5-dichloro-1-oxido-pyridin-1-ium-4-yl)-1-(3,4-dimethoxyphenyl)ethyl]5-[(2,3-dihydroxyphenyl)-N-[(3R)-quinuclidin-3-yl]oxycarbonyl-anilino)methyl]thiophene-2-carboxylate;

Epimeric mixture 1 of [1-[3-(cyclopentoxy)-4-methoxy-phenyl]-2-(3,5-dichloro-1-oxido-pyridin-1-ium-4-yl)ethyl]5-[[[2-oxo-1-phenyl-2-[(3R)-quinuclidin-3-yl]oxy-ethyl]amino]methyl]thiophene-2-carboxylate;

Epimeric mixture 2 of [1-[3-(cyclopentoxy)-4-methoxy-phenyl]-2-(3,5-dichloro-1-oxido-pyridin-1-ium-4-yl)ethyl]5-[[[2-oxo-1-phenyl-2-[(3R)-quinuclidin-3-yl]oxy-ethyl]amino]methyl]thiophene-2-carboxylate;

[(1S)-2-(3,5-dichloro-1-oxido-pyridin-1-ium-4-yl)-1-[4-(difluoromethoxy)-3-isopropoxy-phenyl]ethyl]5-[[[2-oxo-1-phenyl-2-[(3R)-quinuclidin-3-yl]oxy-ethyl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[[2-[[(3R)-1-methyl-3-piperidyl]oxy]-2-oxo-1-phenyl-ethyl]amino]methyl]thiophene-2-carboxylate;

and pharmaceutically acceptable salts and solvates thereof.

The term "single diastereoisomer" or "diastereoisomer" was reported near the chemical name of each compound isolated as single diastereoisomer whose absolute configuration at a stereogenic centre was not determined. For example, the term "single diastereoisomer" was reported near the chemical name of each compound isolated as single diastereoisomer whose absolute configuration at the stereogenic centre at carbon atom of X (when X is [1]-N(R$_{19}$)—CH<[2]) was not determined. By analogy the term "diastereoisomer" was reported also near the chemical name of each compound isolated as single diastereoisomer whose absolute configuration was not determined at the stereogenic centre at carbon (1) of compounds of formula (I)', as above defined. An asterisk "*" was introduced in the chemical structures on a stereogenic center that was isolated as single diastereoisomer or enantiomer but without assignment of the absolute configuration.

The present invention also provides processes for the preparation of compounds of the invention.

Processes of preparation described below and reported in the following Schemes should not be viewed as limiting the scope of the synthetic methods available for the preparation of the compounds of the invention.

In the following Schemes, for compounds of formula I to XXVI, unless otherwise indicated, $R_1, R_2, R_3, R_4, R_5, L_1, W_1, L_2, W_2$, X, A, n, m and k are as above defined.

Compounds of formula (I) can be obtained according to general synthetic routes reported in Scheme A, B, and C or following the same procedures of Scheme A, B, and C starting from slightly modified reagents, easily identifiable by the skilled person and/or following slightly modified procedures that the skilled person can easily apply.

Scheme A
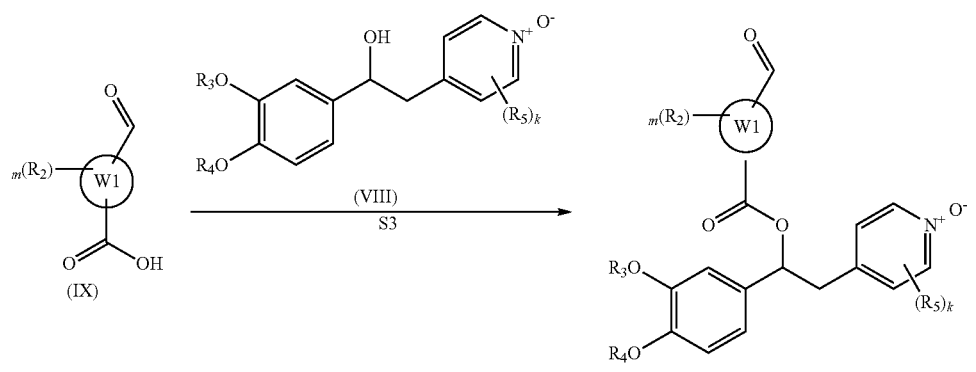
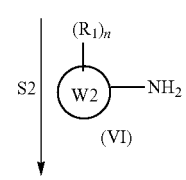
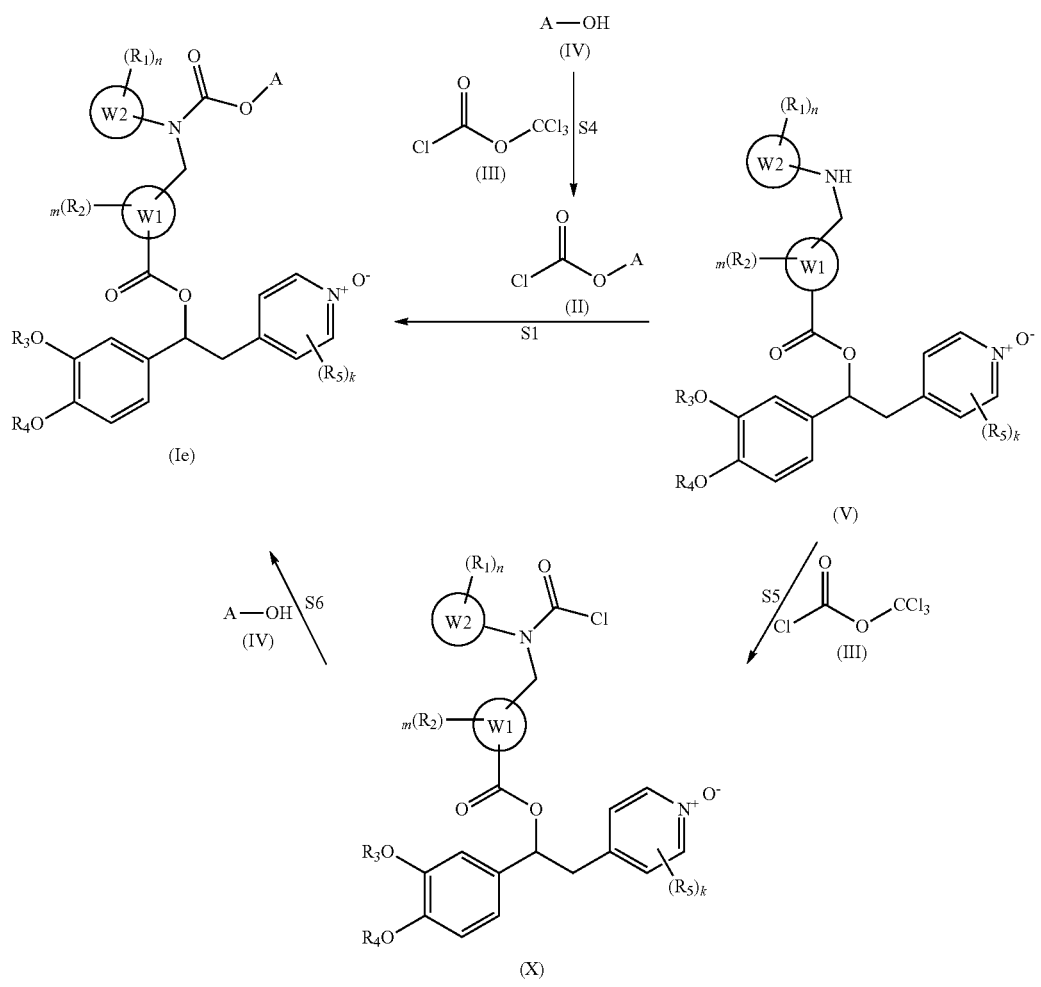

Compounds of formula (Ie), i.e. compounds of formula (I) which are in the form of N-oxide on the pyridine ring and wherein $L_1$ is absent (i.e. $L_1$ is $(CH_2)_p$ and p is 0) and $L_2$ is $CH_2$ and X is a N atom may be prepared according to Scheme A.

In sub-schemes S1 to S6 are described single steps that are represented in scheme A Aldehydes of formula (VII) may be obtained following sub-scheme (S3) by reacting a carboxylic acid of formula (IX) with an alcohol of formula (VIII) in a suitable solvent, such as DCM or DMF in the presence of a coupling agent, such as EDC/DMAP or HATU, at an appropriate temperature, such as room (or ambient) temperature.

Amines of formula (V) may be obtained following sub-scheme (S2) by reacting an aldehyde of formula (VII) with an amine of formula (VI) in a suitable solvent, such as DCM, in the presence of an acid, such as acetic acid, under reducing conditions, for example with sodium borohydride, sodium triacetoxyborohydride, sodium cyanoborohydride or by catalytic hydrogenation, and an optional catalyst, such as DMAP, at an appropriate temperature such as room (or ambient) temperature or 0° C. or 40° C. or 50° C.

Chloroformates of formula (II) may be obtained following sub-scheme S4 by reacting an alcohol of formula (IV) with trichloromethyl chloroformate in a suitable solvent, such as MeCN, at an appropriate temperature, such as 0° C. or room temperature Carbamoylchlorides of formula (X) may be obtained following sub-scheme S5 by reacting an amine of formula (V) with trichloromethyl chloroformate in a suitable solvent, such as MeCN, at an appropriate temperature, such as 0° C. or room temperature.

Compounds of formula (Ie) may be obtained following sub-scheme S1 by reacting an amine of formula (V) with a chloroformate of formula (II) in a suitable solvent, such as THF or pyridine or $CH_3CN$, at high temperatures, typically between 70° C. and 150° C. or by microwave irradiation.

Compounds of formula (Ie) may also be obtained following sub-scheme S6 by reacting a carbamoyl chloride of formula (X) with an alcohol of formula (IV) in a suitable solvent, such as THF or pyridine or $CHCl_3$, at an appropriate temperature, such as room temperature.

Compounds of formula (Ie), i.e. compounds of formula (I) which are in the form of N-oxide on the pyridine ring and wherein $L_1$ is absent (i.e. $L_1$ is $(CH_2)_p$ and p is 0) and $L_2$ is $CH_2$ and X is a N atom may also be prepared according to Scheme B.

Scheme B

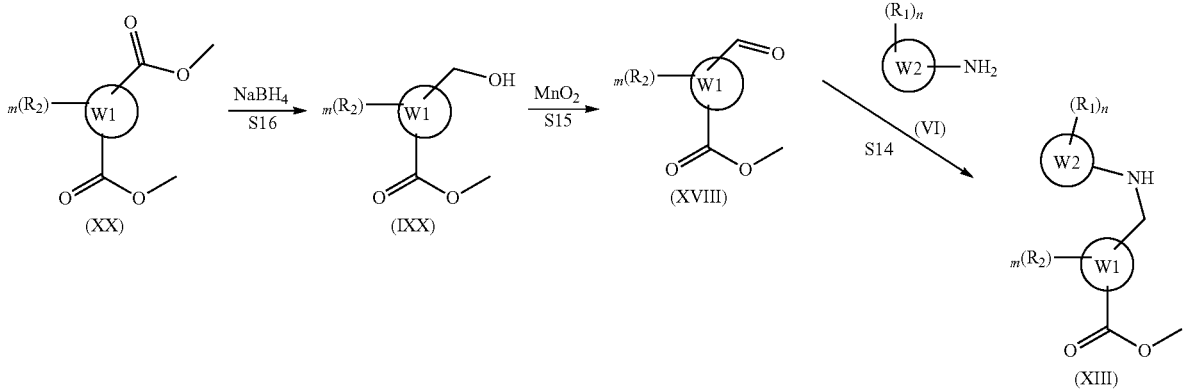

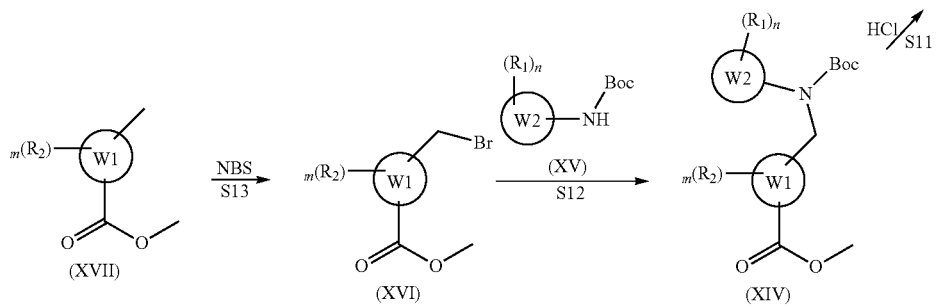

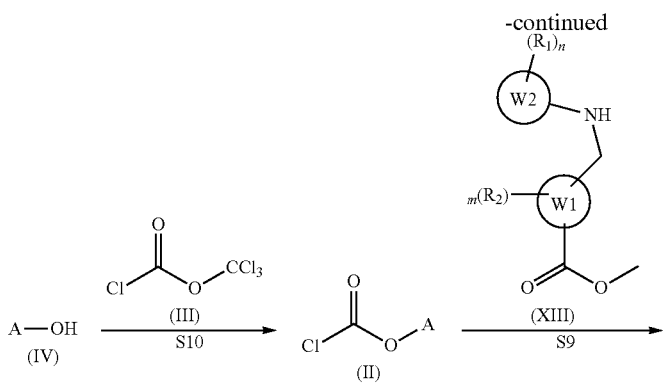
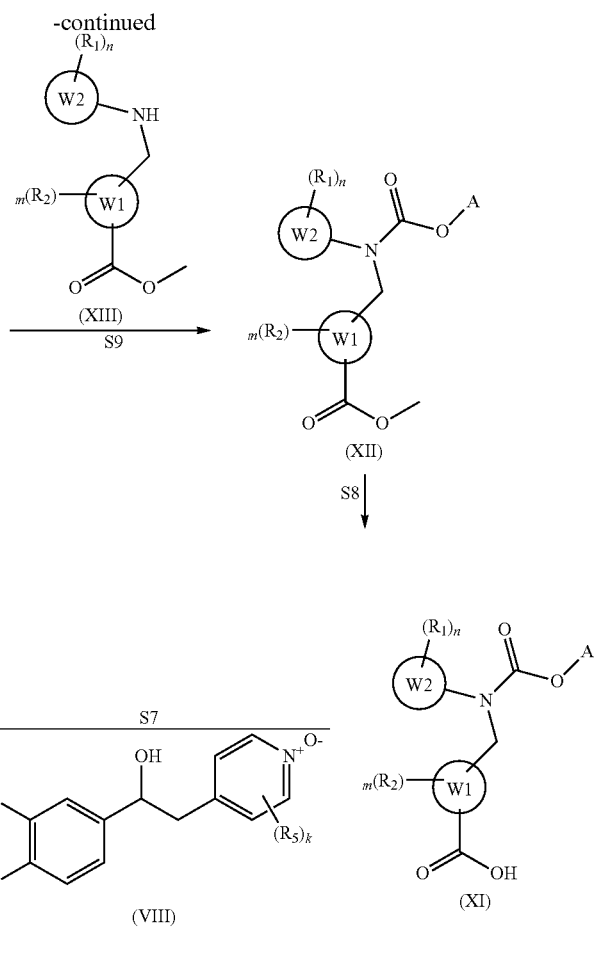

In sub-schemes S7 to S16 are described single steps represented in scheme B

Alcohols of formula (IXX) may be obtained following sub-scheme S16 by reaction of an ester of formula (XX) with a reducing agent such as sodium borohydride in a solvent such as THF.

Aldehydes of formula (XVII) may be obtained following sub-scheme S15 by oxidation of alcohols of formula (IXX) with an oxidising agent such as MnO2 under solvent free conditions or in a suitable solvent such as DCM at room temperature or at higher temperatures such as 50° C.

Intermediates of formula (XIII) may be obtained following sub-scheme S14 by reaction of an amine of formula (VI) with an aldehyde of formula (XVIII) in a suitable solvent, such as acetonitrile in the presence of an acid, such as acetic acid, and a reducing agent, such as NaB(OAc)$_3$H, at an appropriate temperature, such as room (or ambient) temperature or 0° C. or 40° C.

Intermediates of formula (XIII) may also be obtained following sub-scheme S11 by reaction of a compound of formula (XIV) with an acid such as HCl in a suitable solvent, such as dioxane or DCM at an appropriate temperature, such as room (or ambient) temperature or 0° C.

Intermediates (XIV) may be obtained following sub-scheme S12 by alkylation of a compound of formula (XV) with a bromide of formula (XVI) in a suitable aprotic solvent such as DMF or THF in the presence of a strong base such as NaH at an appropriate temperature, such as room (or ambient) temperature or 0° C.

Intermediates of formula (XVI) may be obtained following sub-scheme S13 by reaction of a compound of formula (XVII) with a brominating agent such as NBS or bromine in a suitable solvent such as DCM at an appropriate temperature, such as room (or ambient) temperature or 0° C.

Chloroformates of formula (II) may be obtained following sub-scheme S10 by reacting an alcohol of formula (IV) with trichloromethyl chloroformate (III) in a suitable solvent, such as MeCN, at an appropriate temperature, such as 0° C.

Intermediates of formula (XII) may be obtained following sub-scheme S9 by reaction of an amine of formula (XIII) with a chloroformate of formula (II) in a suitable solvent, such as THF or pyridine or CH$_3$CN, at high temperatures, typically between 70° C. and 150° C. or by microwave irradiation.

Intermediates of formula (XI) may be obtained following sub-scheme S8 by hydrolysis of a compound of formula (XII) in a suitable solvent mixture, such as THF/MeOH/water, in the presence of a suitable base, such as lithium hydroxide, at an appropriate temperature such as room temperature or 40° C.

Compounds of formula (Ie) may be obtained following sub-scheme S7 by reacting an alcohol of formula (VIII) with a carboxylic acid of formula (XI) in a suitable solvent, such as DMF, in the presence of a coupling agent, such as EDC/DMAP or HATU, at an appropriate temperature such as room (or ambient) temperature or 40° C.

Compounds of formula (If), i.e. compounds of formula (I) which are in the form of N-oxide on the pyridine ring and wherein $L_1$ is absent (i.e. $L_1$ is $(CH_2)_p$ and p is 0) and $L_2$ is $CH_2$, and X is a group [1]-$N(R_{19})$—CH<[2] (wherein $R_{19}$ is selected from hydrogen, ($C_1$-$C_6$) alkyl and benzyl and wherein [1] represents the point of attachment of group X to $L_2$ and [2] represents the point of attachment of group X to the group $W_2$ and to the carbonyl group) may be prepared according to Scheme C.

Scheme C
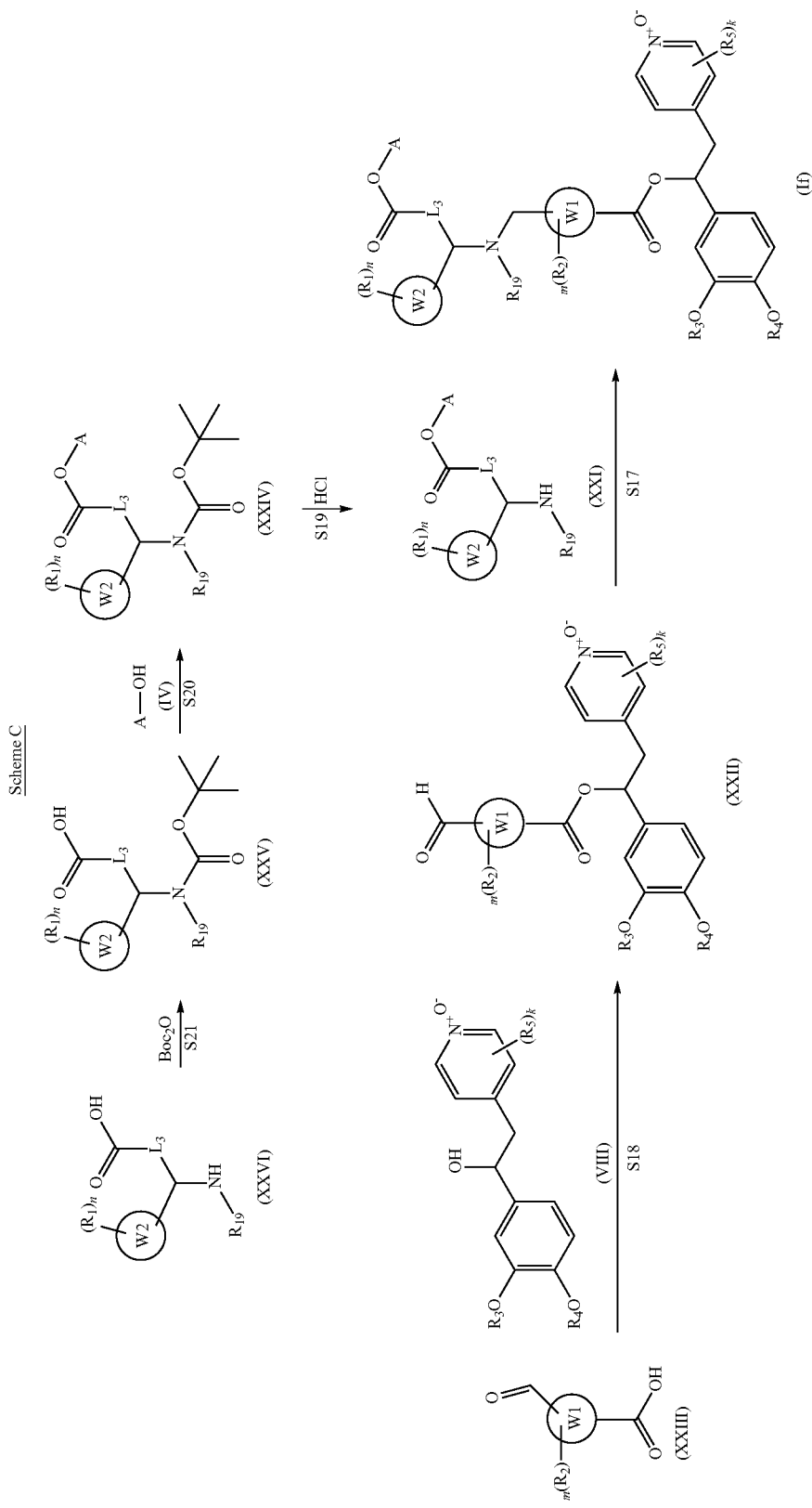

In sub-schemes S17 to S21 are described single steps that are represented in scheme C Intermediates of formula (XXV) may be commercially available or intermediates of formula (XXV) may be obtained following sub-scheme S21 by reaction of a glycine derivative of formula (XXVI) with di-tert-butyl dicarbonate in a suitable solvent, such as dioxane/water in the presence of a base such as NaOH at 0° C. or at room temperature.

Intermediates of formula (XXIV) may be obtained following sub-scheme S20 by reaction of an alcohol of formula (IV) with an intermediate of formula (XXV) in a solvent such as THF, in the presence of a condensing agent and a dehydrating agent such as 1-hydroxybenzotriazole and N,N'-dicyclohexylcarbodiimide at 0° C. or at room temperature.

Intermediates of formula (XXI) may be obtained following sub-scheme S19 by reaction of an intermediate of formula (XXIV) with an acid such as HCl in a suitable solvent, such as dioxane or DCM at an appropriate temperature, such as room (or ambient) temperature or 0° C. Intermediates of formula (XXI) may be directly used in the following step (subscheme S17) without isolation Intermediates of formula (XXII) may be obtained following sub-scheme S18 by reaction of an alcohol of formula (VIII) with a carboxylic acid of formula (XXIII) in a suitable solvent, such as DMF, in the presence of a coupling agent, such as EDC/DMAP or HATU, at an appropriate temperature such as room (or ambient) temperature or 40° C.

Compounds of formula (If) may be obtained following sub-scheme S17 by reaction of an intermediate of formula (XXII) with an intermediate of formula (XXI) in a suitable solvent, such as DCM or ethanol or CH$_3$CN, in the presence of an acid such as acetic acid, or using a salt of (XXI), under reducing conditions, for example with sodium borohydride, sodium triacetoxyborohydride, sodium cyanoborohydride or by catalytic hydrogenation, and an optional catalyst, such as DMAP, at an appropriate temperature such as room (or ambient) temperature or 0° C. or 40° C. or 50° C.

The processes described are particularly advantageous as they are susceptible of being properly modulated, through any proper variant known to the skilled person, so as to obtain any of the desired compounds of the invention. Such variants are comprised within the scope of the present invention. Synthetic procedures not comprise in the above described schemes are precisely described for the specific compounds From all of the above, it should be clear to the skilled person that any of the described groups may be present as such or in any properly protected form.

In particular, functional groups present in the compounds of formula II to XXVI and which could generate unwanted side reactions and by-products, need to be properly protected before the alkylation, acylation, coupling, oxidation or sulfonylation takes place. Likewise, subsequent deprotection of those same protected groups may follow upon completion of the said reactions.

According to the invention, unless otherwise indicated, the term "protecting group" designates a protective group adapted to preserve the function of the group it is bound to. Typically, protective groups are used to preserve amino, hydroxy, or carboxyl functions. Appropriate protecting groups may thus include, for example, benzyl, benzyloxycarbonyl, t-butoxycarbonyl, alkyl or benzyl esters or the like, which are well known to those skilled in the art [see, for a general reference, T. W. Green; Protective Groups in Organic Synthesis (Wiley, N.Y. 1999) which is incorporated herein by reference in its entirety].

Likewise, selective protection and deprotection of any of the said groups, for instance including carbonyl, hydroxy or amino groups, may be accomplished according to very well-known methods commonly employed in organic synthetic chemistry.

The N-oxides on the 4-pyridinyl ring of the compounds of general formula (I) and embodiments thereof may be prepared according to methods available in the literature and well known to the skilled person. For instance they may be prepared by dissolving the compound of general formula (I) or embodiments thereof in CH$_2$Cl$_2$ or CHCl$_3$, then adding an oxidizing agent such as m-chloro perbenzoic acid (mCPBA) to the resulting solution. Other oxidizing agents which may be used are hydrogen peroxide, perbenzoic acid and peracetic acid.

Alternatively, in particular for those compounds comprising functional groups sensitive to oxidation, the corresponding N-oxides are prepared by carrying out the oxidation step before further functional groups are introduced.

In a preferred embodiment, the process for preparation of compounds of formula (I) or embodiments thereof is performed starting from N-oxide on the pyridine ring of compound of formula (VIII), thus allowing the preparation of compound of formula (I) or embodiments thereof in the form of N-oxides on the pyridine ring.

Optional salification of the compounds of formula (I) or N-oxides on the pyridine ring thereof may be carried out by properly converting any of the free acidic or amino groups into the corresponding pharmaceutically acceptable salts. In this case too, the operative conditions being employed for the optional salification of the compounds of the present invention are all within the ordinary knowledge of the skilled person.

From all of the above, it should be clear to the skilled person that the above process, comprehensive of any variant thereof for the preparation of suitable compounds of the present invention, may be conveniently modified so that to adapt the reaction conditions to the specific needs, for instance by choosing appropriate condensing agents, solvents and protective groups, as the case may be.

The present invention also provides pharmaceutical compositions of compounds of the present invention in admixture with one or more pharmaceutically acceptable carriers, for example those described in Remington's Pharmaceutical Sciences Handbook, XVII Ed., Mack Pub., N.Y., U.S.A., which is incorporated herein by reference in its entirety.

Administration of the compounds of the present invention or may be accomplished according to patient needs, for example, orally, nasally, parenterally (subcutaneously, intravenously, intramuscularly, intrasternally and by infusion), by inhalation, rectally, vaginally, topically, locally, transdermally, and by ocular administration. Various solid oral dosage forms may be used for administering compounds of the present invention including such solid forms as tablets, gelcaps, capsules, caplets, granules, lozenges and bulk powders. The compounds of the present invention may be administered alone or combined with various pharmaceutically acceptable carriers, diluents (such as sucrose, mannitol, lactose, starches) and excipients known in the art, including but not limited to suspending agents, solubilizers, buffering agents, binders, disintegrants, preservatives, colorants, flavorants, lubricants and the like. Time release capsules, tablets and gels are also advantageous in administering the compounds of the present invention.

Various liquid oral dosage forms may also be used for administering compounds of the present invention, including aqueous and non-aqueous solutions, emulsions, suspensions, syrups, and elixirs. Such dosage forms can also contain suitable inert diluents known in the art such as water and suitable excipients known in the art such as preservatives, wetting agents, sweeteners, flavorants, as well as agents for emulsifying and/or suspending the compounds of the invention. The compounds of the present invention may be injected, for example, intravenously, in the form of an isotonic sterile solution. Other preparations are also possible.

Suppositories for rectal administration of the compounds of the present invention may be prepared by mixing the compound with a suitable excipient such as cocoa butter, salicylates and polyethylene glycols.

Formulations for vaginal administration may be in the form of cream, gel, paste, foam, or spray formula containing, in addition to the active ingredient, such suitable carriers as are known in the art.

For topical administration the pharmaceutical composition may be in the form of creams, ointments, liniments, lotions, emulsions, suspensions, gels, solutions, pastes, powders, sprays, and drops suitable for administration to the skin, eye, ear or nose. Topical administration may also involve transdermal administration via means such as transdermal patches.

For the treatment of the diseases of the respiratory tract, the compounds according to the present invention are preferably administered by inhalation.

Inhalable preparations include inhalable powders, propellant-containing metered aerosols or propellant-free inhalable formulations and may be administered through a suitable inhalation device which may be respectively selected from dry powder inhaler, pressurized metered dosed inhaler, or a nebulizer.

For administration as a dry powder, single- or multi-dose inhalers known from the prior art may be utilized. In that case the powder may be filled in gelatine, plastic or other capsules, cartridges or blister packs or in a reservoir.

A diluent or carrier, generally non-toxic and chemically inert to the compounds of the present invention, e.g. lactose or any other additive suitable for improving the respirable fraction may be added to the powdered compounds of the present invention.

Inhalation aerosols containing propellant gas such as hydrofluoroalkanes may contain the compounds of the invention either in solution or in dispersed form. The propellant-driven formulations may also contain other ingredients such as co-solvents, stabilizers and optionally other excipients.

The propellant-free inhalable formulations comprising the compounds of the present invention may be in form of solutions or suspensions in an aqueous, alcoholic or hydroalcoholic medium and they may be delivered by jet or ultrasonic nebulizers known from the prior art or by soft-mist nebulizers such as Respimat®.

The compounds of the present invention may be administered as the sole active agent or in combination with other pharmaceutical active ingredients including those currently used in the treatment of respiratory disorders, e.g. beta2-agonists, antimuscarinic agents, corticosteroids, mitogen-activated protein kinases (P38 MAP kinase) inhibitors, nuclear factor kappa-B kinase subunit beta (IKK2) inhibitors, human neutrophil elastase (HNE) inhibitors, phosphodiesterase 4 (PDE4) inhibitors, leukotriene modulators, non-steroidal anti-inflammatory agents (NSAIDs) and mucus regulators.

The present invention also provides combinations of a compound of the present invention, with a β2-agonist selected from the group consisting of carmoterol, vilanterol (GSK-642444), indacaterol, milveterol, arformoterol, formoterol, salbutamol, levalbuterol, terbutaline, AZD-3199, olodaterol (BI-1744-CL), abediterol (LAS-100977), bambuterol, isoproterenol, procaterol, clenbuterol, reproterol, fenoterol and ASF-1020 and salts thereof.

The present invention also provides combinations of a compound of the present invention, with a corticosteroid selected from the group consisting of fluticasone propionate, fluticasone furoate, mometasone furoate, beclometasone dipropionate, ciclesonide, budesonide, GSK 685698, and GSK 870086.

The present invention also provides combinations of a compound of the present invention, with an antimuscarinic agent selected from the group consisting of aclidinium, tiotropium, ipratropium, trospium, glycopyrronium and oxitropium salts.

The present invention also provides combinations of a compound of the present invention, with a PDE4 inhibitor selected from the group consisting of AN-2728, AN-2898, CBS-3595, apremilast, ELB-353, KF-66490, K-34, LAS-37779, IBFB-211913, AWD-12-281, cipamfylline, cilomilast, roflumilast, BAY19-8004 and SCH-351591, AN-6415, indus-82010, TP1-PD3, ELB-353, CC-11050, GSK-256066, oglemilast, OX-914, tetomilast, MEM-1414, and RPL-554.

The present invention also provides combinations of a compound of the present invention, with a P38 MAP kinase inhibitor selected from the group consisting of semapimod, talmapimod, pirfenidone, PH-797804, GSK-725, minokine and losmapimod and salts thereof.

In a preferred embodiment, the present invention provides combinations of a compound of the present invention with an IKK2 inhibitor.

The present invention also provides combinations of a compound of the present invention with a HNE inhibitor selected from the group consisting of AAT, ADC-7828, Aeriva, TAPI, AE-3763, KRP-109, AX-9657, POL-6014, AER-002, AGTC-0106, respriva, AZD-9668, zemaira, AAT IV, PGX-100, elafin, SPHD-400, prolastin C and prolastin inhaled.

The present invention also provides combinations of a compound of the present invention with a leukotriene modulator selected from the group consisting of montelukast, zafirlukast and pranlukast.

The invention also provides combinations of a compound of the present invention with a NSAID selected from the group consisting of ibuprofen and ketoprofen.

The invention also provides combinations of a compound of the present invention with a mucus regulator selected from the group consisting of INS-37217, diquafosol, sibenadet, CS-003, talnetant, DNK-333, MSI-1956 and gefitinib.

The dosages of the compounds of the present invention depend upon a variety of factors including the particular disease to be treated, the severity of the symptoms, the route of administration, the frequency of the dosage interval, the particular compound utilized, the efficacy, toxicology profile, and pharmacokinetic profile of the compound.

Advantageously, the compounds of the present invention may be administered for example, at a dosage of 0.001 to 1000 mg/day, preferably 0.1 to 500 mg/day.

When they are administered by inhalation route, the dosage of the compounds of the present invention is advantageously 0.01 to 20 mg/day, preferably between 0.1 to 10 mg/day.

Preferably, the compounds of the present invention alone or combined with other active ingredients may be administered for the prevention and/or treatment of any obstructive respiratory disease such as asthma, chronic bronchitis and chronic obstructive pulmonary disease (COPD).

The compounds of the present invention may be administered for the prevention and/or treatment of any disease wherein PDE4 inhibition or M3 antagonism is required. Said disease include: allergic disease states such as atopic dermatitis, urticaria, allergic rhinitis, allergic conjunctivitis, vernal conjunctivitis, eosinophilic granuloma, psoriasis, inflammatory arthritis, rheumatoid arthritis, septic shock, ulcerative colitis, Crohn's disease, reperfusion injury of the myocardium and brain, chronic glomerulonephritis, endotoxic shock, cystic fibrosis, arterial restenosis, artherosclerosis, keratosis, rheumatoid spondylitis, osteoarthritis, pyresis, diabetes mellitus, pneumoconiosis, toxic and allergic contact eczema, atopic eczema, seborrheic eczema, lichen simplex, sunburn, pruritus in the anogenital area, alopecia greata, hypertrophic scars, discoid lupus erythematosus, systemic lupus erythematosus, follicular and wide-area pyodermias, endogenous and exogenous acne, acne rosacea, Behçet's disease, anaphylactoid purpura nephritis, inflammatory bowel disease, leukemia, multiple sclerosis, gastrointestinal diseases, autoimmune diseases and the like.

They also include neurological and psychiatric disorders such as Alzheimer's disease, multiple sclerosis, amylolaterosclerosis (ALS), multiple systems atrophy (MSA), schizophrenia, Parkinson's disease, Huntington's disease, Pick's disease, depression, stroke, and spinal cord injury.

Other features of the invention will become apparent in the course of the following descriptions of exemplary embodiments which are given for illustration of the invention and are not intended to be limiting thereof.

EXAMPLES

Abbreviations

DCC=N,N'-dicyclohexylcarbodiimide;
HOBt=hydroxybenzotriazole;
HATU=(dimethylamino)-N,N-dimethyl(3H-[1,2,3]triazolo[4,5-b]pyridin-3-yloxy)methaniminium hexafluorophosphate;
CDI=camonyldiimidazole;
EDC=1-ethyl-3-(3-dimethylaminopropyl) carbodiimide hydrochloride;
DMAP=4-dimethylaminopyridine;
DMF=dimethylformamide;
DMSO=dimethyl sulfoxide;
EtOAc=ethyl acetate;
RT=room temperature;
THF=tetrahydrofuran;
DCM=dichloromethane;
MeOH=methyl alcohol;
EtOH=ethyl alcohol;
LHMDS=lithium bis(trimethylsilyl)amide;
m-CPBA=meta-Chloroperoxybenzoic acid;
TFA=trifluoroacetic acid;
LC-MS=liquid chromatography/mass spectrometry;
NMR=nuclear magnetic resonance;
HPLC=high pressure liquid chromatography;
MPLC=medium pressure liquid chromatography;
SFC=supercritical fluid chromatography
General Experimental Details
Analytical Methods
Liquid Chromatography-Mass Spectrometry
Method 1

LC-MS was performed on a Waters 2795 Alliance HT HPLC with Waters 2996 Diode Array Detector coupled to a Micromass ZQ, single quadrapole mass spectrometer using a Phenomenex Luna C18 (2) column (5 µm, 100×4.6 mm plus guard cartridge) with a linear gradient of 5-95% acetonitrile/water (with 0.1% formic acid in each mobile phase) within 3.5 minutes and held at 95% for 2.0 minutes.

Method 2

LC-MS was performed on a Waters 2795 Alliance HT HPLC with Waters 2996 Diode Array Detector coupled to a Micromass ZQ, single quadrapole mass spectrometer using a Waters Xterra MS C18 column (5 µm, 100×4.6 mm plus guard cartridge) being initially held at 5% acetonitrile/water (with 10 mM ammonium bicarbonate in the aqueous mobile phase) for 0.5 minutes, followed by a linear gradient of 5-95% within 3.5 minutes and then held at 95% for 1.5 minutes.

Method 3

UPLC-MS was performed on a UPLC Acquity with AcquityPDA Detector coupled to a Micromass ZQ, Acquity QDA detector single quadrapole mass spectrometer using a Waters BEH column C18 (1.7 µm, 50×2.1 mm) with a linear gradient of 1-99.9% acetonitrile/water (with 0.05% formic acid in each mobile phase) within 4 minutes and held at 99.9% for 3.5 minutes; F=1 ml/min Method 4

UPLC-MS was performed on a Waters UPLC H Class with a Diode Array Detector coupled to a Waters XEVO-TQS, triple quadrupole mass spectrometer with an electrospray ionization (ESI) source, using a Aquity UPLC CSH C18 1.7 µm 50×2.10 (Waters). Mobile phase A consisted of Ammonium Formiate buffer (25 mM at pH 3) and mobile phase B of 0.1% formic acid in acetonitrile. The flow rate was 0.35 ml/min and the gradient started from 20% to 80% of mobile phase B in 5.5 min followed by an isocratic step at 80% for 2 minutes. The mass spectrometer operated switching between positive and negative ion mode (mass range 150-1000).

Chiral Separation Protocol

The diastereomeric separation of compounds was achieved either by chiral High Performance Liquid Chromatography (HPLC) using a Gilson Trilution preparative HPLC system (322 pump, 155 UV/VIS, GX281 liquid handler and fraction collector) or by Supercritical Fluid Chromatography (SFC) using a Waters Thar Prep100 preparative SFC system (P200 $CO_2$ pump, 2545 modifier pump, 2998 UV/VIS detector, 2767 liquid handler with Stacked Injection Module). The Waters 2767 liquid handler acted as both auto-sampler and fraction collector.

The column used for the preparative purification of the compounds was a Diacel Chiralpak IA/IB/IC, a Phenomenex Lux Cellulose-4, an YMC Amylose-C or an YMC Cellulose-C at 5 µm 250×20–21.2 mm ID.

Appropriate isocratic methods were selected based on methanol, ethanol or isopropanol solvent systems under unmodified or basic conditions.

The standard SFC method used was modifier, $CO_2$, 100 mL/min, 120 Bar backpressure, 40° C. column temperature.

The standard HPLC method used was modifier, heptane, 5 mL/min and room temperature.

The modifier used under basic conditions was diethylamine (0.1% V/V). The modifier used under acidic conditions was either formic acid (0.1% V/V) or trifluoroacetic acid (0.1% V/V).

The SFC purification was controlled by Waters Fractionlynx software through monitoring at 210-400 nm and triggered at a threshold collection value, typically 260 nm. Collected fractions were analysed by SFC (Waters/Thar SFC systems with Waters SQD). The fractions that contained the desired product were concentrated by vacuum centrifugation.

HPLC purification was controlled by Gilson Trilution software monitoring two wavelengths and triggered at a threshold collection value, typically 260 nm. Collected fractions were analysed by HPLC (Agilent 1200 series HPLC system). The fractions that contained the desired product were concentrated by vacuum centrifugation.

Supercritical Fluid Chromatography—Mass Spectrometry Analytical Conditions

Method 5

SFC-MS was performed on a Waters/Thar SFC systems with Waters SQD using a YMC Cellulose-C column with a 40% iso-propyl alcohol/$CO_2$ (with 0.1% diethylamine) isocratic run at 5 mL/min, 120 Bar backpressure, 40° C. column temperature.

Method 6

SFC-MS was performed on a Waters/Thar SFC systems with Waters SQD using a YMC Cellulose-C column with a 25% ethanol/$CO_2$ (with 0.1% diethylamine) isocratic run at 5 mL/min, 120 Bar backpressure, 40° C. column temperature.

Method 7

SFC-MS was performed on a Waters/Thar SFC systems with Waters SQD using a Chiralpak IA column with a 45% iso-propyl alcohol/$CO_2$ (with 0.1% diethylamine) isocratic run at 5 mL/min, 120 Bar backpressure, 40° C. column temperature.

Method 8

SFC-MS was performed on a Waters/Thar SFC systems with Waters SQD using a Chiralpak IA column with a 55% iso-propyl alcohol/$CO_2$ (with 0.1% diethylamine) isocratic run at 5 mL/min, 120 Bar backpressure, 40° C. column temperature.

Method 9

SFC-MS was performed on a Waters/Thar SFC systems with Waters SQD using a Chiralpak IA column with a 30% ethanol/$CO_2$ (with 0.1% diethylamine) isocratic run at 5 mL/min, 120 Bar backpressure, 40° C. column temperature.

Method 10

SFC-MS was performed on a Waters/Thar SFC systems with Waters SQD using a Chiralpak IA column with a 40% ethanol/$CO_2$ (with 0.1% diethylamine) isocratic run at 5 mL/min, 120 Bar backpressure, 40° C. column temperature.

Method 11

SFC-MS was performed on a Waters/Thar SFC systems with Waters SQD using a Chiralpak IB column with a 30% ethanol/$CO_2$ (with 0.1% diethylamine) isocratic run at 5 mL/min, 120 Bar backpressure, 40° C. column temperature.

Method 12

SFC-MS was performed on a Waters/Thar SFC systems with Waters SQD using a YMC Amylose-C column with a 30% iso-propyl alcohol/$CO_2$ (with 0.1% diethylamine) isocratic run at 5 mL/min, 120 Bar backpressure, 40° C. column temperature.

Method 13

SFC-MS was performed on a Waters/Thar SFC systems with Waters SQD using a YMC Amylose-C column with a 40% iso-propyl alcohol/$CO_2$ (with 0.1% diethylamine) isocratic run at 5 mL/min, 120 Bar backpressure, 40° C. column temperature.

Method 14

SFC-MS was performed on a Waters/Thar SFC systems with Waters SQD using a YMC Amylose-C column with a 45% iso-propyl alcohol/$CO_2$ (with 0.1% diethylamine) isocratic run at 5 mL/min, 120 Bar backpressure, 40° C. column temperature.

Method 15

SFC-MS was performed on a Waters/Thar SFC systems with Waters SQD using a YMC Amylose-C column with a 55% iso-propyl alcohol/$CO_2$ (with 0.1% diethylamine) isocratic run at 5 mL/min, 120 Bar backpressure, 40° C. column temperature.

Method 16

SFC-MS was performed on a Waters/Thar SFC systems with Waters SQD using a YMC Cellulose-C column with a 35% ethanol/$CO_2$ (with 0.1% diethylamine) isocratic run at 5 mL/min, 120 Bar backpressure, 40° C. column temperature.

Method 17

SFC-MS was performed on a Waters/Thar SFC systems with Waters SQD using a YMC Cellulose-C column with a 40% iso-propyl alcohol/$CO_2$ (with 0.1% diethylamine) isocratic run at 5 mL/min, 120 Bar backpressure, 40° C. column temperature.

Method 18

SFC-MS was performed on a Waters/Thar SFC systems with Waters SQD using a YMC Amylose-C column with a 35% iso-propyl alcohol/$CO_2$ (with 0.1% diethylamine) isocratic run at 5 mL/min, 120 Bar backpressure, 40° C. column temperature.

Method 23

SFC-MS was performed on a Waters/Thar SFC systems with Waters SQD using a Chiralpak IA column with a 40% iso-propyl alcohol/$CO_2$ (with 0.1% diethylamine) isocratic run at 5 mL/min, 120 bar backpressure, 40° C. column temperature.

Method 24

SFC-MS was performed on a Waters/Thar SFC systems with Waters SQD using a Chiralpak IA column with a 35% iso-propyl alcohol/$CO_2$ (with 0.1% diethylamine) isocratic run at 5 mL/min, 120 bar backpressure, 40° C. column temperature.

Method 25

SFC-MS was performed on a Waters/Thar SFC systems with Waters SQD using a Chiralpak IB column with a 35% ethanol/$CO_2$ (with 0.1% diethylamine) isocratic run at 5 mL/min, 120 bar backpressure, 40° C. column temperature.

Method 26

SFC-MS was performed on a Waters/Thar SFC systems with Waters SQD using a YMC cellulose column with a 30% iso-propyl alcohol/$CO_2$ (with 0.1% diethylamine) isocratic run at 5 mL/min, 120 bar backpressure, 40° C. column temperature.

Method 27

SFC-MS was performed on a Waters/Thar SFC systems with Waters SQD using a Chiralpak IC column with a 55% iso-propyl alcohol/$CO_2$ (with 0.1% diethylamine) isocratic run at 5 mL/min, 120 bar backpressure, 40° C. column temperature.

Method 28

SFC-MS was performed on a Waters/Thar SFC systems with Waters SQD using a Lux Cellulose-4 column with a 35% iso-propyl alcohol/$CO_2$ (with 0.1% diethylamine) isocratic run at 5 mL/min, 120 bar backpressure, 40° C. column temperature.

Method 29

SFC-MS was performed on a Waters/Thar SFC systems with Waters SQD using a Lux Cellulose-4 column with a 55% ethanol/$CO_2$ (with 0.1% diethylamine) isocratic run at 5 mL/min, 120 bar backpressure, 40° C. column temperature.

Chiral HPLC—Analytical Conditions

Method 19

Chiral HPLC was performed on an Agilent 1200 series HPLC system using a Chiralpak IA column with 50% iso-propyl alcohol/heptane (with 0.1% diethylamine) at 1 mL/min.

Method 20

Chiral HPLC was performed on an Agilent 1200 series HPLC system using a Chiralpak IC column with 50% tetrahydrofuran/heptane (with 0.1% diethylamine) at 1 mL/min.

Method 21

Chiral HPLC was performed on an Agilent 1200 series HPLC system using a Chiralpak IB column with 50% ethanol/heptane (with 0.1% diethylamine) at 1 mL/min.

Method 22

Chiral HPLC was performed on an Agilent 1200 series HPLC system using a Chiralpak IB column with 30% ethanol/70% heptane (with 0.1% diethylamine) at 1 mL/min.

NMR $^1$H Nuclear magnetic resonance (NMR) spectroscopy was carried out using a Bruker instrument operating at 400 MHz using the stated solvent at around room temperature unless otherwise stated. In all cases, NMR data were consistent with the proposed structures. Characteristic chemical shifts (δ) are given in parts-per-million using conventional abbreviations for designation of major peaks: e.g. s, singlet; d, doublet; t, triplet; q, quartet; dd, doublet of doublets; dt, doublet of triplets; m, multiplet; br, broad.

Preparative Reverse-Phase HPLC Conditions

Preparative HPLC purification was performed by reverse phase HPLC using a Waters Fractionlynx preparative HPLC system (2525 pump, 2996/2998 UV/VIS detector, 2767 liquid handler) or an equivalent HPLC system such as a Gilson Trilution UV directed system. The Waters 2767 liquid handler acted as both auto-sampler and fraction collector.

The columns used for the preparative purification of the compounds were a Waters Sunfire OBD Phenomenex Luna Phenyl Hexyl or Waters Xbridge Phenyl at 10 μm 19×150 mm or Waters CSH Phenyl Hexyl, 19×150, 5 μm column.

Appropriate focused gradients were selected based on acetonitrile and methanol solvent systems under either acidic or basic conditions.

The modifiers used under acidic/basic conditions were formic acid or trifluoroacetic acid (0.1% V/V) and ammonium bicarbonate (10 mM) respectively.

The purification was controlled by Waters Fractionlynx software through monitoring at 210-400 nm, and triggered a threshold collection value at 260 nm and, when using the Fractionlynx, the presence of target molecular ion as observed under APi conditions. Collected fractions were analysed by LCMS (Waters Acquity systems with Waters SQD).

Compound Preparation

Where the preparation of starting materials is not described, these are commercially available, known in the literature, or readily obtainable by those skilled in the art using standard procedures. Where it is stated that compounds were prepared "analogously" or "similarly" to earlier examples or intermediates, it will be appreciated by the skilled person that the reaction time, number of equivalents of reagents and temperature can be modified for each specific reaction and that it may be necessary or desirable to employ different work-up or purification techniques.

Flash chromatography refers to silica gel chromatography and is carried out using an Isolera MPLC system (manufactured by Biotage); pre-packed silica gel cartridges (supplied by Biotage); or using conventional glass column chromatography.

In the procedures that follow, after each starting material, reference to a compound number may be provided. This is provided merely for assistance to the skilled chemist. The starting material may not necessarily have been prepared from the batch referred to.

Many of the compounds described in the following Examples have been prepared from stereochemically pure starting materials, for example 95% enantiomeric excess (ee). The stereochemistry of the compounds in the Examples, where indicated, has been assigned on the assumption that absolute configuration at resolved stereogenic centers of staring materials is maintained throughout any subsequent reaction conditions.

Compounds isolated as single diastereoisomers whose absolute configuration at stereogenic center (2) in general formula (IE) was not determined, are herebelow referred to as Single Diastereoisomers without mention in their chemical name of absolute configuration for the unknown stereogenic centre.

Intermediate 1/A (1-1/A). (S)-3,5-Dichloro-4-(2-(3,4-dimethoxyphenyl)-2-hydroxyethyl)pyridine 1-oxide

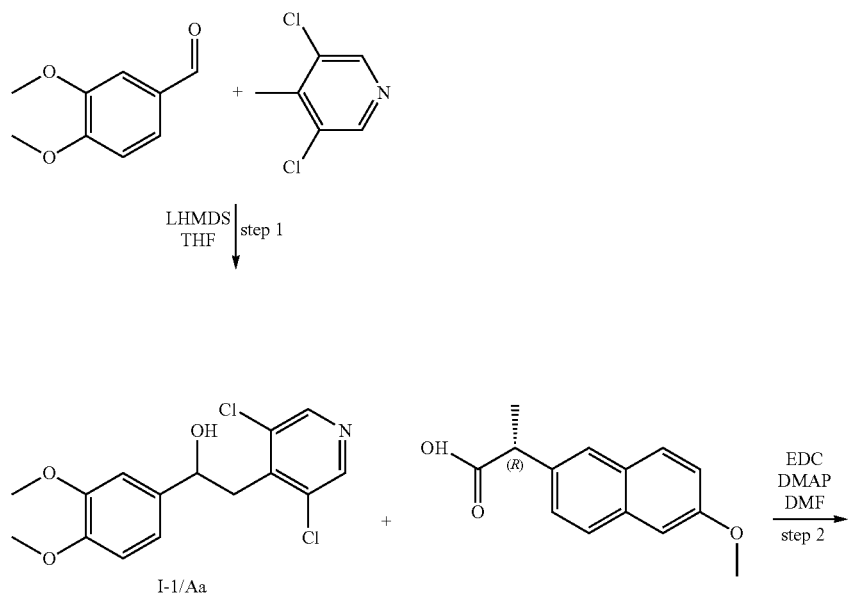

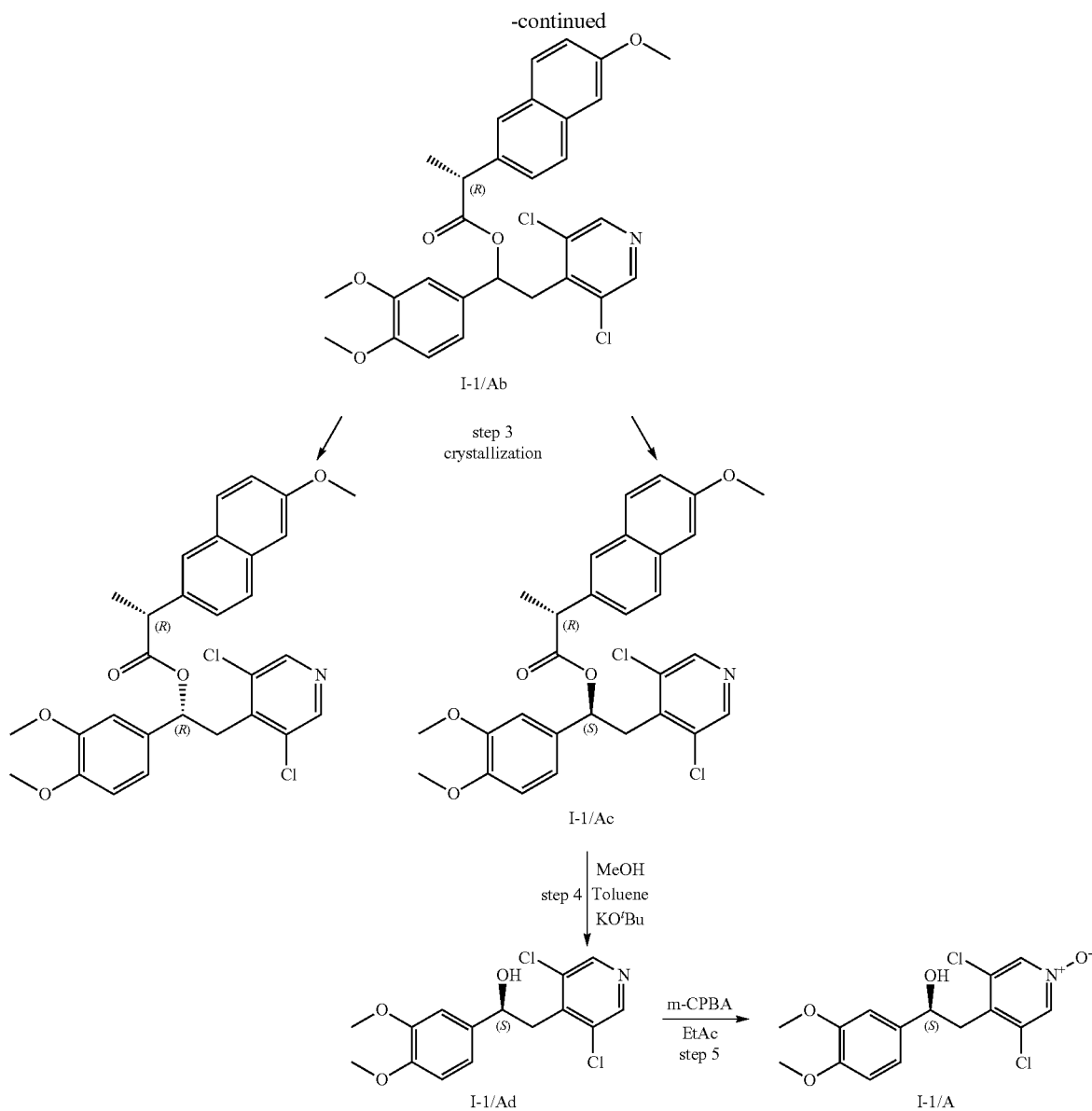

Step 1: Preparation of (R,S)-2-(3,5-dichloropyridin-4-yl)-1-(3,4-dimethoxyphenyl)ethanol (1-1/Aa)

3,5-Dichloro-4-methylpyridine (54 g, 331 mmol) was dissolved in dry THF (480 mL) under argon atmosphere and cooled at −78° C. in dry-ice/acetone bath. LHMDS1N THF solution (331 mL, 331 mmol) was added drop-wise keeping the temperature at −78°. The mixture was stirred at −78° for 1 h. Thereafter, a solution of 3,4-dimethoxybenzaldehyde (50 g, 301 mmol) in dry THF (120 mL) was added drop-wise keeping the temperature at −78° C. When the addition was completed, the mixture was allowed to warm at RT.

The reaction was poured into ice and water (1 L) and the mixture was stirred until a copious precipitate formed. The solid was filtered, and dissolved in ethyl acetate (500 mL), dried over Na$_2$SO$_4$ and the solvent evaporated under vacuum. The crude was crystallized in CHCl$_3$/hexane. The precipitate was filtered, washed with hexane and dried under vacuum at 40° C. for 8 h to give 55 g of the title compound (45% yield).

The mother liquor solution was evaporated under vacuum at 40° C., dissolved in ethyl acetate (200 mL) and extracted with 200 mL of water. The organic solution was dried over Na$_2$SO$_4$ and the solvent evaporated under vacuum at 40° C. The crude was crystallized in CHCl$_3$/hexane, and additional 15 g of the title product were obtained (70% overall yield).

Step 2: Preparation of (R,S)-2-(3,5-dichloropyridin-4-yl)-1-(3,4-dimethoxyphenyl)ethyl) (R)-2-(6-methoxynaphthalen-2-yl)propanoate (1-1/Ab)

(R,S)-2-(3,5-Dichloropyridin-4-yl)-1-(3,4-dimethoxyphenyl)ethanol (50 g, 152 mmol), (R)-2-(6-methoxynaphthalen-2-yl)propanoic acid (38.6 g, 168 mmol), DMAP (20.5 g, 168 mmol) and EDC (43.8 g, 229 mmol) were dissolved in DMF (300 mL) and the reaction mixture was stirred at RT for 2 h. Thereafter, water (500 mL) was added, and the solution stirred till complete precipitation occurs. The solid was filtered and dissolved in DCM (500 mL). The organic solution was washed with aqueous HCl 1N (2×500 mL), saturated aqueous NaHCO$_3$ solution (500 mL) and dried over Na$_2$SO$_4$. The solvent was evaporated under vacuum and the solid residue sonicated in EtOH (300 mL) and triturated for 1 h. The resulting precipitate was collected by filtration and dried under vacuum at 40° C. for 4 h to give 79 g (99% yield) of the title compound, as diastereoisomeric mixture.

Step 3: Preparation of (S)-2-(3,5-dichloropyridin-4-yl)-1-(3,4-dimethoxyphenyl)ethyl) (R)-(2-(6-methoxynaphthalen-2-yl)propanoate (1-1/Ac)

(R,S)-2-(3,5-Dichloropyridin-4-yl)-1-(3,4-dimethoxyphenyl)ethyl) (R)-(6-methoxynaphthalen-2-yl)propanoate (diastereoisomeric mixture, 79 g, 146 mmol) was dissolved in CHCl$_3$ (100 mL) and MeOH (30 mL) was slowly added up to persistent opalescence and the mixture left at RT for 2 h. The solid formed was collected by filtration and re-crystallized by CHCl$_3$/MeOH (70 mL/20 mL) solvent system to obtain 35 g of the desired compound (yield 88%, ee 98%). Chiral HPLC analysis: Chiralcel OD column, 10 μm, 250×4.6 mm; Flow=0.8 ml/min; eluent=hexane:isopropanol 97/3; R$_t$=42.33 min;

$^1$H NMR (600 MHz, CHLOROFORM-d) δ ppm 8.04 (s, 2H), 7.67 (d, J=8.79 Hz, 1H), 7.58 (d, J=8.52 Hz, 1H), 7.53 (m, 1H), 7.12-7.20 (m, 3H), 6.95 (dd, J=8.24, 1.92 Hz, 1H), 6.78-6.88 (m, 2H), 6.14 (dd, J=10.44, 4.12 Hz, 1H), 3.95 (s, 3H), 3.88 (s, 3H), 3.78-3.81 (m, 4H), 3.55 (dd, J=13.73, 10.44 Hz, 1H), 3.14 (dd, J=13.60, 4.26 Hz, 1H), 1.44 (d, J=7.14 Hz, 3H).

Step 4: Preparation of (S)-2-(3,5-dichloropyridin-4-yl)-1-(3,4-dimethoxyphenyl)ethanol, (1-1/Ad)

(S)-2-(3,5-Dichloropyridin-4-yl)-1-(3,4-dimethoxyphenyl)ethyl) (R)-2-(6-methoxynaphthalen-2-yl)propanoate (30 g, 56 mmol) was dissolved in MeOH, and toluene was slowly added. Potassium tert-butoxide was slowly added to the suspension. The reaction mixture was stirred for 24 h at RT. The reaction was diluted with water (500 mL) and the aqueous mixture was extracted with CHCl$_3$ (500 mL). The organic layer was dried over Na$_2$SO$_4$ and the solvent was evaporated under vacuum. The residue was crystallized from CHCl$_3$ (100 mL) and hexane (20 mL). The mother liquor was concentrated and recrystallized with an analogous procedure giving a second crop of desired compound. In total, 16 g of the title compound (87% yield) were obtained. Chiral HPLC analysis: Chiralcel OD column, 10 μm, 250×4.6 mm; flow=0.8 ml/min; eluent=hexane:isopropanol 95/5; R$_t$=58.03 min; [α]$_D^{20}$=+10.21 (c=0.506, Methanol); $^1$H NMR (400 MHz, acetone) δ ppm 8.47 (s, 2H), 6.96-7.15 (m, 1H), 6.87 (m, 2H), 4.93-5.21 (m, 1H), 4.50 (d, J=3.97 Hz, 1H), 3.78 (s, 6H), 3.44 (dd, J=12.79, 8.38 Hz, 1H), 3.22 (dd, J=13.01, 5.51 Hz, 1H). MS/ESI$^+$[MH]$^+$: 328.19.

Step 5: Preparation of (S)-3,5-dichloro-4-(2-(3,4-dimethoxyphenyl)-2-hydroxyethyl)pyridine 1-oxide (1-1/A)

(S)-2-(3,5-Dichloropyridin-4-yl)-1-(3,4-dimethoxyphenyl)ethanol (4 g, 12 mmol) was dissolved in ethyl acetate, and m-CPBA was added to the solution. The mixture was stirred at RT for 5 h. The formed solid was collected by filtration, washed with ethyl acetate and dried under vacuum to give 1.72 g of (S)-2-(3,5-dichloropyridin-4-yl)-1-(3,4-dimethoxyphenyl)ethanol (41% yield). Chiral HPLC analysis: Chiralcel OD column, 10 μm, 250×4.6 mm; Flow=0.8 ml/min; eluent=hexane:isopropanol 60/40; R$_t$=22.16 min; [α]$_D^{20}$=+68.91 (c=0.253, Methanol/CHCl$_3$ 1:1); $^1$H NMR (400 MHz, CHLOROFORM-d) δ ppm 8.15 (s, 2H), 6.99 (m, 1H), 6.79-6.88 (m, 2H), 5.03 (dd, J=8.50, 5.32 Hz, 1H), 3.75-3.98 (m, 6H), 3.42 (dd, J=13.57, 8.56 Hz, 1H), 3.19 (dd, J=13.51, 5.32 Hz, 1H), 2.06-2.15 (m, 1H); MS/ESI$^+$[MH]$^+$: 344

Intermediate 1/O (1-1/O). (R)-3,5-Dichloro-4-(2-(3,4-dimethoxyphenyl)-2-hydroxyethyl)pyridine 1-oxide

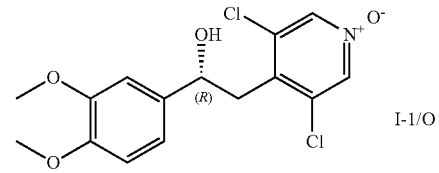

I-1/O

Analogously as described for I-1/A, using (S)-2-(6-methoxynaphthalen-2-yl)propanoic acid in Step 2, (R)-3,5-Dichloro-4-(2-(3,4-dimethoxyphenyl)-2-hydroxyethyl)pyridine 1-oxide was obtained. Chiral HPLC analysis: Lux Cellulose-1 column, 5 μm, 250×4.6 mm; Flow=0.8 ml/min; eluent=hexane:isopropanol 60/40; R$_t$=32.7 min; [α]$_D^{20}$=−70.04 (c=0.25, Methanol/CHCl$_3$ 1:1)

Under these conditions the R$_t$ of (S)-enantiomer is 27 min.

Intermediates I-1/B, I-1/C, I-1/D, I-1/E, I-1/F

The racemic alcohol intermediates reported in table below are described in patent application WO2009/018909, which is incorporated herein by reference in its entirety, or may be obtained following the above procedure (only step 1 followed by step 5) substituting 3,4-dimethoxybenzaldehyde with the suitable 3,4-dialkoxybenzaldehyde.

Table of Racemic Alcohol Intermediates

| Structure | Name | Intermediate | Analytical data |
|---|---|---|---|
| ![structure] | (R,S)-3,5-dichloro-4-(2-(3,4-dimethoxyphenyl)-2-hydroxyethyl)pyridine 1-oxide | I-1/B | $^1$H NMR (400 MHz, (CDCl3) δ ppm 8.15 (s, 2 H), 6.99 (m, 1 H), 6.79-6.88 (m, 2 H), 5.03 (dd, J = 8.50, 5.32 Hz, 1 H), 3.75-3.98 (m, 6 H), 3.42 (dd, J = 13.57, 8.56 Hz, 1 H), 3.19 (dd, J = 13.51, 5.32 Hz, 1 H), 2.06-2.15 (m, 1 H); MS/ESI$^+$ [MH]$^+$: 344 |

-continued

| Structure | Name | Intermediate | Analytical data |
|---|---|---|---|
| 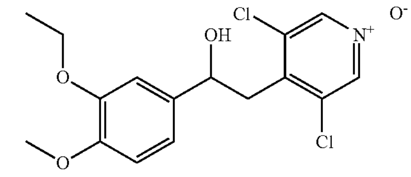 | (R,S)-3,5-dichloro-4-(2-(3-ethoxy-4-methoxyphenyl)-2-hydroxyethyl)pyridine 1-oxide | I-1/C | MS/ESI+ [MH]+: 358 |
| 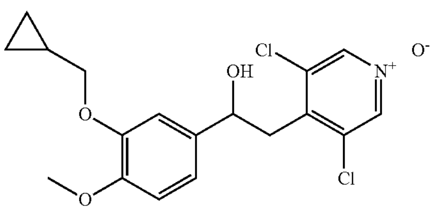 | (R,S)-3,5-dichloro-4-(2-(3-cyclopropylmethoxy-4-methoxyphenyl)-2-hydroxyethyl)pyridine 1-oxide | I-1/D | $^1$H NMR (400 MHz, CDCl3): δ 8.13 (s, 2 H), 6.97 (s, 1 H), 6.83-6.81 (m, 2 H), 5.00-4.97 (m, 1 H), 3.87-3.84 (m, 5 H), 3.41-3.13 (m, 1 H), 3.18-3.13 (m, 1 H), 2.13-2.11 (br s, 1 H), 1.35-1.31 (m, 1 H), 0.68-0.63 (m, 2 H), 0.37-0.35 (m, 2 H). LCMS (Method 1): [MH+] = 384 at 3.21 min. |
| 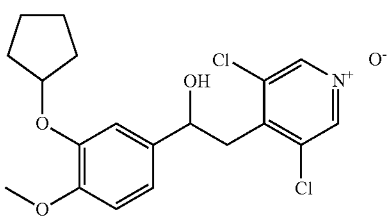 | (R,S)-3,5-dichloro-4-(2-(3-(cyclopentyloxy)-4-methoxyphenyl)-2-hydroxyethyl)pyridine 1-oxide | I-1/E | $^1$H NMR (400 MHz, CDCl3): δ 8.13 (s, 2 H), 6.94 (s, 1 H), 6.82-6.81 (m, 2 H), 5.01-4.80 (m, 1 H), 4.79-4.76 (m, 1 H), 3.42 (s, 3 H), 3.41-3.36 (m, 1 H), 3.19-3.14 (m, 1 H), 1.95-1.79 (m, 6 H), 1.65-1.57 (m, 3 H). LCMS (Method 2): [MH+] = 398 at 3.13 min. |
| 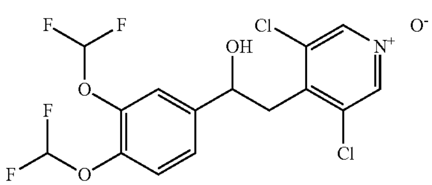 | (R,S)-4-(2-(3,4-bis(difluoromethoxy)phenyl)-2-hydroxyethyl)-3,5-dichloropyridine 1-oxide | I-1/F | $^1$H NMR (400 MHz, CDCl3): δ 8.15 (s, 2 H), 7.33 (s, 1 H), 7.28-7.19 (m, 2 H), 6.55 (t, J = 73.4 Hz, 1 H), 6.53 (t, J = 73.4 Hz, 1 H), 5.08 (app t, J = 6.4 Hz, 1 H), 3.38 (dd, J = 13.6, 8.7 Hz, 1 H), 3.17 (dd, J = 13.6, 5.2 Hz, 1 H), 2.29 (s, 1 H). LCMS (Method 1): [MH+] = 416 at 3.54 min. |

Intermediate 1/G (1-1/G). (S)-3,5-Dichloro-4-(2-(3-(cyclopropylmethoxy)-4-(difluoromethoxy)phenyl)-2-hydroxyethyl)pyridine 1-oxide The intermediate I-1/G may be obtained following the procedure described in patent application WO2010/089107, which is incorporated herein by reference in its entirety.

Intermediate 1/H (1-1/H). (S)-3,5-Dichloro-4-(2-(4-(difluoromethoxy)-3-methoxyphenyl)-2-hydroxyethyl)pyridine 1-oxide

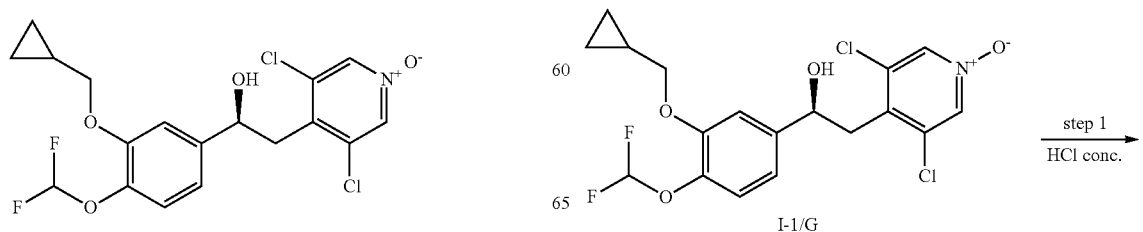

I-1/G step 1
HCl conc.

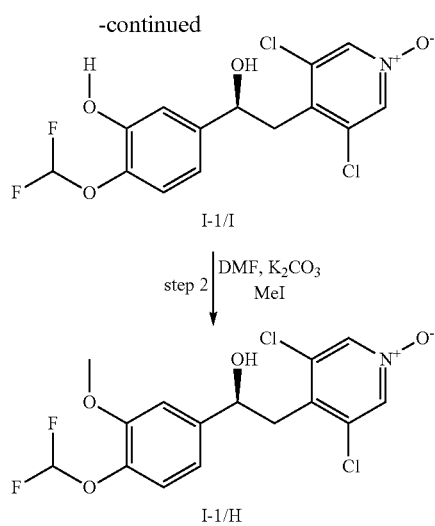

Step 1: (S)-3,5-Dichloro-4-(2-(4-(difluoromethoxy)-3-hydroxyphenyl)-2-hydroxyethyl)pyridine 1-oxide (1-1/I)

(S)-3,5-Dichloro-4-(2-(3-(cyclopropylmethoxy)-4-(difluoromethoxy)phenyl)-2-hydroxyethyl)pyridine 1-oxide (5 g, 11.90 mmol) was added to 100 mL of 37% HCl and stirred at room temperature for about 3 min., obtaining a yellow solution. After stirring for further 3 min. the solution was poured into a solution of NaOH (48 g) in water (500 mL). The red solution was added with 1 M HCl to pH 1. The brown solid was filtered, washed with water and triturated with hot EtOH (50 mL). After stirring at r.t. for 1 h the solid was filtered, washed with EtOH and dried under vacuum at 40 C yielding 2.4 of the title compound.

$^1$H NMR (400 MHz, DMSO-$d_6$) δ ppm 9.84 (br. s., 1H), 8.54 (s, 2H), 7.03 (d, J=8.38 Hz, 1H), 6.98 (t, J=75.00 Hz, 1H), 6.95 (d, J=1.76 Hz, 1H), 6.74 (dd, J=8.16, 1.54 Hz, 1H), 5.54 (br. s., 1H), 4.78 (t, J=6.39 Hz, 1H), 3.14 (dd, J=13.23, 8.38 Hz, 1H), 2.97 (dd, J=13.23, 5.29 Hz, 1H)

MS/ESI$^+$[MH]$^+$:366

Step 2: (S)-3,5-Dichloro-4-(2-(4-(difluoromethoxy)-3-methoxyphenyl)-2-hydroxyethyl)pyridine 1-oxide (1-1/H)

(S)-3,5-Dichloro-4-(2-(4-(difluoromethoxy)-3-hydroxyphenyl)-2-hydroxyethyl)pyridine 1-oxide (2 g, 5.46 mmol) was dissolved in DMF (16 mL) then K$_2$CO$_3$ (2 g, 14.47 mmol) and iodomethane (1.72 g, 12.12 mmol) were added and the mixture was stirred at r.t. for 4 h. The mixture was poured into 200 mL of water, filtered, washed with water and dried under vacuum at 40° C. 1.98 g of whitish solid was obtained.

$^1$H NMR (400 MHz, DMSO-$d_6$): δ ppm 8.53 (s, 2H), 7.08-7.13 (m, 2H), 7.01 (t, J=75.00 Hz, 1H), 6.88 (dd, J=7.94, 1.76 Hz, 1H), 5.64 (d, J=4.41 Hz, 1H), 4.77-4.94 (m, 1H), 3.81 (s, 3H), 3.17 (d, J=8.38 Hz, 1H), 3.05 (d, J=5.73 Hz, 1H)

MS/ESI$^+$[MH]$^+$:380

Intermediates I-1/J, I-1/K, I-1/L, I-1/M, I-1/N

The intermediates reported in table below, I-1/J, I-1/K, I-1/L, I-1/M, I-1/N, may be obtained following the procedure described above for intermediate 1/H, by reacting intermediate 1/I with a suitable alkylating agent.

| Structure | Name | Intermediate | Analytical data |
|---|---|---|---|
| ![structure] | (S)-3,5-dichloro-4-(2-(4-(difluoromethoxy)-3-trideuteromethoxyphenyl)-2-hydroxyethyl)-pyridine 1-oxide | I-1/J | $^1$H NMR (400 MHz, DMSO-d6): δ ppm 8.53 (s, 2 H), 7.06-7.13 (m, 2 H), 7.01 (t, J = 75.00 Hz, 1 H), 6.88 (dd, J = 8.38, 1.76 Hz, 1 H), 5.63 (d, J = 4.41 Hz, 1 H), 4.64-4.91 (m, 1 H), 3.19 (dd, J = 13.23, 8.38 Hz, 1 H), 3.05 (d, J = 5.73 Hz, 1 H) MS/ESI+ [MH]$^+$: 383 |
| ![structure] | (S)-3,5-dichloro-4-(2-(4-(difluoromethoxy)-3-ethoxyphenyl)-2-hydroxyethyl)-pyridine 1-oxide | I-1/K | $^1$H NMR (400 MHz, DMSO-d6): δ ppm 8.53 (s, 2 H), 7.06-7.13 (m, 2 H), 7.01 (t, J = 75.00 Hz, 1 H), 6.86 (dd, J = 8.16, 1.54 Hz, 1 H), 5.62 (d, J = 3.97 Hz, 1 H), 4.72-4.97 (m, 1 H), 3.91-4.19 (m, 2 H), 3.18 (dd, J = 13.23, 8.38 Hz, 1 H), 3.02 (dd, J = 13.23, 5.29 Hz, 1 H), 1.33 (t, J = 7.06 Hz, 3 H) MS/ESI+ [MH]$^+$: 394 |
| ![structure] | (S)-3,5-dichloro-4-(2-(4-(difluoromethoxy)-3-isopropoxyphenyl)-2-hydroxyethyl)-pyridine 1-oxide | I-1/L | $^1$H NMR (400 MHz, DMSO-d6): δ ppm 8.52 (s, 2 H), 7.04-7.13 (m, 2 H), 6.97 (t, J = 75.00 Hz, 1 H), 6.86 (dd, J = 7.94, 1.76 Hz, 1 H), 5.63 (d, J = 3.53 Hz, 1 H), 4.81-4.90 (m, 1 H), 4.46-4.65 (m, 1 H), 3.16 (d, J = 7.94 Hz, 1 H), 3.04 (d, J = 6.17 Hz, 1 H), 1.26 (dd, J = 13.67, 6.17 Hz, 6 H) MS/ESI+ [MH]$^+$: 408 |

| Structure | Name | Intermediate | Analytical data |
|---|---|---|---|
| (structure) | (S)-3,5-dichloro-4-(2-(4-(difluoromethoxy)-3-propoxyphenyl)-2-hydroxyethyl)-pyridine 1-oxide | I-1/M | $^1$H NMR (400 MHz, DMSO-$d_6$): δ ppm 7.14 (m, 1 H), 7.04-7.08 (m, 1 H), 6.99 (t, J = 75.00 Hz, 1 H), 6.84-6.91 (m, 1 H), 5.55-5.70 (m, 1 H), 4.79-4.99 (m, 1 H), 3.88-4.06 (m, 2 H), 3.12-3.22 (m, 1 H), 2.91-3.10 (m, 1 H), 1.60-1.86 (m, 2 H), 0.98 (m, 3 H) MS/ESI+ [MH]$^+$: 408 MS/ESI+ [MH]$^+$: 408 |
| (structure) | (S)-3,5-dichloro-4-(2-(3-(cyclopentyloxy)-4-(difluoromethoxy)-phenyl)-2-hydroxyethyl)-pyridine 1-oxide | I-1/N | MS/ESI+ [MH]$^+$: 434 |

Intermediate 2. (R)-Quinuclidin-3-yl carbonochloridate hydrochloride (1-2)

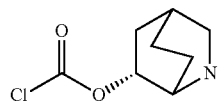 [SMILES: O=C(Cl)O[C@@H]1CC2CCC1NC2]

A stirred solution of (R)-3-quinuclidinol (2.5 g, 19.66 mmol) in acetonitrile (200 mL) was added with trichloromethyl chloroformate (3.06 mL, 25.57 mmol) dropwise at 0° C. and the mixture was allowed to stir at 0° C. for 1 h. The reaction mixture was then stirred at room temperature for 16 h and then the solvent was removed in vacuo to afford the title compound as a white solid (4.39 g, 98%).

$^1$H NMR (400 MHz, DMSO): δ 10.29 (s, 1H), 4.05-3.95 (m, 1H), 3.43 (t, J=10.8 Hz, 1H), 3.12 (m, 3H), 3.10-2.95 (m, 1H), 2.79 (d, J=13.3 Hz, 1H), 2.12-2.02 (m, 1H), 1.98 (m, J=3.4 Hz, 1H), 1.89-1.78 (m, 1H), 1.75-1.59 (m, 2H).

Intermediate 62. Tert-butyl 2-(4-formylpyrazol-1-yl)acetate

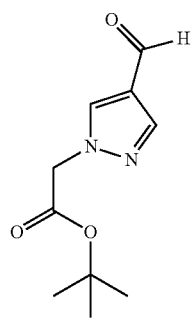

A mixture of 1H-pyrazole-4-carbaldehyde (0.5 g, 5.2 mmol), potassium tert-butoxide (0.7 g, 6.25 mmol) in N,N-dimethylformamide (6 mL) was stirred at room temperature for 5 minutes. Tert-butylbromoacetate (1.11 g, 5.72 mmol) was added and the resulting mixture was stirred for 2 hours at room temperature. The reaction was partitioned between ethyl acetate and saturated aqueous sodium bicarbonate solution. The organic layer was collected, washed with water then brine, passed through a hydrophobic frit and the solvent was removed in vacuo. The crude material was purified by silica gel column chromatography, eluting with 15-100% ethyl acetate in iso-hexane, to afford the title compound (0.678 g, 62%) as colorless oil.

$^1$H NMR (400 MHz, CDCl$_3$): δ 9.89 (s, 1H), 8.02-8.00 (m, 2H), 4.86 (s, 2H), 1.48 (s, 9 H).

Intermediate 63. 2-(4-formylpyrazol-1-yl)acetic acid

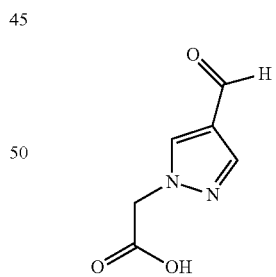

To a solution of tert-butyl 2-(4-formylpyrazol-1-yl)acetate (0.67 g, 3.19 mmol) in dioxane (10 mL) was added a 4N solution of HCl in dioxane (10 mL) and the mixture was stirred at room temperature for three days. The solvent was removed by evaporation under reduced pressure to afford the title compound (0.41 g, 98%) as a yellow oil.

¹H NMR (400 MHz, DMSO): δ 13.21 (brs, 1H), 9.83 (s, 1H), 8.46 (s, 1H), 8.00 (s, 1H), 5.07 (s, 2H). LCMS (Method 1): [MH−]=153 at 1.64 min.

Intermediate 3. [(1S)-2-(3,5-Dichloro-1-oxido-pyridin-1-ium-4-yl)-1-(3,4-dimethoxyphenyl)ethyl]5-formylthiophene-2-carboxylate (I-3)

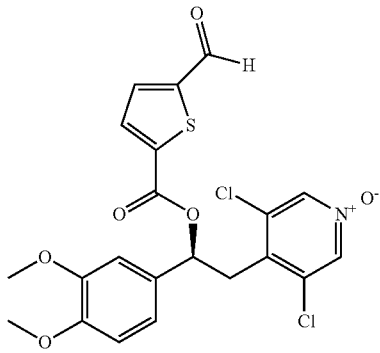

A stirred solution of 5-formyl-2-thiophenecarboxylic acid (400 mg, 2.56 mmol) in dichloromethane (20 mL) was added with (1S)-2-(3,5-dichloro-1-oxido-pyridin-1-ium-4-yl)-1-(3,4-dimethoxyphenyl)ethanol I-1/A (881 mg, 2.56 mmol) followed by 4-(dimethylamino)-pyridine (156 mg, 1.28 mmol) and N-(3-dimethylaminopropyl)-N'-ethylcarbodiimide hydrochloride (983 mg, 5.12 mmol). The resulting mixture was stirred at room temperature for 18 h. The reaction was partitioned between dichloromethane and saturated aqueous sodium bicarbonate solution. The organic layer was washed with brine, passed through a hydrophobic frit and the solvent was removed in vacuo. The crude material was purified by silica gel column chromatography, eluting with 0-100% EtOAc in DCM, to afford the title compound (488 mg, 39%) as yellow oil.

¹H NMR (400 MHz, CDCl₃): δ 9.97 (s, 1H), 8.15 (s, 2H), 7.81 (d, J=3.6 Hz, 1H), 7.72 (d, J=3.6 Hz, 1H), 7.03-6.99 (m, 2H), 6.87 (d, J=8.7 Hz, 1H), 6.26 (dd, J=4.4, 10.0 Hz, 1H), 3.91 (s, 3H), 3.88 (s, 3H), 3.72 (dd, J=10.0, 14.0 Hz, 1H), 3.33 (dd, J=4.4, 14.0 Hz, 1H). LCMS (Method 2): [MH+]=482 at 3.38 min.

The following intermediates were synthesized via the same procedure reacting the suitable carboxylic acid intermediate with the suitable alcohol intermediate:

| Structure | Intermediate number | Analytical Data |
|---|---|---|
| 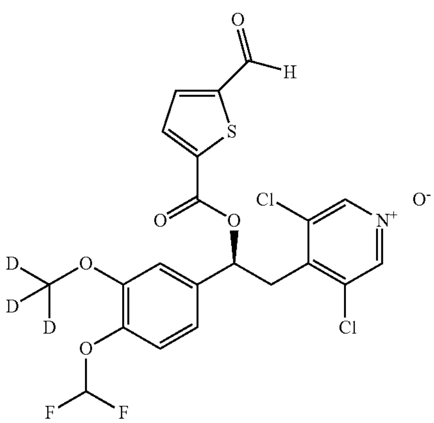 | Intermediate 4 | ¹H NMR (400 MHz, CDCl3): δ 9.98 (s, 1 H), 8.16 (s, 2 H), 7.82 (d, J = 4.0 Hz, 1 H), 7.72 (d, J = 4.0 Hz, 1 H), 7.25-7.18 (m, 1 H), 7.05-7.03 (m, 2 H), 6.55 (t, J = 75.2 Hz, 1 H), 6.22 (dd, J = 4.4, 9.6 Hz, 1 H), 3.62 (dd, J = 9.6, 14.0 Hz, 1 H), 3.33 (dd, J = 4.4, 14.0 Hz, 1 H). LCMS (Method 1): [MH+] = 521 at 3.85 min. |
| 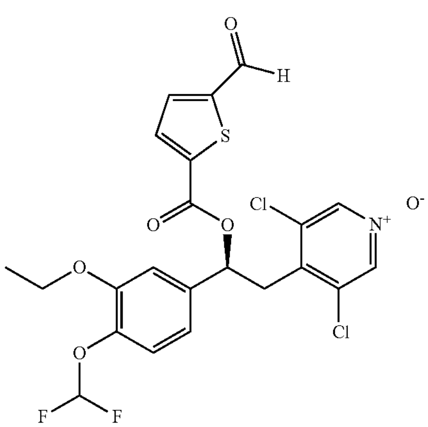 | Intermediate 5 | ¹H NMR (400 MHz, CDCl3): δ 9.98 (s, 1 H), 8.15 (s, 2 H), 7.82 (d, J = 4.0 Hz, 1 H), 7.71 (d, J = 4.0 Hz, 1 H), 7.18 (d, J = 8.0 Hz, 1 H), 7.03-7.01 (m, 2 H), 6.57 (t, J = 75.0 Hz, 1 H), 6.23 (dd, J = 4.4, 9.6 Hz, 1 H), 4.16-4.09 (m, 2 H), 3.67 (dd, J = 9.6, 14.0 Hz, 1 H), 3.31 (dd, J = 4.4, 14.0 Hz, 1 H), 1.46 (t, J = 6.8 Hz, 3 H). LCMS (Method 1): [MH+] = 532 at 4.03 min. |

-continued

| Structure | Intermediate number | Analytical Data |
|---|---|---|
| 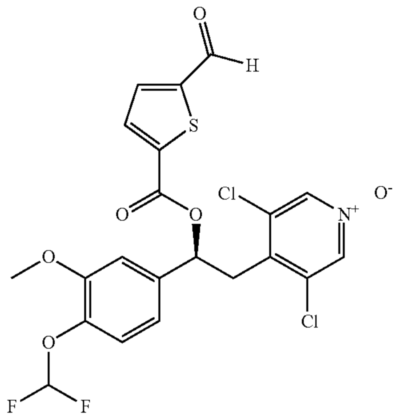 | Intermediate 6 | $^1$H NMR (400 MHz, CDCl3): δ 9.98 (s, 1 H), 8.16 (s, 2 H), 7.82 (d, J = 4.0 Hz, 1 H), 7.72 (d, J = 4.0 Hz, 1 H), 7.19 (d, J = 8.0 Hz, 1 H), 7.05-7.03 (m, 2 H), 6.54 (t, J = 75.0 Hz, 1 H), 6.24 (dd, J = 4.4, 9.6 Hz, 1 H), 4.13 (s, 3 H), 3.67 (dd, J = 9.6, 14.0 Hz, 1 H), 3.32 (dd, J = 4.4, 14.0 Hz, 1 H). LCMS (Method 1): [MH+] = 518 at 3.86 min. |
| 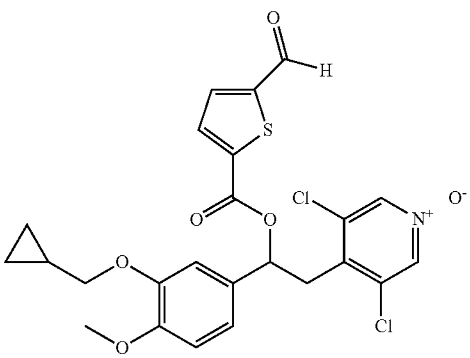 | Intermediate 7 | $^1$H NMR (400 MHz, CDCl3): δ 9.97 (s, 1 H), 8.14 (s, 2 H), 7.81 (d, J = 4.0 Hz, 1 H), 7.72 (d, J = 4.0 Hz, 1 H), 7.02-6.97 (m, 2 H), 6.87 (d, J = 8.0 Hz, 1 H), 6.22 (dd, J = 4.4, 9.6 Hz, 1 H), 3.73-3.70 (m, 5 H), 3.69 (dd, J = 9.6, 14.0 Hz, 1 H), 3.31 (dd, J = 4.4, 14.0 Hz, 1 H), 1.34-1.29 (m, 1 H), 0.68-0.63 (m, 2 H), 0.40-0.38 (m, 2 H). LCMS (Method 1): [MH+] = 522 at 3.95 min. |
| 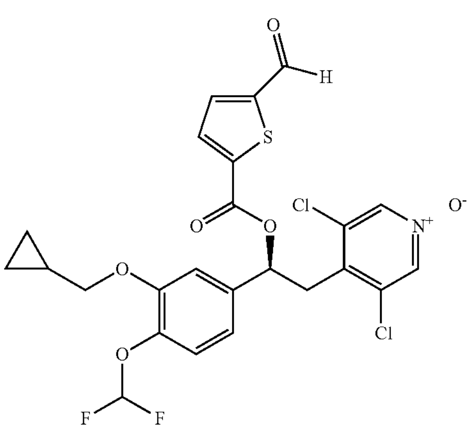 | Intermediate 8 | $^1$H NMR (400 MHz, CDCl3): δ 9.98 (s, 1 H), 8.15 (s, 2 H), 7.81 (d, J = 3.6 Hz, 1 H), 7.71 (d, J = 3.6 Hz, 1 H), 7.19 (d, J = 8.0 Hz, 1 H), 7.05-7.02 (m, 2 H), 6.62 (t, J = 75.2 Hz, 1 H), 6.22 (dd, J = 4.4, 9.6 Hz, 1 H), 3.91-3.89 (m, 2 H), 3.68 (dd, J = 9.6, 14.0 Hz, 1 H), 3.30 (dd, J = 4.4, 14.0 Hz, 1 H), 1.29-1.26 (m, 1 H), 0.68-0.65 (m, 2 H), 0.40-0.38 (m, 2 H). LCMS (Method 1): [MH+] = 558 at 4.17 min. |

| Structure | Intermediate number | Analytical Data |
|---|---|---|
| 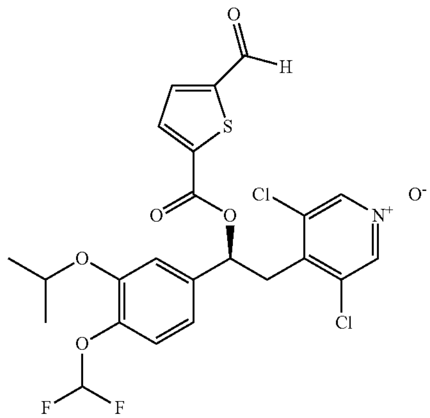 | Intermediate 9 | ¹H NMR (400 MHz, CDCl3): δ 9.99 (s, 1 H), 8.16 (s, 2 H), 7.83 (d, J = 4.0 Hz, 1 H), 7.73 (d, J = 4.0 Hz, 1 H), 7.19 (d, J = 8.2 Hz, 1 H), 7.07-7.01 (m, 2 H), 6.56 (t, J = 75.2 Hz, 1 H), 6.23 (dd, J = 10.0, 4.2 Hz, 1 H), 4.59 (h, J = 6.2 Hz, 1 H), 3.68 (dd, J = 14.2, 10.1 Hz, 1 H), 3.32 (dd, J = 14.2, 4.2 Hz, 1 H), 1.37 (dd, J = 13.0, 6.1 Hz, 6 H). LCMS (Method 1): [MH+] = 546 at 4.14 min. |
| 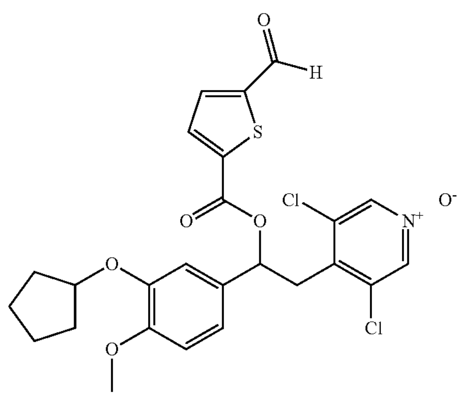 | Intermediate 64 | LCMS (Method 1): [MH+] = 536 at 4.15 min |
| 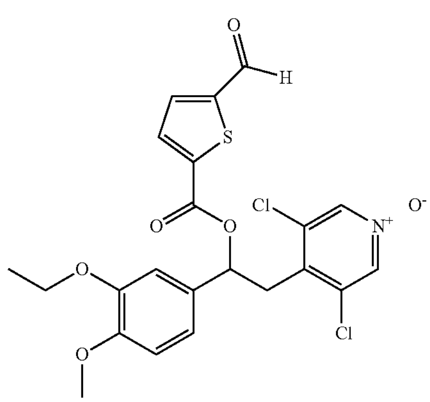 | Intermediate 65 | LCMS (Method 1): [MH+] = 496 at 3.71 min. |

| Structure | Intermediate number | Analytical Data |
|---|---|---|
| 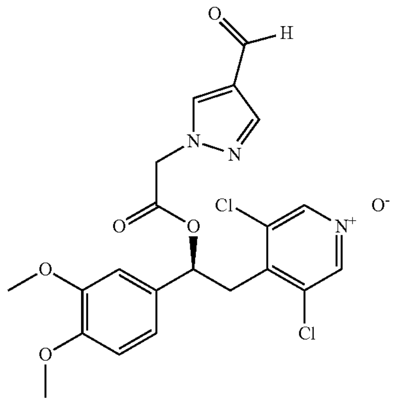 | Intermediate 66 | $^1$H NMR (400 MHz, CDCl$_3$): δ 9.89 (s, 1 H), 8.14 (s, 2 H), 8.01-7.96 (m, 2 H), 6.87-6.81 (m, 3 H), 6.12 (dd, J = 4.8, 8.8 Hz, 1 H), 4.97-4.85 (m, 2 H), 3.89 (s, 3 H), 3.87 (s, 3 H), 3.55 (dd, J = 8.8, 13.6 Hz, 1 H), 3.29 (dd, J = 4.8, 13.6 Hz, 1 H).<br>LCMS (Method 1): [MH+] = 480 at 3.14 min. |
| 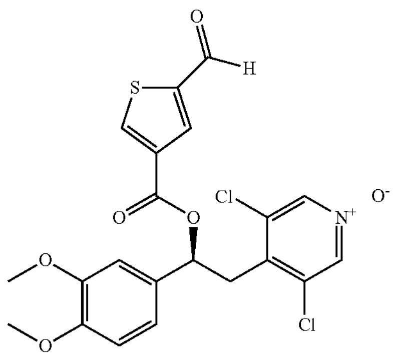 | Intermediate 67 | $^1$H NMR (400 MHz, CDCl$_3$): δ 9.93 (d, J = 1.4 Hz, 1 H), 8.46 (dd, J = 1.4, 1.4 Hz, 1 H), 8.16 (s, 2 H), 8.13 (d, J = 1.3 Hz, 1 H), 7.03 (dd, J = 2.0, 8.3 Hz, 1 H), 6.97 (d, J = 2.0 Hz, 1 H), 6.88 (d, J = 8.3 Hz, 1 H), 6.26 (dd, J = 4.5, 9.9 Hz, 1 H), 3.91 (s, 3 H), 3.88 (s, 3 H), 3.72 (dd, J = 9.9, 14.1 Hz, 1 H), 3.36 (dd, J = 4.4, 14.0 Hz, 1 H).<br>LCMS (Method 1): [MH+] = 482 at 3.52 min. |
| 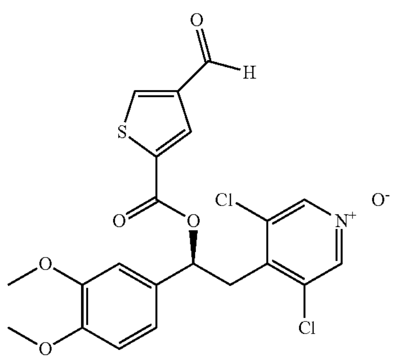 | Intermediate 68 | $^1$H NMR (400 MHz, CDCl$_3$): δ 9.90 (d, J = 2.0 Hz, 1 H), 8.30 (d, J = 1.5 Hz, 1 H), 8.17-8.15 (m, 3 H), 7.01 (d, J = 8.1 Hz, 1 H), 6.97 (d, J = 1.8 Hz, 1 H), 6.87 (d, J = 8.3 Hz, 1 H), 6.25 (dd, J = 4.4, 9.7 Hz, 1 H), 3.92 (s, 3 H), 3.89 (s, 3 H), 3.71 (dd, J = 9.9, 14.1 Hz, 1 H), 3.35 (dd, J = 4.4, 14.0 Hz, 1 H).<br>LCMS (Method 2): [MH+] = 482 at 2.69 min. |
| 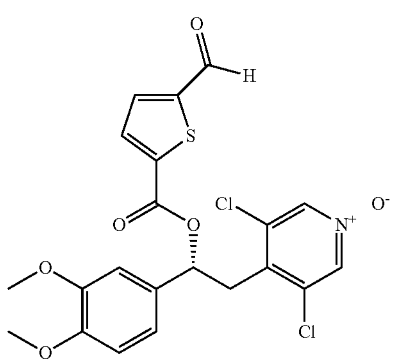 | Intermediate 69 | $^1$H NMR (400 MHz, CDCl$_3$): δ 9.97 (s, 1 H), 8.15 (s, 2 H), 7.82 (d, J = 4.0 Hz, 1 H), 7.72 (d, J = 4.0 Hz, 1 H), 7.04-6.97 (m, 2 H), 6.87 (d, J = 8.3 Hz, 1 H), 6.26 (dd, J = 4.3, 9.9 Hz, 1 H), 3.92 (s, 3 H), 3.88 (s, 3 H), 3.72 (dd, J = 10.0, 14.0 Hz, 1 H), 3.34 (dd, J = 4.3, 14.1 Hz, 1 H).<br>LCMS (Method 1): [MH+] = 482 at 3.57 min. |

The following intermediates were obtained by SFC purification of the appropriate racemic mixture hereabove described.

| Structure | Intermediate number | Analytical Data |
|---|---|---|
| 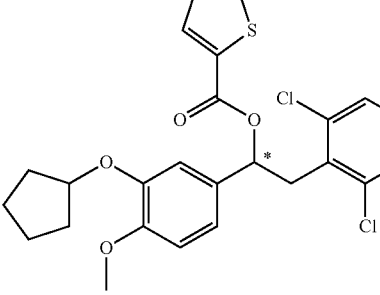<br>Enantiomer 1 of Intermediate 64 | Intermediate 70 | LCMS (Method 1): [MH+] = 536 at 4.15 min.<br>SFC/MS (Method 26): [MH + NHEt$_2$]$^+$ = 609 at 3.84 min. |
| 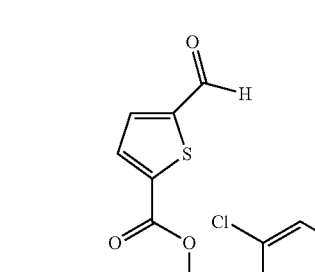<br>Enantiomer 2 of Intermediate 64 | Intermediate 71 | LCMS (Method 1): [MH+] = 536 at 4.15 min.<br>SFC/MS (Method 26): [MH + NHEt$_2$]$^+$ = 609 at 4.62 min. |
| 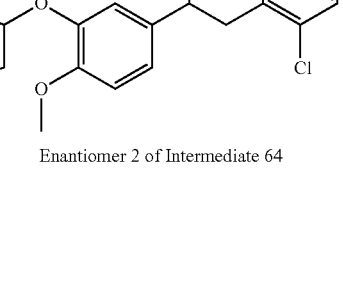<br>Enantiomer 1 of Intermediate 7 | Intermediate 72 | LCMS (Method 2): [MH+] = 522 at 3.26 min.<br>SFC/MS (Method 27): [MH + NHEt$_2$]$^+$ = 595 at 7.10 min. |

-continued

| Structure | Intermediate number | Analytical Data |
|---|---|---|
| 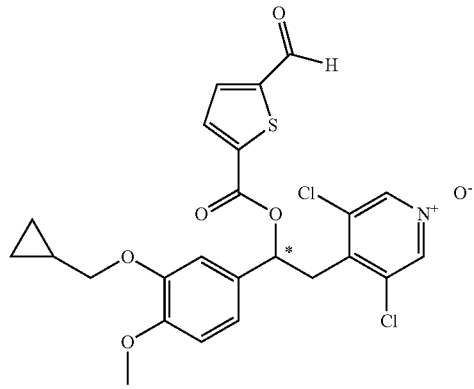Enantiomer 2 of Intermediate 7 | Intermediate 73 | LCMS (Method 2): [MH+] = 522 at 3.26 min.<br>SFC/MS (Method 27): [MH + NHEt$_2$]$^+$ = 595 at 9.00 min. |
| 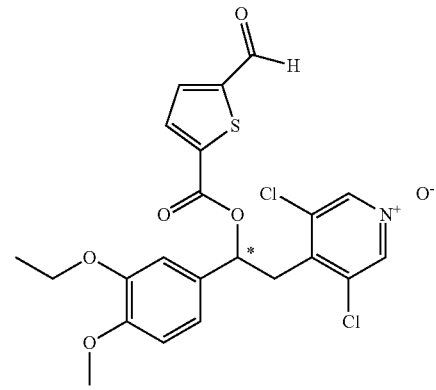Enantiomer 1 of Intermediate 65 | Intermediate 74 | LCMS (Method 1): [MH+] = 496 at 3.71 min.<br>SFC/MS (Method 28): [MH + NHEt$_2$]$^+$ = 569 at 6.10 min. |
| 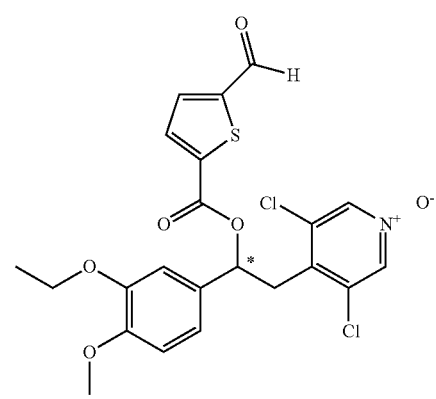Enantiomer 2 of Intermediate 65 | Intermediate 75 | LCMS (Method 1): [MH+] = 496 at 3.71 min.<br>SFC/MS (Method 28): [MH + NHEt$_2$]$^+$ = 569 at 7.70 min. |

Intermediate 10. [(1S)-2-(3,5-Dichloro-1-oxido-pyridin-1-ium-4-yl)-1-(3,4-dimethoxyphenyl)ethyl]5-[(2-fluoroanilino)methyl]thiophene-2-carboxylate (I-10)

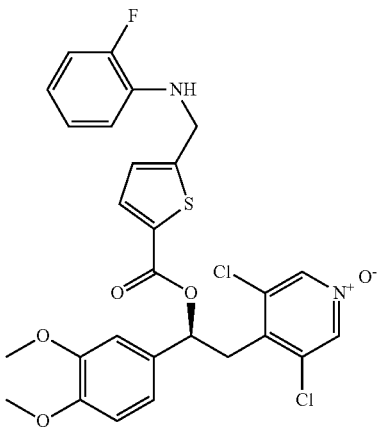

A stirred solution of [(1S)-2-(3,5-dichloro-1-oxidopyridin-1-ium-4-yl)-1-(3,4-dimethoxyphenyl)ethyl]5-formylthiophene-2-carboxylate (128 mg, 0.265 mmol) in dichloromethane (5 mL) was added with 2-fluoroaniline (29 mg, 0.265 mmol) followed by glacial acetic acid (0.015 mL, 0.265 mmol). The reaction was stirred at room temperature for 6 h. Sodium triacetoxyborohydride (140 mg, 0.662 mmol) was added and the reaction was stirred at room temperature for 18 h. Water was added to quench the reaction and the organic layer was washed with brine, passed through a hydrophobic frit and the solvent was removed in vacuo. The crude material was purified by silica gel column chromatography, eluting with 0-100% EtOAc in DCM, to afford the title compound (50 mg, 32%) as a yellow oil.

$^1$H NMR (400 MHz, CDCl$_3$): δ 8.11 (s, 2H), 7.65 (d, J=4.0 Hz, 1H), 7.02-6.95 (m, 5H), 6.84 (d, J=8.0 Hz, 1H), 6.71-6.65 (m, 2H), 6.18 (dd, J=4.4, 9.6 Hz, 1H), 4.57-4.56 (m, 2H), 4.51-4.48 (m, 1H), 3.87 (s, 3H), 3.86 (s, 3H), 3.64 (dd, J=9.6, 14.0 Hz, 1H), 3.29 (dd, J=4.4, 14.0 Hz, 1H). LCMS (Method 1): [MH+]=577 at 4.08 min.

The following intermediates were synthesized via the same procedure.

| Structure | Intermediate number | Precursor | Analytical Data |
|---|---|---|---|
| (structure with d3-methoxy and OCHF2 groups) | Intermediate 11 | Intermediate 4 | $^1$H NMR (400 MHz, CDCl$_3$): δ 8.16 (s, 2 H), 7.65 (d, J = 3.6 Hz, 1 H), 7.17-7.15 (m, 1 H), 7.03-6.95 (m, 6 H), 6.72-6.67 (m, 1 H), 6.53 (t, J = 75.2 Hz, 1 H), 6.21 (dd, J = 4.4, 9.6 Hz, 1 H), 4.58 (brs, 2 H), 4.49 (brs, 1 H), 3.60 (dd, J = 9.6, 14.0 Hz, 1 H), 3.25 (dd, J = 4.4, 14.0 Hz, 1 H). LCMS (Method 2): [MH+] = 616 at 3.93 min. |
| (structure with ethoxy and OCHF2 groups) | Intermediate 12 | Intermediate 5 | $^1$H NMR (400 MHz, CDCl$_3$): δ 8.15 (s, 2 H), 7.68 (d, J = 3.6 Hz, 1 H), 7.21-7.14 (m, 1 H), 7.05-6.95 (m, 6 H), 6.74-6.57 (m, 1 H), 6.55 (t, J = 75.2 Hz, 1 H), 6.18 (dd, J = 4.4, 9.6 Hz, 1 H), 4.59 (brs, 2 H), 4.47 (brs, 1 H), 4.14-4.03 (m, 2 H), 3.63 (dd, J = 9.6, 14.0 Hz, 1 H), 3.26 (dd, J = 4.4, 14.0 Hz, 1 H), 1.48-1.43 (m, 3 H). LCMS (Method 2): [MH+] = 627 at 4.28 min. |

-continued

| Structure | Intermediate number | Precursor | Analytical Data |
|---|---|---|---|
| 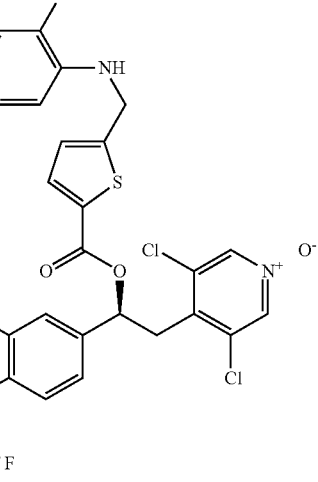 | Intermediate 13 | Intermediate 6 | $^1$H NMR (400 MHz, CDCl$_3$): δ 8.16 (s, 2 H), 7.68 (d, J = 3.6 Hz, 1 H), 7.21-7.15 (m, 1 H), 7.06-6.95 (m, 6 H), 6.71-6.65 (m, 1 H), 6.53 (t, J = 75.2 Hz, 1 H), 6.19 (dd, J = 4.4, 9.6 Hz, 1 H), 4.58 (brs, 2 H), 4.48 (brs, 1 H), 3.91 (s, 3 H), 3.63 (dd, J = 9.6, 14.0 Hz, 1 H), 3.26 (dd, J = 4.4, 14.0 Hz, 1 H). LCMS (Method 2): [MH+] = 613 at 4.08 min. |
| 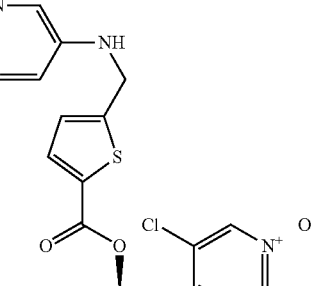 | Intermediate 14 | Intermediate 3 | $^1$H NMR (400 MHz, CDCl$_3$): δ 8.12 (s, 2 H), 8.11-8.10 (m, 1 H), 8.02-8.01 (m, 1 H), 7.65 (d, J = 4.0 Hz, 1 H), 7.12-7.08 (m, 1 H), 6.99-6.90 (m, 4 H), 6.89-6.83 (m, 1 H), 6.20 (dd, J = 4.4, 9.6 Hz, 1 H), 4.54 (brs, 2 H), 4.50 (brs, 1 H), 3.92 (s, 3 H), 3.88 (s, 3 H), 3.66 (dd, J = 9.6, 14.0 Hz, 1 H), 3.32 (dd, J = 4.4, 14.0 Hz, 1 H). LCMS (Method 1): [MH+] = 560 at 2.53 min. |
| 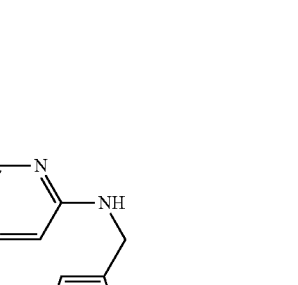 | Intermediate 15 | Intermediate 3 | $^1$H NMR (400 MHz, CDCl$_3$): δ 8.14-8.13 (m, 1 H), 8.11 (s, 2 H), 7.61 (d, J = 4.0 Hz, 1 H), 7.45-7.40 (m, 1 H), 6.97-6.95 (m, 3 H), 6.81 (d, J = 8.0 Hz, 1 H), 6.66-6.62 (m, 1 H), 6.51-6.41 (m, 1 H), 6.20 (dd, J = 4.4, 9.6 Hz, 1 H), 4.98 (t, J = 6.0 Hz, 1 H), 4.73 (d, J = 6.0 Hz, 2 H), 3.88 (s, 3 H), 3.86 (s, 3 H), 3.66 (dd, J = 9.6, 14.0 Hz, 1 H), 3.31 (dd, J = 4.4, 14.0 Hz, 1 H). LCMS (Method 1): [MH+] = 560 at 2.54 min. |

-continued

| Structure | Intermediate number | Precursor | Analytical Data |
|---|---|---|---|
| 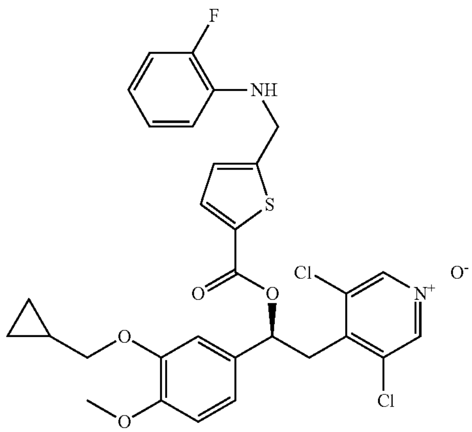 | Intermediate 16 | Intermediate 7 | $^1$H NMR (400 MHz, CDCl$_3$): δ 8.11 (s, 2 H), 7.65-7.64 (m, 1 H), 7.03-6.95 (m, 5 H), 6.85-6.83 (m, 1 H), 6.71-6.65 (m, 2 H), 6.19-6.15 (m, 1 H), 4.57 (s, 2 H), 3.87-3.86 (m, 5 H), 3.67-3.61 (m, 1 H), 3.30-3.25 (m, 1 H), 0.87-0.82 (m, 1 H), 0.65-0.61 (m, 2 H), 0.37-0.33 (m, 2 H). NH not observed. LCMS (Method 1): [MH+] = 617 at 4.39 min. |
| 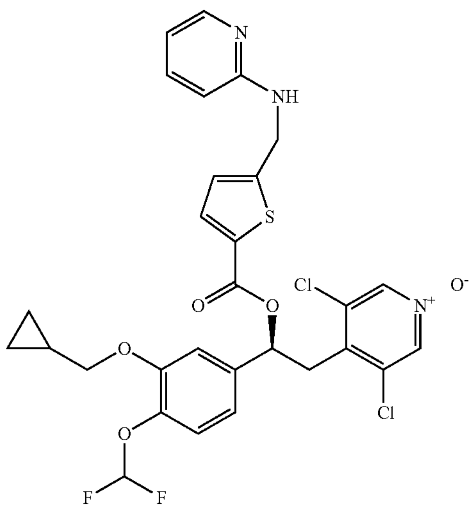 | Intermediate 17 | Intermediate 8 | LCMS (Method 1): [MH+] = 636 at 2.98 min. |
| 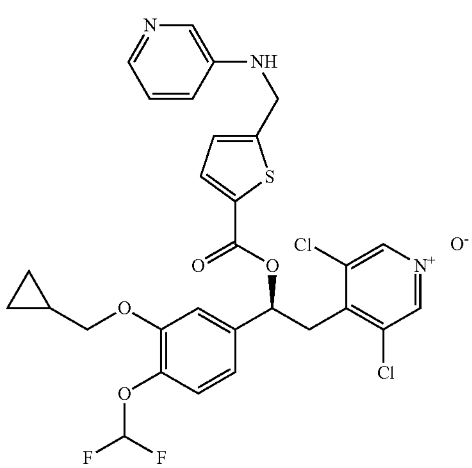 | Intermediate 18 | Intermediate 8 | $^1$H NMR (400 MHz, CDCl$_3$): δ 8.12-8.04 (m, 3 H), 8.04-8.03 (m, 1 H), 7.66 (d, J = 3.6 Hz, 1 H), 7.17-7.15 (m, 1 H), 7.11-7.08 (m, 1 H), 7.03-6.99 (m, 3 H), 6.92-6.89 (m, 1 H), 6.60 (t, J = 75.2 Hz, 1 H), 6.18 (dd, J = 4.4, 9.6 Hz, 1 H), 4.56 (d, J = 6.0 Hz, 2 H), 4.30-4.28 (m, 1 H), 4.04-4.01 (m, 2 H), 3.62 (dd, J = 9.6, 14.0 Hz, 1 H), 3.28 (dd, J = 4.4, 14.0 Hz, 1 H), 1.26-1.19 (m, 1 H), 0.66-0.62 (m, 2 H), 0.37-0.33 (m, 2 H). LCMS (Method 2): [MH+] = 636 at 3.85 min. |

-continued

| Structure | Intermediate number | Precursor | Analytical Data |
|---|---|---|---|
| 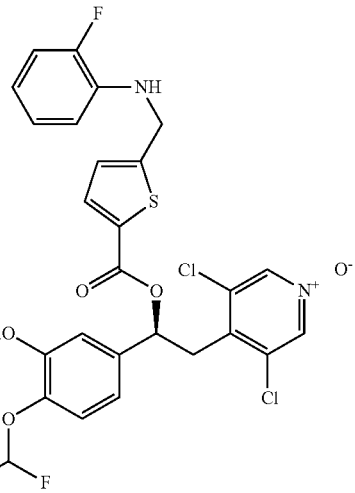 | Intermediate 19 | Intermediate 8 | $^1$H NMR (400 MHz, CDCl$_3$): δ 8.12 (s, 2 H), 7.65 (d, J = 4.0 Hz, 1 H), 7.17-7.15 (m, 1 H), 7.03-6.95 (m, 5 H), 6.71-6.69 (m, 2 H), 6.60 (t, J = 75.6 Hz, 1 H), 6.18 (dd, J = 4.4, 9.6 Hz, 1 H), 4.58-4.56 (m, 2 H), 4.49-4.47 (m, 1 H), 3.88-3.86 (m, 2 H), 3.62 (dd, J = 9.6, 14.0 Hz, 1 H), 3.25 (dd, J = 4.4, 14.0 Hz, 1 H), 1.27-1.24 (m, 1 H), 0.66-0.61 (m, 2 H), 0.37-0.33 (m, 2 H). LCMS (Method 2): [MH+] = 653 at 3.78 min. |
| 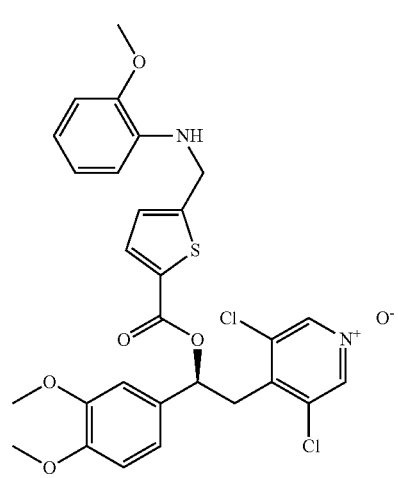 | Intermediate 20 | Intermediate 3 | $^1$H NMR (400 MHz, CDCl$_3$): δ 7.99 (s, 2 H), 7.53 (d, J = 3.8 Hz, 1 H), 6.93-6.81 (m, H), 6.80 (d, J = 7.6 Hz, 1 H), 6.67 (d, J = 4.3 Hz, 1 H), 6.64 (s, 1 H), 6.59 (d, J = 7.6 Hz, 1 H), 6.45 (d, J = 7.8 Hz, 1 H), 6.07 (dd, J = 9.7, 4.5 Hz, 1 H), 4.39 (s, 2 H), 3.71 (s, 3 H), 3.67 (s, 3 H), 3.50 (dd, J = 14.0, 9.6 Hz, 1 H), 3.15 (dd, J = 14.0, 4.6 Hz, 1 H). LCMS (Method 1): [MH+] = 589 at 4.09 min. |
| 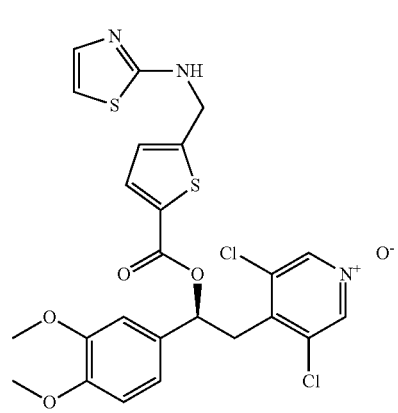 | Intermediate 21 | Intermediate 3 | $^1$H NMR (400 MHz, CDCl$_3$): δ 8.14 (s, 2 H), 7.64 (d, J = 3.8 Hz, 1 H), 7.13 (d, J = 3.6 Hz, 1 H), 7.04-7.00 (m, 1 H), 6.97-6.95 (m, 2 H), 6.85 (d, J = 8.1 Hz, 1 H), 6.54 (d, J = 3.6 Hz, 1 H), 6.20 (dd, J = 9.8, 4.4 Hz, 1 H), 4.70-4.65 (m, 3 H), 3.89 (s, 3 H), 3.87 (s, 3 H), 3.66 (dd, J = 14.2, 10.2 Hz, 1 H), 3.30 (dd, J = 14.3, 4.4 Hz, 1 H). LCMS (Method 1): [MH+] = 566 at 2.90 min. |

-continued

| Structure | Intermediate number | Precursor | Analytical Data |
|---|---|---|---|
| 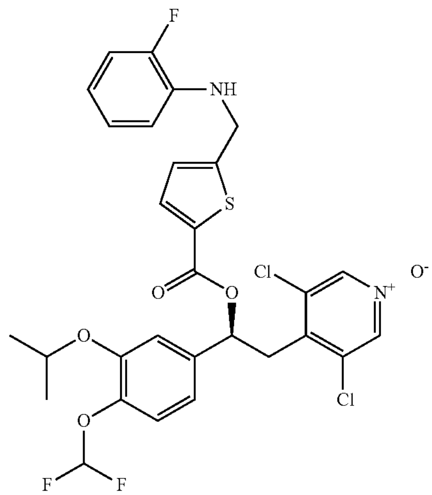 | Intermediate 22 | Intermediate 9 | $^1$H NMR (400 MHz, CDCl$_3$): δ 8.13 (s, 2 H), 7.67 (d, J = 3.8 Hz, 1 H), 7.18-7.11 (m, 1 H), 7.05-6.95 (m, 5 H), 6.73-6.65 (m, 2 H), 6.54 (t, J = 75 Hz, 1 H), 6.18 (dd, J = 10.0, 4.3 Hz, 1 H), 4.60-4.49 (m, 4 H), 3.67-3.56 (m, 1 H), 3.27 (dd, J = 14.0, 4.4 Hz, 1 H), 1.36 (d, J = 6.1 Hz, 3 H), 1.31 (d, J = 6.0 Hz, 3 H). LCMS (Method 2): [MH+] = 641 at 4.38 min. |
| 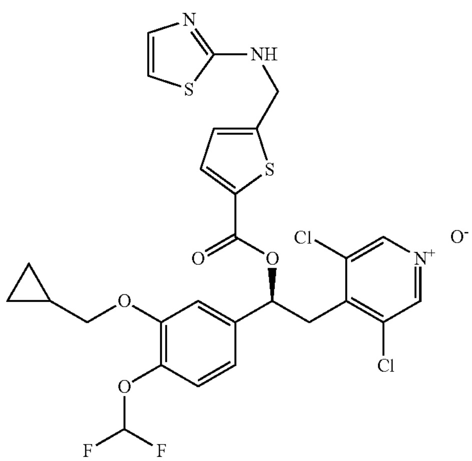 | Intermediate 23 | Intermediate 8 | $^1$H NMR (400 MHz, CDCl$_3$): δ 8.16 (s, 2 H), 7.78 (d, J = 3.9 Hz, 1 H), 7.69 (d, J = 3.5 Hz, 1 H), 7.56 (d, J = 4.0 Hz, 1 H), 7.31 (d, J = 3.5 Hz, 1 H), 7.19 (d, J = 8.9 Hz, 1 H), 7.07-6.99 (m, 2 H), 6.62 (t, J = 75 Hz, 1 H), 6.24 (dd, J = 10.0, 4.3 Hz, 1 H), 4.72 (s, 2 H), 3.91 (d, J = 7.0 Hz, 2 H), 3.68 (dd, J = 14.2, 10.0 Hz, 1 H), 3.31 (dd, J = 14.3, 4.0 Hz, 1 H), 1.33-1.21 (m, 1 H), 0.68-0.71 (m, 2 H), 0.41-0.34 (m, 2 H), NH not observed. LCMS (Method 2): [MH+] = 642 at 3.92 min. |
| 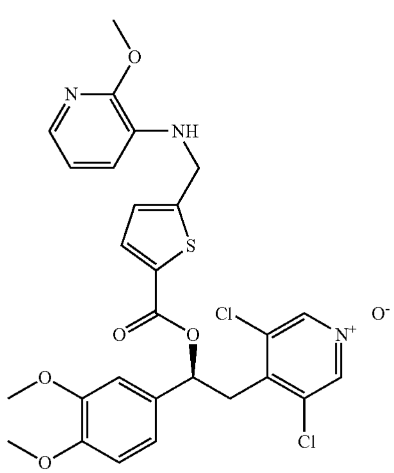 | Intermediate 24 | Intermediate 3 | $^1$H NMR (400 MHz, CDCl$_3$): δ 8.12 (s, 2 H), 7.66 (d, J = 3.8 Hz, 1 H), 7.55 (dd, J = 4.9, 1.7 Hz, 1 H), 6.99-6.94 (m, 3 H), 6.85 (d, J = 8.2 Hz, 1 H), 6.75 (dd, J = 7.6, 4.9 Hz, 1 H), 6.70 (dd, J = 7.6, 1.7 Hz, 1 H), 6.20 (dd, J = 9.9, 4.5 Hz, 1 H), 4.76 (t, J = 5.9 Hz, 1 H), 4.54 (d, J = 5.9 Hz, 2 H), 4.00 (s, 3 H), 3.89 (s, 3 H), 3.87 (s, 3 H), 3.66 (dd, J = 14.0, 9.9 Hz, 1 H), 3.30 (dd, J = 14.0, 4.5 Hz, 1 H). LCMS (Method 1): [MH+] = 590 at 3.79 min. |

-continued

| Structure | Intermediate number | Precursor | Analytical Data |
|---|---|---|---|
| (structure) | Intermediate 25 | Intermediate 3 | $^1$H NMR (400 MHz, CDCl$_3$): δ 8.12 (s, 2 H), 7.66 (d, J = 3.8 Hz, 1 H), 7.24 (d, J = 7.8 Hz, 1 H), 7.03 (d, J = 7.6 Hz, 1 H), 7.01-6.97 (m, 2 H), 6.96 (d, J = 2.0 Hz, 1 H), 6.85 (t, J = 3.9 Hz, 3 H), 6.21 (dd, J = 9.9, 4.4 Hz, 1 H), 4.64-4.47 (m, 3 H), 3.89 (s, 3 H), 3.87 (s, 3 H), 3.67 (dd, J = 14.0, 9.9 Hz, 1 H), 3.31 (dd, J = 14.0, 4.5 Hz, 1 H). LCMS (Method 1): [MH+] = 584 at 3.88 min. |
| (structure) | Intermediate 26 | Intermediate 3 | $^1$H NMR (400 MHz, CDCl$_3$): δ 8.12 (s, 2 H), 7.65 (d, J = 3.8 Hz, 1 H), 7.17-7.10 (m, 1 H), 6.99-6.94 (m, 2 H), 6.84 (dd, J = 8.3, 3.0 Hz, 2 H), 6.48-6.38 (m, 2 H), 6.34 (dt, J = 11.5, 2.4 Hz, 1 H), 6.19 (dd, J = 14.0, 4.0 Hz, 1 H), 5.68 (s, 1 H), 4.50 (s, 2 H), 3.89 (s, 3 H), 3.88 (s, 3 H), 3.65 (dd, J = 13.9, 10.1 Hz, 1 H), 3.29 (dd, J = 13.9, 4.6 Hz, 1 H). LCMS (Method 1): [MH+] = 577 at 3.81 min. |
| (structure) | Intermediate 27 | Intermediate 3 | $^1$H NMR (400 MHz, CDCl$_3$): δ 8.11 (s, 2 H), 7.65 (d, J = 3.8 Hz, 1 H), 7.50 (d, J = 8.1 Hz, 2 H), 7.30 (t, J = 7.7 Hz, 2 H), 7.13-7.05 (m, 1 H), 6.99-6.94 (m, 3 H), 6.84 (d, J = 8.1 Hz, 1 H), 6.20 (dd, J = 9.9, 4.5 Hz, 1 H), 4.53 (s, 2 H), 4.24 (s, 1 H), 3.87 (s, 3 H), 3.87 (s, 3 H), 3.65 (dd, J = 14.0, 9.9 Hz, 1 H), 3.29 (dd, J = 14.0, 4.5 Hz, 1 H). LCMS (Method 2): [MH+] = 559 at 3.83 min. |

-continued
| Structure | Intermediate number | Precursor | Analytical Data |
|---|---|---|---|
| 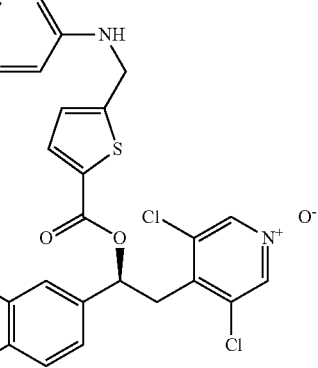 | Intermediate 28 | Intermediate 3 | $^1$H NMR (400 MHz, CDCl$_3$): δ 8.11 (s, 2 H), 7.66 (d, J = 3.8 Hz, 1 H), 7.30-7.21 (m, 1 H), 6.99-6.94 (m, 3 H), 6.89 (d, J = 7.6 Hz, 1 H), 6.84 (d, J = 8.2 Hz, 1 H), 6.79 (s, 1 H), 6.73 (d, J = 8.3 Hz, 1 H), 6.56 (t, J = 56.6 Hz, 1 H), 6.21 (dd, J = 9.8, 4.5 Hz, 1 H), 4.56 (d, J = 5.9 Hz, 2 H), 4.34 (t, J = 5.9 Hz, 1 H), 3.88 (s, 3 H), 3.87 (s, 3 H), 3.65 (dd, J = 14.0, 9.9 Hz, 1 H), 3.30 (dd, J = 14.0, 4.5 Hz, 1 H). LCMS (Method 1): [MH+] = 609 at 4.09 min |
| 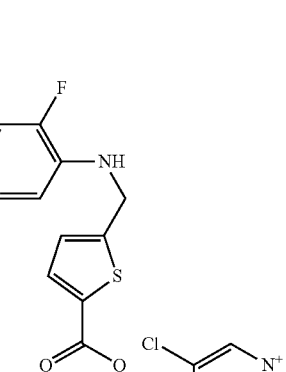 | Intermediate 76 | Intermediate 3 | LCMS (Method 2): [MH+] = 593 at 3.01 min. |
| 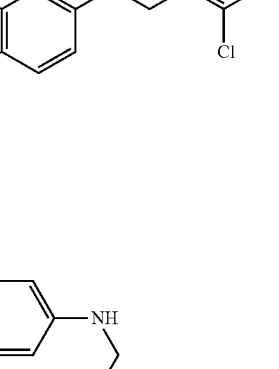 | Intermediate 77 | Intermediate 3 | LCMS (Method 2): [MH+] = 593 at 3.06 min. |

-continued

| Structure | Intermediate number | Precursor | Analytical Data |
|---|---|---|---|
| (structure) | Intermediate 78 | Intermediate 3 | LCMS (Method 2): [MH+] = 589 at 3.54 min. |
| (structure) | Intermediate 79 | Intermediate 3 | LCMS (Method 2): [MH+] = 589 at 3.58 min. |
| (structure) | Intermediate 80 | Intermediate 66 | $^1$H NMR (400 MHz, CDCl$_3$): δ 8.12 (s, 2 H), 7.52 (s, 1 H), 7.37 (s, 1 H), 6.99-6.94 (m, 2 H), 6.85-6.80 (m, 3 H), 6.75-6.71 (m, 1 H), 6.66-6.61 (m, 1 H), 6.12 (dd, J = 5.2, 9.2 Hz, 1 H), 4.89-4.79 (m, 2 H), 4.23 (s, 2 H), 4.14-4.11 (m, 1 H), 3.89 (s, 3 H), 3.87 (s, 3 H), 3.54 (dd, J = 9.2, 14.0 Hz, 1 H), 3.25 (dd, J = 5.2, 14.0 Hz, 1 H). LCMS (Method 1): [MH+] = 575 at 3.71 min. |

-continued

| Structure | Intermediate number | Precursor | Analytical Data |
|---|---|---|---|
| 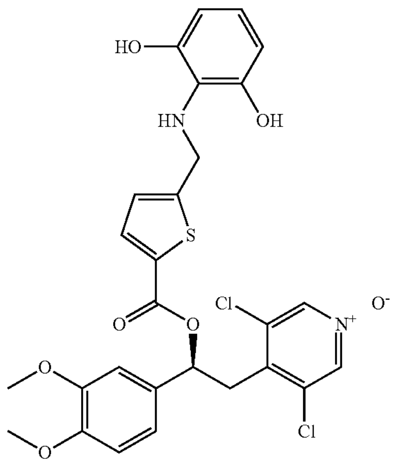 | Intermediate 81 | Intermediate 3 | LCMS (Method X): [MH+] = 591 |
| 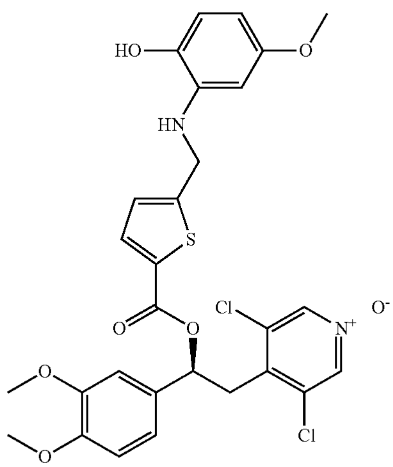 | Intermediate 82 | Intermediate 3 | LCMS (Method X): [MH+] = 605 |
| 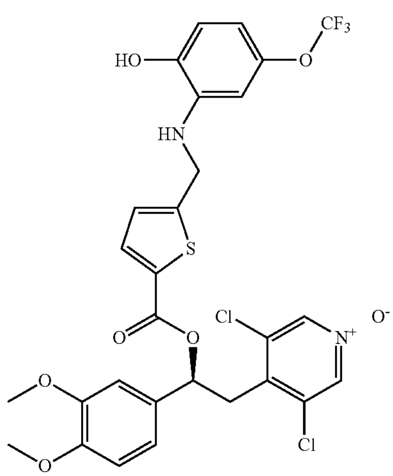 | Intermediate 83 | Intermediate 3 | LCMS (Method X): [MH+] = 659 |

-continued

| Structure | Intermediate number | Precursor | Analytical Data |
|---|---|---|---|
| (structure shown) | Intermediate 84 | Intermediate 3 | LCMS (Method X): [MH+] = 591 |

Example 1

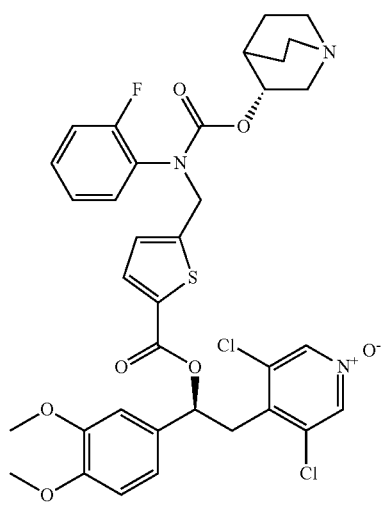

[(1S)-2-(3,5-dichloro-1-oxido-pyridin-1-ium-4-yl)-1-(3,4-dimethoxyphenyl)ethyl]5-[(2-fluoro-N-[(3R)-quinuclidin-3-yl]oxycarbonyl-anilino)methyl]thiophene-2-carboxylate formate salt (E1)

A microwave tube was charged with [(1S)-2-(3,5-dichloro-1-oxido-pyridin-1-ium-4-yl)-1-(3,4-dimethoxyphenyl)ethyl]5-[(2-fluoroanilino)methyl]thiophene-2-carboxylate (50 mg, 0.09 mmol), (R)-quinuclidin-3-yl carbonochloridate hydrochloride (81 mg, 0.36 mmol) and anhydrous acetonitrile (0.8 mL). The mixture was heated at 80° C. for 3 minutes under microwave irradiation. The reaction was evaporated to dryness. The residue was dissolved in DMSO (1.5 mL) and purified by preparative HPLC to afford [(1S)-2-(3,5-dichloro-1-oxido-pyridin-1-ium-4-yl)-1-(3,4-dimethoxyphenyl)ethyl]5-[(2-fluoro-N-[(3R)-quinuclidin-3-yl]oxycarbonyl-anilino)methyl]-thiophene-2-carboxylate formate salt as a white solid (26 mg, 41%).

$^1$H NMR (400 MHz, CDCl$_3$): δ 8.40 (s, 1H), 8.15 (s, 2H), 7.59 (d, J=3.6 Hz, 1H), 7.32-7.28 (m, 1H), 7.15-7.11 (m, 3H), 6.99-6.96 (m, 2H), 6.86-6.84 (m, 2H), 6.20 (dd, J=4.8, 10.0 Hz, 1H), 4.95-4.93 (m, 3H), 3.90 (s, 3H), 3.88 (s, 3H), 3.66 (dd, J=10.0, 14.0 Hz, 1H), 3.38-3.28 (m, 2H), 2.97-2.91 (m, 3H), 2.83-2.61 (m, 2H), 2.18-2.16 (m, 1H), 1.84-1.79 (m, 1H), 1.78-1.70 (m, 1H), 1.50-1.37 (m, 2H). LCMS (Method 2): [MH+]=730 at 3.21 min.

Compounds herebelow reported were prepared starting from the appropriate starting materials according to analogous procedures as those hereabove described to obtain Example 1. The single diastereoisomers were obtained by chiral SFC purification.

| Structure | Example | Precursor | Analytical Data |
|---|---|---|---|
| 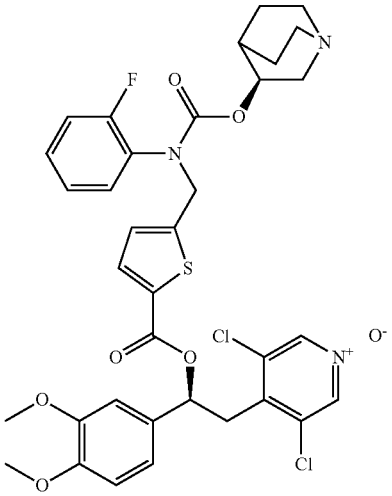 [(1S)-2-(3,5-dichloro-1-oxido-pyridin-1-ium-4-yl)-1-(3,4-dimethoxyphenyl)ethyl]5-[(2-fluoro-N-[(3S)-quinuclidin-3-yl]oxycarbonyl-anilino)methyl]thiophene-2-carboxylate formate salt | Example 2 | Intermediate 10 | $^1$H NMR (400 MHz, acetone) δ ppm 8.25 (s, 2 H), 8.12 (s, 1 H), 7.56-7.77 (m, 1 H), 7.29-7.41 (m, 2 H), 7.15-7.26 (m, 2 H), 7.11 (d, J = 1.76 Hz, 1 H), 7.02-7.08 (m, 1 H), 6.97 (m, 2 H), 6.15-6.37 (m, 1 H), 4.94-5.19 (m, 2 H), 4.73-4.92 (m, 1 H), 3.81 and 3.80 (m, 7 H), 3.17-3.47 (m, 2 H), 2.53-2.91 (m, 5 H), 1.52-1.83 (m, 3 H), 1.18-1.46 (m, 2 H). [MH+] = 730 |
| 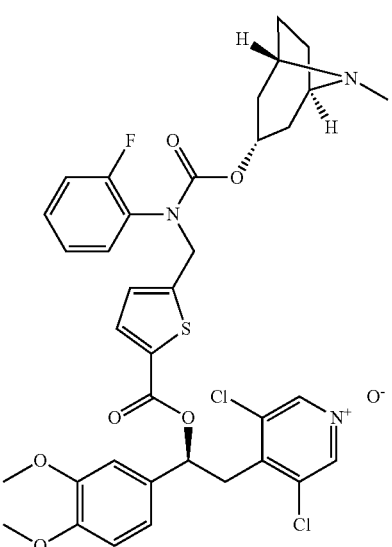 [(1S)-2-(3,5-dichloro-1-oxido-pyridin-1-ium-4-yl)-1-(3,4-dimethoxyphenyl)ethyl]5-[[2-fluoro-N-[[(1R,5S)-8-methyl-8-azabicyclo[3.2.1]octan-3-yl]oxycarbonyl]anilino]methyl]thiophene-2-carboxylate formate salt | Example 3 | Intermediate 10 | $^1$H NMR (400 MHz, acetone) δ ppm 8.24 (s, 2 H), 8.13 (s, 1 H), 7.56-7.71 (m, 1 H), 7.19-7.44 (m, 4 H), 7.09-7.13 (m, 1 H), 6.90-7.08 (m, 3 H), 6.18-6.33 (m, 1 H), 4.84-5.16 (m, 3 H), 3.81 and 3.63 (m, 7 H), 3.32-3.42 (m, 1 H), 3.08-3.29 (m, 2 H), 2.37-2.50 (m, 2 H), 2.30-2.38 (m, 3 H), 1.57-1.83 (m, 4 H), 1.24-1.40 (m, 2 H). [MH+] = 744 |

-continued

| Structure | Example | Precursor | Analytical Data |
|---|---|---|---|
| 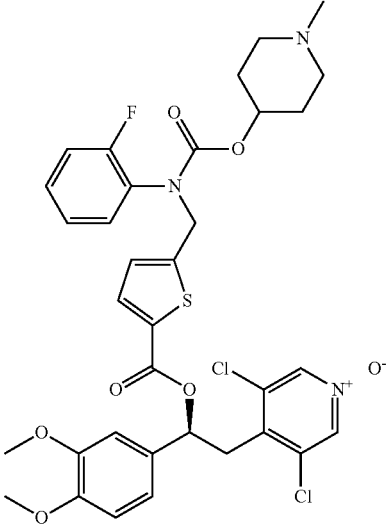 [(1S)-2-(3,5-dichloro-1-oxido-pyridin-1-ium-4-yl)-1-(3,4-dimethoxyphenyl)ethyl]5-[[2-fluoro-N-[(1-methyl-4-piperidiyl)oxycarbonyl]anilino]methyl]thiophene-2-carboxylate formate salt | Example 4 | Intermediate 10 | $^1$H NMR (400 MHz, acetone) δ ppm 8.32 (s, 2 H), 8.12 (s, 1 H), 7.58-7.68 (m, 1 H), 7.25-7.41 (m, 2 H), 7.13-7.23 (m, 2 H), 7.09-7.13 (m, 1 H), 7.01-7.08 (m, 1 H), 6.90-6.99 (m, 1 H), 6.79-6.88 (m, 1 H), 6.17-6.32 (m, 1 H), 5.09 (s, 2 H), 4.57-4.81 (m, 1 H), 3.81 (m, 7 H), 3.25-3.44 (m, 1 H), 2.08-2.37 (m, 7 H), 1.37-1.92 (m, 4H) [MH+] = 718 |
| 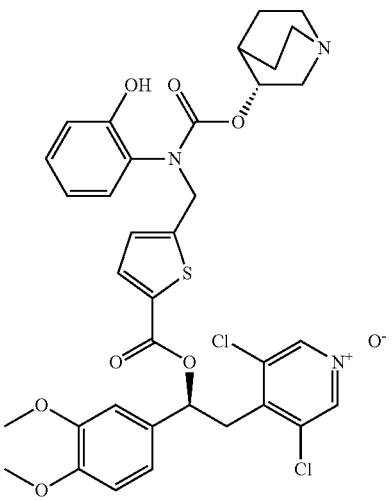 [(1S)-2-(3,5-dichloro-1-oxido-pyridin-1-ium-4-yl)-1-(3,4-dimethoxyphenyl)ethyl]5-[(2-hydroxy-N-[(3R)-quinuclidin-3-yl]oxycarbonyl-anilino)methyl]thiophene-2-carboxylate | Example 5 | 2 steps from Intermediate 3 | $^1$H NMR (400 MHz, DMSO-d6) δ ppm 9.77 (s, 1 H), 8.54 (s, 2 H), 7.52-7.69 (m, 1 H), 7.04-7.17 (m, 1 H), 6.83-7.02 (m, 6 H), 6.62-6.79 (m, 1 H), 5.99-6.26 (m, 1 H), 4.33-5.18 (m, 3 H), 3.70 and 3.86 (2 s, 6 H), 3.45-3.63 (m, 1 H), 2.85-3.16 (m, 1 H), 2.53-2.73 (m, 3 H), 2.26-2.47 (m, 3 H), 1.89-2.03 (m, 1 H), 0.94-1.84 (m, 4H). [MH+] = 728, 364 |

| Structure | Example | Precursor | Analytical Data |
|---|---|---|---|
| 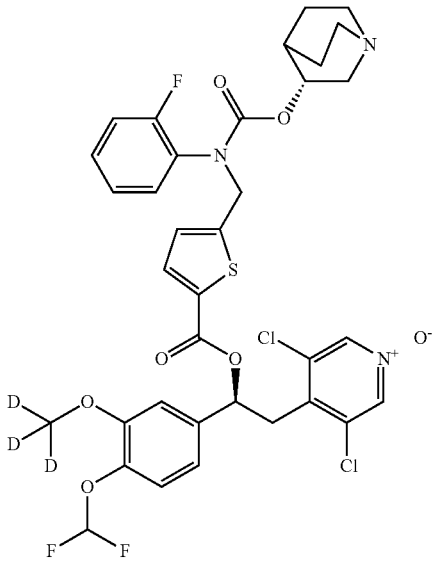 [(1S)-2-(3,5-dichloro-1-oxido-pyridin-1-ium-4-yl)-1-[4-(difluoromethoxy)-3-(trideuteriomethoxy)phenyl]ethyl]5-[(2-fluoro-N-[(3R)-quinuclidin-3-yl]oxycarbonyl-anilino)methyl]thiophene-2-carboxylate | Example 6 | Intermediate 11 | $^1$H NMR (400 MHz, DMSO) δ 8.52 (s, 2 H), 7.66 (d, J = 3.7 Hz, 1 H), 7.38-7.33 (m, 2 H), 7.28-7.18 (m, 4 H), 7.05-6.98 (m, 3 H), 6.15 (dd, J = 4.0, 9.4 Hz, 1 H), 5.05-4.95 (m, 2 H), 4.68-4.66 (m, 1 H), 3.60-3.54 (m, 1 H), 3.32 (dd, J = 4.0, 14.2 Hz, 1 H), 3.17-3.14 (m, 1 H), 2.81-2.59 (m, 4 H), 2.49-2.40 (m, 1 H), 1.89-1.87 (m, 1 H), 1.75-1.66 (m, 2 H), 1.29-1.06 (m, 2 H). LCMS (Method 2): [MH+] = 769 at 3.41 min. |
| 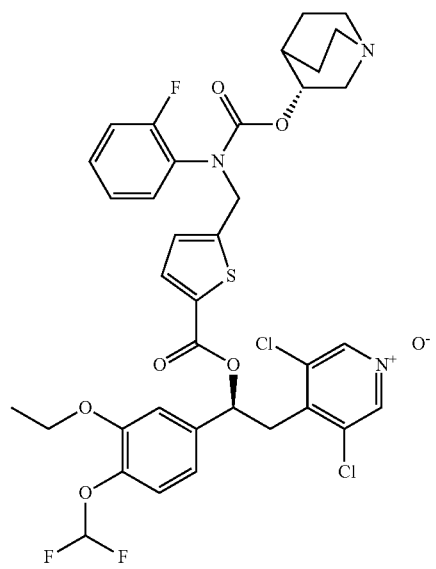 [(1S)-2-(3,5-dichloro-1-oxido-pyridin-1-ium-4-yl)-1-[4-(difluoromethoxy)-3-ethoxy-phenyl]ethyl]5-[(2-fluoro-N-[(3R)-quinuclidin-3-yl]oxycarbonyl-anilino)methyl]thiophene-2-carboxylate formate salt | Example 7 | Intermediate 12 | $^1$H NMR (400 MHz, DMSO) δ 8.53 (s, 2 H), 8.20 (s, 1 H), 7.66 (d, J = 3.6 Hz, 1 H), 7.38-7.33 (m, 2 H), 7.27-7.18 (m, 4 H), 7.05-6.98 (m, 3 H), 6.13 (dd, J = 4.0, 9.2 Hz, 1 H), 5.04-4.97 (m, 2 H), 4.72-4.68 (m, 1 H), 4.15-4.06 (m, 2 H), 3.59-3.52 (m, 1 H), 3.32 (dd, J = 4.0, 14.2 Hz, 1 H), 3.15-3.12 (m, 1 H), 2.76-2.63 (m, 4 H), 2.49-2.42 (m, 1 H), 1.89-1.73 (m, 1 H), 1.65-1.42 (m, 2 H), 1.32 (t, J = 7.0 Hz, 3 H), 1.24-1.09 (m, 2 H). LCMS (Method 2): [MH+] = 780 at 3.56 min. |

-continued

| Structure | Example | Precursor | Analytical Data |
|---|---|---|---|
| 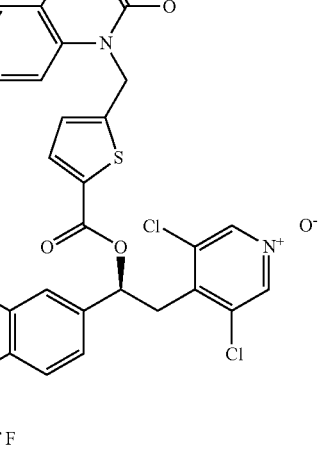 [(1S)-2-(3,5-dichloro-1-oxido-pyridin-1-ium-4-yl)-1-[4-(difluoromethoxy)-3-methoxy-phenyl]ethyl]5-[(2-fluoro-N-[(3R)-quinuclidin-3-yl]oxycarbonyl-anilino)methyl]thiophene-2-carboxylate formate salt | Example 8 | Intermediate 13 | $^1$H NMR (400 MHz, DMSO) δ 8.55 (s, 2 H), 8.20 (s, 1 H), 7.66 (d, J = 3.6 Hz, 1 H), 7.39-7.30 (m, 2 H), 7.28-7.20 (m, 4 H), 7.07-6.88 (m, 3 H), 6.15 (dd, J = 4.0, 9.2 Hz, 1 H), 5.05-4.96 (m, 2 H), 4.71-4.67 (m, 1 H), 3.85 (s, 3 H), 3.60-3.54 (m, 1 H), 3.35-3.30 (m, 1 H), 3.16-3.13 (m, 1 H), 2.81-2.61 (m, 4 H), 2.50-2.35 (m, 1 H), 1.98-1.86 (m, 1 H), 1.67-1.40 (m, 2 H), 1.24-1.15 (m, 2 H). LCMS (Method 2): [MH+] = 766 at 3.41 min. |
|  [(1S)-2-(3,5-dichloro-1-oxido-pyridin-1-ium-4-yl)-1-(3,4-dimethoxyphenyl)ethyl]5-[[3-pyridyl-[(3R)-quinuclidin-3-yl]oxycarbonyl-amino]methyl]thiophene-2-carboxylate | Example 9 | Intermediate 14 | $^1$H NMR (400 MHz, DMSO) δ 8.56 (s, 2 H), 8.50 (brs, 1 H), 8.44 (d, J = 4.4 Hz, 1 H), 7.72-7.70 (m, 1 H), 7.66-7.65 (m, 1 H), 7.44-7.41 (m, 1 H), 7.04-6.97 (m, 4 H), 6.12 (dd, J = 4.0, 9.6 Hz, 1 H), 5.11 (brs, 2 H), 4.707-4.688 (m, 1 H), 3.77 (s, 3 H), 3.75 (s, 3 H), 3.60-3.54 (dd, J = 9.6, 14.0 Hz, 1 H), 3.31-3.26 (m, 1 H), 3.13-3.07 (m, 1 H), 2.67-2.54 (m, 6 H), 1.81-1.79 (m, 1 H), 1.58-1.56 (m, 1 H), 1.55-1.50 (m, 1 H), 1.24-1.22 (m, 1 H). LCMS (Method 1): [MH+] = 713 at 2.52 min. |

| Structure | Example | Precursor | Analytical Data |
|---|---|---|---|
| 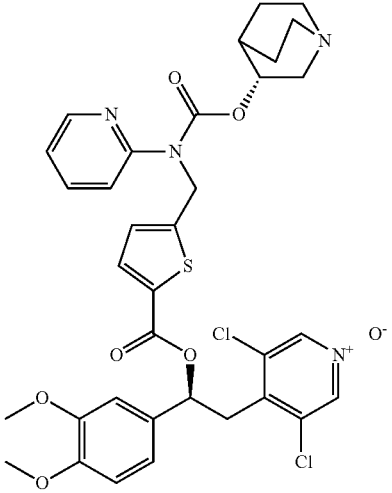<br>[(1S)-2-(3,5-dichloro-1-oxido-pyridin-1-ium-4-yl)-1-(3,4-dimethoxyphenyl)ethyl]5-[[2-pyridyl-[(3R)-quinuclidin-3-yl]oxycarbonyl-amino]methyl]thiophene-2-carboxylate formate salt | Example 10 | Intermediate 15 | $^1$H NMR (400 MHz, DMSO) δ 8.54 (s, 2 H), 8.45-8.44 (m, 1 H), 7.86-7.82 (m, 1 H), 7.75-7.73 (m, 1 H), 7.66 (d, J = 3.7 Hz, 1 H), 7.23-7.20 (m, 1 H), 7.10 (d, J = 3.7 Hz, 1 H), 6.99-6.96 (m, 3 H), 6.11 (dd, J = 4.1, 9.7 Hz, 1 H), 5.37-5.28 (m, 2 H), 4.78-4.76 (m, 1 H), 3.75 (s, 3 H), 3.74 (s, 3 H), 3.56 (dd, J = 9.7, 14.2 Hz, 1 H), 3.33-3.28 (m, 1 H), 3.18-3.13 (m, 1 H), 2.80-2.63 (m, 5 H), 1.96-1.95 (m, 1 H), 1.67-1.61 (m, 1 H), 1.59-1.51 (m, 2 H), 1.30-1.29 (m, 1 H). LCMS (Method 1): [MH+] = 713 at 2.66 min. |
| 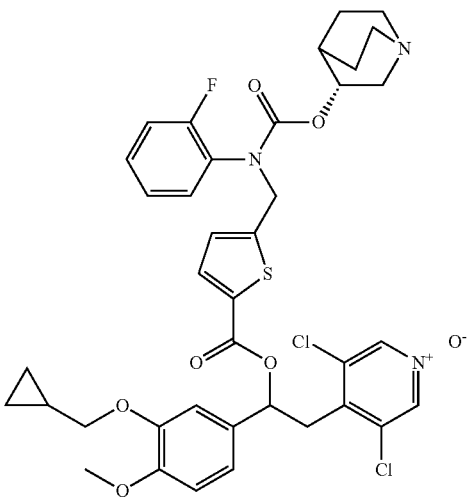<br>[1-[3-(cyclopropylmethoxy)-4-methoxy-phenyl]-2-(3,5-dichloro-1-oxido-pyridin-1-ium-4-yl)ethyl]5-[(2-fluoro-N-[(3R)-quinuclidin-3-yl]oxycarbonyl-anilino)methyl]thiophene-2-carboxylate formate salt | Example 11 | Intermediate 16 | $^1$H NMR (400 MHz, CD$_3$CN): δ 8.33 (s, 1 H), 8.20*or (s, 2 H), 8.18* $^{or}$ †(s, 2 H), 7.65-7.59 (m, 1 H), 7.42-7.14 (m, 4 H), 7.08-6.93 (m, 4 H), 6.15-6.11 (m, 1 H), 5.01-4.93 (m, 3 H), 3.82-3.81 (m, 5 H) 3.66-3.60 (m, 1 H), 3.44-2.71 (m, 6 H), 2.11-2.01 (m, 1 H), 1.97-1.66 (m, 4 H), 1.58-1.33 (m, 1 H), 1.23-1.19 (m, 1 H), 0.61-0.57 (m, 2 H), 0.34-0.20 (m, 2 H). † and * refer to different isomers (arbitrarily assigned). LCMS (Method 1): [MH+] = 770 at 2.91 min |

-continued

| Structure | Example | Precursor | Analytical Data |
|---|---|---|---|
| 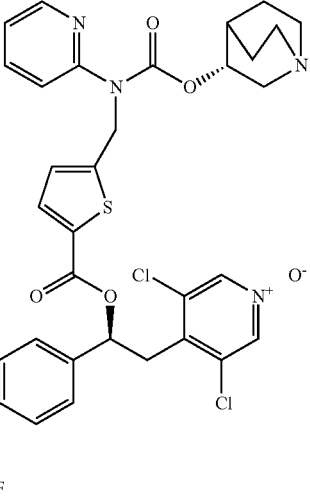<br>[(1S)-1-[3-(cyclopropylmethoxy)-4-(difluoromethoxy)phenyl]-2-(3,5-dichloro-1-oxido-pyridin-1-ium-4-yl)ethyl]5-[[2-pyridyl-[(3R)-quinuclidin-3-yl]oxycarbonyl-amino]methyl]thiophene-2-carboxylate trifluoroacetate salt | Example 12 | Intermediate 17 | $^1$H NMR (400 MHz, CDCl$_3$): δ 8.46 (d, J = 4.7 Hz, 1 H), 8.19 (s, 2 H), 7.74 (t, J = 7.6 Hz, 1 H), 7.60 (d, J = 3.9 Hz, 2 H), 7.20-7.14 (m, 2 H), 7.05-6.95 (m, 3 H), 6.61 (t, J = 75.3 Hz, 1 H), 6.15 (dd, J = 9.9, 4.2 Hz, 1 H), 5.37-5.26 (m, 2 H), 5.17-5.11 (m, 1 H), 3.88 (d, J = 6.9 Hz, 2 H), 3.70-3.59 (m, 2 H), 3.34-3.08 (m, 5 H), 2.49-2.43 (m, 1 H), 2.10-1.98 (m, 1 H), 1.97-1.83 (m, 2 H), 1.80-1.67 (m, 1 H), 1.63-1.54 (m, 1 H), 1.31-1.21 (m, 1 H), 0.68-0.61 (m, 2 H), 0.39-0.33 (m, 2 H). LCMS (Method 1): [MH+] = 789 at 2.98 min. |
| 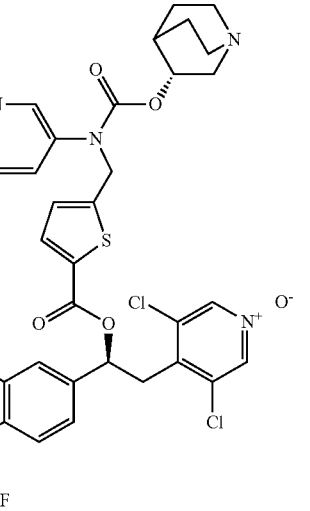<br>[(1S)-1-[3-(cyclopropylmethoxy)-4-(difluoromethoxy)phenyl]-2-(3,5-dichloro-1-oxido-pyridin-1-ium-4-yl)ethyl]5-[[3-pyridyl-[(3R)-quinuclidin-3-yl]oxycarbonyl-amino]methyl]thiophene-2-carboxylate bis trifluoroacetate salt | Example 13 | Intermediate 18 | $^1$H NMR (400 MHz, CDCl$_3$): δ 8.60 (m, 2 H), 8.28 (s, 2 H), 7.79 (brs, 1 H), 7.67-7.57 (m, 2 H), 7.19 (d, J = 8.1 Hz, 1 H), 7.08-7.00 (m, 2 H), 6.94-6.90 (m, 1 H), 6.63 (t, J = 75.3 Hz, 1 H), 6.18 (dd, J = 10.1, 4.2 Hz, 1 H), 5.15 (m, 2 H), 5.04 (m, 2 H), 3.90 (d, J = 6.9 Hz, 2 H), 3.74-3.62 (m, 2 H), 3.42-3.20 (m, 5 H), 2.43 (s, 1 H), 2.11-1.88 (m, 2 H), 1.73 (s, 2 H), 1.28 (t, J = 7.3 Hz, 1 H), 0.69-0.63 (m, 2 H), 0.39-0.34 (m, 2 H). LCMS (Method 1) : [MH+] = 789 at 2.88 min. |

-continued

| Structure | Example | Precursor | Analytical Data |
|---|---|---|---|
| 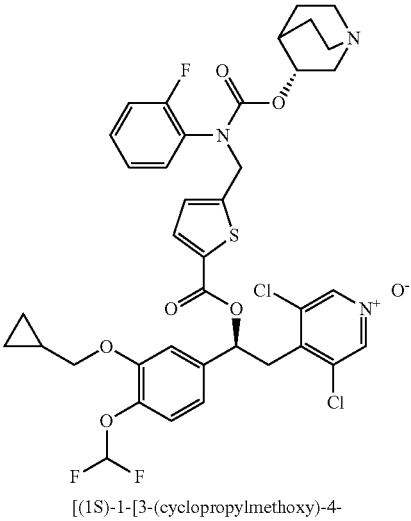<br>[(1S)-1-[3-(cyclopropylmethoxy)-4-(difluoromethoxy)phenyl]-2-(3,5-dichloro-1-oxido-pyridin-1-ium-4-yl)ethyl]5-[(2-fluoro-N-[(3R)-quinuclidin-3-yl]oxycarbonyl-anilino)methyl]thiophene-2-carboxylate formate salt | Example 14 | Intermediate 19 | $^1$H NMR (400 MHz, CDCl$_3$): δ 8.43 (s, 1 H), 8.16 (s, 2 H), 7.60 (d, J = 3.8 Hz, 1 H), 7.34-7.27 (m, 1 H), 7.21-7.09 (m, 4 H), 7.06-7.00 (m, 2 H), 6.87 (d, J = 3.8 Hz, 1 H), 6.62 (t, J = 75.3 Hz, 1 H), 6.18 (dd, J = 10.0, 4.2 Hz, 1 H), 4.94 (m, 3 H), 3.89 (d, J = 6.9 Hz, 2 H), 3.64 (dd, J = 14.1, 10.1 Hz, 1 H), 3.36-3.23 (m, 3 H), 2.87 (m, 3 H), 2.76 (m, 1 H), 2.09 (s, 1 H), 1.82-1.55 (m, 2 H) 1.32-1.24 (m, 3 H), 0.68-0.62 (m, 2 H), 0.40-0.35 (m, 2 H). LCMS (Method 1): [MH+] = 806 at 3.02 min. |
| 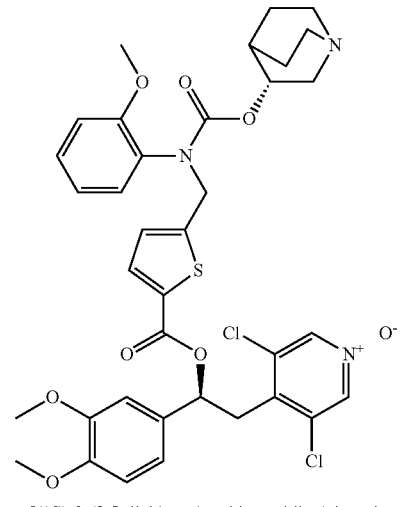<br>[(1S)-2-(3,5-dichloro-1-oxido-pyridin-1-ium-4-yl)-1-(3,4-dimethoxyphenyl)ethyl]5-[(2-methoxy-N-[(3R)-quinuclidin-3-yl]oxycarbonyl-anilino)methyl]thiophene-2-carboxylate | Example 15 | Intermediate 20 | $^1$H NMR (400 MHz, DMSO at 105° C.): δ 8.35 (s, 2 H), 7.60 (d, J = 3.8 Hz, 1 H), 7.29-7.24 (m, 1 H), 7.08-7.03 (m, 2 H), 7.02-6.95 (m, 3 H), 6.98-6.84 (m, 2 H), 6.19 (dd, J = 9.2, 4.7 Hz, 1 H), 4.86 (s, 2 H), 4.66-4.61 (m, 1 H), 3.78 (s, 3 H), 3.78 (s, 3 H), 3.73 (s, 3 H), 3.59 (dd, J = 14.3, 9.3 Hz, 1 H), 3.34 (dd, J = 14.9, 5.2 Hz, 1 H), 3.06 (dd, J = 15.3, 8.4 Hz, 1 H), 2.64-2.49 (m, 3 H), 2.54-2.41 (m, 2 H), 1.82 (s, 1 H), 1.60-1.52 (m, 1 H), 1.50-1.42 (m, 1 H), 1.38-1.25 (m, 1 H), 1.22-1.11 (m, 1 H). LCMS (Method 1): [MH+] = 741 at 2.77 min. |

-continued

| Structure | Example | Precursor | Analytical Data |
|---|---|---|---|
| 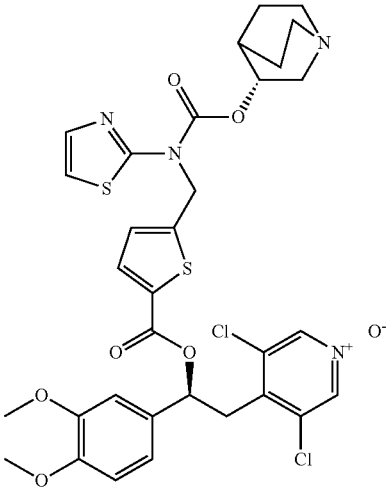<br>[(1S)-2-(3,5-dichloro-1-oxido-pyridin-1-ium-4-yl)-1-(3,4-dimethoxyphenyl)ethyl]5-[[[(3R)-quinuclidin-3-yl]oxycarbonyl-thiazol-2-yl-amino]methyl]thiophene-2-carboxylate | Example 16 | Intermediate 21 | $^1$H NMR (400 MHz, CDCl$_3$): δ 8.13 (s, 2 H), 7.61 (d, J = 3.8 Hz, 1 H), 7.49 (d, J = 3.6 Hz, 1 H), 7.09 (d, J = 3.7 Hz, 1 H), 7.01 (d, J = 3.6 Hz, 1 H), 6.98-6.93 (m, 2 H), 6.84 (d, J = 8.1 Hz, 1 H), 6.18 (dd, J = 9.8, 4.5 Hz, 1 H), 5.52 (s, 2 H), 4.97 (s, 1 H), 3.88 (s, 3 H), 3.87 (s, 3 H), 3.64 (dd, J = 14.0, 9.8 Hz, 1 H), 3.33 (dd, J = 14.9, 8.6 Hz, 1 H), 3.29 (dd, J = 14.0,4.3 Hz, 1 H), 2.92-2.73 (m, 5 H), 2.19-2.14 (m, 1 H), 1.80-1.69 (m, 1 H), 1.66-1.53 (m, 1 H), 1.52-1.40 (m, 1 H), 1.31-1.23 (m, 1 H). LCMS (Method 2): [MH+] = 719 at 3.58 min. |
| 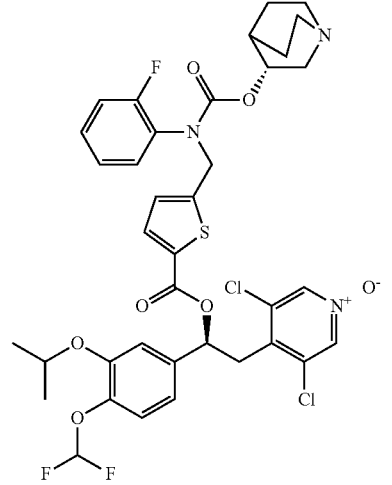<br>[(1S)-2-(3,5-dichloro-1-oxido-pyridin-1-ium-4-yl)-1-[4-(difluoromethoxy)-3-isopropoxy-phenyl]ethyl]5-[(2-fluoro-N-[(3R)-quinuclidin-3-yl]oxycarbonyl-anilino)methyl]thiophene-2-carboxylate trifluoroacetate salt | Example 17 | Intermediate 22 | $^1$H NMR (400 MHz, CDCl$_3$): δ 8.22 (s, 2 H), 7.60 (d, J = 3.8 Hz, 1 H), 7.38-7.30 (m, 1 H), 7.19-7.10 (m, 4 H), 7.05-6.98 (m, 2 H), 6.88 (d, J = 3.8 Hz, 1 H), 6.56 (t, J = 75.3 Hz, 1 H), 6.19 (dd, J = 9.9, 4.4 Hz, 1 H), 5.14-5.06 (m, 1 H), 4.97-4.89 (m, 2 H), 4.57 (h, J = 5.96 Hz, 1 H), 3.66 (dd, J = 14.1, 10.0 Hz, 1 H), 3.62-3.54 (m, 1 H), 3.32 (dd, J = 14.5, 4.6 Hz, 1 H), 3.28-3.14 (m, 3 H), 3.10 (d, J = 15.2 Hz, 1 H), 2.96-2.89 (m, 1 H), 2.39-2.31 (m, 1 H), 2.02-1.93 (m, 1 H), 1.91-1.81 (m, 1 H), 1.71-1.58 (m, 2 H), 1.36 (dd, J = 11.4, 6.0 Hz, 6 H). LCMS (Method 2): [MH+] = 794 at 3.72 min |

-continued

| Structure | Example | Precursor | Analytical Data |
|---|---|---|---|
| 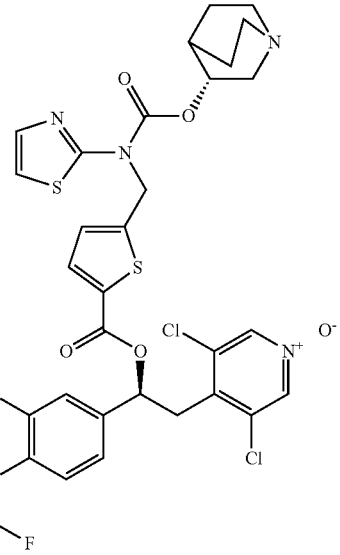<br>[(1S)-1-[3-(cyclopropylmethoxy)-4-(difluoromethoxy)phenyl]-2-(3,5-dichloro-1-oxido-pyridin-1-ium-4-yl)ethyl]5-[[[(3R)-quinuclidin-3-yl]oxycaronyl-thiazol-2-yl-amino]methyl]thiophene-2-carboxylate | Example 18 | Intermediate 23 | $^1$H NMR (400 MHz, CDCl$_3$): δ 8.14 (s, 2 H), 7.62 (d, J = 3.8 Hz, 1 H), 7.50 (d, J = 3.6 Hz, 1 H), 7.16 (d, J = 8.1 Hz, 1 H), 7.13-7.06 (m, 1 H), 7.04 (d, J = 3.6 Hz, 1 H), 7.02-6.97 (m, 2 H), 6.61 (t, J = 75.3 Hz, 1 H), 6.14 (dd, J = 10.1, 4.1 Hz, 1 H), 5.52 (s, 2 H), 5.09-4.98 (m, 1H), 3.87 (d, J = 6.9 Hz, 2 H), 3.62 (dd, J = 14.1, 10.1 Hz, 1 H), 3.40 (dd, J= 8.6, 8.1 Hz, 1 H), 3.26 (dd, J = 14.1, 4.2 Hz, 1 H), 3.04-2.84 (m, 5 H), 2.40-2.03 (m, 1 H), 1.89-1.77 (m, 2 H), 1.73-1.61 (m, 1 H), 1.60-1.49 (m, 1 H), 1.33-1.20 (m, 1 H), 0.68-0.61 (m, 2 H), 0.38-0.33 (m, 2 H). LCMS (Method 1): [MH+] = 794 at 3.05 min. |
| 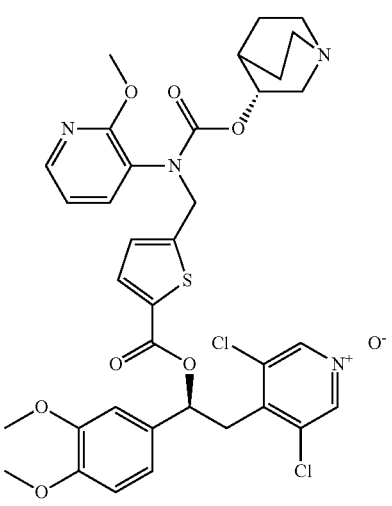<br>[(1S)-2-(3,5-dichloro-1-oxido-pyridin-1-ium-4-yl)-1-(3,4-dimethoxyphenyl)ethyl]5-[[(2-methoxy-3-pyridyl)-[(3R)-quinuclidin-3-yl]oxycarbonyl-amino]methyl]thiophene-2-carboxylate formate salt | Example 19 | Intermediate 24 | $^1$H NMR (400 MHz, CDCl$_3$): δ 8.45 (s, 1 H), 8.15 (s, 2 H), 8.12 (dd, J = 5.0, 1.8 Hz, 1 H), 7.59 (d, J = 3.8 Hz, 1 H), 7.28-7.21 (m, 1 H), 7.00-6.94 (m, 2 H), 6.89-6.81 (m, 3 H), 6.21 (dd, J = 9.7, 4.5 Hz, 1 H), 4.94-4.82 (m, 3 H), 3.93 (s, 3 H), 3.90 (s, 3 H), 3.88 (s, 3 H), 3.66 (dd, J = 14.1, 9.8 Hz, 1 H), 3.31 (dd, J = 14.0, 4.9 Hz, 1 H), 3.31-3.25 (m, 1 H), 2.86 (t, J = 8.3 Hz, 3 H), 2.73 (d, J = 14.8 Hz, 1 H), 2.68-2.57 (m, 1 H), 2.09-2.01 (m, 1 H), 1.80-1.69 (m, 1 H), 1.68-1.57 (m, 1 H), 1.41-1.29 (m, 2 H). LCMS (Method 1): [MH+] = 743 at 2.68 min. HPLC (Method 1): [MH+] = 743 at 2.68 min. |

-continued

| Structure | Example | Precursor | Analytical Data |
|---|---|---|---|
| 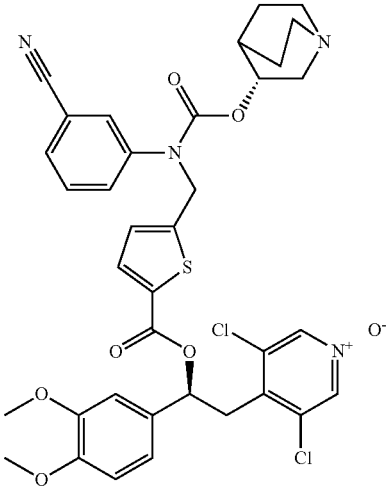<br>[(1S)-2-(3,5-dichloro-1-oxido-pyridin-1-ium-4-yl)-1-(3,4-dimethoxyphenyl)ethyl]5-[(3-cyano-N-[(3R)-quinuclidin-3-yl]oxycarbonyl-anilino)methyl]thiophene-2-carboxylate | Example 20 | Intermediate 25 | $^1$H NMR (400 MHz, CDCl$_3$): δ 8.16 (s, 2 H), 7.62 (d, J = 3.8 Hz, 1 H), 7.56 (d, J = 7.6 Hz, 1 H), 7.53-7.50 (m, 1 H), 7.47 (t, J = 7.8 Hz, 1 H), 7.44-7.38 (m, 1 H), 7.01-6.95 (m, 2 H), 6.86 (dd, J = 6.0, 2.2 Hz, 2 H), 6.22 (dd, J = 9.8, 4.5 Hz, 1 H), 5.00 (s, 2 H), 4.86-4.80 (m, 1 H), 3.90 (s, 3 H), 3.88 (s, 3 H), 3.67 (dd, J = 14.0, 9.9 Hz, 1 H), 3.31 (dd, J = 14.0, 4.5 Hz, 1 H), 3.25 (dd, J = 14.9, 8.3 Hz, 1 H), 2.81-2.68 (m, 3 H), 2.70-2.60 (m, 2 H), 2.03-1.97 (m, 1 H), 1.72-1.65 (m, 2 H), 1.46-1.37 (m, 1 H), 1.36-1.26 (m, 1 H). LCMS (Method 1): [MH+] = 737 at 2.69 min. |
| 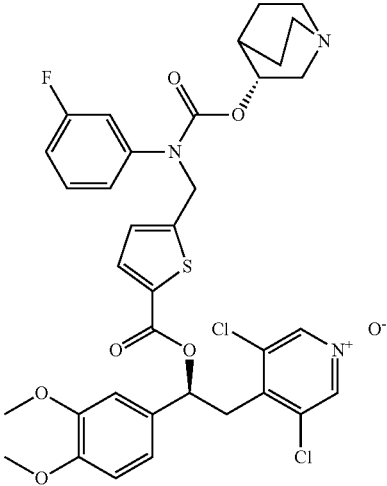<br>[(1S)-2-(3,5-dichloro-1-oxido-pyridin-1-ium-4-yl)-1-(3,4-dimethoxyphenyl)ethyl]5-[(3-fluoro-N-[(3R)-quinuclidin-3-yl]oxycarbonyl-anilino)methyl]thiophene-2-carboxylate | Example 21 | Intermediate 26 | $^1$H NMR (400 MHz, CDCl$_3$): δ 8.15 (s, 2 H), 7.61 (d, J = 3.8 Hz, 1 H), 7.34 (td, J = 8.2, 6.2 Hz, 1 H), 7.05-6.94 (m, 3 H), 6.95-6.88 (m, 1 H), 6.91-6.80 (m, 3 H), 6.21 (dd, J = 9.8, 4.5 Hz, 1 H), 5.04-4.97 (m, 1 H), 4.98-4.91 (m, 2 H), 3.91 (s, 3 H), 3.88 (s, 3 H), 3.68 (dd, J = 14.0, 9.8 Hz, 1 H), 3.45-3.38 (m, 1 H), 3.32 (dd, J = 14.0, 4.6 Hz, 1 H), 3.08-2.88 (m, 3 H), 2.90-2.76 (m, 2 H), 2.29-2.21 (m, 1 H), 1.91-1.86 (m, 1 H), 1.82-1.69 (m, 1 H), 1.68-1.46 (m, 2 H). LCMS (Method 2): [MH+] = 730 at 3.16 min. |

-continued

| Structure | Example | Precursor | Analytical Data |
|---|---|---|---|
| 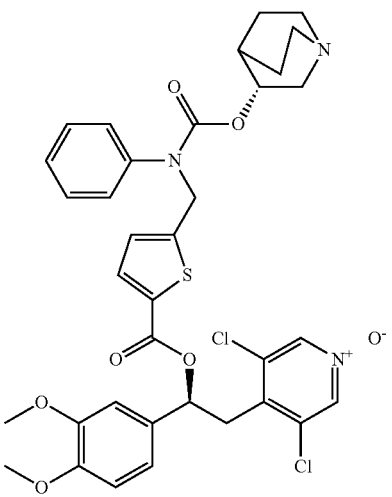<br>[(1S)-2-(3,5-dichloro-1-oxido-pyridin-1-ium-4-yl)-1-(3,4-dimethoxyphenyl)ethyl]5-[(N-[(3R)-quinuclidin-3-yl]oxycarbonylanilino)methyl]thiophene-2-carboxylate formate salt | Example 22 | Intermediate 27 | $^1$H NMR (400 MHz, CDCl$_3$): δ 8.42 (s, 1 H), 8.15 (s, 2 H), 7.60 (d, J = 3.8 Hz, 1 H), 7.39-7.32 (m, 2 H), 7.29 (d, J = 7.2 Hz, 1 H), 7.17-7.06 (m, 2 H), 7.00-6.95 (m, 2 H), 6.85 (dd, J = 5.9, 2.2 Hz, 2 H), 6.21 (dd, J = 9.8, 4.5 Hz, 1 H), 5.02-4.93 (m, 2 H), 4.94-4.87 (m, 1 H), 3.90 (s, 3 H), 3.88 (s, 3 H), 3.67 (dd, J = 14.0, 9.8 Hz, 1 H), 3.37-3.27 (m, 1 H), 3.31 (dd, J = 13.9, 4.9 Hz, 1 H), 2.92-2.84 (m, 3 H), 2.79 (d, J = 15.5 Hz, 1 H), 2.74-2.62 (m, 1H), 2.17-2.07 (m, 1 H), 1.82-1.72 (m, 1 H), 1.71-1.58 (m, 1 H), 1.56-1.31 (m, 2 H). LCMS (Method 1): [MH+] = 712 at 2.73 min. |
| 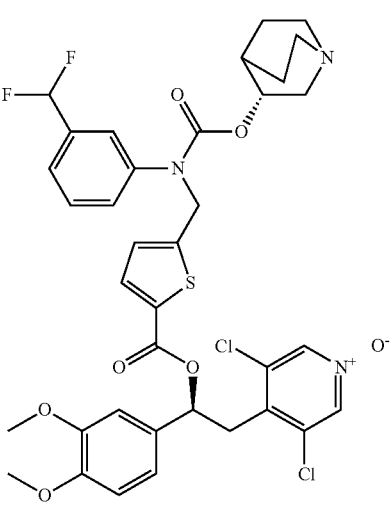<br>[(1S)-2-(3,5-dichloro-1-oxido-pyridin-1-ium-4-yl)-1-(3,4-dimethoxyphenyl)ethyl]5-[[3-(difluoromethyl)-N-[(3R)-quinuclidin-3-yl]oxycarbonyl-anilino]methyl]thiophene-2-carboxylate formate salt | Example 23 | Intermediate 28 | $^1$H NMR (400 MHz, CDCl$_3$): δ 8.41 (s, 1 H), 8.15 (s, 2 H), 7.61 (d, J = 3.8 Hz, 1 H), 7.48-7.39 (m, 2 H), 7.33 (s, 1 H), 7.26 (s, 1 H), 7.01-6.95 (m, 2 H), 6.88-6.81 (m, 2 H), 6.64 (t, J = 56.3 Hz, 1 H), 6.21 (dd, J = 9.8, 4.5 Hz, 1 H), 5.02-4.90 (m, 3 H), 3.90 (s, 3 H), 3.88 (s, 3 H), 3.67 (dd, J = 14.5, 9.7 Hz, 1 H), 3.39-3.26 (m, 2 H), 2.99-2.71 (m, 5 H), 2.14 (s, 1 H), 1.82-1.76 (m, 1 H), 1.72-1.60 (m, 1 H), 1.63-1.34 (m, 2 H). LCMS (Method 2): [MH+] = 762 at 3.05 min |

| Structure | Example | Precursor | Analytical Data |
|---|---|---|---|
| 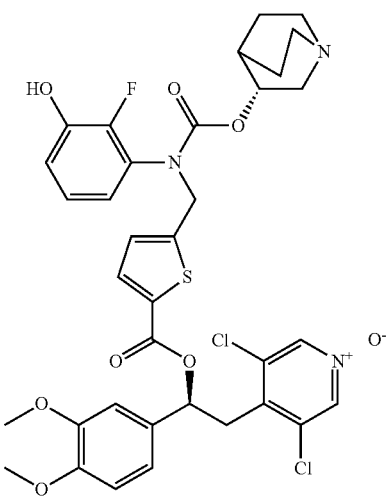<br>[(1S)-2-(3,5-dichloro-1-oxido-pyridin-1-ium-4-yl)-1-(3,4-dimethoxyphenyl)ethyl]5-[(2-fluoro-3-hydroxy-N-[(3R)-quinuclidin-3-yl]oxycarbonyl-anilino)methyl]thiophene-2-carboxylate | Example 59 | Intermediate 76 | $^1$H NMR (400 MHz, DMSO): δ 9.59 (s, 1 H), 8.40 (s, 2 H), 7.64 (d, J = 3.8 Hz, 1 H), 7.02 (s, 1 H), 6.99 (d, J = 4.0 Hz, 3 H), 6.97-6.88 (m, 2 H), 6.73-6.67 (m, 1 H), 6.19 (dd, J = 4.6, 9.3 Hz, 1 H), 4.97 (d, J = 2.5 Hz, 2 H), 4.74-4.70 (m, 1 H), 3.79 (s, 3 H), 3.79 (s, 3 H), 3.60 (dd, J = 9.3, 14.2 Hz, 1 H), 3.35 (dd, J = 4.7, 14.2 Hz, 1 H), 3.15 (ddd, J = 2.2, 8.1, 14.6 Hz, 1 H), 2.75-2.58 (m, 4 H), 1.92-1.88 (m, 1 H), 1.66-1.46 (m, 3 H), 1.29-1.22 (m, 2 H). LCMS (Method 1): [MH+] = 746 at 2.64 min. |
| 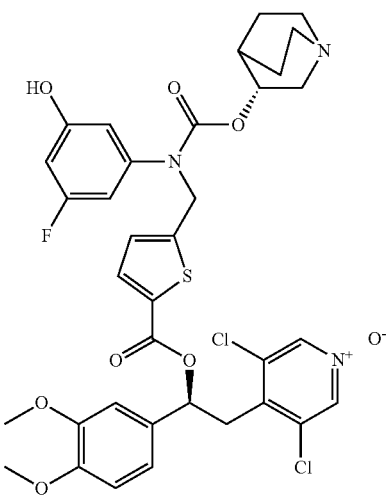<br>[(1S)-2-(3,5-dichloro-1-oxido-pyridin-1-ium-4-yl)-1-(3,4-dimethoxyphenyl)ethyl]5-[(3-fluoro-5-hydroxy-N-[(3R)-quinuclidin-3-yl]oxycarbonyl-anilino)methyl]thiophene-2-carboxylate | Example 60 | Intermediate 77 | $^1$H NMR (400 MHz, DMSO): δ 10.13-10.04 (m, 1 H), 8.55 (s, 2 H), 7.68 (d, J = 3.8 Hz, 1 H), 7.05-6.99 (m, 2 H), 6.98 (s, 2 H), 6.62 (d, J = 10.9 Hz, 1 H), 6.51 (s, 1 H), 6.48-6.44 (m, 1 H), 6.13 (dd, J = 4.0, 9.6 Hz, 1 H), 5.03 (s, 2 H), 4.72-4.66 (m, 1 H), 3.77 (s, 3 H), 3.75 (s, 3 H), 3.64-3.53 (m, 1 H), 3.33-3.23 (m, 1 H), 3.15-3.08 (m, 1 H), 2.67-2.56 (m, 5 H), 1.91-1.90 (m, 1 H), 1.62-1.42 (m, 3 H), 1.26-1.21 (m, 1 H). LCMS (Method 1): [MH+] = 746 at 2.69 min. |

| Structure | Example | Precursor | Analytical Data |
|---|---|---|---|
| 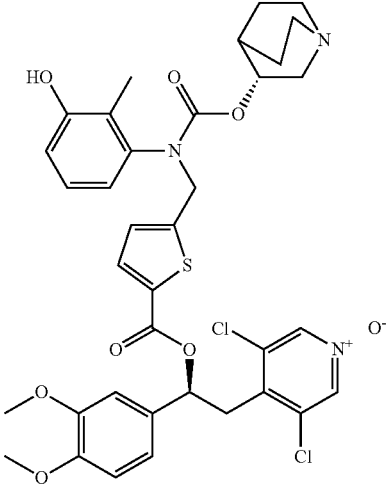<br>[(1S)-2-(3,5-dichloro-1-oxido-pyridin-1-ium-4-yl)-1-(3,4-dimethoxyphenyl)ethyl]5-[(3-hydroxy-2-methyl-N-[(3R)-quinuclidin-3-yl]oxycarbonyl-anilino)methyl]thiophene-2-carboxylate | Example 61 | Intermediate 78 | $^1$H NMR (400 MHz, 110° C., DMSO): δ 8.94 (br s, 1 H), 8.35 (s, 2 H), 7.63 (d, J = 3.8 Hz, 1 H), 7.05-6.94 (m, 5 H), 6.79 (dd, J = 0.9, 8.1 Hz, 1 H), 6.53 (d, J = 8.1 Hz, 1 H), 6.22 (dd, J = 4.7, 9.3 Hz, 1 H), 5.14-4.73 (m, 2 H), 4.72-4.68 (m, 1 H), 3.80 (s, 3 H), 3.80 (s, 3 H), 3.61 (dd, J = 9.7, 14.7 Hz, 1 H), 3.37 (dd, J = 5.0, 14.1 Hz, 1 H), 3.12 (ddd, J = 2.0, 8.1, 14.5 Hz, 1 H), 2.70-2.61 (m, 4 H), 2.57-2.54 (m, 1 H), 1.91 (s, 3 H), 1.89-1.85 (m, 1 H), 1.65-1.56 (m, 1 H), 1.55-1.46 (m, 1 H), 1.44-1.34 (m, 1 H), 1.27-1.18 (m, 1 H). LCMS (Method 1): [MH+] = 742 at 2.64 min. |
| 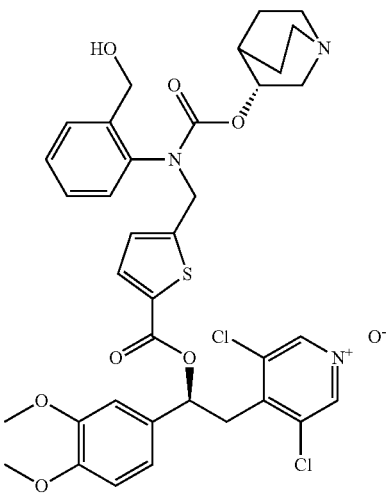<br>[(1S)-2-(3,5-dichloro-1-oxido-pyridin-1-ium-4-yl)-1-(3,4-dimethoxyphenyl)ethyl]5-[[2-(hydroxymethyl)-N-[(3R)-quinuclidin-3-yl]oxycarbonyl-anilino]methyl]thiophene-2-carboxylate | Example 62 | Intermediate 79 | $^1$H NMR (400 MHz, DMSO): δ 8.58 (s, 2 H), 7.63 (d, J = 3.6 Hz, 1 H), 7.49 (d, J = 7.7 Hz, 1 H), 7.37-7.30 (m, 1 H), 7.30-7.20 (m, 1 H), 7.01-6.86 (m, 5 H), 6.20-6.10 (m, 1 H), 5.30-5.15 (m, 1H), 5.15-5.00 (m, 1 H), 4.78-4.55 (m, 2 H); 4.36-4.21 (m, 2 H), 3.80 (s, 3 H), 3.75 (s, 3H), 3.64-3.56 (m, 1 H), 3.35-3.25 (m, 1H), 3.20-3.00 (m, 1 H), 3.20-3.00 (m, 1 H), 2.80-2.55 (m, 3 H), 2.42-2.25 (m, 2 H), 1.85-1.35 (m, 4 H), 1.15-0.9 (m, H). LCMS (Method 1): [MH+] = 742 at 2.63 min. |

-continued

| Structure | Example | Precursor | Analytical Data |
|---|---|---|---|
| 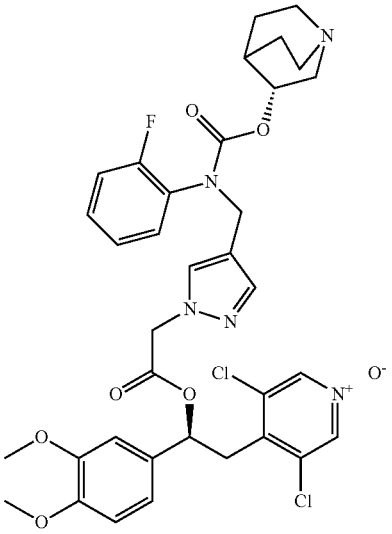 [(1S)-2-(3,5-dichloro-1-oxido-pyridin-1-ium-4-yl)-1-(3,4-dimethoxyphenyl)ethyl]2-[4-[(2-fluoro-N-[(3R)-quinuclidin-3-yl]oxycarbonyl-anilino)methyl]pyrazol-1-yl]acetate formate salt | Example 63 | Intermediate 80 | $^1$H NMR (400 MHz, CDCl3): δ 8.39 (s, 1 H), 8.16 (s, 2 H), 7.37-7.25 (m, 3 H), 7.15-7.05 (m, 3 H), 6.88-6.79 (m, 3 H), 6.09 (dd, J = 9.1, 5.1 Hz, 1 H), 4.97 (s, 1 H), 4.84-4.83 (m, 2 H), 4.74-4.72 (m, 1 H), 4.58-4.54 (m, 1 H), 3.89 (s, 3 H), 3.87 (s, 3 H), 3.54 (dd, J = 14.0, 9.1 Hz, 1 H), 3.44-3.41 (m, 1 H), 3.27 (dd, J = 14.0, 5.1 Hz, 1 H), 3.29-2.65 (m, 5 H), 2.23-2.22 (m, 1 H), 1.89-1.87 (m, 1 H), 1.78-1.76 (m, 1 H), 1.56-1.50 (m, 2 H). LCMS (Method 1): [MH+] = 728 at 2.57 min. |
| 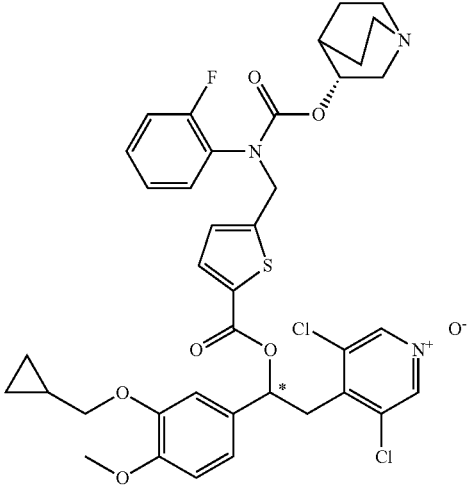 Diastereoisomer 1 of [1-[3-(cyclopropylmethoxy)-4-methoxy-phenyl]-2-(3,5-dichloro-1-oxido-pyridin-1-ium-4-yl)ethyl] 5-[(2-fluoro-N-[(3R)-quinuclidin-3-yl]oxycarbonyl-anilino)methyl]thiophene-2-carboxylate | Example 64 | Example 11 | $^1$H NMR (400 MHz, DMSO): δ 8.32 (s, 2 H), 7.40 (d, J = 3.3 Hz, 1 H), 7.15-7.09 (m, 2 H), 7.07-6.95 (m, 2 H), 6.74 (s, 4 H), 5.87 (dd, J = 4.2, 9.7 Hz, 1 H), 4.85-4.63 (m, 2 H), 4.50-4.36 (m, 1 H), 3.59-3.54 (m, 2 H), 3.53 (s, 3 H), 3.33 (dd, J = 9.9, 14.1 Hz, 1 H), 3.08-2.97 (m, 1 H), 2.90-2.84 (m, 1 H), 2.40-2.30 (m, 3 H), 2.23-2.13 (m, 1 H), 1.61-1.47 (m, 1 H), 1.36-1.15 (m, 2 H), 1.03-0.84 (m, 4 H), 0.35-0.29 (m, 2 H), 0.10-0.05 (m, 2 H). LCMS (Method 1): [MH+] = 770 at 2.9 min. Chiral analysis (Method 22) at 22.97 min |

-continued

| Structure | Example | Precursor | Analytical Data |
|---|---|---|---|
| 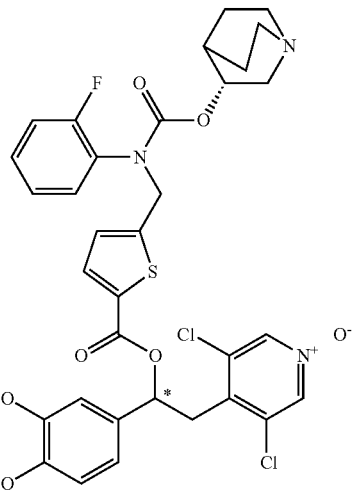<br>Diastereoisomer 2 of [1-[3-(cyclopropylmethoxy)-4-methoxy-phenyl]-2-(3,5-dichloro-1-oxido-pyridin-1-ium-4-yl)ethyl] 5-[(2-fluoro-N-[(3R)-quinuclidin-3-yl]oxycarbonyl-anilino)methyl]thiophene-2-carboxylate | Example 65 | Example 11 | $^1$H NMR (400 MHz, DMSO): δ 8.55 (s, 2 H), 7.64 (d, J = 3.8 Hz, 1 H), 7.40-7.32 (m, 2 H), 7.31-7.20 (m, 2 H), 7.00-6.96 (m, 4 H), 6.10 (dd, J = 4.0, 9.6 Hz, 1 H), 5.04-4.95 (m, 2 H), 4.69-4.66 (m, 1 H), 3.83-3.78 (m, 2 H), 3.78 (s, 3 H), 3.61-3.53 (m, 1 H), 3.30-3.24 (m, 1 H), 3.11-3.11 (m, 1 H), 2.73-2.53 (m, 3 H), 2.47-2.38 (m, 1 H), 1.82-1.78 (m, 1 H), 1.45 (s, 2 H), 1.25-1.02 (m, 4 H), 0.59-0.53 (m, 2 H), 0.33-0.31 (m, 2 H). LCMS (Method 1) : [MH+] = 770 at 2.9 min. Chiral analysis (Method 22) at 20.19 min. |
| 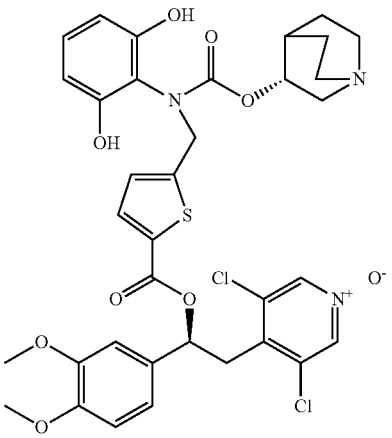<br>[(1S)-2-(3,5-dichloro-1-oxido-pyridin-1-ium-4-yl)-1-(3,4-dimethoxyphenyl)ethyl]5-[(2,6-dihydroxyphenyl)-N-[(3R)-quinuclidin-3-yl]oxycarbonyl-anilino)methyl]thiophene-2-carboxylate formate salt | Example 66 | Intermediate 81 | 1H NMR (400 MHz, DMSO-d6) d ppm 9.22-9.58 (bs, 1 H), 8.51 (s, 2 H), 8.27 (s, 2 H), 7.56 (d, J = 3.53 Hz, 1 H), 6.74-7.03 (m, 5 H), 6.24 (m, 2 H), 6.07 (dd, J = 9.48, 4.19 Hz, 1 H), 4.55-4.93 (m, 2 H), 4.39-4.54 (m, 1 H), 3.63 and 3.82 (2 s, 3 H each, 6 H), 3.51 (m, 1 H), 2.97 (m, 4 H), 2.55-2.73 (m, 3 H), 1.69 (m, 1 H), 1.46 (m, 3 H), 0.90-1.08 (m, 1 H). LCMS (Method A): [MH+] = 744 at 2.64 min. |

-continued

| Structure | Example | Precursor | Analytical Data |
|---|---|---|---|
| 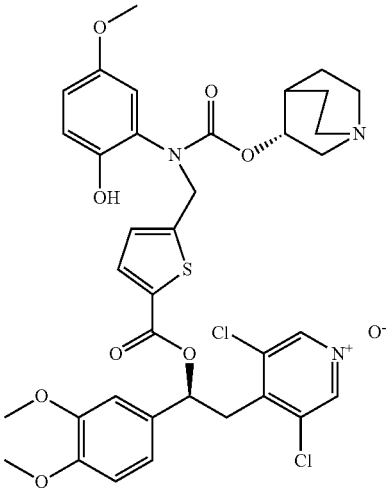<br>[(1S)-2-(3,5-dichloro-1-oxido-pyridin-1-ium-4-yl)-1-(3,4-dimethoxyphenyl)ethyl]5-[(2-hydroxy-5-methoxyphenyl)-N-[(3R)-quinuclidin-3-yl]oxycarbonyl-anilino) methyl]thiophene-2-carboxylate | Example 67 | Intermediate 82 | 1H NMR (400 MHz, acetone) δ ppm 8.29 (s, 2 H), 7.52-7.73 (m, 1 H), 7.11-7.16 (m, 1 H), 7.03-7.10 (m, 1 H), 6.98 (s, 2 H), 6.81-6.90 (m, 1 H), 6.67-6.79 (m, 1 H), 6.53-6.64 (m, 1 H), 6.24-6.32 (m, 1 H), 4.86-5.23 (m, 1 H), 4.49-4.79 (m, 1 H), 3.83 (d, J = 10.14 Hz, 6 H), 3.65 (s, 4 H), 3.29-3.46 (m, 1 H), 3.02-3.18 (m, 1 H), 2.80 (br. s., 15 H), 1.27-1.93 (m, 4 H), 1.04-1.26 (m, 1 H) LCMS (Method A): [MH+] = 758 at 2.97 min. |
| 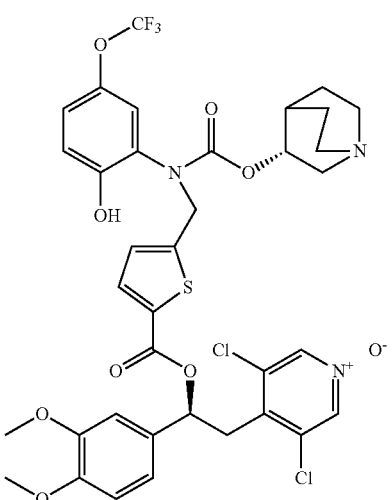<br>[(1S)-2-(3,5-dichloro-1-oxido-pyridin-1-ium-4-yl)-1-(3,4-dimethoxyphenyl)ethyl]5-[(2-hydroxy-5-(trifluoromethoxy)phenyl)-N-[(3R)-quinuclidin-3-yl]oxycarbonyl-anilino)methyl]thiophene-2-carboxylate formate salt | Example 68 | Intermediate 83 | 1H NMR (400 MHz, acetone) d ppm 8.27 (s, 2 H), 7.58-7.66 (m, 1 H), 6.88-7.17 (m, 7 H), 6.19-6.32 (m, 1 H), 4.88-5.15 (m, 1 H), 4.67-4.82 (m, 2 H), 4.58-4.65 (m, 1 H), 3.812 and 3.79 (2 s, 6 H, 3 H each), 3.61-3.74 (m, 1 H), 3.32-3.47 (m, 1 H), 3.01-3.27 (m, 4 H), 2.53-2.84 (m, 2 H), 1.95-2.00 (m, 1 H), 1.47-1.91 (m, 5 H) LCMS (Method A): [MH+] = 812 at 3.47 min. |

| Structure | Example | Precursor | Analytical Data |
|---|---|---|---|
| 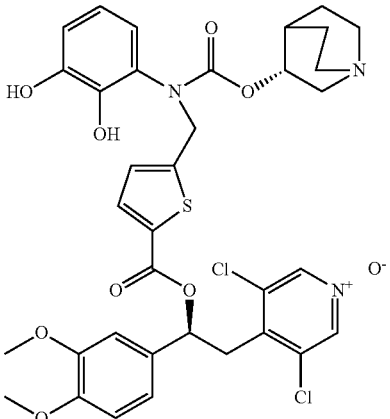 [(1S)-2-(3,5-dichloro-1-oxido-pyridin-1-ium-4-yl)-1-(3,4-dimethoxyphenyl)ethyl]5-[(2,3-dihydroxyphenyl)-N-[(3R)-quinuclidin-3-yl]oxycarbonyl-anilino)methyl]thiophene-2-carboxylate formate salt | Example 69 | Intermediate 84 | 1H NMR (400 MHz, acetone) d ppm 8.72-9.14 (bs, 1 H), 8.33 (s, 2 H), 7.55-7.71 (m, 1 H), 7.10-7.14 (m, 1 H), 7.01-7.08 (m, 1 H), 6.90-7.00 (m, 2 H), 6.75-6.81 (m, 1 H), 6.52-6.68 (m, 2 H), 6.19-6.28 (m, 1 H), 4.97-5.08 (m, 2 H), 3.81 and 3.79 (2 s , 3 H each, 6 H), 3.64 -3.73 (m, 2 H), 3.04-3.46 (m, 6 H), 2.05-2.20 (m, 3 H), 1.50- 1.76 (m, 2 H)<br>LCMS (Method A): [MH+] = 744 at 2.70 min. |

Intermediate 29. 3-((Trimethylsilyl)oxy)aniline (I-29)

$^1$H NMR (400 MHz, CDCl$_3$): δ 7.26 (s, 1H), 7.00 (t, J=7.99 Hz, 1H), 6.34-6.20 (m, 3H), 3.60 (s, 2H), 0.28-0.21 (m, 9H).
LCMS (Method 2): [MH+]=182 at 3.28 min.

Example 24

[(1S)-2-(3,5-Dichloro-1-oxido-pyridin-1-ium-4-yl)-1-(3,4-dimethoxyphenyl)ethyl]5-[(3-hydroxy-N-[(3R)-quinuclidin-3-yl]oxycarbonyl-anilino)methyl]thiophene-2-carboxylate (E24)

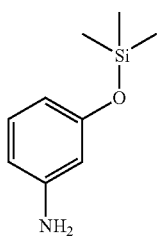

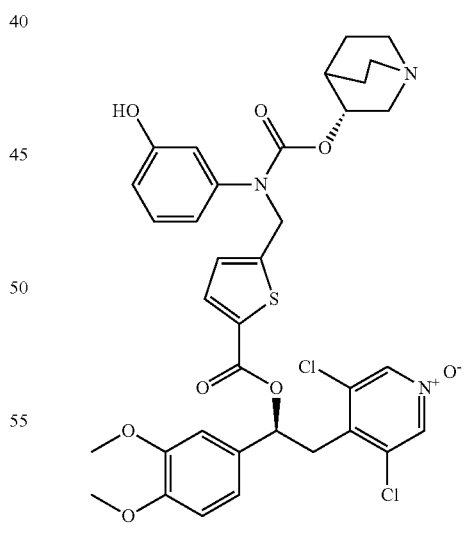

A mixture of 3-aminophenol (0.67 g, 6.15 mmol) and hexamethyldisilazane (10 mL) was added with a catalytic amount of concentrated sulfuric acid (0.05 mL) and the mixture was heated at reflux for 18 h. The mixture was cooled and excess solvent was removed in vacuo. Trituration with diethyl ether gave a precipitate which was filtered and the filtrate was evaporated in vacuo. The crude material was purified by silica gel column chromatography, eluting with 0-100% EtOAc in isohexane, to give the title product as a red-brown oil (782 mg, 70%).

A mixture of 3-((trimethylsilyl)oxy)aniline (0.14 g, 0.77 mmol) and [(1S)-2-(3,5-dichloro-1-oxido-pyridin-1-ium-4-yl)-1-(3,4-dimethoxyphenyl)ethyl]5-formylthiophene-2-carboxylate (0.186 g, 0.39 mmol) in DCM (5 mL) was stirred at room temperature for 18 h. NaBH(OAc)$_3$ (0.206 g, 0.97 mmol) and acetic acid (0.043 mL, 0.75 mmol) was added and the reaction mixture was stirred at room temperature for a further 3 h. The reaction mixture was diluted with DCM (10 mL) and washed with saturated aqueous NaHCO₃ solution (25 mL). The aqueous phase was further extracted with DCM (10 mL), and the combined organic phases were washed with brine (20 mL), filtered through a phase separator cartridge and the solvent was removed in vacuo, co-evaporated with MeCN to give [(1S)-2-(3,5-dichloro-1-oxido-pyridin-1-ium-4-yl)-1-(3,4-dimethoxyphenyl)ethyl]5-[(3-trimethylsilyloxyanilino)methyl]thiophene-2-carboxylate as a light brown gum. A mixture of this material (0.185 g, 0.29 mmol) and (R)-quinuclidin-3-yl carbonochloridate (0.162 g, 0.72 mmol) in MeCN (5 mL) was heated in a microwave at 80° C. for 6 min. Additional (R)-quinuclidin-3-yl carbonochloridate (0.08 g, 0.35 mmol) was added and heated in the microwave at 80° C. for a further 6 min. The solvent was removed in vacuo and the residue was partitioned between EtOAc (20 mL) and water (20 mL). The separated aqueous phase was basified by the addition of saturated aqueous NaHCO₃ solution and extracted with EtOAc (2×20 mL). The organic extracts were combined and filtered through a phase separator and the solvent was removed in vacuo. Purification by preparative HPLC gave the title compound as a white solid (0.02 g, 9.6%).

¹H NMR (400 MHz, DMSO-d₆): δ 9.53 (s, 1H), 8.55 (s, 2H), 7.66 (d, J=3.78 Hz, 1H), 7.15 (t, J=8.00 Hz, 1H), 7.03-6.96 (m, 4H), 6.70-6.61 (m, 3H), 6.14 (dd, J=9.71, 4.26 Hz, 1H), 5.00 (s, 2H), 4.68-4.63 (m, 1H), 3.76 (d, J=6.84 Hz, 6H), 3.58 (dd, J=14.23, 9.79 Hz, 1H), 3.54 (dd, J=14.19, 9.83 Hz, 1H), 3.25 (dd, J=14.20, 4.22 Hz, 1H), 3.10 (dd, J=14.57, 7.97 Hz, 1H), 2.69-2.55 (m, 4H), 1.87 (s, 1H), 1.62-1.42 (m, 3H), 1.21 (s, 1H). LCMS (Method 1): [MH+]=728 at 2.66 min.

The following compound was synthesized in a similar way.

Example 26

[(1S)-2-(3,5-Dichloro-1-oxido-pyridin-1-ium-4-yl)-1-(3,4-dimethoxyphenyl)ethyl]5-[(2-fluoro-N-[(3R)-1-methylpyrrolidin-3-yl]oxycarbonyl-anilino)methyl]thiophene-2-carboxylate formate salt (E26)

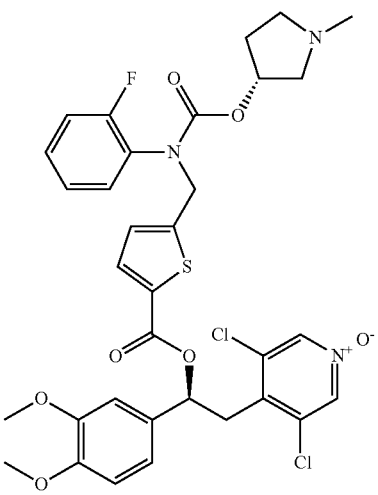

| Structure | Example | Precursor | Analytical Data |
|---|---|---|---|
| [(1S)-1-[3-(cyclopropylmethoxy)-4-(difluoromethoxy)phenyl]-2-(3,5-dichloro-1-oxido-pyridin-1-ium-4-yl)ethyl] 5-[(3-hydroxy-N-[(3R)-quinuclidin-3-yl]oxycarbonyl-anilino)methyl]thiophene-2-carboxylate formate salt | Example 25 | 2 steps from Intermediate 8 and Intermediate 29 | ¹H NMR (400 MHz, DMSO): δ 9.88 (br s, 1H), 8.56 (s, 2 H), 8.21 (s, 1 H), 7.71-7.67 (m, 1 H), 7.29-6.90 (m, 6 H), 6.70-6.62 (m, 3 H), 6.14 (dd, J = 9.60, 4.25 Hz, 1 H), 5.07-4.97 (m, 2 H), 4.70-4.65 (m, 1 H), 3.92 (d, J = 6.94 Hz, 2 H), 3.65-3.57 (m, 1 H), 3.19-3.09 (m, 2 H), 2.73-2.53 (m, 5 H), 1.89 (s, 1 H), 1.65-1.15 (m, 4 H), 0.59-0.53 (m, 2 H), 0.38-0.32 (m, 2 H). LCMS (Method 1): [MH+] = 804 at 2.97 min. |

A solution of [(1S)-2-(3,5-dichloro-1-oxido-pyridin-1-ium-4-yl)-1-(3,4-dimethoxyphenyl)ethyl]5-[(2-fluoroanilino)methyl]thiophene-2-carboxylate (177 mg, 0.306 mmol) in acetonitrile (6 mL) was added with diphosgene (75 μL, 0.61 mmol) and the reaction mixture was stirred at room temperature for 5 minutes. After which time, a solution of diisopropylethylamine (341 μl, 2.0 mmol) and (R)-1-methylpyrrolidin-3-ol (220 μl, 2.0 mmol) in acetonitrile (3 mL) was added over 10 minutes. The brown mixture was stirred at room temperature for 1 h and then the solvent was removed in vacuo. The crude product was dissolved in chloroform (70 mL) and the organic layer was washed with HCl 1M (50 mL). The organic layer was dried over sodium sulfate and evaporated under vacuum. The crude material was purified by flash chromatography (on a reverse phase C18 60 g column). The collected fractions were evaporated under vacuum and the product was further purified by means of preparative HPLC (Fraction Lynx). The collected fractions were evaporated in vacuo at 45° C. The residue was treated with acetone and diethyl ether to give the title compound as a formate salt as a foam (32 mg, 15%).

¹H NMR (400 MHz, acetone) δ ppm 8.25 (s, 2H), 8.13 (s, 1H), 7.52-7.72 (m, 1H), 7.24-7.41 (m, 2H), 7.16-7.22 (m, 2H), 7.09-7.14 (m, 1H), 6.96 (m, 3H), 6.20-6.29 (m, 1H), 5.10-5.22 (m, 1H), 5.00 (s, 2H), 3.81 and 3.78 (2s, 6H, 3H each), 3.60-3.71 (m, 1H), 3.18-3.46 (m, 1H), 2.64-2.89 (m, 2H), 2.09-2.54 (m, 7H)

[MH+]=704.

Intermediate 30. Methyl 6-(anilinomethyl)pyridine-3-carboxylate hydrochloride (I-30)

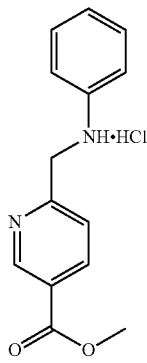

A mixture of N-Boc-aniline (350 mg, 1.81 mmol) and methyl 6-(bromomethyl)pyridine-3-carboxylate (500 mg, 2.17 mmol) in THF (10 mL) at 0° C. was added with sodium hydride (108 mg, 60% dispersion in mineral oil, 2.71 mmol). The reaction was stirred for 1 h at room temperature was then heated at 60° C. for 5 h. The reaction was cooled to room temperature and quenched with water. The mixture was partitioned between ethyl acetate and saturated aqueous ammonium chloride solution. The organic phase was washed with brine, dried over MgSO₄ then evaporated to dryness. The residue was taken up with 4N solution of HCl in dioxane (5.5 mL) and the resulting mixture was stirred at room temperature for 2 h. The reaction was concentrated under reduced pressure and the residue was triturated with diethyl ether to provide the title compound (394 mg, 78%) as an off-white solid.

¹H NMR (400 MHz, DMSO): δ 9.07 (d, J=2.0 Hz, 1H), 8.33 (dd, J=2.0, 8.0 Hz, 1H), 7.59 (d, J=8.4 Hz, 1H), 7.14-7.10 (m, 2H), 6.74-6.70 (m, 3H), 4.54 (s, 2H), 3.88 (s, 3H), NH not observed.

The following intermediates were synthesized via the same procedure.

| Structure | Intermediate | Analytical data |
|---|---|---|
| 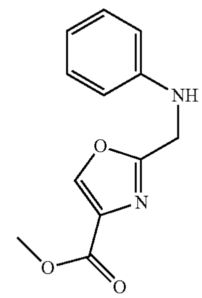 [SMILES: COC(=O)c1coc(CNc2ccccc2)n1] | Intermediate 31 | ¹H NMR (400 MHz, CDCl₃): δ 8.19 (s, 1 H), 7.22 (dd, J = 8.4, 7.2 Hz, 2 H), 6.83 (t, J = 7.4 Hz, 1 H), 6.77 (d, J = 8.0 Hz, 2 H), 5.80 (s, 1 H), 4.54 (s, 2 H), 3.91 (s, 3 H). LCMS (Method 1): [MH+] = 233 at 2.58 min. |
| 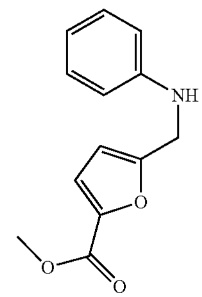 [SMILES: COC(=O)c1ccc(CNc2ccccc2)o1] | Intermediate 32 | ¹H NMR (400 MHz, CDCl₃): δ 7.19-7.15 (m, 2 H), 7.10 (d, J = 3.6 Hz, 1 H), 6.76-6.73 (m, 1 H), 6.65-6.63 (m, 2 H), 6.33 (d, J = 3.6 Hz, 1 H), 4.04 (s, 2 H), 4.12 (brs, 1 H), 3.88 (s, 3 H). |

Intermediate 33. Methyl 6-((phenylamino)methyl)picolinate (I-33)

Step 1: Preparation of methyl 6-formylpyridine-2-carboxylate (I-33a)

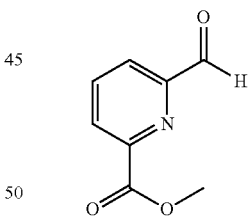

A suspension of dimethylpyridine-2,6-dicarboxylate (1.0 g, 5.12 mmol) in methanol (8 mL) and THF (3 mL) was heated at 75° C. until the solid was dissolved. NaBH₄ (184 mg, 4.87 mmol) was then added portion-wise. The mixture was stirred at 70° C. for 1 h. The mixture was cooled to room temperature and 10% citric acid (1.6 mL) was added. The solution was filtered and the filtrate was evaporated to dryness, taken up in dichloromethane, dried over MgSO₄ and the solvent was removed in vacuo. The residue was purified by silica gel chromatography, eluting with 0-100% EtOAc in isohexane, to provide a colourless oil which was then dissolved in toluene (20 mL) and chloroform (20 mL). MnO₂ (194 mg, 22.2 mmol) was added and the mixture was stirred at room temperature for 18 h. The mixture was filtered through a pad of fluorosil, eluting with chloroform (30 mL)

and the solvent was removed in vacuo to provide the title compound (249 mg, 29%) as white solid.

$^1$H NMR (400 MHz, CDCl$_3$): δ 10.20 (s, 1H), 8.37 (dd, J=1.2, 7.6 Hz, 1H), 8.17 (dd, J=1.2, 7.6 Hz, 1H), 8.08-8.04 (m, 1H), 4.07 (s, 3H).

Step 2: Preparation of methyl 6-((phenylamino)methyl)picolinate (I-33)

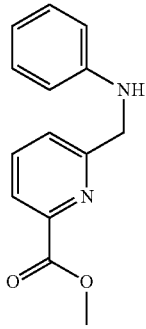 [SMILES: COC(=O)c1cccc(CNc2ccccc2)n1]

A mixture of aniline (128 mg, 1.38 mmol), methyl 6-formylpyridine-2-carboxylate (217 mg, 1.31 mmol) and acetic acid (75 μL, 1.31 mmol) in dichloromethane (10 mL) was stirred at room temperature for 24 h. After this time, sodium triacetoxyborohydride (695 mg, 3.28 mmol) was added in one portion and the resulting mixture was stirred at room temperature for 18 h. The reaction was partitioned between dichloromethane and saturated aqueous sodium bicarbonate solution. The organic layer was washed with brine, passed through a hydrophobic fit and the solvent was removed in vacuo to afford the title compound (310 mg, 97%) as yellow oil.

$^1$H NMR (400 MHz, CDCl$_3$): δ 8.03-8.02 (m, 1H), 8.00-7.99 (m, 1H), 7.80-7.76 (m, 1H), 7.19-7.14 (m, 2H), 6.74-6.70 (m, 1H), 6.64-6.62 (m, 2H), 4.58 (s, 2H), 4.02 (s, 3H). NH not observed.

The following intermediates were synthesized via the same procedure used for the preparation of Intermediate 10 (or Intermediate 33, step 2).

| Structure | Intermediate number | Analytical Data |
|---|---|---|
| (structure with 2-fluorophenyl-NH-CH2-thiophene-methyl carboxylate) | Intermediate 34 | $^1$H NMR (400 MHz, CDCl$_3$): δ 7.74 (d, J = 1.6 Hz, 1 H), 7.37 (s, 1 H), 7.01-6.91 (m, 2 H), 6.66-6.59 (m, 2 H), 4.32 (s, 2 H), 3.85 (s, 3 H), NH not observed. LCMS (Method 1): [MH+] = 266 at 4.26 min. |
| (structure with 2-pyridyl-NH-CH2-thiophene-methyl carboxylate) | Intermediate 35 | $^1$H NMR (400 MHz, DMSO): δ 8.00-7.99 (m, 1 H), 7.64 (d, J = 3.8 Hz, 1 H), 7.42-7.38 (m, 1 H), 7.35-7.20 (m, 1 H), 7.07 (d, J = 3.8 Hz, 1 H), 6.55-6.51 (m, 2 H), 4.68-4.66 (m, 2 H), 3.76 (s, 3 H). LCMS (Method 2): [MH+] = 249 at 3.37 min. |
| (structure with 2-fluorophenyl-NH-CH2-thiophene-methyl carboxylate isomer) | Intermediate 36 | $^1$H NMR (400 MHz, CDCl$_3$): δ 7.96 (d, J = 1.4 Hz, 1 H), 7.00-6.93 (m, 2 H), 6.73-6.61 (m, 2 H), 4.50 (s, 2 H), 4.44 (d, J = 12.7 Hz, 1 H), 3.83 (s, 3 H). LCMS (Method 1): [MH+] = 266 at 4.23 min. |

The following intermediates were synthesized by reaction of intermediate 2 with the appropriate secondary amine, indicated as precursor in the table below, following the same procedure used for the preparation of Example 1:

| Structure | Intermediate number | Precursor | Analytical Data |
|---|---|---|---|
| (quinuclidinyl carbamate structure with pyridyl-N-CH2-thiophene-methyl carboxylate) | Intermediate 37 | Intermediate 35 | $^1$H NMR (400 MHz, CDCl$_3$): δ 8.48-8.46 (m, 1 H), 7.75-7.67 (m, 1 H), 7.61 (d, J = 3.8 Hz, 1 H), 7.24-7.16 (m, 1 H), 6.96-6.95 (m, 1 H), 5.34-5.28 (m, 2 H), 5.14-5.12 (m, 1 H), 3.86 (s, 3 H), 3.62-3.51 (m, 1 H), 3.26-3.07 (m, 6 H), 2.51-2.49 (m, 1 H), 2.11-1.71 (m, 4 H). LCMS (Method 1): [MH+] = 402 at 2.47 min. |

-continued

| Structure | Intermediate number | Precursor | Analytical Data |
|---|---|---|---|
| 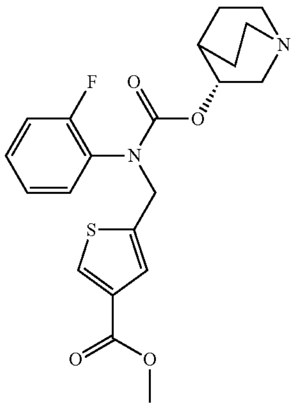 [SMILES: COC(=O)c1csc(CN(C(=O)O[C@H]2CN3CCC2CC3)c2ccccc2F)c1] | Intermediate 38 | Intermediate 36 | ¹H NMR (400 MHz, CDCl₃): δ 7.96 (d, J = 1.4 Hz, 1 H), 7.27-7.19 (m, 2 H), 7.10-6.99 (m, 3 H), 4.88 (s, 2 H), 4.90-4.67 (m, 1 H), 3.78 (s, 3 H), 2.91-2.50 (m, 5 H), 2.00-1.82 (m, 1 H), 1.66-1.54 (m, 1H), 1.54-1.43 (m, 1H), 1.34-1.23 (m, 1 H), 1.22-1.10 (m, 1 H). LCMS (Method 1): [MH+] = 419 at 2.60 min. |
| 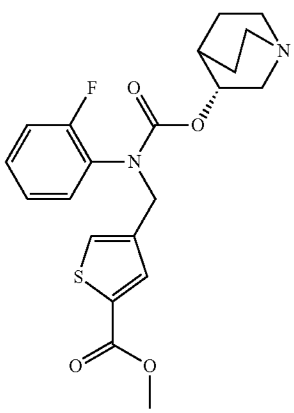 [SMILES: COC(=O)c1cc(CN(C(=O)O[C@H]2CN3CCC2CC3)c2ccccc2F)cs1] | Intermediate 39 | Intermediate 34 | ¹H NMR (400 MHz, CDCl₃): δ 7.69 (d, J = 1.5 Hz, 1 H), 7.34-7.30 (m, 1 H), 7.30-7.22 (m, 1 H), 7.13-7.02 (m, 3 H), 4.83-4.76 (m, 3 H), 3.86 (s, 3 H), 3.31-3.14 (m, 1 H), 2.82-2.50 (m, 5 H), 1.97-1.88 (m, 1 H), 1.7-1.58 (m, 1 H), 1.58-1.46 (m, 1 H), 1.38-1.28 (m, 1 H), 1.27-1.15 (m, 1 H). LCMS (Method 1): [MH+]= 419 at 2.63 min. |
| 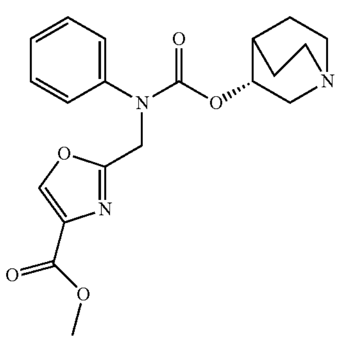 [SMILES: COC(=O)c1coc(CN(C(=O)O[C@H]2CN3CCC2CC3)c2ccccc2)n1] | Intermediate 40 | Intermediate 31 | ¹H NMR (400 MHz, CDCl₃): δ 8.30-8.15 (m, 1 H), 7.39-7.12 (m, 5 H), 5.01 (s, 2 H), 4.81-4.76 (m, 1 H), 3.89 (s, 3 H), 3.19 (dd, J = 16.0, 8.5 Hz, 1 H), 2.83-2.59 (m, 5 H), 2.01-1.94 (m, 1 H), 1.73-1.59 (m, 1 H), 1.57-1.46 (m, 1 H), 1.46-1.36 (m, 1 H), 1.3-1.19 (m, 1 H). LCMS (Method 2): [MH+] = 286 at 2.43 min |

Example 27

[(1S)-2-(3,5-Dichloro-1-oxido-pyridin-1-ium-4-yl)-1-(3,4-dimethoxyphenyl)ethyl]-4-[(2-fluoro-N-[(3R)-quinuclidin-3-yl]oxycarbonyl-anilino)methyl]thiophene-2-carboxylate formate salt (E27)

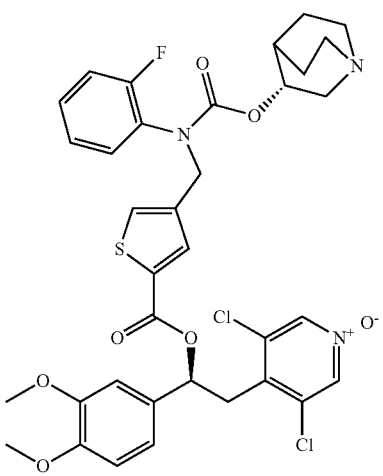

A solution of (R)-methyl 4-(((2-fluorophenyl)((quinuclidin-3-yloxy)carbonyl)amino)methyl)-thiophene-2-carboxylate (370 mg, 0.88 mmol) in MeOH (2.5 mL) and THF (2.5 mL), was added with an aqueous solution of LiOH (1 N, 1.76 mL, 1.76 mmol) at room temperature. The resulting mixture was stirred for 16 h and additional LiOH (1 N, 0.8 mL, 0.8 mmol) was added and stirring was continued for 3 h. The solution was then cooled to 0° C. and the pH was adjusted to 2 with 2 N HCl. The solvent was removed in vacuo and the mixture was azeotroped to dryness with toluene. The resulting thick oil was dissolved in DMF (8 mL) and half of the material was used in the next step.

To a solution of the carboxylic acid in DMF (4 mL, 0.44 mmol) was added (1S)-2-(3,5-dichloro-1-oxido-pyridin-1-ium-4-yl)-1-(3,4-dimethoxyphenyl)ethanol I-1/A (181 mg, 0.53 mmol), DMAP (27 mg, 0.22 mmol) followed by EDC.HCl (169 mg, 0.88 mmol). The resulting mixture was stirred at room temperature for 16 h and partitioned between EtOAc (50 mL) and water (20 mL). The layers were separated and the aqueous phase extracted with EtOAc (3×30 mL). The combined organic phases were dried over $MgSO_4$. The solvent was removed in vacuo and the residue was purified via preparative HPLC to give the [(1S)-2-(3,5-dichloro-1-oxido-pyridin-1-ium-4-yl)-1-(3,4-dimethoxyphenyl)ethyl]-4-[(2-fluoro-N-[(3R)-quinuclidin-3-yl]oxycarbonyl-anilino)methyl]thiophene-2-carboxylate formate salt (E27) as a white solid (48 mg, 15% over two steps).

$^1$H NMR (400 MHz, $CDCl_3$): δ 8.14 (s, 2H), 7.67 (s, 1H), 7.33 (s, 1H), 7.31-7.27 (m, 1H), 7.11 (t, J=8.1 Hz, 2H), 7.04 (t, J=7.4 Hz, 1H), 7.00-6.96 (m, 2H), 6.86 (d, J=8.1 Hz, 1H), 6.20 (dd, J=9.8, 4.4 Hz, 1H), 4.93-4.87 (m, 1H), 4.78 (d, J=15.1 Hz, 1H), 4.72 (d, J=15.3 Hz, 1H), 3.91 (s, 3H), 3.88 (s, 3H), 3.67 (dd, J=14.0, 9.9 Hz, 1H), 3.31 (dd, J=14.0, 4.9 Hz, 1H), 3.35-3.26 (m, 1H), 2.95-2.83 (m, 3H), 2.76 (d, J=15.3 Hz, 1H), 2.72-2.62 (m, 1H), 2.13-2.06 (m, 1H), 1.77-1.72 (m, 1H), 1.68-1.62 (m, 1H), 1.48-1.40 (m, 1H), 1.39-1.34 (m, 1H). LCMS (Method 1): [MH+]=730 at 2.72 min.

The following compounds were synthesized via the same procedure.

| Structure | Example number | Precursor | Analytical Data |
|---|---|---|---|
| [(1S)-2-(3,5-dichloro-1-oxido-pyridin-1-ium-4-yl)-1-[4-(difluoromethoxy)-3-methoxy-phenyl]ethyl] 5-[[2-pyridyl-[(3R)-quinuclidin-3-yl]oxycarbonyl-amino]methyl]thiophene-2-carboxylate trifluoroacetate salt | Example 28 | Intermediate 37 | $^1$H NMR (400 MHz, $CD_3CN$): δ 8.46-8.45 (m, 1 H), 8.22 (brs, 2 H), 7.84-7.80 (m, 1 H), 7.79-7.73 (m, 1 H), 7.68-7.66 (m, 1 H), 7.23-7.17 (m, 3 H), 7.09-7.04 (m, 2 H), 6.74 (t, J = 75.2 Hz, 1 H), 6.16 (dd, J = 4.4, 9.6 Hz, 1 H), 5.37 (s, 2 H), 5.11-5.09 (m, 1 H), 3.87 (s, 3 H), 3.68-3.62 (m, 2 H), 3.37-3.34 (m, 1 H), 3.25-3.00 (m, 5 H), 2.37-2.36 (m, 1 H), 1.98-1.74 (m, 4 H). LCMS (Method 1): [MH+] = 749 at 2.85 min. |

| Structure | Example number | Precursor | Analytical Data |
|---|---|---|---|
| [(1S)-2-(3,5-dichloro-1-oxido-pyridin-1-ium-4-yl)-1-[4-(difluoromethoxy)-3-isopropoxy-phenyl]ethyl] 5-[[2-pyridyl-[(3R)-quinuclidin-3-yl]oxycarbonyl-amino]methyl]thiophene-2-carboxylate trifluoroacetate salt | Example 29 | Intermediate 37 | $^1$H NMR (400 MHz, CD$_3$CN): δ 8.46-8.45 (m, 1 H), 8.27 (brs, 2 H), 7.84-7.80 (m, 1 H), 7.76-7.72 (m, 1 H), 7.68-7.67 (m, 1 H), 7.23-7.15 (m, 3 H), 7.08-7.03 (m, 2 H), 6.73 (t, J = 75.2 Hz, 1 H), 6.13 (dd, J = 4.4, 9.6 Hz, 1 H), 5.41 (s, 2 H), 5.11-5.09 (m, 1 H), 4.69-4.61 (m, 1H), 3.67-3.60 (m, 2 H), 3.49-3.46 (m, 1 H), 3.37-3.06 (m, 5 H), 2.37-2.36 (m, 1 H), 1.99-1.76 (m, 4 H), 1.48-1.32 (m, 3 H), 1.27-1.10 (m, 3 H). LCMS (Method 1): [MH+] = 777 at 2.97 min. |
| [(1S)-2-(3,5-dichloro-1-oxido-pyridin-1-ium-4-yl)-1-[4-(difluoromethoxy)-3-isopropoxy-phenyl]ethyl] 5-[(2-fluoro-N-[(3R)-quinuclidin-3-yl]oxycarbonyl-anilino)methyl]-thiophene-3-carboxylate formate salt | Example 30 | Intermediate 38 | $^1$H NMR (400 MHz, CDCl$_3$): δ 8.42 (s, 1 H), 8.14 (s, 2 H), 8.03 (d, J = 1.4 Hz, 1 H), 7.34-7.29 (m, 1 H), 7.22 (s, 1 H), 7.19-7.08 (m, 4 H), 7.01 (s, 1 H), 7.00-6.98 (m, 1 H), 6.55 (t, J = 75.3 Hz, 1 H), 6.15 (dd, J = 9.9, 4.2 Hz, 1 H), 4.97-4.83 (m, 3 H), 4.59-4.52 (m, 1 H), 3.62 (dd, J = 14.0, 10.0 Hz, 1 H), 3.32-3.23 (m, 1 H), 3.28 (dd, J = 14.0, 4.6 Hz, 1 H), 2.89-2.77 (m, 3 H), 2.71 (d, J = 15.8 Hz, 1 H), 2.67-2.58 (m, 1 H), 2.08-2.02 (m, 1 H), 2.00-1.77 (m, 2 H), 1.77-1.67 (m, 1 H), 1.66-1.56 (m, 1 H), 1.37 (d, J = 6.1 Hz, 3 H), 1.33 (d, J = 6.1 Hz, 3 H). LCMS (Method 2): [MH+] = 794 at 4.15 min. |

-continued

| Structure | Example number | Precursor | Analytical Data |
|---|---|---|---|
| [(1S)-2-(3,5-dichloro-1-oxido-pyridin-1-ium-4-yl)-1-[4-(difluoromethoxy)-3-isopropoxy-phenyl]ethyl] 4-[(2-fluoro-N-[(3R)-quinuclidin-3-yl]oxycarbonyl-anilino)methyl]thiophene-2-carboxylate | Example 31 | Intermediate 39 | $^1$H NMR (400 MHz, CDCl$_3$): δ 8.15 (s, 2 H), 7.68 (s, 1 H), 7.36-7.34 (m, 1 H), 7.31-7.26 (m, 1 H), 7.17 (d, J = 8.2 Hz, 1 H), 7.15-7.04 (m, 3 H), 7.04 (d, J = 2.2 Hz, 1 H), 7.00 (dd, J = 8.2, 2.0 Hz, 1 H), 6.56 (t, J = 75.3 Hz, 1 H), 6.18 (dd, J = 9.9, 4.2 Hz, 1 H), 4.91-4.84 (m, 1 H), 4.80 (d, J = 15.3 Hz, 1 H), 4.72 (d, J = 15.3 Hz, 1 H), 4.58 (h, J = 5.9 Hz, 1 H), 3.63 (dd, J = 14.1, 10.0 Hz, 1 H), 3.29 (dd, J = 14.1, 4.6 Hz, 1 H), 3.32-3.24 (m, 1 H), 2.88-2.80 (m, 3 H), 2.73 (d, J = 15.2 Hz, 1 H), 2.72-2.57 (m, 1 H), 2.06 (s, 1 H), 1.76-1.69 (m, 1 H), 1.68-1.56 (m, 1 H), 1.47-1.38 (m, 1 H), 1.38 (d, J = 6.1 Hz, 3 H), 1.36-1.27 (m, 1 H), 1.34 (d, J = 6.1 Hz, 3 H). LCMS (Method 1): [MH+] = 794 at 3.78 min. |
| [(1S)-2-(3,5-dichloro-1-oxido-pyridin-1-ium-4-yl)-1-(3,4-dimethoxyphenyl)ethyl] 5-[(2-fluoro-N-[(3R)-quinuclidin-3-yl]oxycarbonyl-anilino)methyl]thiophene-3-carboxylate | Example 32 | Intermediate 38 | $^1$H NMR (400 MHz, CDCl$_3$): δ 8.13 (s, 2 H), 8.03 (d, J = 1.4 Hz, 1 H), 7.39-7.18 (m, 1 H), 7.23 (s, 1 H), 7.16-7.06 (m, 3 H), 6.98 (dd, J = 8.5, 2.1 Hz, 1 H), 6.94 (d, J = 2.0 Hz, 1 H), 6.85 (d, J = 8.2 Hz, 1 H), 6.18 (dd, J = 9.9, 4.4 Hz, 1 H), 4.96-4.83 (m, 3 H), 3.90 (s, 3 H), 3.88 (s, 3 H), 3.65 (dd, J = 13.9, 10.0 Hz, 1 H), 3.34-3.26 (m, 1 H), 3.30 (dd, J = 13.9, 4.7 Hz, 1 H), 2.94-2.82 (m, 3 H), 2.77 (d, J = 14.9 Hz, 1 H), 2.72-2.62 (m, 1 H), 2.12-2.06 (m, 1 H), 1.86-1.59 (m, 2 H), 1.48-1.39 (m, 1 H), 1.39-1.32 (m, 1 H). LCMS (Method 1): [MH+] = 730 at 2.70 min. |

| Structure | Example number | Precursor | Analytical Data |
|---|---|---|---|
| 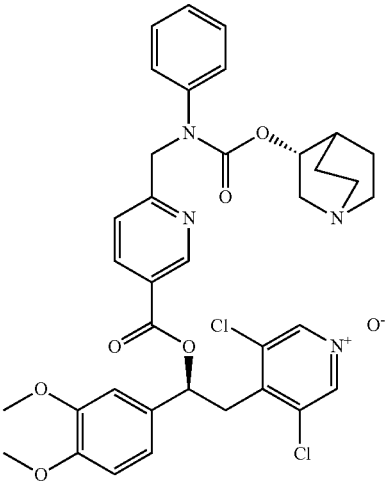<br>[(1S)-2-(3,5-dichloro-1-oxido-pyridin-1-ium-4-yl)-1-(3,4-dimethoxyphenyl)ethyl] 6-[(N-[(3R)-quinuclidin-3-yl]oxycarbonylanilino)methyl]pyridine-3-carboxylate formate salt | Example 33 | 3 steps from Intermediate 30 | $^1$H NMR (400 MHz, DMSO): δ 9.31 (s, 1 H), 8.58 (s, 2 H), 8.31 (dd, J = 2.0, 8.2 Hz, 1 H), 8.21 (s, 1 H), 7.60 (d, J = 8.2 Hz, 1 H), 7.50-7.35 (m, 4 H), 7.28-7.22 (m, 1 H), 7.11-7.05 (m, 2 H), 6.99 (m, 1 H), 6.25 (dd, J = 9.6, 4.1 Hz, 1 H), 5.08-5.01 (m, 2 H), 4.74-4.72 (m, 1 H), 3.81 (s, 3 H), 3.76 (s, 3 H), 3.74-3.67 (m, 2 H), 3.35 (dd, J = 4.1, 14.2 Hz, 1 H), 3.22-3.17 (m, 1 H), 2.75-2.63 (m, 4 H), 1.93-1.87 (m, 1 H), 1.68-1.59 (m, 1 H), 1.58-1.49 (m, 1 H), 1.34-1.22 (m, 2 H). LCMS (Method 1): [MH+] = 707 at 2.68 min. |
| 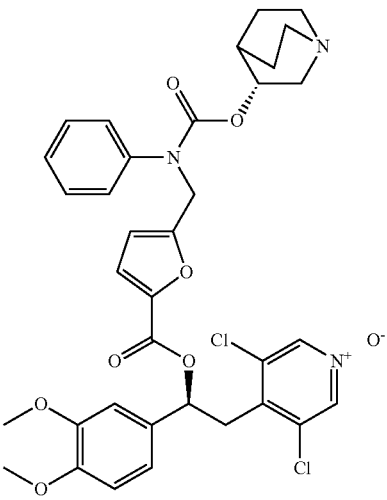<br>[(1S)-2-(3,5-dichloro-1-oxido-pyridin-1-ium-4-yl)-1-(3,4-dimethoxyphenyl)ethyl] 5-[(N-[(3R)-quinuclidin-3-yl]oxycarbonylanilino)methyl]-furan-2-carboxylate | Example 34 | 3 steps from Intermediate 32 | $^1$H NMR (400 MHz, DMSO): δ 8.66 (s, 2 H), 7.41-7.37 (m, 2 H), 7.31-7.25 (m, 4 H), 7.03-6.99 (m, 3 H), 6.52 (d, J = 3.6 Hz, 1 H), 6.15 (dd, J = 4.4, 9.6 Hz, 1 H), 4.93 (s, 2 H), 4.67-4.65 (m, 1 H), 3.79 (s, 3 H), 3.78 (s, 3 H), 3.62-3.56 (m, 1 H), 3.37-3.30 (m, 1 H), 3.10-3.04 (m, 1 H), 2.65-2.49 (m, 5 H), 1.88-1.83 (m, 1 H), 1.61-1.51 (m, 1 H), 1.50-1.41 (m, 1 H), 1.38-1.29 (m, 1 H), 1.22-1.17 (m, 1 H). LCMS (Method 2): [MH+] = 696 at 3.01 min. |

| Structure | Example number | Precursor | Analytical Data |
|---|---|---|---|
| 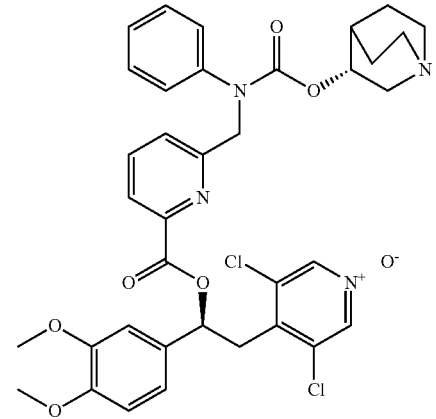 [(1S)-2-(3,5-dichloro-1-oxido-pyridin-1-ium-4-yl)-1-(3,4-dimethoxyphenyl)ethyl] 6-[(N-[(3R)-quinuclidin-3-yl]oxycarbonylanilino)methyl]pyridine-2-carboxylate | Example 35 | 3 steps from Intermediate 33 | $^1$H NMR (400 MHz, CD$_3$CN): δ 8.18 (s, 2 H), 8.01 (d, J = 7.5 Hz, 1 H), 7.90 (m, 1 H), 7.59 (d, J = 7.7 Hz, 1 H), 7.49-7.47 (m, 2 H), 7.35 (m, 2 H), 7.24 (m, 1 H), 7.07-7.04 (m, 2 H), 6.92 (d, J = 8.1 Hz, 1 H), 6.28 (dd, J = 5.0, 9.1 Hz, 1 H), 5.02-5.01 (m, 2 H), 4.70-4.67 (m, 1 H), 3.81 (s, 3 H), 3.79 (s, 3 H), 3.70 (dd, J = 9.1, 14.1 Hz, 1 H), 3.40 (dd, J = 5.0, 14.1 Hz, 1 H), 3.11-3.05 (m, 1 H), 2.65-2.52 (m, 5 H), 1.83-1.82 (m, 1 H), 1.61-1.56 (m, 1 H), 1.51-1.47 (m, 1 H), 1.33-1.27 (m, 1 H), 1.21-1.13 (m, 1 H). LCMS (Method 1): [MH+] = 707 at 2.71 min. |
| 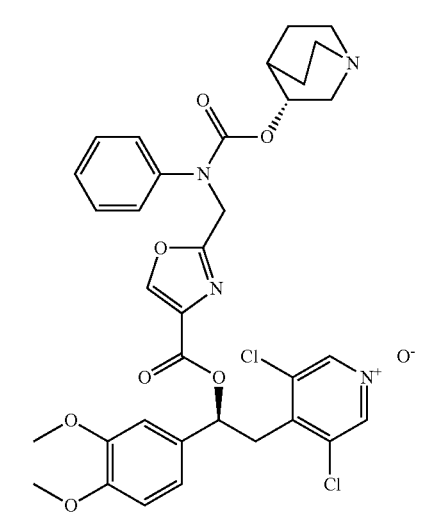 [(1S)-2-(3,5-dichloro-1-oxido-pyridin-1-ium-4-yl)-1-(3,4-dimethoxyphenyl)ethyl] 2-[(N-[(3R)-quinuclidin-3-yl]oxycarbonylanilino)methyl]oxazole-4-carboxylate formate salt | Example 36 | Intermediate 40 | $^1$H NMR (400 MHz, CDCl$_3$): δ 8.41 (s, 1 H), 8.24 (s, 1 H), 8.15 (s, 2 H), 7.40-7.31 (m, 2 H), 7.34-7.26 (m, 1 H), 7.27-7.20 (m, 2 H), 6.99-6.94 (m, 2 H), 6.84 (d, J = 8.2 Hz, 1 H), 6.25 (dd, J = 9.4, 4.9 Hz, 1 H), 5.01 (s, 1 H), 4.95 (d, J = 3.2 Hz, 2 H), 3.89 (s, 3 H), 3.88 (s, 3 H), 3.68 (dd, J = 14.4, 9.3 Hz, 1 H), 3.48-3.37 (m, 1 H), 3.36 (dd, J = 13.9, 5.1 Hz, 1 H), 3.10-2.96 (m, 4 H), 2.80 (s, 1 H), 2.27 (s, 1 H), 1.89 (s, 1 H), 1.77 (s, 1 H), 1.56 (s, 2 H). LCMS (Method 1): [MH+] = 697 at 2.58 min. |

Intermediate 41. 2-((tert-Butoxycarbonyl)amino)-2-phenylacetic acid (I-41)

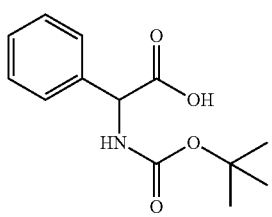 [SMILES: CC(C)(C)OC(=O)NC(C(=O)O)c1ccccc1]

Phenylglycine (1.51 g, 10 mmol) was dissolved in a mixture of dioxane and water (2:1, 30 mL) and 1.0 N aqueous sodium hydroxide, and the resulting mixture was cooled to 0° C. Di-tert-butyl dicarbonate (3.27 g, 15 mmol) and sodium hydrogen carbonate (0.84 g, 10 mmol) were added in one portion and the mixture was stirred at 0° C. for 10 minutes. The ice bath was removed and the reaction mixture was stirred at room temperature for 24 h. After this time, the reaction mixture was concentrated under reduced pressure and partitioned between ethyl acetate and water. The aqueous layer was acidified with 1.0 N aqueous potassium hydrogen sulfate solution (pH 2.5) and washed with ethyl acetate (2×40 mL). The combined organic fractions were dried over magnesium sulfate and the solvent was removed in vacuo to yield the title compound (1.8 g, 72%) as a clear oil, which solidified on standing.

$^1$H NMR (400 MHz, CDCl$_3$): δ 8.08 (s, 1H), 7.47-7.27 (m, 5H), 5.48* or † (dd, J=72.0 Hz, 6.5 Hz, 1H), 5.13*$^{or}$ † (d, J=5.6 Hz, 1H), 3.71 (s, 1H), 1.43 (s, 3H), 1.21 (s, 6H). * and † refer to different isomers.

The following intermediates were synthesized via a similar method.

| Structure | Intermediate number | Analytical Data |
|---|---|---|
| 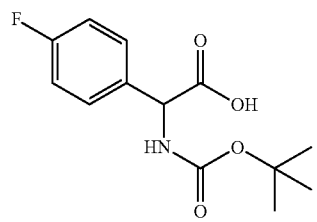 [SMILES: CC(C)(C)OC(=O)NC(C(=O)O)c1ccc(F)cc1] | Intermediate 42 | $^1$H NMR (400 MHz, CDCl$_3$): δ 7.79-7.69* $^{or\,+}$ (m, 1 H), 7.43-7.35 (m, 2 H), 7.09-6.99 (m, 2 H), 5.55-5.46* $^{or\,+}$ (m, 1 H), 5.36-5.28* $^{or\,+}$ (m, 1 H), 5.15-5.06* $^{or\,+}$ (m, 1 H), 1.43 (s, 3H), 1.23 (s, 6 H). |
| 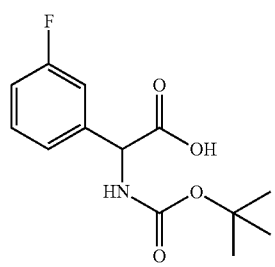 | Intermediate 43 | $^1$H NMR (400 MHz, CDCl$_3$): δ 7.37-7.30 (m, 1 H), 7.17 (d, J = 7.8 Hz, 1 H), 7.12-7.07 (m, 1 H), 7.05-6.99 (m, 1 H), 5.63 (br s, 1 H), 5.32 (d, J = 7.0 Hz, 1 H), 4.84-4.79 (m, 1 H), 3.10 (ddd, J = 14.9, 8.2, 2.3 Hz, 1 H), 2.79-2.62 (m, 3 H), 2.61-2.51 (m, 1 H), 2.32 (d, J = 14.9 Hz, 1 H), 2.05-1.99 (m, 1 H), 1.78-1.62 (m, 2 H), 1.56-1.47 (m, 1 H), 1.44 (s, 9 H), 1.41-1.31 (m, 1 H).<br>LCMS (Method 1): [MH+] = 379 at 2.62 min. |
| 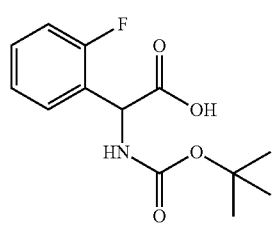 | Intermediate 44 | $^1$H NMR (400 MHz, CDCl$_3$): δ 7.38-7.27 (m, 2 H), 7.17-7.05 (m, 2 H), 5.67-5.60 (m, 1 H), 5.57 (d, J = 8.0 Hz, 1 H), 4.84-4.79 (m, 1 H), 3.10 (dd, J = 14.9, 8.1 Hz, 1 H), 2.77-2.61 (m, 3 H), 2.52-2.42 (m, 1 H), 2.36 (d, J = 15.1 Hz, 1 H), 2.01-1.96 (m, 1 H), 1.73-1.61 (m, 2 H), 1.54-1.46 (m, 1 H), 1.44 (s, 9 H), 1.39-1.25 (m, 1 H).<br>LCMS (Method 2): [MH+] = 379 at 3.65 min. |
| 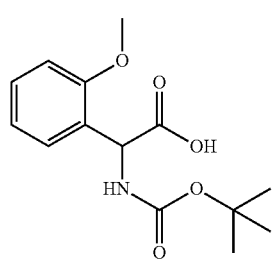 | Intermediate 45 | $^1$H NMR (400 MHz, CDCl$_3$): δ 7.34-7.27 (m, 2 H), 6.95 (t, J = 7.5 Hz, 1 H), 6.87 (d, J = 8.1 Hz, 1 H), 5.69 (d, J = 9.0 Hz, 1 H), 5.46 (d, J = 9.1 Hz, 1 H), 4.79-4.74 (m, 1 H), 3.83 (s, 3 H), 3.13 (ddd, J = 14.8, 8.0, 2.3 Hz, 1 H), 2.76-2.62 (m, 3 H), 2.40 (d, J = 14.7 Hz, 2 H), 1.97-1.89 (m, 1 H), 1.73-1.63 (m, 1 H), 1.54-1.46 (m, 1 H), 1.44 (s, 9 H), 1.30-1.17 (m, 2 H).<br>LCMS (Method 1): [MH+] = 391 at 2.57 min. |
| 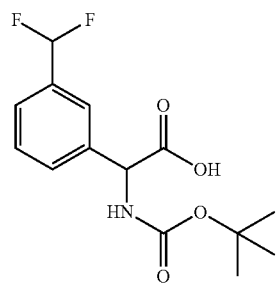 [SMILES: CC(C)(C)OC(=O)NC(C(=O)O)c1cccc(C(F)F)c1] | Intermediate 85 | LCMS (Method 1): [MH−] = 300 at 3.77 min. |

Intermediate 86 and intermediate 87. (1R,3r,5S)-8-benzyl-8-azabicyclo[3.2.1]octan-3-ol (Intermediate 86) and (1R,3s,5S)-8-benzyl-8-azabicyclo[3.2.1]octan-3-ol (Intermediate 87)

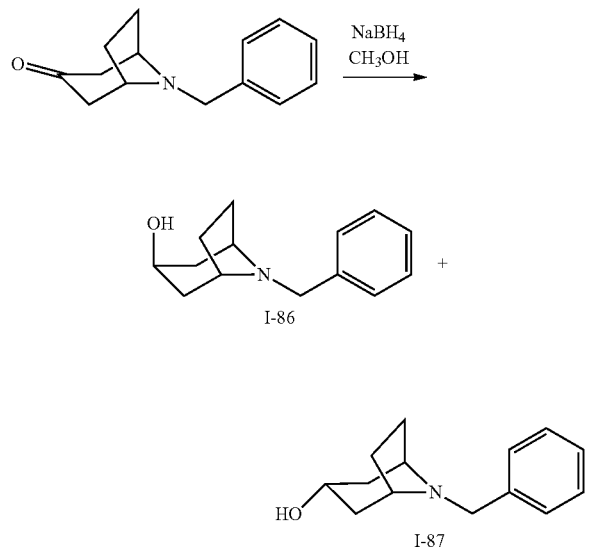

To a solution of (1R,5R)-8-benzyl-8-azabicyclo[3.2.1]octan-3-one (540 mg, 2.51 mmol) in methanol (10 mL) was added sodium borohydride (100 mg, 2.64 mmol), portionwise over a period of three minutes. After stirring for one hour at room temperature the mixture was diluted with saturated sodium chloride solution (50 mL) and extracted with ethyl acetate (3×25 mL). The organic extracts were combined, dried over magnesium sulfate, filtered and the solvent was removed in vacuo. The crude material was purified by silica gel column chromatography eluting with 0-100% (20% methanol/10% triethylamine/70% dichloromethane) in dichloromethane to give the title compound, I-86 (281 mg, 51%) as white solid. Mixed fractions were further purified on KP-NH column eluting with 0-50% ethyl acetate in iso-hexane to give title compound I-87 (183 mg, 34%) as white solid.

Intermediate 86: LCMS (Method 2): [MH+]=218 at 2.53 min

Intermediate 87: LCMS (Method 2): [MH+]=218 at 2.69 min

Intermediate 46. (R)—(R)-Quinuclidin-3-yl 2-((tert-butoxycarbonyl)amino)-2-phenylacetate (I-46)

A mixture of (R)-2-((tert-Butoxycarbonyl)amino)-2-phenylacetic acid (5.0 g, 19.9 mmol), (R) enantiomeric pure form commercially available or obtainable from I-41 with known methods e.g. chiral preparative SFC, (R)-quinuclidin-3-ol (3.8 g, 29.8 mmol), N,N'-Dicyclohexylcarbodiimide (4.72 g, 22.9 mmol) and 1-hydroxybenzotriazole hydrate (3.09 g, 22.9 mmol) in tetrahydrofuran (175 mL) was stirred at room temperature for 18 h. After this time the reaction mixture was filtered through a pad of Celite® and concentrated in vacuo. The residue was partitioned between ethyl acetate (100 mL) and 10% aqueous sodium carbonate solution (50 mL), and the organic fractions were dried over magnesium sulfate, filtered and the solvent was removed in vacuo. Trituration with cold methanol gave the title compound as a white solid (898 mg, 17%) as a single diastereoisomer.

$^1$H NMR (400 MHz, CDCl$_3$): δ 7.84 (d, J=7.8 Hz, 1H), 7.49-7.31 (m, 5H), 5.22 (d, J=8.2 Hz, 1H), 4.73-4.66 (m, 1H), 3.02 (ddd, J=14.5 Hz, 7.8 Hz, 1.5 Hz, 1H), 2.69-2.51 (m, 3H), 2.46-2.33 (m, 1H), 2.19 (d, J=14.5, 1 H), 1.98-1.87 (m, 1H), 1.70-1.53 (m, 2H), 1.53-1.30 (m, 1H), 1.43 (s, 9H), 1.34-1.23 (m, 1H).

The following intermediates were synthesized via a similar method, reacting the suitable precursor, commercially available or above described, with the suitable amino-alcohol, commercially available or above described.

| Structure | Intermediate number | Precursor | Analytical Data |
|---|---|---|---|
| 4-F-phenyl Boc-amino quinuclidinyl ester | Intermediate 47 | Intermediate 42 | $^1$H NMR (400 MHz, CDCl$_3$): δ 7.38-7.32 (m, 2 H), 7.09-7.02 (m, 2 H), 5.59 (br s, 1 H), 5.29 (d, J = 7.0 Hz, 1 H), 4.83-4.78 (m, 1 H), 3.14-3.06 (m, 1 H), 2.80-2.62 (m, 3 H), 2.59-2.50 (m, 1 H), 2.35-2.28 (m, 1 H), 2.04-1.98 (m, 1 H), 1.76-1.28 (m, 13 H). LCMS (Method 2): [MH+] = 379 at 3.65 min. |
| 3-F-phenyl Boc-amino quinuclidinyl ester | Intermediate 48 | Intermediate 43 | $^1$H NMR (400 MHz, DMSO): δ 10.50 (br s, 1 H), 9.30 (br s, 3 H), 7.62-7.52 (m, 2 H), 7.48 (d, J = 7.7 Hz, 1 H), 7.40-7.32 (m, 1 H), 5.41 (s, 1 H), 5.17 (br s, 1 H), 3.69-3.59 (m, 1 H), 3.30-3.11 (m, 5 H), 2.38-2.31 (m, 1 H), 2.15-2.05 (m, 1 H), 1.99-1.89 (m, 1 H), 1.88-1.80 (m, 1 H), 1.80-1.70 (m, 1 H). LCMS (Method 1): [MH+] = 379 at 2.62 min. |

| Structure | Intermediate number | Precursor | Analytical Data |
|---|---|---|---|
| 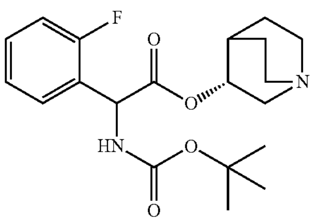 [SMILES: CC(C)(C)OC(=O)NC(C(=O)O[C@H]1CN2CCC1CC2)c1ccccc1F] | Intermediate 49 | Intermediate 44 | $^1$H NMR (400 MHz, DMSO): δ 10.81 (br s, 1 H), 9.32 (br s, 3 H), 7.78-7.72 (m, 1 H), 7.62-7.55 (m, 1 H), 7.44-7.34 (m, 2 H), 5.52 (s, 1 H), 5.23-5.17 (m, 1 H), 3.66 (dd, J = 14.0, 8.5 Hz, 1 H), 3.32-3.10 (m, 5 H), 2.36-2.29 (m, 1 H), 2.12-2.00 (m, 1 H), 1.99-1.90 (m, 1 H), 1.90-1 79 (m, 1 H), 1.79-1.71 (m, 1 H). LCMS (Method 2): [MH+] = 379 at 3.65 min. |
| 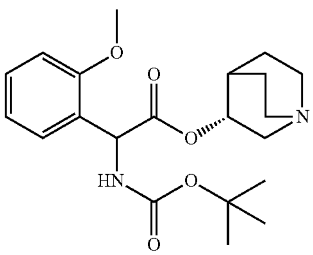 [SMILES: COc1ccccc1C(NC(=O)OC(C)(C)C)C(=O)O[C@H]1CN2CCC1CC2] | Intermediate 50 | Intermediate 45 | $^1$H NMR (400 MHz, DMSO): δ 10.82 (s, 1 H), 8.91 (s, 3 H), 7.54-7.47 (m, 2 H), 7.17 (d, J = 8.2 Hz, 1 H), 7.08 (t, J = 7.5 Hz, 1 H), 5.42-5.35 (m, 1 H), 5.21-5.15 (m, 1 H), 3.86 (s, 3 H), 3.72-3.63 (m, 1 H), 3.30-3.07 (m, 4 H), 3.03-2.92 (m, 1 H), 2.32-2.26 (m, 1 H), 1.98-1.79 (m, 3 H), 1.79-1.65 (m, 1 H). LCMS (Method 1): [MH+] = 391 at 2.57 min. |
| 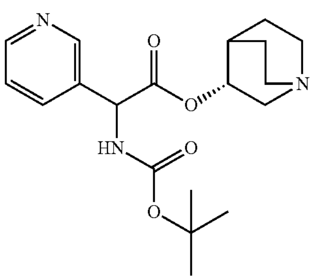 [SMILES: CC(C)(C)OC(=O)NC(C(=O)O[C@H]1CN2CCC1CC2)c1cccnc1] | Intermediate 51 | 2-((Tert-butoxycarbonyl) amino)-2-(pyridin-3-yl) acetic acid | $^1$H NMR (400 MHz, DMSO-d$_6$): δ 8.63 (t, J = 2.50 Hz, 1 H), 8.52 (td, J = 4.55, 1.60 Hz, 1 H), 7.95 (d, J = 8.08 Hz, 1 H), 7.86-7.81 (m, 1 H), 7.43-7.36 (m, 1 H), 5.31 (dd, J = 8.04, 3.97 Hz, 1 H), 4.72 (t, J = 9.02 Hz, 1 H), 3.11-2.96 (m, 1 H), 2.65-2.53 (m, 4 H), 2.47-2.10 (m, 1 H), 1.89-1.65 (m, 1 H), 1.63-1.47 (m, 2 H), 1.41 (s, 9 H), 1.36-1.22 (m, 2 H), |
| 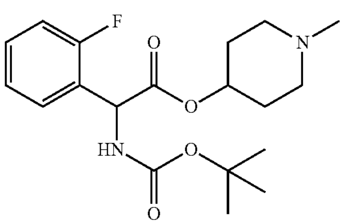 [SMILES: CN1CCC(OC(=O)C(NC(=O)OC(C)(C)C)c2ccccc2F)CC1] | Intermediate 52 | Intermediate 44 | LCMS (Method 1) : [MH+] = 367 at 2.52 min. |
| 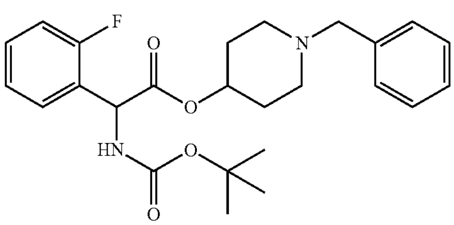 [SMILES: CC(C)(C)OC(=O)NC(C(=O)OC1CCN(Cc2ccccc2)CC1)c1ccccc1F] | Intermediate 53 | Intermediate 44 | LCMS (Method 1) : [MH+] = 443 at 2.79 min. |
| 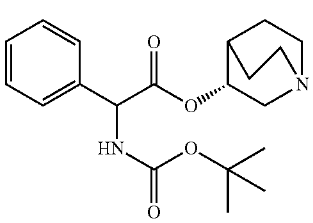 [SMILES: CC(C)(C)OC(=O)NC(C(=O)O[C@H]1CN2CCC1CC2)c1ccccc1] | Intermediate 88 | Intermediate 41 and (R)-quinuclidin-3-ol | LCMS (Method 2): [MH+] = 361 at 3.30 min. |

-continued

| Structure | Intermediate number | Precursor | Analytical Data |
|---|---|---|---|
| 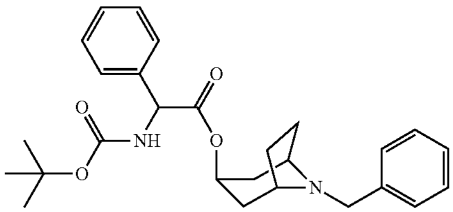 [SMILES: CC(C)(C)OC(=O)NC(C(=O)OC1CC2CCC(C1)N2Cc1ccccc1)c1ccccc1] | Intermediate 89 (endo) | Intermediate 41 and intermediate 86 | LCMS (Method 2): [MH+] = 451 at 4.63 min. |
| 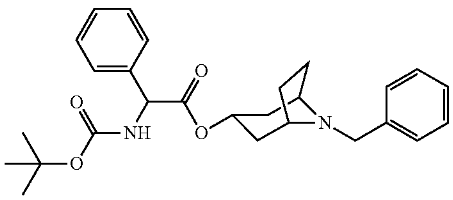 [SMILES: CC(C)(C)OC(=O)NC(C(=O)OC1CC2CCC(C1)N2Cc1ccccc1)c1ccccc1] | Intermediate 90 (exo) | Intermediate 41 and intermediate 87 | LCMS (Method 2): [MH+] = 451 at 4.73 min. |
| 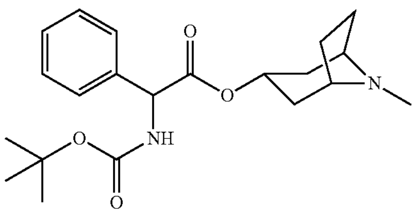 [SMILES: CN1C2CCC1CC(OC(=O)C(NC(=O)OC(C)(C)C)c1ccccc1)C2] | Intermediate 91 (exo) | Intermediate 41 and (1R,3s,5S)-8-methyl-8-azabicyclo[3.2.1]octan-3-ol | LCMS (Method 2): [MH+] = 375 at 3.60 min. |
| 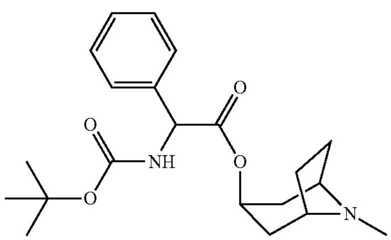 [SMILES: CN1C2CCC1CC(OC(=O)C(NC(=O)OC(C)(C)C)c1ccccc1)C2] | Intermediate 92 (endo) | Intermediate 41 and (1R,3r,5S)-8-methyl-8-azabicyclo[3.2.1]octan-3-ol | LCMS (Method 2): [MH+] = 375 at 3.36 min. |
| 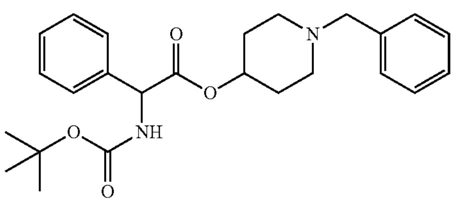 [SMILES: CC(C)(C)OC(=O)NC(C(=O)OC1CCN(Cc2ccccc2)CC1)c1ccccc1] | Intermediate 93 | Intermediate 41 and 1-benzylpiperidin-4-ol | LCMS (Method 2): [MH+] = 425 at 4.52 min. |
| 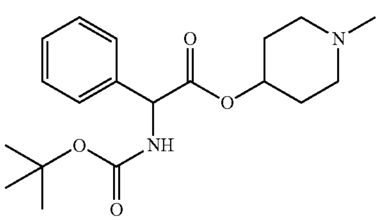 [SMILES: CN1CCC(OC(=O)C(NC(=O)OC(C)(C)C)c2ccccc2)CC1] | Intermediate 94 | Intermediate 41 and 1-methylpiperidin-4-ol | LCMS (Method 2): [MH+] = 349 at 3.63 min. |
| 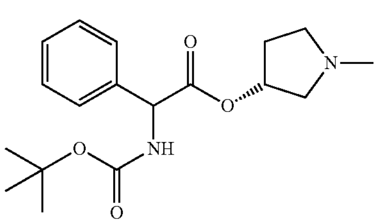 | Intermediate 95 | Intermediate 41 and (3R)-1-methylpyrrolidin-3-ol | LCMS (Method 2): [MH+] = 335 at 3.15 min. |

-continued

| Structure | Intermediate number | Precursor | Analytical Data |
|---|---|---|---|
| 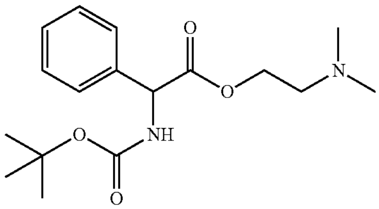 [SMILES: CN(C)CCOC(=O)C(NC(=O)OC(C)(C)C)c1ccccc1] | Intermediate 96 | Intermediate 41 and 2-(dimethylamino)ethanol | LCMS (Method 2): [MH+] = 323 at 3.50 min. |
| 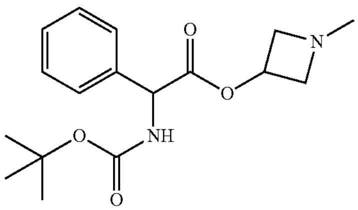 [SMILES: CN1CC(OC(=O)C(NC(=O)OC(C)(C)C)c2ccccc2)C1] | Intermediate 97 | Intermediate 41 and 1-methylazetidin-3-ol | LCMS (Method 2): [MH+] = 321 at 2.88 min. |
| 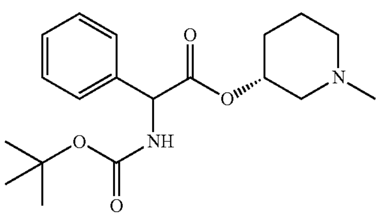 [SMILES: CN1CCC[C@@H](OC(=O)C(NC(=O)OC(C)(C)C)c2ccccc2)C1] | Intermediate 98 | Intermediate 41 and (3R)-1-methylpiperidin-3-ol | LCMS (Method 2): [MH+] = 349 at 3.72 min. |
| 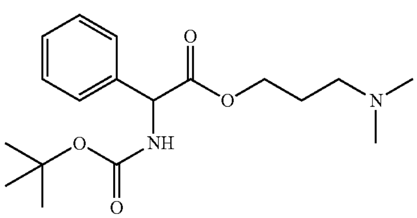 [SMILES: CN(C)CCCOC(=O)C(NC(=O)OC(C)(C)C)c1ccccc1] | Intermediate 99 | Intermediate 41 and 3-(dimethylamino)propanol | LCMS (Method 2): [MH+] = 337 at 2.93 min. |
| 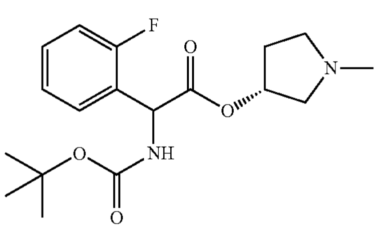 [SMILES: CN1CC[C@@H](OC(=O)C(NC(=O)OC(C)(C)C)c2ccccc2F)C1] | Intermediate 100 | Intermediate 44 and (3R)-1-methylpyrrolidin-3-ol | LCMS (Method 2): [MH+] = 353 at 3.63 min. |
| 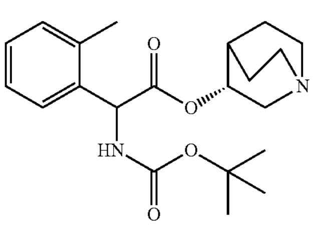 [SMILES: Cc1ccccc1C(NC(=O)OC(C)(C)C)C(=O)O[C@H]1CN2CCC1CC2] | Intermediate 101 | 2-(tert-butoxycarbonyl-amino)-2-(o-tolyl)acetic acid and (R)-quinuclidin-3-ol | LCMS (Method 2): [MH+] = 375 at 3.62 min. |

-continued

| Structure | Intermediate number | Precursor | Analytical Data |
|---|---|---|---|
| 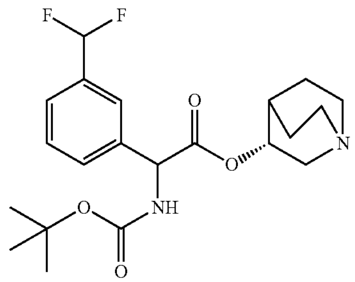 [SMILES: CC(C)(C)OC(=O)NC(C(=O)O[C@H]1CN2CCC1CC2)c1cccc(C(F)F)c1] | Intermediate 102 | Intermediate 85 and (R)-quinuclidin-3-ol | LCMS (Method 1): [MH+] = 411 at 2.66 min. |
| 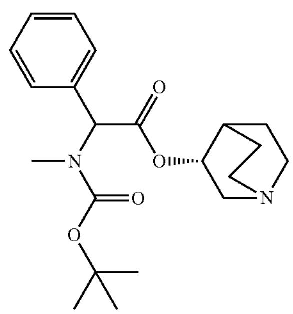 [SMILES: CN(C(=O)OC(C)(C)C)C(C(=O)O[C@H]1CN2CCC1CC2)c1ccccc1] | Intermediate 103 | 2-[tert-butoxycarbonyl(methyl)amino]-2-phenyl-acetic acid and (R)-quinuclidin-3-ol | LCMS (Method 1): [MH+] = 375 at 2.66 min. |
| 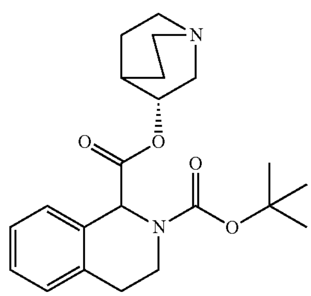 [SMILES: CC(C)(C)OC(=O)N1CCc2ccccc2C1C(=O)O[C@H]1CN2CCC1CC2] | Intermediate 104 | 2-tert-butoxycarbonyl-3,4-dihydro-1H-isoquinoline-1-carboxylic acid and (R)-quinuclidin-3-ol | LCMS (Method 2): [MH+] = 387 at 3.40 min. |
| 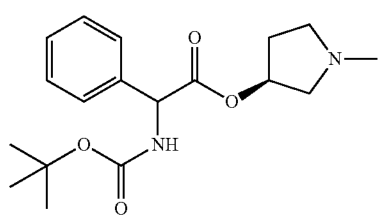 [SMILES: CN1CC[C@H](OC(=O)C(NC(=O)OC(C)(C)C)c2ccccc2)C1] | Intermediate 105 | Intermediate 41 and (3S)-1-methylpyrrolidin-3-ol | $^1$H NMR (400 MHz, CDCl$_3$): δ 7.37-7.31 (m, 5 H), 5.58 (d, J = 7.1 Hz, 1 H), 5.29 (d, J = 7.3 Hz, 1 H), 5.26-5.16 (m, 2 H), 4.18† (d, J = 8.7 Hz, 1 H), 3.53-3.43* (m, 1 H), 2.76-2.62 (m, 3 H), 2.45-2.35 (m, 2 H), 2.33 (s, 3 H), 2.27 (s, 3 H), 1.96-1.82 (m, 3 H), 1.71-1.57 (m, 3 H), 1.43 (s, 9 H), 1.43 (s, 9 H), 1.39-1.23 (m, 9 H), 1.21-1.01 (m, 2 H), 0.93-0.81 (m, 1 H), † and * refer to different isomers (arbitrarily assigned). LCMS (Method 2): [MH+] = 335 at 3 min. |
| 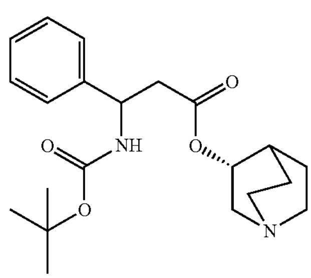 [SMILES: CC(C)(C)OC(=O)NC(CC(=O)O[C@H]1CN2CCC1CC2)c1ccccc1] | Intermediate 106 | 3-(tert-butoxycarbonyl-amino)-3-phenyl-propanoic acid and (R)-quinuclidin-3-ol | LCMS (Method 2): [MH+] = 375 at 3.40 min. |

| Structure | Intermediate number | Precursor | Analytical Data |
|---|---|---|---|
| 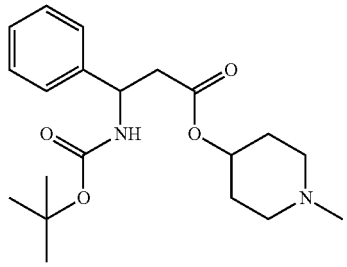 [SMILES: CN1CCC(OC(=O)CC(NC(=O)OC(C)(C)C)c2ccccc2)CC1] | Intermediate 107 | 3-(tert-butoxycarbonyl-amino)-3-phenyl-propanoic acid and 1-methylpiperidin-4-ol | LCMS (Method 2): [MH+] = 363 at 2.94 min. |
| 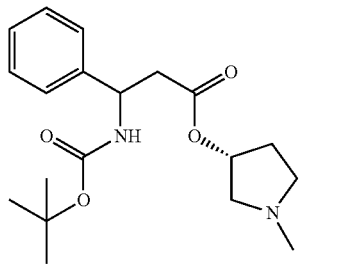 [SMILES: CN1CC[C@@H](OC(=O)CC(NC(=O)OC(C)(C)C)c2ccccc2)C1] | Intermediate 108 | 3-(tert-butoxycarbonyl-amino)-3-phenyl-propanoic acid and (3R)-1-methylpyrrolidin-3-ol | LCMS (Method 2): [MH+] = 349 at 2.96 min |
| 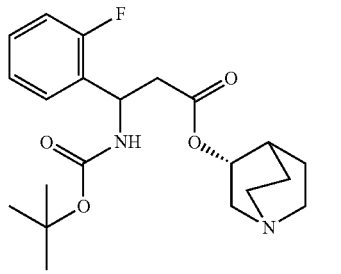 [SMILES: CC(C)(C)OC(=O)NC(CC(=O)O[C@H]1CN2CCC1CC2)c1ccccc1F] | Intermediate 109 | 3-(tert-butoxycarbonyl-amino)-3-(2-fluorophenyl)propanoic acid and (R)-quinuclidin-3-ol | LCMS (Method 2): [MH+] = 393 at 3.27 min. |
| 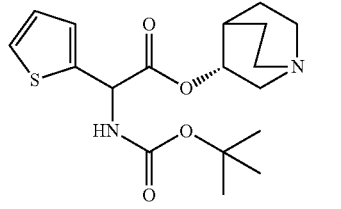 [SMILES: CC(C)(C)OC(=O)NC(C(=O)O[C@H]1CN2CCC1CC2)c1cccs1] | Intermediate 110 | 2-((tert-butoxycarbonyl)amino)-2-(thiophen-2-yl)acetic acid and (R)-quinuclidin-3-ol | LCMS (Method 3): [MH+] = 367 at 1.14 min |

Intermediate 54. (R)—(R)-Quinuclidin-3-yl 2-amino-2-phenylacetate bis hydrochloride (I-54)

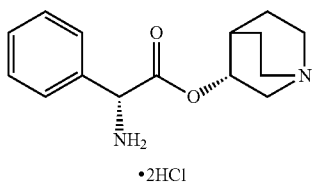 [SMILES: N[C@@H](C(=O)O[C@H]1CN2CCC1CC2)c1ccccc1]

A solution of (R)—(R)-quinuclidin-3-yl2-((tert-butoxy-carbonyl)amino)-2-phenylacetate I-46 (0.608 g, 1.687 mmol) in anhydrous dioxane (6 mL) was added with 2M HCl in ether (5.2 mL, 10.4 mmol). The reaction mixture was stirred at room temperature for 20 h. The solvent was removed in vacuo to afford the title compound as a white solid (0.564 g, quantitative yield).

$^1$H NMR (400 MHz, DMSO): δ 10.56 (br s, 1H), 9.24 (br s, 3H), 7.65-7.59 (m, 2H), 7.56-7.49 (m, 3H), 5.34 (s, 1H), 5.20-5.15 (m, 1H), 3.69-3.60 (m, 1H), 3.32-3.10 (m, 5H), 2.37-2.30 (m, 1H), 2.15-2.04 (m, 1H), 1.99-1.89 (m, 1H), 1.89-1.80 (m, 1H), 1.79-1.70 (m, 1H). LCMS (Method 2): [MH+]=261 at 2.11 min.

The following intermediates were synthesized via a similar method.

| Structure | Intermediate number | Precursor | Analytical Data |
|---|---|---|---|
| (4-F-phenyl structure) ·2HCl | Intermediate 55 | Intermediate 47 | ¹H NMR (400 MHz, DMSO): δ 10.74 (br s, 1 H), 9.33 (br s, 3 H), 7.73-7.67 (m, 2 H), 7.41-7.34 (m, 2 H), 5.37 (s, 1 H), 5.19-5.13 (m, 1 H), 3.68-3.60 (m, 1 H), 3.30-3.10 (m, 5 H), 2.35-2.30 (m, 1 H), 2.19-2.08 (m, 1 H), 1.99-1.60 (m, 3 H). LCMS (Method 2): [MH+] = 279 at 2.62 min. |
| (3-F-phenyl structure) ·2HCl | Intermediate 56 | Intermediate 48 | ¹H NMR (400 MHz, DMSO): δ 10.50 (br s, 1 H), 9.30 (br s, 3 H), 7.62-7.52 (m, 2 H), 7.48 (d, J = 7.7 Hz, 1 H), 7.40-7.32 (m, 1 H), 5.41 (s, 1 H), 5.17 (br s, 1 H), 3.69-3.59 (m, 1 H), 3.30-3.11 (m, 5 H), 2.38-2.31 (m, 1 H), 2.15-2.05 (m, 1 H), 1.99-1.89 (m, 1 H), 1.88-1.80 (m, 1 H), 1.80-1.70 (m, 1 H). LCMS (Method 2): [MH+] = 279 at 2.57 min. |
| (2-F-phenyl structure) ·2HCl | Intermediate 57 | Intermediate 49 | ¹H NMR (400 MHz, DMSO): δ 10.81 (br s, 1 H), 9.32 (br s, 3 H), 7.78-7.72 (m, 1 H), 7.62-7.55 (m, 1 H), 7.44-7.34 (m, 2 H), 5.52 (s, 1 H), 5.23-5.17 (m, 1 H), 3.66 (dd, J = 14.0, 8.5 Hz, 1 H), 3.32-3.10 (m, 5 H), 2.36-2.29 (m, 1 H), 2.12-2.00 (m, 1 H), 1.99-1.90 (m, 1 H), 1.90-1 79 (m, 1 H), 1.79-1.71 (m, 1 H). LCMS (Method 2): [MH+] = 279 at 2.59 min. |
| (2-OMe-phenyl structure) ·2HCl | Intermediate 58 | Intermediate 50 | ¹H NMR (400 MHz, DMSO): δ 10.82 (s, 1 H), 8.91 (s, 3 H), 7.54-7.47 (m, 2 H), 7.17 (d, J = 8.2 Hz, 1 H), 7.08 (t, J = 7.5 Hz, 1 H), 5.42-5.35 (m, 1 H), 5.21-5.15 (m, 1 H), 3.86 (s, 3 H), 3.72-3.63 (m, 1 H), 3.30-3.07 (m, 4 H), 3.03-2.92 (m, 1 H), 2.32-2.26 (m, 1 H), 1.98-1.79 (m, 3 H), 1.79-1.65 (m, 1 H). LCMS (Method 2): [MH+] = 291 at 2.49 min. |
| (3-pyridyl structure) ·2HCl | Intermediate 59 | Intermediate 51 | LCMS (Method 2): [MH+] = 262 at 2.13 min. |
| (2-F-phenyl, N-Me piperidine structure) ·2HCl | Intermediate 60 | Intermediate 52 | LCMS (Method 2): [MH+] = 267 at 1.94 min. |
| (2-F-phenyl, N-benzyl piperidine structure) ·2HCl | Intermediate 61 | Intermediate 53 | LCMS (Method 2): [MH+] = 343 at 3.08 min. |
| (phenyl structure) ·2HCl | Intermediate 111 | Intermediate 88 | LCMS (Method 2): [MH+] = 261 at 2.05 min. |

-continued

| Structure | Intermediate number | Precursor | Analytical Data |
|---|---|---|---|
| (1-methylpyrrolidin-3-yl) 2-amino-2-phenylacetate ·2HCl | Intermediate 112 | Intermediate 95 | LCMS (Method 2): [MH+] = 235 at 2.54 min. |
| 2-(dimethylamino)ethyl 2-amino-2-phenylacetate ·2HCl | Intermediate 113 | Intermediate 96 | LCMS (Method 2): [MH+] = 223 at 1.90 min. |
| (1-methylazetidin-3-yl) 2-amino-2-phenylacetate ·2HCl | Intermediate 114 | Intermediate 97 | LCMS (Method 2): [MH+] = 221 at 2.37 min. |
| (1-methylpiperidin-3-yl) 2-amino-2-phenylacetate ·2HCl | Intermediate 115 | Intermediate 98 | LCMS (Method 2): [MH+] = 249 at 2.67 min. |
| 3-(dimethylamino)propyl 2-amino-2-phenylacetate ·2HCl | Intermediate 116 | Intermediate 99 | LCMS (Method 2): [MH+] = 237 at 2.33 min. |
| (1-methylpyrrolidin-3-yl) 2-amino-2-(2-fluorophenyl)acetate ·2HCl | Intermediate 117 | Intermediate 100 | LCMS (Method 2): [MH+] = 253 at 1.92 min. |
| quinuclidin-3-yl 2-amino-2-(3-(difluoromethyl)phenyl)acetate ·2HCl | Intermediate 118 | Intermediate 102 | LCMS (Method 2): [MH+] = 311 at 2.75 min. |
| quinuclidin-3-yl 2-(methylamino)-2-phenylacetate ·2HCl | Intermediate 119 | Intermediate 103 | LCMS (Method 2): [MH+] = 275 at 2.62 min. |

| Structure | Intermediate number | Precursor | Analytical Data |
|---|---|---|---|
| (phenyl-CH(NH₂)-C(O)-O-(1-methylpyrrolidin-3-yl)) ·2HCl | Intermediate 120 | Intermediate 105 | LCMS (Method 2): [MH+] = 235 at 2.42 min. |
| (thiophen-2-yl-CH(NH₂)-C(O)-O-(quinuclidin-3-yl)) 2HCl | Intermediate 121 | Intermediate 110 | LCMS (Method X): [MH+] = 267 at 0.15 min. |

Intermediate 122. (8-benzyl-8-azabicyclo[3.2.1]octan-3-yl) 2-amino-2-phenyl-acetate (endo) (I-122)

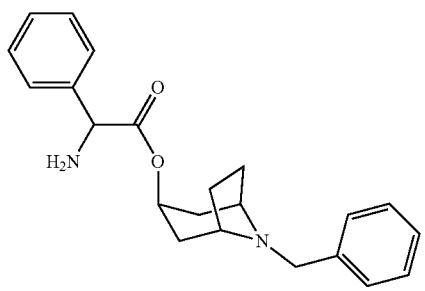 [SMILES: NC(C(=O)OC1CC2CCC(C1)N2Cc1ccccc1)c1ccccc1]

To (1R,3r,5S)-8-benzyl-8-azabicyclo[3.2.1]octan-3-yl) 2-(tert-butoxycarbonylamino)-2-phenyl-acetate (Intermediate 89, 0.390 g, 0.84 mmol) was added a 4N solution of HCl in dioxane (3 mL) and the mixture was stirred at room temperature overnight. The solvent was removed by evaporation under reduced pressure, co-evaporated with diethyl ether. The residue was loaded on a 10 g SCX column and eluted with acetonitrile then with 10% triethylamine/acetonitrile. The solvent was removed by evaporation under reduced pressure to give the free base of the title compound as a yellow gum (0.280 g, 95%).

LCMS (Method 2): [MH+]=351 at 3.14 min.

The following intermediates were synthesized via the same method.

| Structure | Intermediate number | Precursor | Analytical Data |
|---|---|---|---|
| (phenyl-CH(NH₂)-C(O)-O-(8-benzyl-8-azabicyclo[3.2.1]octan-3-yl), exo) | Intermediate 123 (exo) | Intermediate 90 | LCMS (Method 2): [MH+] = 351 at 3.14 min. |
| (phenyl-CH(NH₂)-C(O)-O-(8-methyl-8-azabicyclo[3.2.1]octan-3-yl), endo) | Intermediate 124 (endo) | Intermediate 92 | LCMS (Method 2): [MH+] = 275 at 1.92 min. |
| (phenyl-CH(NH₂)-C(O)-O-(8-methyl-8-azabicyclo[3.2.1]octan-3-yl), exo) | Intermediate 125 (exo) | Intermediate 91 | LCMS (Method 2): [MH+] = 275 at 2.00 min. |

-continued
| Structure | Intermediate number | Precursor | Analytical Data |
|---|---|---|---|
| 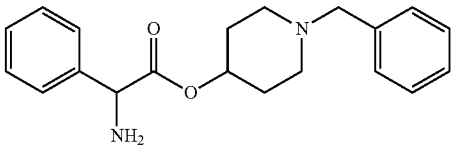 [SMILES: NC(C(=O)OC1CCN(Cc2ccccc2)CC1)c1ccccc1] | Intermediate 126 | Intermediate 93 | LCMS (Method 2): [MH+] = 325 at 3.11 min. |
| 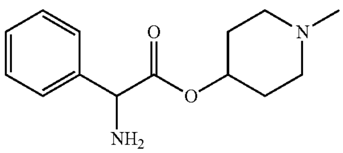 [SMILES: CN1CCC(OC(=O)C(N)c2ccccc2)CC1] | Intermediate 127 | Intermediate 94 | LCMS (Method 2): [MH+] = 249 at 2.09 min. |
Intermediate 128. [(3R)-quinuclidin-3-yl]2-amino-2-(3-hydroxyphenyl)acetate (I-128)
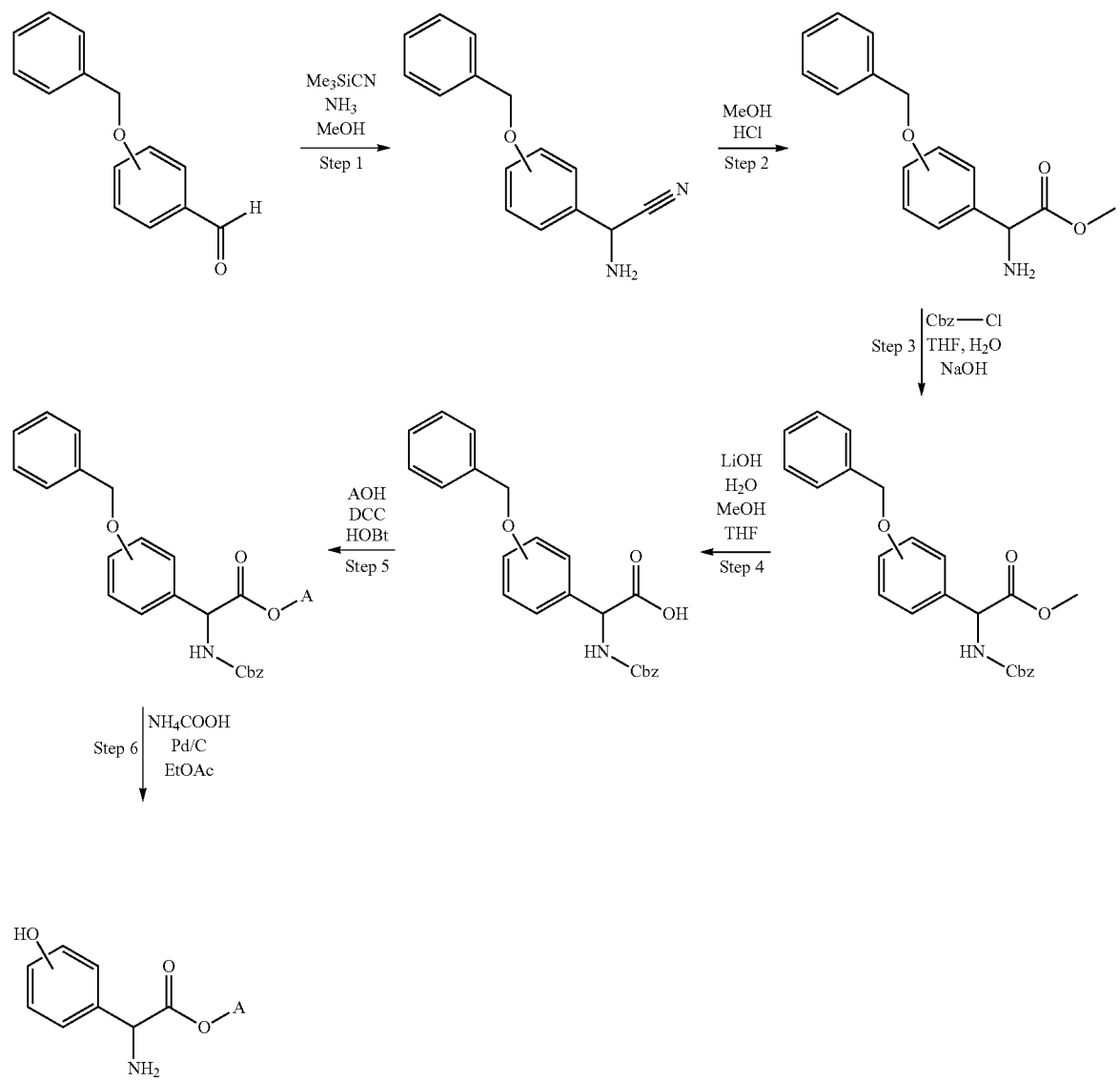

Step 1: Preparation of 2-amino-2-(3-(benzyloxy)phenyl)acetonitrile

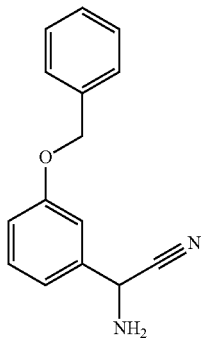 [SMILES: N#CC(N)c1cccc(OCc2ccccc2)c1]

To a stirred solution of 3-benzyloxybenzaldehyde (2.12 g, 10 mmol) in a 7N ammonia solution in methanol (50 mL) at 0° C. was added trimethylsilyl cyanide (1.11 mL, 15 mmol) dropwise. The resulting mixture was stirred at 0° C. for 10 min, warmed to 45° C. for 18 h and concentrated to dryness. The crude material was purified by silica gel column chromatography, eluting with 0-100% dichloromethane/10% methanol in dichloromethane, to afford the title compound (1.26 g, 53%) as a thick orange oil.

$^1$H NMR (400 MHz, CDCl$_3$): δ 7.44-7.29 (m, 6H), 7.16 (dd, J=2.1, 2.1 Hz, 1H), 7.11 (d, J=7.6 Hz, 1H), 6.97 (dd, J=2.4, 8.2 Hz, 1H), 5.08 (s, 2H), 4.86 (s, 1H), 1.92 (bs, 2H). LCMS (Method 2): [MH+]=238 at 3.65 min.

Step 2: Preparation of methyl 2-amino-2-(3-(benzyloxy)phenyl)acetate

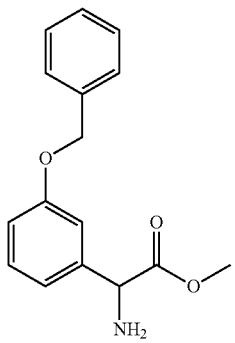 [SMILES: COC(=O)C(N)c1cccc(OCc2ccccc2)c1]

To a stirred solution of 2-amino-2-(3-(benzyloxy)phenyl) acetonitrile (1.22 g, 5.3 mmol) in methanol (10 mL) at room temperature was added 2 N HCl in ether (10 mL, 20 mmol). The resulting mixture was heated under reflux for 18 h and concentrated to dryness. The crude material was taken up in ethyl acetate (200 mL) and washed with saturated aqueous sodium bicarbonate (100 mL). The layers were separated and the organic phase dried over magnesium sulfate, filtered and the solvent was removed in vacuo. The residue was loaded onto a SCX cartridge eluting with dichloromethane/methanol followed by 7N ammonia in methanol to afford the title compound (1.0 g, 70%) as a thick orange oil.

$^1$H NMR (400 MHz, CDCl$_3$): δ 7.44-7.20 (m, 6H), 7.01 (dd, J=2.0, 2.0 Hz, 1H), 6.95 (d, J=7.8 Hz, 1H), 6.89 (dd, J=1.9, 8.2 Hz, 1H), 5.03 (s, 2H), 4.57 (s, 1H), 3.65 (s, 3H), 2.17 (s, 2H). LCMS (Method 2): [MH+]=272 at 3.53 min.

Step 3: Preparation of methyl 2-(benzyloxycarbonylamino)-2-(3-benzyloxyphenyl)acetate

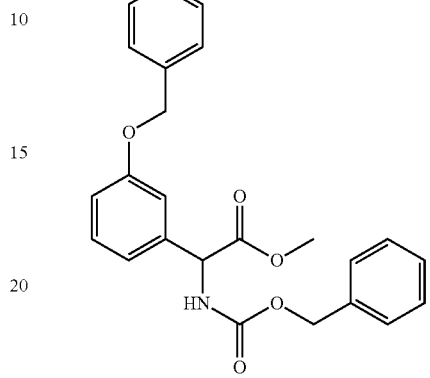

To a solution of methyl 2-amino-2-(3-(benzyloxy)phenyl) acetate (1.09 g, 4 mmol) in a mixture of tetrahydrofuran and water (1:1, 90 mL) at 0° C. was added benzyl chloroformate (0.57 mL, 4 mmol) and aqueous sodium hydroxide (4 N, 1 mL, 4 mmol) simultaneously. The mixture was stirred at 0° C. for one hour. The ice bath was removed and the reaction mixture was stirred at room temperature for 16 h. The solvent was removed in vacuo and ethyl acetate (100 mL) and water (30 mL) were added. The layers were separated and the aqueous phase re-extracted with ethyl acetate (2×50 mL). The combined organic fractions were dried over magnesium sulfate, filtered and the solvent removed in vacuo. The residue was purified by silica gel column chromatography, eluting with 0-40% ethyl acetate in iso-hexane to afford the title compound (900 mg, 56%) as a brown oil.

$^1$H NMR (400 MHz, CDCl$_3$): δ 7.47-7.20 (m, 11H), 7.04-6.90 (m, 3H), 5.88 (d, J=7.1 Hz, 1H), 5.35 (d, J=7.3 Hz, 1H), 5.13 (d, J=12.9 Hz, 1H), 5.06 (d, J=12.0 Hz, 1H), 5.02 (s, 2H), 3.68 (s, 3H). LCMS (Method 2): [MH+]=406 at 3.67 min.

Step 4: Preparation of 2-(((benzyloxy)carbonyl)amino)-2-(3-(benzyloxy)phenyl)acetic acid

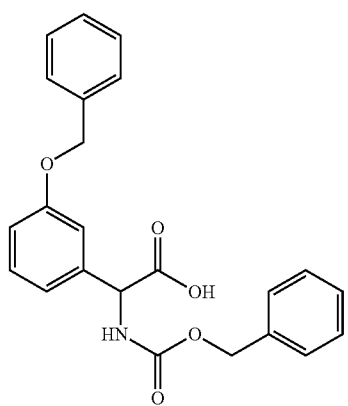 [SMILES: O=C(NC(C(=O)O)c1cccc(OCc2ccccc2)c1)OCc1ccccc1]

A solution of methyl 2-(benzyloxycarbonylamino)-2-(3-benzyloxyphenyl)acetate (640 mg, 1.75 mmol) and aqueous lithium hydroxide (1 N, 3.50 mL, 3.50 mmol) in methanol (5 mL) and tetrahydrofuran (5 mL) was stirred at room temperature for one hour. The mixture was concentrated in vacuo and the residue diluted with dichloromethane (30 mL) and acidified to pH 0.5 with 2 N HCl. The aqueous phase was re-extracted with dichloromethane (2×50 mL). The combined organic fractions were dried over a hydrophobic frit and the solvent was removed in vacuo to give the title compound as a light brown oil (460 mg, 67%). This was used in the next step without further purification.

$^1$H NMR (400 MHz, CDCl$_3$): δ 7.37-7.24 (m, 9H), 7.21-7.12 (m, 2H), 7.01-6.90 (m, 2H), 6.86 (dd, J=1.6, 8.2 Hz, 1H), 5.91 (d, J=7.1 Hz, 1H), 5.32 (d, J=7.1 Hz, 1H), 5.18 (d, J=5.6 Hz, 1H), 5.01-4.87 (m, 4H). LCMS (Method 2): [MH+]=391 at 2.4 min.

Step 5: Preparation of [(3R)-quinuclidin-3-yl]2-(benzyloxycarbonylamino)-2-(3-benzyloxyphenyl)acetate

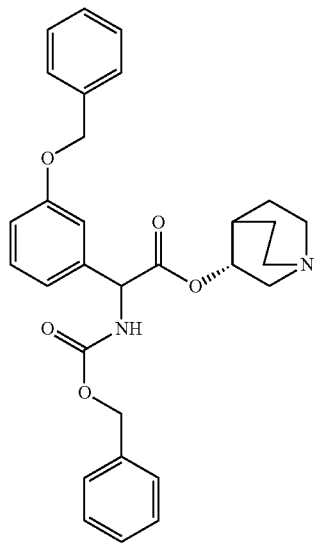 [SMILES: O=C(NC(C(=O)O[C@H]1CN2CCC1CC2)c1cccc(OCc2ccccc2)c1)OCc1ccccc1]

A solution of 2-(((benzyloxy)carbonyl)amino)-2-(3-(benzyloxy)phenyl)acetic acid (2.1 g, 5.3 mmol), N,N'-dicyclohexylcarbodiimide (1.20 g, 5.83 mmol), 1-hydroxybenzotriazole hydrate (787 mg, 5.83 mmol) and (R)-quinuclidin-3-ol (1.70 g, 13.5 mmol) in dry tetrahydrofuran (27 mL) was stirred at room temperature for 18 h. Additional (R)-quinuclidin-3-ol (1.70 g, 13.5 mmol) was then added to the mixture and stirred for 4 days. The white slurry was then filtered through a pad of Celite®, rinsed with ethyl acetate (100 mL) and the solvent was removed in vacuo. The residue was partitioned between ethyl acetate (100 mL) and saturated sodium carbonate (50 mL). The layers were separated and the aqueous phase back-extracted with ethyl acetate (2×50 mL). The combined organic fractions were dried over magnesium sulfate, filtered and the solvent was removed in vacuo. The residue was purified by silica gel column chromatography, eluting with 0-40% ethyl acetate/10% methanolic ammonia solution in ethyl acetate to afford the title compound (1.5 g, 56%) as a clear thick oil.

$^1$H NMR (400 MHz, CDCl$_3$): δ 7.43-7.27 (m, 11H), 7.02-6.90 (m, 3H), 5.83 (d, J=6.6 Hz, 1H), 5.34 (d, J=6.1 Hz, 1H), 5.12-5.02 (m, 4H), 4.84-4.77 (m, 1H), 3.19*$^{or}$ † (dd, J=9.8, 12.8 Hz, 1H), 3.08*$^{or}$ † (dd, J=8.8, 15.5 Hz, 1H), 2.77-2.67 (m, 4H), 2.56-2.51*$^{or}$ † (m, 1H), 2.34*$^{or}$ † (d, J=15.2 Hz, 1H), 2.04-1.99*$^{or}$ † (m, 1H), 1.83-1.78*$^{or}$ † (m, 1H), 1.71-1.57 (m, 2H), 1.50-1.43 (m, 1H), 1.35-1.23*$^{or}$ † (m, 1H), 1.18-1.10*$^{or}$ † (m, 1H), † and * refer to different isomers (arbitrarily assigned). LCMS (Method 1): [MH+]=501 at 2.93 min.

Step 6: Preparation of [(3R)-quinuclidin-3-yl]2-amino-2-(3-hydroxyphenyl)acetate (Intermediate 128)

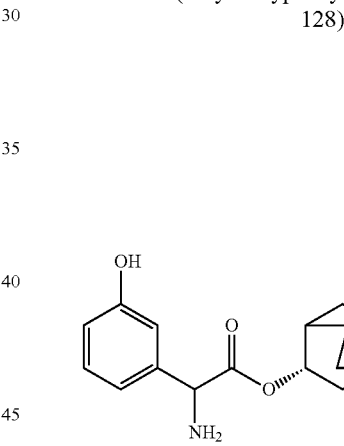

To a solution of [(3R)-quinuclidin-3-yl]2-(benzyloxycarbonylamino)-2-(3-benzyloxyphenyl)acetate (1.5 g, 3.0 mmol) in ethyl acetate (30 mL) were added ammonium formate (945 mg, 15 mmol) and 10% Pd/C (400 mg). The mixture was heated to 60° C. for 16 h. Additional ammonium formate (400 mg, 6.3 mmol) and 10% Pd/C (200 mg) were added and the black slurry stirred at 60° C. for 4 h. After cooling the slurry to room temperature and filtration through a pad of Celite®, the solids were washed with ethyl acetate/ethanol (1:1, 250 mL). The solvent was removed in vacuo to yield the title compound as a yellow oil (800 mg, 97%) which was used in the next step without further purification.

LCMS (Method 2): [MH+]=277 at 1.92 min.

Intermediate 129. [(1S)-2-(3,5-dichloro-1-oxido-pyridin-1-ium-4-yl)-1-(3,4-dimethoxyphenyl)ethyl] 2-(5-formyl-2-thienyl)acetate (I-129)
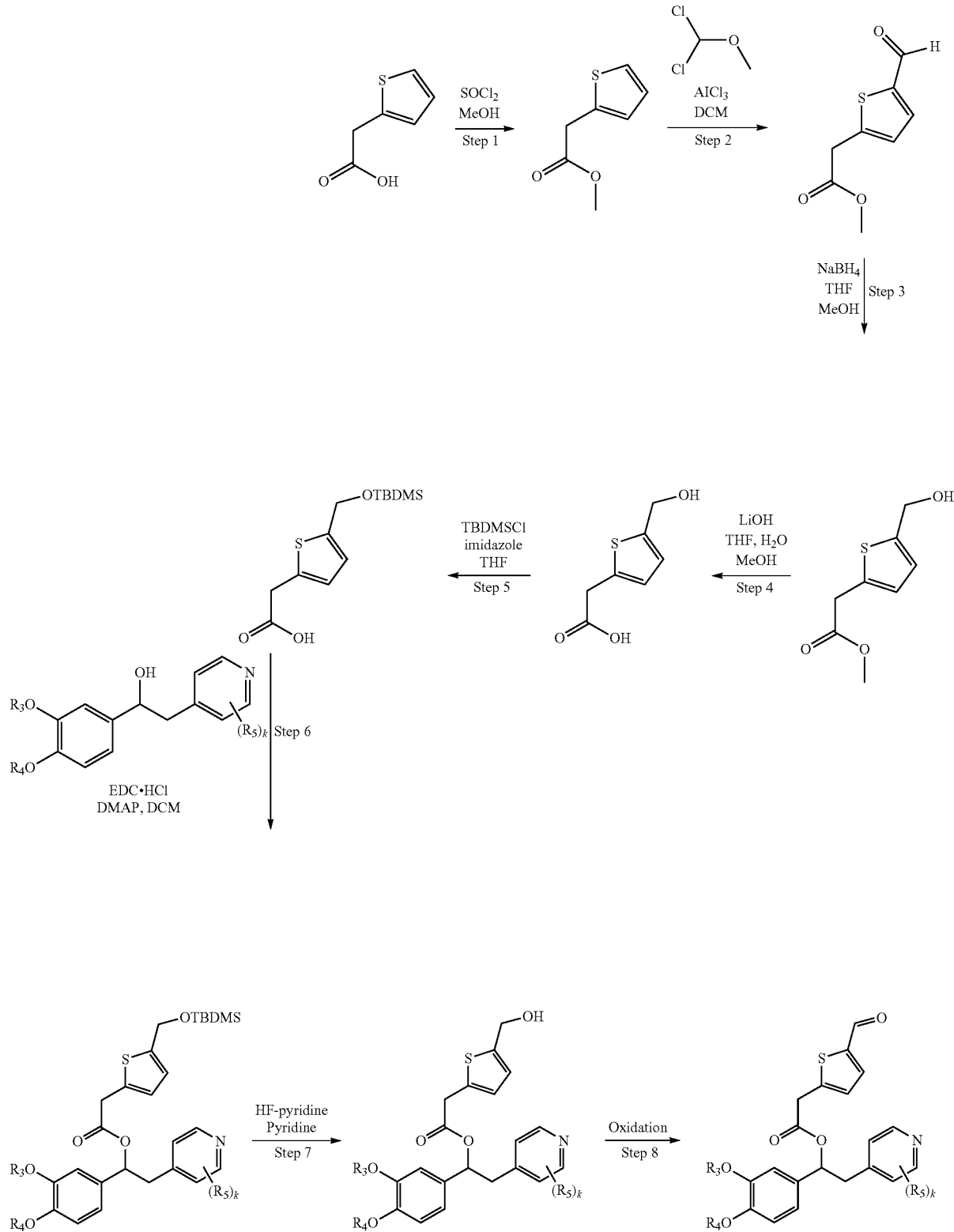

Step 1: Preparation of methyl 2-(2-thienyl)acetate

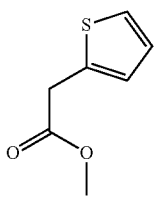

To a solution of 2-thiopheneacetic acid (1.50 g, 10.6 mmol) in MeOH (20 mL) was added thionyl chloride (3.80 mL, 53 mmol) dropwise at 0° C. The resulting solution was stirred at room temperature for 18 h. The reaction mixture was concentrated in vacuo to give the title compound as a dark brown oil (1.65 g, quantitative yield) which was used in the next step without further purification.

$^1$H NMR (400 MHz, CDCl$_3$): δ 7.22 (dd, J=1.6, 5.1 Hz, 1H), 6.98-6.93 (m, 2H), 3.85 (s, 2H), 3.73 (s, 3H).

Step 2: Preparation of methyl 2-(5-formyl-2-thienyl)acetate

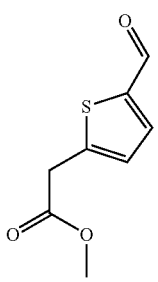

To a suspension of aluminium trichloride (853 mg, 6.4 mmol) in dichloromethane (4 mL) at −10° C. was added a solution of methyl 2-(2-thienyl)acetate (500 mg, 3.2 mmol) in dichloromethane (3 mL). The resulting solution was stirred at −10° C. for 10 minutes. A solution of dichloro(methoxy)methane (434 μL, 4.8 mmol) in dichloromethane (3 mL) was then added dropwise over 30 minutes. The reaction mixture was stirred at −10° C. for 1 h. The resulting solution was poured into a flask containing water (20 mL), crushed ice and concentrated HCl (1 mL) and stirred vigorously for 30 minutes. The solution was washed with dichloromethane (3×20 mL) and the combined organic phases washed with aqueous saturated sodium bicarbonate (30 mL) followed by brine (30 mL). The phases were separated over a hydrophobic frit and concentrated in vacuo to give the title compound as a red oil (533 mg, 91%) which was used in the next step without further purification.

LCMS (Method 1): [MH+]=185 at 3.15 min

Step 3: Preparation of methyl 2-[5-(hydroxymethyl)-2-thienyl]acetate

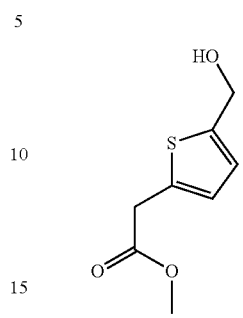

To a solution of methyl 2-(5-formyl-2-thienyl)acetate (3.88 g, 21.1 mmol) in methanol (4 mL) and tetrahydrofuran (16 mL) was added sodium borohydride (399 mg, 10.5 mmol) at −10° C. The reaction mixture was stirred at 0° C. for 1 h. Sodium borohydride (399 mg, 10.5 mmol) was added and the mixture left to stir at 0° C. for 2 h. Acetic acid (1.2 mL) was added and the reaction solution concentrated in vacuo. The residue was diluted with water (30 mL) and extracted with ethyl acetate (3×30 mL). The combined organic phases were washed with brine (20 mL), dried over magnesium sulfate and concentrated in vacuo. The residue was purified by silica gel chromatography, eluting with 0-30% ethyl acetate in isohexane to give the title compound as a yellow oil (1.1 g, 28%).

$^1$H NMR (400 MHz, CDCl$_3$): δ 6.86 (d, J=3.4 Hz, 1H), 6.80 (d, J=3.4 Hz, 1H), 4.78 (s, 2H), 3.81 (s, 2H), 3.73 (s, 3H), OH proton not visible.

Step 4: Preparation of 2-[5-(hydroxymethyl)-2-thienyl]acetic acid

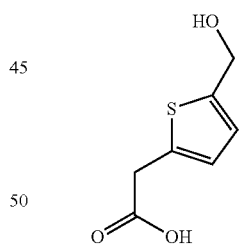

To a solution of methyl 2-[5-(hydroxymethyl)-2-thienyl]acetate in tetrahydrofuran (10 mL) and methanol (10 mL) was added 1 N aqueous solution of lithium hydroxide (11.83 mL) and the resulting solution was stirred at room temperature for 4 h. The reaction mixture was cooled to 0° C. and acidified to pH 1 with 2 N aqueous solution of HCl. The solution was concentrated in vacuo and the residue partitioned between ethyl acetate (30 mL) and water (30 mL). The organic phases were dried over magnesium sulfate, filtered and concentrated in vacuo to give the title compound as an orange solid (1.02 g, quantitative yield) which was used in the next step without further purification.

LCMS (Method 1): [MH−]=171 at 2.30 min

Step 5: Preparation of 2-[5-[[tert-butyl(dimethyl)silyl]oxymethyl]-2-thienyl]acetic acid

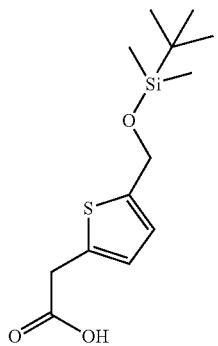 [SMILES: CC(C)(C)[Si](C)(C)OCc1ccc(CC(=O)O)s1]

To a solution of 2-[5-(hydroxymethyl)-2-thienyl]acetic acid (500 mg, 2.91 mmol) and imidazole (415 mg, 6.11 mmol) was added tert-butyldimethylsilyl chloride (916 mg, 6.11 mmol) portionwise over 20 minutes. The resultant solution was stirred at room temperature for one hour, tetrahydrofuran (10 mL) was then added and the reaction mixture cooled in an ice-bath. A solution of potassium carbonate (500 mg, 3.62 mmol) in water (10 mL) was added and the reaction mixture stirred for 20 minutes. The reaction solution was diluted with ethyl acetate (30 mL) and washed with brine (2×30 mL). The organic phase was dried over magnesium sulfate, filtered and concentration in vacuo. The residue was purified by silica gel chromatography, eluting with 0-50% ethyl acetate in iso-hexane to give the title compound as a yellow oil (200 mg, 24%) which was used in the next step without further purification.

LCMS (Method 2): [MH−]=285 at 2.90 min.

Step 6: Preparation of [(1S)-2-(3,5-dichloro-1-oxido-pyridin-1-ium-4-yl)-1-(3,4-dimethoxyphenyl)ethyl] 2-[5-[[tert-butyl(dimethyl)silyl]oxymethyl]-2-thienyl]acetate

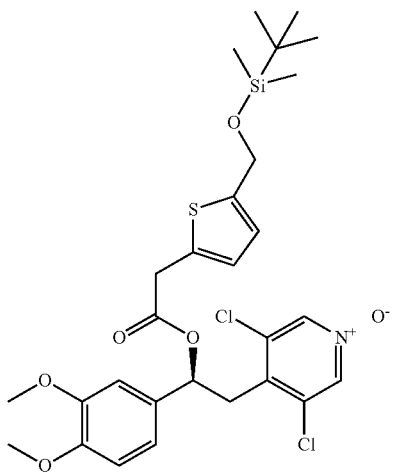

To a solution of 2-[5-[[tert-butyl(dimethyl)silyl]oxymethyl]-2-thienyl]acetic acid (995 mg, 3.48 mmol) in dichloromethane (40 mL) was added (S)-3,5-dichloro-4-(2-(3,4-dimethoxyphenyl)-2-hydroxyethyl)pyridine 1-oxide (1.43 g, 4.17 mmol), followed by 4-(dimethylamino)-pyridine (212 mg, 1.74 mmol) and N-(3-dimethylaminopropyl)-N'-ethyl-carbodiimide hydrochloride (1.33 g, 6.96 mmol). The resultant solution was stirred at room temperature for 72 h. The reaction solution was washed with saturated aqueous sodium bicarbonate (2×30 mL), the organic phase passed through a hydrophobic frit and concentrated in vacuo. The residue was purified by silica gel chromatography, eluting with 0-100% ethyl acetate in iso-hexane to give the title compound as a pale yellow oil (980 mg, 46%).

LCMS (Method 2): [MH+]=612 at 4.08 min.

Step 7: Preparation of [(1S)-2-(3,5-dichloro-1-oxido-pyridin-1-ium-4-yl)-1-(3,4-dimethoxyphenyl)ethyl] 2-[5-(hydroxymethyl)-2-thienyl]acetate

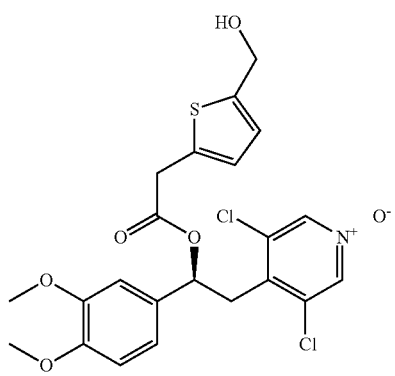

To a solution of [(1S)-2-(3,5-dichloro-1-oxido-pyridin-1-ium-4-yl)-1-(3,4-dimethoxyphenyl)ethyl]2-[5-[[tert-butyl(dimethyl)silyl]oxymethyl]-2-thienyl]acetate (400 mg, 0.65 mmol) in pyridine (5 mL) was added HF.pyridine (0.88 mL) drop wise. The resultant solution was stirred at room temperature for 3 h. The reaction solution was cooled to 0° C. and quenched with saturated aqueous sodium bicarbonate (5 mL). The aqueous phase was extracted with ethyl acetate (3×10 mL) and the organic phases combined, dried over magnesium sulfate, filtered and concentrated in vacuo to give the title compound as a pale yellow solid (270 mg, 84%) which was used in the next step without further purification.

LCMS (Method 2): [MH+]=498 at 3.07 min.

Step 8: Preparation of [(1S)-2-(3,5-dichloro-1-oxido-pyridin-1-ium-4-yl)-1-(3,4-dimethoxyphenyl)ethyl] 2-(5-formyl-2-thienyl)acetate (Intermediate 129)

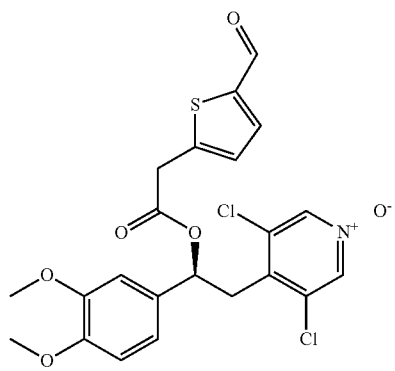

To a solution of [(1S)-2-(3,5-dichloro-1-oxido-pyridin-1-ium-4-yl)-1-(3,4-dimethoxyphenyl)ethyl]2-[5-(hydroxymethyl)-2-thienyl]acetate (100 mg, 0.20 mmol) in dichloromethane (2 mL) was added Dess-Martin periodinane (102 mg, 0.24 mmol) at −78° C. The reaction was stirred at room temperature for 30 min. The reaction solution was washed with saturated aqueous Na$_2$S$_2$O$_3$ (5 mL) and saturated aqueous sodium bicarbonate (5 mL). The organic phase was passed through a hydrophobic fit and concentrated in vacuo to give the title compound as a pale yellow oil (100 mg, quantitative yield) which was used in the next step without further purification.

LCMS (Method 2): [MH+]=496 at 2.69 min.

Example 37

[(1S)-2-(3,5-dichloro-1-oxido-pyridin-1-ium-4-yl)-1-(3,4-dimethoxyphenyl)ethyl]5-[[[1-(3-fluorophenyl)-2-oxo-2-[(3R)-quinuclidin-3-yl]oxy-ethyl]amino]methyl]thiophene-2-carboxylate (E37)

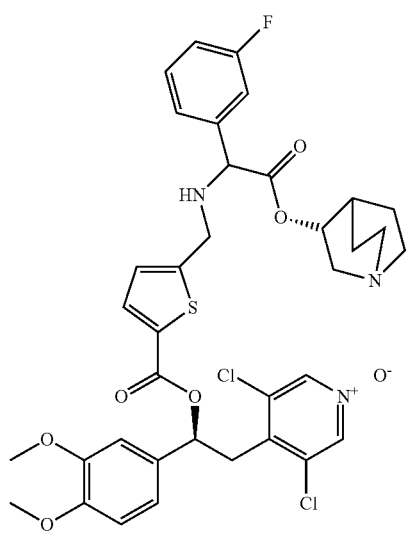

A suspension of (R)-quinuclidin-3-yl 2-amino-2-(3-fluorophenyl)acetate bis hydrochloride salt (0.176 g, 0.500 mmol) in EtOAc (5 mL) was added with Et$_3$N (0.150 mL, 1.10 mmol). The reaction mixture was stirred at room temperature for 2 h. The precipitate obtained was filtered, washed with EtOAc (~5 mL) and the solvent was removed in vacuo. This residue was dissolved in CH$_3$CN (5 mL) and to the solution was added [(1S)-2-(3,5-dichloro-1-oxido-pyridin-1-ium-4-yl)-1-(3,4-dimethoxyphenyl)ethyl]5-formylthiophene-2-carboxylate (0.220 g, 0.456 mmol) followed by acetic acid (0.026 mL, 0.456 mmol). The reaction mixture was stirred at room temperature for 20 h. NaBH(OAc)$_3$ (0.265 g, 1.25 mmol) was added and the reaction mixture was stirred at room temperature for a further 24 h. The excess solvent was removed in vacuo and the residue was partitioned between EtOAc (30 mL) and saturated aqueous NaHCO$_3$ solution (20 mL). The organic layer was washed with saturated brine (2×15 mL), separated and filtered through a phase separator cartridge and the solvent was removed in vacuo. Purification by preparative HPLC gave the title compound (1:1 mixture of diastereoisomers) as a pale yellow solid (200 mg, 59%).

$^1$H NMR (400 MHz, DMSO): δ 8.56*or † (s, 2H), 8.55*or † (s, 2H), 7.69 (dd, J=3.8, 1.6 Hz, 1H), 7.44-7.39 (m, 1H), 7.33-7.26 (m, 2H), 7.18-7.15 (m, 1H), 7.02-6.98 (m, 4H), 6.14 (dd, J=9.7, 4.4 Hz, 1H), 4.71-4.69 (m, 1H), 4.50 (d, J=9.28 Hz, 1H), 3.89-3.88 (m, 2H), 3.78-3.69 (m, 7H), 3.61-3.56 (m, 1H), 3.29-3.28 (m, 1H), 3.10-3.03*or † (m, 1H), 3.03-2.94*or † (m, 1H), 2.65-2.56 (m, 3H), 2.50-2.45 (m, 1H), 2.17 (d, J=14.68 Hz, 1H), 1.88-1.85*or † (m, 1H), 1.76-1.72*or † (m, 1H), 1.61-1.42 (m, 3H), 1.40-1.10 (m, 1H). † and * refer to different isomers (arbitrarily assigned). LCMS (Method 2): [MH+]=744 at 3.77 min.

The following compounds were synthesized via a similar method as 1:1 mixture of diastereoisomers.

| Structure | Example number | Precursor | Analytical Data |
|---|---|---|---|
| 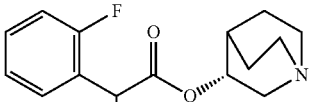<br><br>[(1S)-2-(3,5-dichloro-1-oxido-pyridin-1-ium-4-yl)-1-(3,4-dimethoxyphenyl)ethyl] 5-[[[1-(2-fluorophenyl)-2-oxo-2-quinuclidin-3-yloxy-ethyl]amino]methyl]thiophene-2-carboxylate | Example 38 | Intermediate 3 and Intermediate 57 | $^1$H NMR (400 MHz, CDCl$_3$): δ 8.14 (s, 2 H), 7.64 (dd, J = 3.8, 1.5 Hz, 1 H), 7.42-7.35 (m, 1 H), 7.35-7.29 (m, 1 H), 7.21-7.13 (m, 1 H), 7.13-7.05 (m, 1 H), 7.02-6.96 (m, 2 H), 6.92-6.88 (m, 1 H), 6.85 (d, J = 8.1 Hz, 1 H), 6.22 (dd, J = 9.7, 4.5 Hz, 1 H), 4.90-4.79 (m, 1 H), 4.76 (d, J = 4.2 Hz, 1 H), 3.97 (s, 2 H), 3.90 (s, 3 H), 3.88 (d, J = 1.3 Hz, 3 H), 3.70-3.62 (m, 1 H), 3.35-3.28 (m, 1 H), 3.24-3.09 (m, 1 H), 2.80-2.62 (m, 5 H), 2.54-2.34 (m, 1 H), 2.01-1.85 (m, 1 H), 1.57-1.43 (m, 2 H), 1.36-1.13 (m, 2 H). LCMS (Method 2): [MH+] = 744 at 3.86 min. |
| 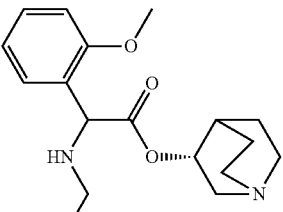<br><br>[(1S)-1-[3-(cyclopropylmethoxy)-4-(difluoromethoxy)phenyl]-2-(3,5-dichloro-1-oxido-pyridin-1-ium-4-yl)ethyl] 5-[[[1-(2-methoxyphenyl)-2-oxo-2-[(3R)-quinuclidin-3-yl]oxy-ethyl]amino]methyl]thiophene-2-carboxylate formate salt | Example 39 | Intermediate 8 and Intermediate 58 | $^1$H NMR (400 MHz, DMSO): δ 8.56 (s, 2 El), 8.19 (s, 1 H), 7.70 (d, J = 3.8 Hz, 1 H), 7.37-7.16 (m, 4 H), 7.08-6.93 (m, 4 H), 7.07 (t, J = 74.8 Hz, 1 H), 6.14 (dd, J = 9.4, 4.4 Hz, 1 H), 4.74-4.68 (m, 1 H), 4.65 (s, 1 H), 3.95-3.89 (m, 4 H), 3.73 (s, 3 H), 3.56 (dd, J = 14.7, 9.7 Hz, 1 H), 3.36-2.91 (m, 3 H), 2.70-2.31 (m, 5 H), 1.78-1.08 (m, 5 H), 0.56-0.55 (m, 2 H), 0.35-0.34 (m, 2 H). LCMS (Method 1): [MH+] = 832 at 2.78 min. |

-continued

| Structure | Example number | Precursor | Analytical Data |
|---|---|---|---|
| 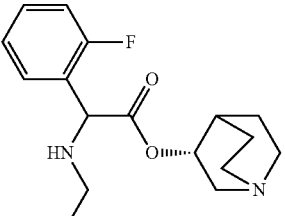 [(1S)-1-[3-(cyclopropylmethoxy)-4-(difluoromethoxy)phenyl]-2-(3,5-dichloro-1-oxido-pyridin-1-ium-4-yl)ethyl] 5-[[[1-(2-fluorophenyl)-2-oxo-2-[(3R)-quinuclidin-3-yl]oxy-ethyl]amino]methyl]thiophene-2-carboxylate formate salt | Example 40 | Intermediate 8 and Intermediate 57 | $^1$H NMR (400 MHz, DMSO): δ 8.55 (s, 2 H), 8.23 (s, 1 H), 7.70 (dd, J = 3.8, 1.9 Hz, 1 H), 7.56-7.50 (m, 1 H), 7.42-7.34 (m, 1 H), 7.27-7.16 (m, 4 H), 7.07 (t, J = 74.6 Hz, 1 H), 7.07-7.01 (m, 2 H), 6.14 (dd, J = 9.5, 4.4 Hz, 1 H), 4.77-4.65 (m, 2 H), 3.96-3.90 (m, 4 H), 3.56 (dd, J = 14.6, 9.3 Hz, 1 H), 3.36-3.27 (m, 1 H), 3.11-3.00 (m, 2 H), 2.70-2.13 (m, 5 H), 1.89-1.07 (m, 5 H), 0.59-0.53 (m, 2 H), 0.37-0.32 (m, 2 H). LCMS (Method 1): [MH+] = 820 at 3.08 min. |
| 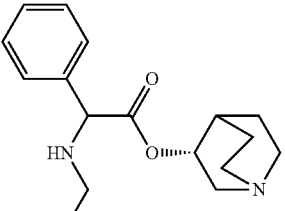 [(1S)-1-[3-(cyclopropylmethoxy)-4-(difluoromethoxy)phenyl]-2-(3,5-dichloro-1-oxido-pyridin-1-ium-4-yl)ethyl] 5-[[[2-oxo-1-phenyl-2-[(3R)-quinuclidin-3-yl]oxy-ethyl]amino]methyl]thiophene-2-carboxylate formate salt | Example 41 | Intermediate 8 and Intermediate 54 | $^1$H NMR (400 MHz, DMSO): δ 8.56 (s, 2 H), 8.23 (s, 1 H), 7.71 (dd, J = 3.8, 2.0 Hz, 1 H), 7.45-7.29 (m, 5 H), 7.24-7.17 (m, 2 H), 7.07 (t, J = 75.2 Hz, 1 H), 7.07-7.01 (m, 2 H), 6.14 (dd, J = 9.5, 4.3 Hz, 1 H), 4.74-4.65 (m, 1 H), 4.43 (s, 1 H), 3.92 (d, J = 7.0 Hz, 2 H), 3.91-3.85 (m, 2 H), 3.57 (dd, J = 14.9, 9.2 Hz, 1 H), 3.34-3.28 (m, 1 H), 3.11-2.95 (m, 2 H), 2.69-2.13 (m, 5 H), 1.90-1.07 (m, 5 H), 0.60-0.53 (m, 2 H), 0.38-0.32 (m, 2 H). LCMS (Method 1): [MH+] = 802 at 3.01 min. |

| Structure | Example number | Precursor | Analytical Data |
|---|---|---|---|
| 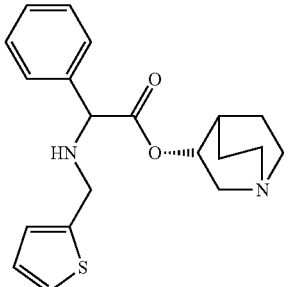<br>[(1S)-2-(3,5-dichloro-1-oxido-pyridin-1-ium-4-yl)-1-(3,4-dimethoxyphenyl)ethyl] 5-[[[2-oxo-1-phenyl-2-[(3R)-quinuclidin-3-yl]oxy-ethyl]amino]methyl]thiophene-2-carboxylate | Example 42 | Intermediate 3 and Intermediate 54 | $^1$H NMR (400 MHz, DMSO): δ 8.56 (s, 2 H), 7.69-7.68 (d, J = 3.8, 1 H), 7.45-7.28 (m, 5 H), 7.04-6.94 (m, 4 H), 6.14 (dd, J = 9.7, 4.3 Hz, 1 H), 4.73-4.65 (m, 1 H), 4.43 (d, J = 9.3, Hz, 1 H), 3.92-3.82 (m, 2 H), 3.80-3.74 (m, 6 H), 3.66-3.54 (m, 2 H), 3.28-3.26 (m, 1 H), 3.10-3.03*or† (m, 1 H), 3.02-2.95*or† (m, 1 H), 2.63-2.50 (m, 3 H), 2.46-2.29 (m, 1 H), 2.16 (m, 1 H), 1.89-1.84*or† (m, 1 H), 1.75-1.71*or† (m, 1 H), 1.61-1.38 (m, 3 H), 1.24-1.18 (m,1 H). † and * refer to different isomers (arbitrarily assigned). LCMS (Method 2): [MH+] = 726 at 3.72 min. |
| 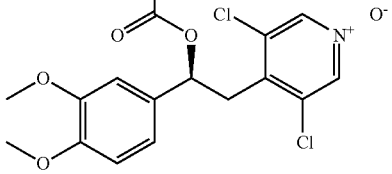<br>[(1S)-1-[3-(cyclopropylmethoxy)-4-(difluoromethoxy)phenyl]-2-(3,5-dichloro-1-oxido-pyridin-1-ium-4-yl)ethyl] 5-[[[1-(3-fluorophenyl)-2-oxo-2-[(3R)-quinuclidin-3-yl]oxy-ethyl]amino]methyl]thiophene-2-carboxylate trifluoroacetate salt | Example 43 | Intermediate 8 and Intermediate 56 | $^1$H NMR (400 MHz, DMSO): δ 9.48 (d, J = 35.2 Hz, 1 H), 8.57* (s, 2 H), 8.56† (s, 2 H), 7.73 (d, J = 3.8 Hz, 1 H), 7.50-7.42 (m, 1 H), 7.38-7.28 (m, 2 H), 7.25-7.17 (m, 3 H), 7.10-7.02 (m, 2 H), 7.07 (t, J = 75.0 Hz, 1 H), 6.15 (dd, J = 9.6, 4.3 Hz, 1 H), 5.09-5.02 (m, 1 H), 4.70-4.62 (m, 1 H), 4.04-3.88 (m, 5 H), 3.74-2.90 (m, 7 H), 2.28-1.15 (m, 6 H), 0.60-0.55 (m, 2 H), 0.38-0.32 (m, 2 H). * and † refer to different isomers. LCMS (Method 2): [MH+] = 820 at 3.86 min. |

-continued

| Structure | Example number | Precursor | Analytical Data |
|---|---|---|---|
| [(1S)-1-[3-(cyclopropylmethoxy)-4-(difluoromethoxy)phenyl]-2-(3,5-dichloro-1-oxido-pyridin-1-ium-4-yl)ethyl] 5-[[[2-oxo-1-(3-pyridyl)-2-[(3R)-quinuclidin-3-yl]oxy-ethyl]amino]methyl]thiophene-2-carboxylate | Example 44 | Intermediate 8 and Intermediate 59 | $^1$H NMR (400 MHz, DMSO): δ 9.86-9.32 (m, 1 H), 8.76-8.49 (m, 2 H), 8.56 (s, 2 H), 8.02-7.95 (m, 1 H), 7.77-7.71 (m, 1 H), 7.59-7.50 (m, 1 H), 7.27-7.03 (m, 4 H), 7.07 (t, J = 74.4 Hz, 1 H), 6.19-6.12 (m, 1 H), 5.11-4.74 (m, 2 H), 4.35-2.81 (m, 12 H), 2.29-1.51 (m, 5 H), 1.26-1.16 (m, 1 H), 0.60-0.54 (m, 2 H), 0.38-0.32 (m, 2 H). LCMS (Method 1): [MH+] = 803 at 2.78 min. |
| [(1S)-2-(3,5-dichloro-1-oxido-pyridin-1-ium-4-yl)-1-(3,4-dimethoxyphenyl)ethyl] 5-[[[1-(2-fluorophenyl)-2-[(1-methyl-4-piperidyl)oxy]-2-oxo-ethyl]amino]methyl]thiophene-2-carboxylate | Example 45 | Intermediate 3 and Intermediate 60 | $^1$H NMR (400 MHz, CDCl$_3$): δ 8.14 (s, 2 H), 7.64 (d, J = 3.7 Hz, 1 H), 7.39-7.26 (m, 2 H), 7.18-7.07 (m, 2 H), 7.01-6.96 (m, 2 H), 6.90-6.81 (m, 2 H), 6.22 (dd, J = 9.7, 4.5 Hz, 1 H), 4.86 (br s, 1 H), 4.72 (d, J = 3.1 Hz, 1 H), 3.96 (s, 2 H), 3.89 (s, 3 H), 3.88 (s, 3 H), 3.66 (dd, J = 14.0, 9.9 Hz, 1 H), 3.31 (dd, J = 14.0, 4.2 Hz, 1 H), 2.49-2.41 (m, 1 H), 2.29-2.20 (m, 6 H), 1.90-1.80 (m, 1 H), 1.80-1.65 (m, 2 H), 1.60-1.45 (m, 1 H). NH not visible LCMS (Method 2): [MH+] = 732 at 3.71 min |

-continued

| Structure | Example number | Precursor | Analytical Data |
|---|---|---|---|
| [(1S)-2-(3,5-dichloro-1-oxido-pyridin-1-ium-4-yl)-1-(3,4-dimethoxyphenyl)ethyl] 5-[[[2-[(1-benzyl-4-piperidyl)oxy]-1-(2-fluorophenyl)-2-oxo-ethyl]amino]methyl]thiophene-2-carboxylate | Example 46 | Intermediate 3 and Intermediate 61 | $^1$H NMR (400 MHz, CDCl$_3$): δ 8.15-8.12 (m, 2 H), 7.64 (d, J = 3.78 Hz, 1 H), 7.35-7.20 (m, 7 H), 7.18-7.08 (m, 2 H), 7.01-6.83 (m, 4 H), 6.22 (dd, J = 9.69, 4.51 Hz, 1 H), 4.86 (s, 1 H), 4.71 (d, J = 3.29 Hz, 1 H), 3.96 (s, 2 H), 3.92-3.86 (m, 7 H), 3.64 (d, J = 11.61 Hz, 1 H), 3.41 (s, 2 H), 3.32 (d, J = 4.54 Hz, 1 H), 2.52 (s, 1 H), 2.23-2.15 (m, 3 H), 1.86-1.5 (m, 4 H), LCMS (Method 2): [MH+] = 808 at 4.39 min |
| [(1R)-2-(3,5-dichloro-1-oxido-pyridin-1-ium-4-yl)-1-(3,4-dimethoxyphenyl)ethyl] 5-[[[2-oxo-1-phenyl-2-[(3R)-quinuclidin-3-yl]oxy-ethyl]amino]methyl]thiophene-2-carboxylate | Example 70 | Intermediate 69 and Intermediate 111 | $^1$H NMR (400 MHz, CD3CN): δ 8.19 (s, 2 H), 7.70 (dd, J = 1.3, 3.8 Hz, 1 H), 7.46-7.33 (m, 5 H), 7.08-7.01 (m, 2 H), 6.98-6.93 (m, 2 H), 6.18 (dd, J = 4.5, 9.6 Hz, 1 H), 4.79-4.72 (m, 1 H), 4.45 (s, 1 H), 4.02-3.91 (m, 2 H), 3.85-3.80 (m, 6 H), 3.67 (ddd, J = 1.8, 9.9, 14.4 Hz, 1 H), 3.34 (dd, J = 4.4, 14.3 Hz, 1 H), 3.17-3.02 (m, 1 H), 2.99-2.83 (m, 1 H), 2.74-2.24 (m, 5 H), 1.82-1.76 (m, 1 H), 1.71-1.16 (m, 4 H). LCMS (Method 1): [MH+] = 726 at 2.57 min. |

The following compounds were synthesized as mixture of diastereoisomers following the same procedure as that described for Example 37 substituting sodium triacetoxyborohydride with sodium cyanoborohydride and substituting acetonitrile with ethanol.

| Structure | Example number | Precursor | Analytical Data |
|---|---|---|---|
| 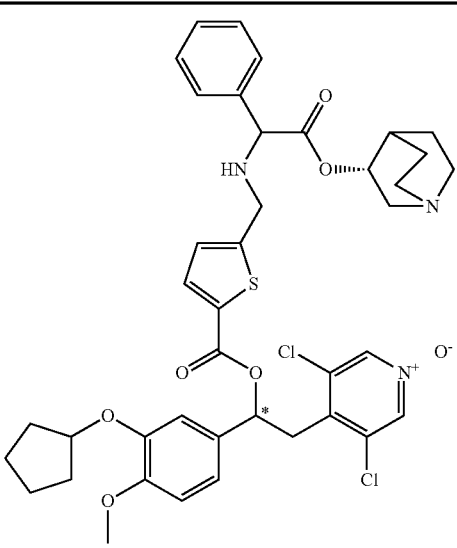<br>Epimeric mixture 1 of [1-[3-(cyclopentoxy)-4-methoxy-phenyl]-2-(3,5-dichloro-1-oxido-pyridin-1-ium-4-yl)ethyl] 5-[[[2-oxo-1-phenyl-2-[(3R)-quinuclidin-3-yl]oxy-ethyl]amino]methyl]thiophene-2-carboxylate dihydrochloride | Example 71 | Intermediate 70 and Intermediate 111 | $^1$H NMR (400 MHz, CD3CN): δ 8.19 (s, 2 H), 7.71-7.69 (m, 1 H), 7.44-7.36 (m, 5 H), 7.00 (d, J = 6.1 Hz, 2 H), 6.98-6.91 (m, 2 H), 6.14 (dd, J = 4.8, 9.1 Hz, 1 H), 4.84-4.72 (m, 2 H), 4.46 (s, 1 H), 3.97-3.93 (m, 2 H), 3.79 (s, 3 H), 3.64 (dd, J = 9.2, 14.0 Hz, 1 H), 3.34 (dd, J = 4.7, 14.0 Hz, 1 H), 3.16-3.01 (m, 1 H), 2.92-2.92 (m, 1 H), 2.73-2.38 (m, 5 H), 1.99-1.92 (m, 5 H), 1.79-1.47 (m, 6 H), 1.44-1.16 (m, 2 H). LCMS (Method 1): [MH+] = 780 at 2.85 min. |
| 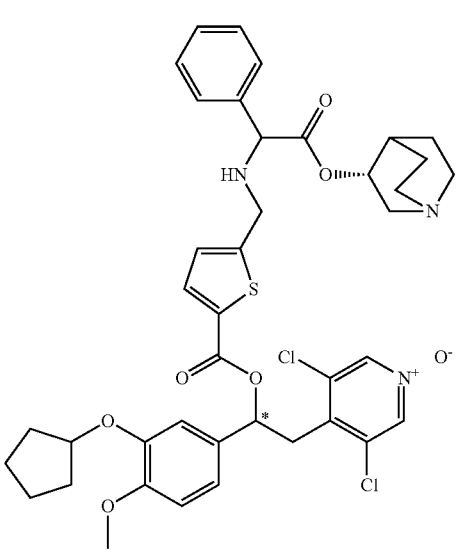<br>Epimeric mixture 2 of [1-[3-(cyclopentoxy)-4-methoxy-phenyl]-2-(3,5-dichloro-1-oxido-pyridin-1-ium-4-yl)ethyl] 5-[[[2-oxo-1-phenyl-2-[(3R)-quinuclidin-3-yl]oxy-ethyl]amino]methyl]thiophene-2-carboxylate dihydrochloride | Example 72 | Intermediate 71 and Intermediate 111 | $^1$H NMR (400 MHz, CD3CN): δ 8.19 (s, 2 H), 7.70-7.68 (m, 1 H), 7.44-7.36 (m, 5 H), 7.02-6.98 (m, 2 H), 6.97-6.92 (m, 2 H), 6.15 (dd, J = 4.8, 9.3 Hz, 1 H), 4.84-4.73 (m, 2 H), 4.46 (s, 1 H), 3.98-3.93 (m, 2 H), 3.79 (s, 3 H), 3.64 (dd, J = 9.3, 14.1 Hz, 1 H), 3.34 (ddd, J = 1.5, 4.8, 14.1 Hz, 1 H), 3.17-3.01 (m, 1 H), 2.93-2.89 (m, 1 H), 2.73-2.38 (m, 5 H), 2.00-1.55 (m, 10 H), 1.55-1.27 (m, 2 H), 1.26-1.14 (m, 1 H). LCMS (Method 1): [MH+] = .780 at 2.85 min. |

| Structure | Example number | Precursor | Analytical Data |
|---|---|---|---|
| Epimeric mixture 1 of [1-[3-(cyclopropylmethoxy)-4-methoxy-phenyl]-2-(3,5-dichloro-1-oxido-pyridin-1-ium-4-yl)ethyl] 5-[[[2-oxo-1-phenyl-2-[(3R)-quinuclidin-3-yl]oxy-ethyl]amino]methyl]thiophene-2-carboxylate | Example 73 | Intermediate 72 and Intermediate 111 | $^1$H NMR (400 MHz, CD3CN): δ 8.07 (s, 2 H), 7.58 (dd, J = 1.0, 3.8 Hz, 1 H), 7.33-7.25 (m, 5 H), 6.95-6.88 (m, 2 H), 6.86-6.82 (m, 2 H), 6.04 (dd, J = 4.5, 9.6 Hz, 1 H), 4.69-4.62 (m, 1 H), 4.35 (d, J = 1.8 Hz, 1 H), 3.86-3.82 (m, 2 H), 3.76-3.67 (m, 5 H), 3.58-3.50 (m, 1 H), 3.21 (dd, J = 3.7, 14.0 Hz, 1 H), 3.07-2.90 (m, 1 H), 2.80 (s, 1 H), 2.63-2.37 (m, 5 H), 1.74-1.66 (m, 1 H), 1.59-1.06 (m, 5 H), 0.53-0.47 (m, 2 H), 0.25-0.19 (m, 2 H). LCMS (Method 1): [MH+] 766 at 2.77 min. |
| Epimeric mixture 2 of [1-[3-(cyclopropylmethoxy)-4-methoxy-phenyl]-2-(3,5-dichloro-1-oxido-pyridin-1-ium-4-yl)ethyl] 5-[[[2-oxo-1-phenyl-2-[(3R)-quinuclidin-3-yl]oxy-ethyl]amino]methyl]thiophene-2-carboxylate | Example 74 | Intermediate 73 and Intermediate 111 | $^1$H NMR (400 MHz, CD3CN): δ 8.08 (d, J = 2.3 Hz, 2 H), 7.58 (dd, J = 1.8, 3.8 Hz, 1 H), 7.33-7.25 (m, 5 H), 6.94-6.89 (m, 2 H), 6.86-6.83 (m, 2 H), 6.04 (dd, J = 4.5, 9.6 Hz, 1 H), 4.69-4.63 (m, 1 H), 4.35 (s, 1 H), 3.87-3.81 (m, 2 H), 3.74-3.70 (m, 5 H), 3.55 (dd, J = 9.7, 14.0 Hz, 1 H), 3.24-3.17 (m, 1 H), 3.06-2.91 (m, 1 H), 2.81-2.75 (m, 1 H), 2.63-2.36 (m, 5 H), 1.72-1.66 (m, 1 H), 1.58-1.07 (m, 5 H), 0.53-0.47 (m, 2 H), 0.25-0.20 (m, 2 H). LCMS (Method 1): [MH+] = 766 at 2.78 min. |

-continued

| Structure | Example number | Precursor | Analytical Data |
|---|---|---|---|
| 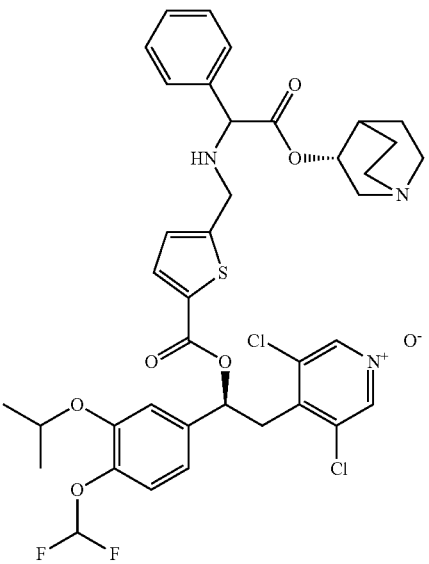<br>[(1S)-2-(3,5-dichloro-1-oxido-pyridin-1-ium-4-yl)-1-[4-(difluoromethoxy)-3-isopropoxy-phenyl]ethyl] 5-[[[2-oxo-1-phenyl-2-[(3R)-quinuclidin-3-yl]oxy-ethyl]amino]methyl]thiophene-2-carboxylate; formate salt | Example 75 | Intermediate 9 and Intermediate 111 | $^1$H NMR (400 MHz, DMSO): δ 8.57 (s, 2 H), 8.18 (s, 1 H), 7.71 (dd, J = 3.8, 1.6 Hz, 1 H), 7.42-7.29 (m, 4 H), 7.27-7.15 (m, 2 H), 7.06-7.00 (m, 2 H), 7.04 (t, J = 74.3 Hz, 1 H), 6.13 (dd, J = 9.3, 4.5 Hz, 1 H), 4.76-4.62 (m, 2 H), 4.43 (d, J = 3.5 Hz, 1 H), 3.98-3.73 (m, 2 H), 3.60-3.50 (m, 1 H), 3.45-3.30 (m, 1 H), 3.16-3.00 (m, 1 H), 2.70-2.55 (m, 4 H), 2.48-2.38 (m, 1H), 2.25-2.17 (m, 1 H), 1.95-1.85†or* (m,, 1 H), 1.80-1.70†or* (m, 1 H) 1.64-1.41 (m, 3 H), 1.30-1.20 (m, 7 H). LCMS (Method 1): [MH+] = 790 at 2.93 min. |
| 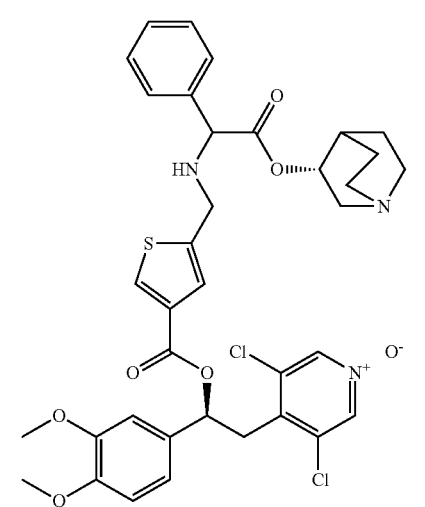<br>[(1S)-2-(3,5-dichloro-1-oxido-pyridin-1-ium-4-yl)-1-(3,4-dimethoxyphenyl)ethyl] 5-[[[2-oxo-1-phenyl-2-[(3R)-quinuclidin-3-yl]oxy-ethyl]amino]methyl]thiophene-3-carboxylate | Example 76 | Intermediate 67 and Intermediate 111 | $^1$H-NMR (400 MHz, DMSO): 5 8.57 (s, 2 H), 8.26*or† (s, 1 H), 8.26*or† (s, 1 H), 7.44-7.30 (m, 5 H), 7.26-7.23 (m, 1 H), 7.03 (s, 1 H), 7.01-6.96 (m, 2 H), 6.12 (dd, J = 4.4, 9.5 Hz, 1 H), 4.71-4.63 (m, 1 H), 4.39 (s, 1 H), 3.89-3.81 (m, 2 H), 3.78 (s, 3 H), 3.75 (s, 3 H), 3.58 (dd, J = 12.1, 12.1 Hz, 1 H), 3.29 (dd, J = 4.2, 14.0 Hz, 1 H), 3.07*or† (ddd, J = 1.8, 7.6, 7.4 Hz, 1 H), 2.98*or† (ddd, J = 3.2, 9.1, 13.5 Hz, 1 H), 2.64-2.44 (m, 4 H), 2.42-2.32 (m, 1 H), 2.15*or† (d, J=15.5 Hz, 1 H), 1.88-1.83*or† (m, 1 H), 1.75-1.71*or† (m, 1 H), 1.60-1.07 (m, 4 H), † and * refer to different isomers (arbitrarily assigned). LCMS (Method 1): [MH+] = 726 at 2.5 min. |

| Structure | Example number | Precursor | Analytical Data |
|---|---|---|---|
| [(1S)-2-(3,5-dichloro-1-oxido-pyridin-1-ium-4-yl)-1-(3,4-dimethoxyphenyl)ethyl] 5-[[[1-(2-fluorophenyl)-2-oxo-2-[(3R)-quinuclidin-3-yl]oxy-ethyl]amino]methyl]thiophene-3-carboxylate | Example 77 | Intermediate 67 and Intermediate 57 | $^1$H NMR (400 MHz, DMSO): δ 8.55*or† (s, 2 H), 8.55*or† (s, 2 H), 8.25*or† (s, 1 H), 8.25*or† (s, 1 H), 7.54-7.49 (m, 1 H), 7.40-7.33 (m, 1 H), 7.27-7.18 (m, 3 H), 7.03-6.95 (m, 3 H), 6.12 (dd, J = 4.3, 9.6 Hz, 1 H), 4.72-4.68*or† (m, 1 H), 4.67-4.64*or† (m, 1 H), 4.66 (d, J = 9.3 Hz, 1 H), 3.88 (d, J = 5.8 Hz, 2 H), 3.77 (s, 3 H), 3.74 (s, 3 H), 3.61-3.52 (m, 2 H), 3.28 (dd, J = 4.5, 14.3 Hz, 1 H), 3.07-2.94 (m, 1 H), 2.62-2.43 (m, 4 H), 2.31-2.25 *or† (m, 1 H), 2.13† (d, J = 14.5 Hz, 1 H), 1.86-1.80*or† (m, 1 H), 1.74-1.68*or† (m, 1 H), 1.55-1.38 (m, 2 H), 1.27-1.09 (m, 2 H), † and * refer to different isomers (arbitrarily assigned). LCMS (Method 2): [MH+] = 744 at 3.52 min. |
| [(1S)-2-(3,5-dichloro-1-oxido-pyridin-1-ium-4-yl)-1-(3,4-dimethoxyphenyl)ethyl] 4-[[[2-oxo-1-phenyl-2-[(3R)-quinuclidin-3-yl]oxy-ethyl]amino]methylthiophene-2-carboxylate | Example 78 | Intermediate 68 and Intermediate 111 | $^1$H NMR (400 MHz, DMSO): δ 8.56 (s, 2 H), 7.78 (dd, J = 1.5, 2.8 Hz, 1 H), 7.71-7.67 (m, 1 H), 7.44-7.29 (m, 5 H), 7.03-6.95 (m, 3 H), 6.14 (dd, J = 4.4, 9.7 Hz, 1 H), 4.67-4.59 (m, 1 H), 4.35 (dd, J = 2.7, 7.7 Hz, 1 H), 3.77 (s, 3 H), 3.75 (s, 3 H), 3.65 (t, J = 5.0 Hz, 2 H), 3.59 (dd, J = 9.9, 14.1 Hz, 1 H), 3.30 (dd, J = 4.1, 14.7 Hz, 1 H), 3.26-3.17 (m, 1 H), 3.03*or† (ddd, J = 2.4, 10.0, 13.1 Hz, 1 H), 2.95*or† (ddd, J = 1.9, 8.1, 14.4 Hz, 1 H), 2.63-2.55 (m, 3 H), 2.63-2.55*or† (m, 1 H), 2.43*or† (d, J = 14.9 Hz, 1 H), 2.37-2.31*or† (m, 1 H), 2.12*or† (d, J = 14.6 Hz, 1 H), 1.86-1.81*or† (m, 1 H), 1.73-1.68*or† (m, 1 H), 1.57-1.37 (m, 2 H), 1.30-1.06 (m, 2 H), † and * refer to different isomers (arbitrarily assigned). LCMS (Method 6): [MH+] = 726 at 3.50 min. |

-continued

| Structure | Example number | Precursor | Analytical Data |
|---|---|---|---|
| 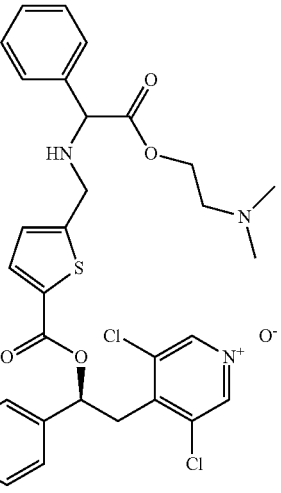<br>[(1S)-2-(3,5-dichloro-1-oxido-pyridin-1-ium-4-yl)-1-(3,4-dimethoxyphenyl)ethyl] 5-[[[2-[2-(dimethylamino)ethoxy]-2-oxo-1-phenyl-ethyl]amino]methyl]thiophene-2-carboxylate | Example 79 | Intermediate 3 and Intermediate 113 | $^1$H NMR (400 MHz, CDCl$_3$): δ 8.14†or* (s, 2 H), 8.13†or* (s, 2 H), 7.64 (d, J = 3.8 Hz, 1 H), 7.38-7.35 (m, 5 H), 7.00-6.96 (m, 2 H), 6.89-6.83 (m, 2 H), 6.24-6.20 (m, 1 H), 4.42 (d, J = 2.8 Hz, 1 H), 4.23-4.09 (m, 2 H), 3.93 (d, J = 5.4 Hz, 2 H), 3.90†or* (s, 3 H), 3.90†or* (s, 3 H), 3.88 (s, 3 H), 3.66 (dd, J = 10.0, 13.8 Hz, 1 H), 3.31 (ddd, J = 2.7, 4.4, 13.9 Hz, 1 H), 2.18-2.15 (m, 2 H), 2.14 (s, 6 H), 1.75-1.69 (m, 2 H). † and * refer to different isomers (arbitrarily assigned), NH not observed. LCMS (Method 2): [MH+] = 688 at 3.1 min. |
| 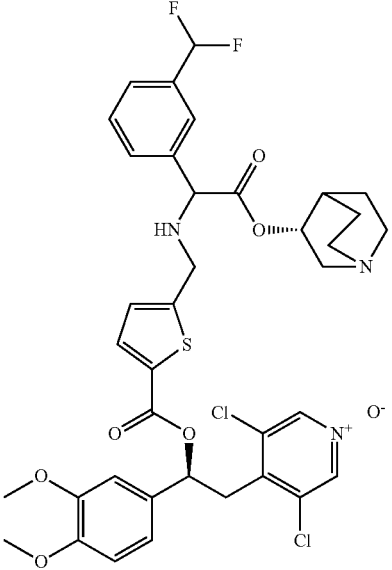<br>[(1S)-2-(3,5-dichloro-1-oxido-pyridin-1-ium-4-yl)-1-(3,4-dimethoxyphenyl)ethyl] 5-[[[1-[3-(difluoromethyl)phenyl]-2-oxo-2-[(3R)-quinuclidin-3-yl]oxy-ethyl]amino]methyl]thiophene-2-carboxylate | Example 80 | Intermediate 3 and Intermediate 118 | $^1$H NMR (400 MHz, CDCl$_3$): δ 8.56†or* (s, 2H), 8.55†or* (s, 2H), 7.70-7.66 (m, 2 H), 7.63-7.58 (m, 1 H), 7.55-7.49 (m, 2 H), 7.05†or* (t, J = 55.3 Hz, 1 H), 7.04†or* (t, J = 55.3 Hz, 1 H), 7.03-6.96 (m, 4 H), 6.14 (dd, J = 4.3, 9.6 Hz, 1 H), 4.73-4.66 (m, 1 H), 4.56-4.52 (m, 1 H), 3.94-3.84 (m, 2 H), 3.77†or* (s, 3 H), 3.76†or* (s, 3 H), 3.75 (s, 3 H), 3.73-3.66 (m, 1 H), 3.58 (dd, J = 9.6, 14.1 Hz, 1 H), 3.33-3.29 (m, 1 H), 3.08-3.02†or* (m, 1 H), 3.01-2.95†or* (m, 1 H), 2.65-2.55 (m, 3 H), 2.45-2.32 (m, 1 H), 2.17-2.11 (m, 1 H), 1.88-1.83†or* (m, 1 H), 1.76-1.70†or* (m, 1 H), 1.57-1.37 (m, 2 H), 1.30-1.06 (m, 2 H). † and * refer to different isomers (arbitrarily assigned); LCMS (Method 2): [MH+] = 776 at 3.75 min |

| Structure | Example number | Precursor | Analytical Data |
|---|---|---|---|
| 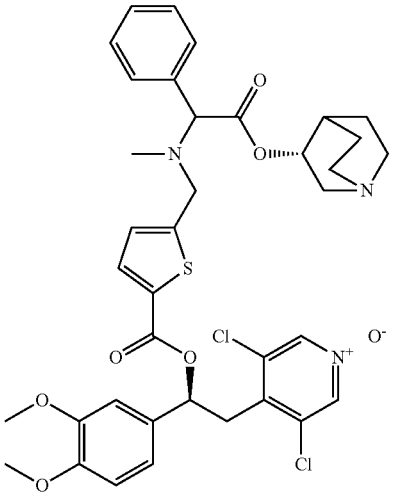<br>[(1S)-2-(3,5-dichloro-1-oxido-pyridin-1-ium-4-yl)-1-(3,4-dimethoxyphenyl)ethyl] 5-[[methyl-[2-oxo-1-phenyl-2-[(3R)-quinuclidin-3-yl]oxy-ethyl]amino]methyl]thiophene-2-carboxylate | Example 81 | Intermediate 3 and Intermediate 119 | $^1$H NMR (400 MHz, DMSO): δ 8.56 (s, 2 H), 7.68 (d, J = 3.8 Hz, 1 H), 7.45-7.36 (m, 5 H), 7.04-7.03 (m, 2 H), 7.01-6.96 (m, 2 H), 6.14 (dd, J = 4.4, 9.7 Hz, 1 H), 4.83-4.76 (m, 1 H), 4.51 (d, J = 6.8 Hz, 1 H), 3.89-3.83 (m, 1 H), 3.78 (s, 3 H), 3.76 (s, 3 H), 3.75-3.72 (m, 1 H), 3.60 (dd, J = 9.9, 14.1 Hz, 1 H), 3.32-3.27 (m, 1 H), 3.16-3.03 (m, 1 H), 2.68-2.58 (m, 4 H), 2.37-2.31 (m, 1 H), 2.22 (s, 3 H), 1.92-1.84 (m, 1 H), 1.62-1.39 (m, 3 H), 1.29-1.21 (m, 1 H). LCMS (Method 1): [MH+] = 740 at 2.82 min. |
| 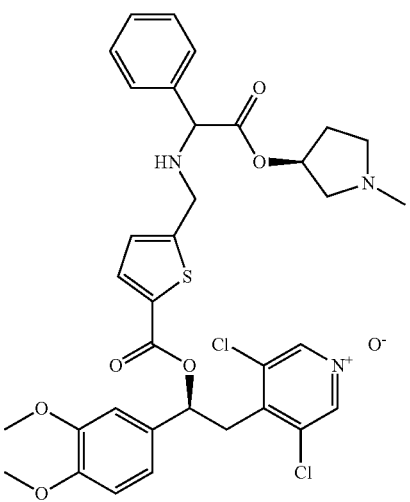<br>[(1S)-2-(3,5-dichloro-1-oxido-pyridin-1-ium-4-yl)-1-(3,4-dimethoxyphenyl)ethyl] 5-[[[2-[(3S)-1-methylpyrrolidin-3-yl]oxy-2-oxo-1-phenyl-ethyl]amino]methyl]thiophene-2-carboxylate | Example 82 | Intermediate 3 and Intermediate 120 | $^1$H NMR (400 MHz, DMSO): δ 8.62*or† (s, 2 H), 8.62*or† (s, 2 H), 7.74 (d, J = 3.8 Hz, 1 H), 7.43 (d, J = 3.0 Hz, 4 H), 7.40-7.35 (m, 1 H), 7.06 (d, J = 3.3 Hz, 2 H), 7.03 (s, 2 H), 6.19 (dd, J = 4.3, 9.6 Hz, 1 H), 5.14-5.08 (m, 1 H), 4.42 (dd, J = 4.3, 9.6 Hz, 1 H), 3.94 (dd, J = 6.4, 15.8 Hz, 1 H), 3.89 (dd, J = 6.3, 15.5 Hz, 1 H), 3.83*or† (s, 3 H), 3.82*or† (s, 3 H), 3.80 (s, 3 H), 3.67-3.55 (m, 2 H), 3.34 (dd, J = 4.3, 14.3 Hz, 1 H), 2.68-2.55 (m, 2 H), 2.39-2.19 (m, 2 H), 2.24*or† (s, 3 H), 2.20*or† (s, 3 H), 2.19-2.08 (m, 1 H), 1.76-1.67*or† (m, 1 H), 1.53-1.45*or† (m, 1 H). † and * refer to different isomers (arbitrarily assigned). LCMS (Method 1): [MH+] = 700 at 2.54 min. |

-continued

| Structure | Example number | Precursor | Analytical Data |
|---|---|---|---|
| 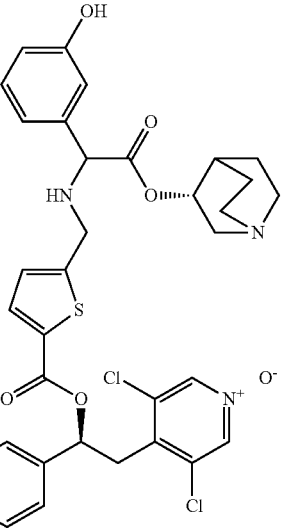 [(1S)-2-(3,5-dichloro-1-oxido-pyridin-1-ium-4-yl)-1-(3,4-dimethoxyphenyl)ethyl] 5-[[[1-(3-hydroxyphenyl)-2-oxo-2-[(3R)-quinuclidin-3-yl]oxy-ethyl]amino]methyl]thiophene-2-carboxylate | Example 83 | Intermediate 3 and Intermediate 128 | $^1$H NMR (400 MHz, DMSO): δ 9.50*or† (s, 1 H), 9.48*or† (s, 1 H), 8.60 (s, 2 H), 7.74 (dd, J = 2.1, 3.7 Hz, 1 H), 7.24-7.17 (m, 1 H), 7.08-7.05 (m, 2 H), 7.04-7.00 (m, 2 H), 6.89-6.84 (m, 2 H), 6.78-6.72 (m, 1 H), 6.19 (dd, J = 4.4, 9.5 Hz, 1 H), 4.79-4.71 (m, 1 H), 4.37 (dd, J = 2.9, 9.0 Hz, 1 H), 4.00-3.89 (m, 2 H), 3.82 (s, 3 H), 3.81 (s, 3 H), 3.67-3.59 (m, 1 H), 3.55-3.45 (m, 1 H), 3.39-3.32 (m, 1 H), 3.14 (dd, J = 8.0, 14.0 Hz, 1 H), 3.06 (ddd, J = 1.8, 8.2, 14.3 Hz, 1 H), 2.72-2.59 (m, 3 H), 2.54-2.46*or† (m, 1 H), 2.25*or† (d, J = 14.1 Hz, 1 H), 1.96-1.91*or† (m, 1 H), 1.85-1.79*or† (m, 1 H), 1.68-1.42 (m, 3 H), 1.34-1.17 (m, 1 H), † and * refer to different isomers (arbitrarily assigned). LCMS (Method 1): [MH+] = 742 at 2.47 min. |
| 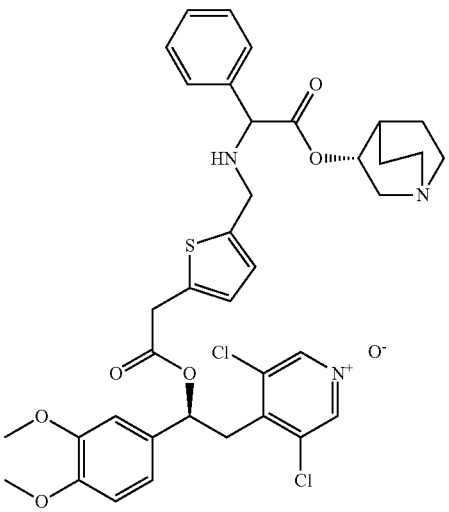 [(3R)-quinuclidin-3-yl] 2-[[5-[2-[(1S)-2-(3,5-dichloro-1-oxido-pyridin-1-ium-4-yl)-1-(3,4-dimethoxyphenyl)ethoxy]-2-oxo-ethyl]-2-thienyl]methylamino]-2-phenyl-acetate | Example 84 | Intermediate 129 and Intermediate 111 | $^1$H NMR (400 MHz, DMSO): δ 8.53 (s, 2 H), 7.48-7.34 (m, 5 H), 6.99-6.91 (m, 3 H), 6.76 (dd, J = 3.7, 11.0 Hz, 2 H), 6.04 (dd, J = 5.4, 8.5 Hz, 1 H), 4.78-4.71 (m, 1 H), 4.45 (s, 1 H), 3.87-3.80 (m, 4 H), 3.80-3.78 (m, 3 H), 3.78-3.77 (m, 3 H), 3.49 (dd, J = 10.4, 14.8 Hz, 1 H), 3.26 (dd, J = 4.9, 14.1 Hz, 1 H), 3.16-3.09*or† (m, 1 H), 3.08-3.00*or† (m, 1 H), 2.73-2.58 (m, 4 H), 2.48-2.37 (m, 1 H), 2.22 (d, J = 16.5 Hz, 1 H), 1.95-1.91*or† (m, 1 H), 1.81-1.77*or† (m, 1 H), 1.67-1.43 (m, 2 H), 1.38-1.13 (m, 2 H), † and * refer to different isomers (arbitrarily assigned). LCMS (Method 1): [MH+] = 740 at 3.65 min. |

The following compounds were synthesized as mixture of diastereoisomers by dissolving or suspending the suitable aldehyde and the suitable glycine ester in EtOH, followed by the a addition of sodium cyanoborohydride, then following the same procedure as that described for Example 37.

| Structure | Example number | Precursor | Analytical Data |
|---|---|---|---|
| 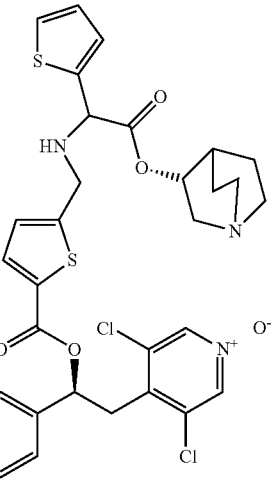<br>[(1S)-2-(3,5-dichloro-1-oxido-pyridin-1-ium-4-yl)-1-(3,4-dimethoxyphenyl)ethyl] 5-[[[1-(thiophen-2-yl)--2-oxo-2-(R)-quinuclidin-3-yloxy-ethyl]amino]methyl]thiophene-2-carboxylate | Example 85 | Intermediate 3 and Intermediate 121 | $^1$H NMR (400 MHz, acetone) d ppm 8.33 (s, 2 H), 7.61-7.77 (m, 1 H), 7.34-7.47 (m, 1 H), 6.88-7.18 (m, 6 H), 6.09-6.40 (m, 1 H), 4.68-4.90 (m, 2 H), 3.93-4.14 (m, 2 H), 3.79 (m, 7 H), 3.25-3.46 (m, 1 H), 2.98-3.22 (m, 2 H), 2.45-2.76 (m, 4 H), 1.45-1.77 (m, 5 H). LCMS (Method 3): [MH+] = 732 at 1.51 min LCMS (Method 4): [MH+] = 732 at 3.08 and 3.12 min |
| 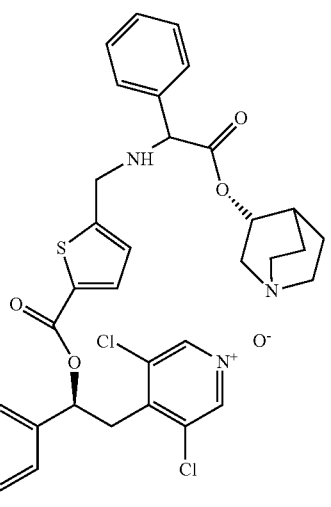<br>[(1S)-2-(3,5-dichloro-1-oxido-pyridin-1-ium-4-yl)-1-[4-(difluoromethoxy)-3-methoxy-phenyl]ethyl] 5-[[[2-oxo-1-phenyl-2-[(3R)-quinuclidin-3-yl]oxy-ethyl]amino]methyl]thiophene-2-carboxylate | Example 86 | Intermediate 6 and Intermediate 54 | 1H NMR (600 MHz, DMSO-d6) d ppm 8.55 (s, 2 H), 7.65-7.78 (m, 1 H), 7.28-7.51 (m, 6 H), 7.16-7.25 (m, 2 H), 6.98-7.09 (m, 3 H), 6.08-6.24 (m, 1 H), 4.64-4.79 (m, 1 H), 4.35-4.51 (m, 1 H), 3.85 (m, 5 H), 3.51-3.69 (m, 2 H), 2.95-3.15 (m, 2 H), 2.58-2.78 (m, 4 H), 1.36 (m, 5 H).<br>LCMS (Method 4): [MH+] = 761.9 at 3.84 and 3.88 min |

The following compounds were synthesized as mixture of diastereoisomers following the same procedure as that described for Example 37 substituting acetonitrile with dichloromethane.

| Structure | Example number | Precursor | Analytical Data |
|---|---|---|---|
| [(1S)-2-(3,5-dichloro-1-oxido-pyridin-1-ium-4-yl)-1-(3,4-dimethoxyphenyl)ethyl] 5-[[[2-[(3R)-1-methylpyrrolidin-3-yl]oxy-2-oxo-1-phenyl-ethyl]amino]methyl]thiophene-2-carboxylate | Example 87 | Intermediate 3 and Intermediate 112 | $^1$H NMR (400 MHz, CDCl$_3$): δ 8.14* or † (s, 2 H), 8.13* or † (s, 2 H), 7.63 (d, J = 3.5 Hz, 1 H), 7.38-7.33 (m, 5 H), 7.01-6.96 (m, 2 H), 6.89-6.83 (m, 2 H), 6.25-6.19 (m, 1 H), 5.26-5.17 (m, 1 H), 4.43 (s, 1 H), 3.95-3.91 (m, 2 H), 3.91* or † (s, 3 H), 3.90* or † (s, 3 H), 3.88 (s, 3 H) 3.66 (dd, J = 9.9, 13.9 Hz, 1 H), 3.35-3.27 (m, 1 H), 2.73-2.58 (m, 3 H), 2.50-2.43 (m, 1 H), 2.29-2.19 (m, 5 H), 1.88-1.79 (m, 1 H). * and † refer to different isomers. NH not visible. LCMS (Method 1): [MH+] = 700 at 2.57 min. |
| [(1S)-2-(3,5-dichloro-1-oxido-pyridin-1-ium-4-yl)-1-(3,4-dimethoxyphenyl)ethyl] 5-[[[2-(1-methylazetidin-3-yl)oxy-2-oxo-1-phenyl-ethyl]amino]methyl]thiophene-2-carboxylate | Example 88 | Intermediate 3 and Intermediate 114 | $^1$H NMR (400 MHz, CDCl$_3$): δ 8.15 † or * (s, 2 H), 8.14† or * (s, 2 H), 7.64 (d, J = 3.8 Hz, 1 H), 7.38-7.35 (m, 5 H), 7.01-6.96 (m, 2 H), 6.89-6.84 (m, 2 H), 6.25-6.21 (m, 1 H), 5.06-5.01 (m, 1 H), 4.44 (d, J = 3.3 Hz, 1 H), 3.95-3.91 (s, 2H), 3.90* or † (s, 3H), 3.90* or † (s, 3H), 3.88* or † (s, 3H), 3.87* or † (s, 3H) 3.71-3.57 (m, 3 H), 3.31 (ddd, J = 2.5, 4.5, 13.9 Hz, 1 H), 3.04-2.99 (m, 1 H), 2.90 (tt, J = 4.0, 4.0 Hz, 1 H), 2.31† or * (s, 3 H). 2.30† or * (s, 3 H). † and * refer to different isomers (arbitrarily assigned). NH not visible. |

-continued

| Structure | Example number | Precursor | Analytical Data |
|---|---|---|---|
| 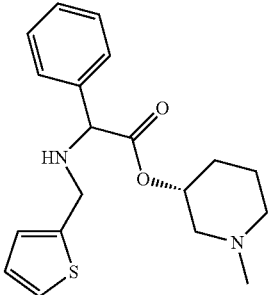<br>[(1S)-2-(3,5-dichloro-1-oxido-pyridin-1-ium-4-yl)-1-(3,4-dimethoxyphenyl)ethyl] 5-[[[2-[[(3R)-1-methyl-3-piperidyl]oxy]-2-oxo-1-phenyl-ethyl]amino]methyl]thiophene-2-carboxylate; formate salt | Example 89 | Intermediate 3 and Intermediate 115 | $^1$H NMR (400 MHz, CDCl$_3$ δ 8.20 (s, 2 H), 8.16† or * (s, 2 H), 8.14† or * (s, 2 H), 7.65-7.63 (m, 1 H), 7.42-7.32 (m, 5 H), 7.01-6.97 (m, 2 H), 6.91-6.84 (m, 2 H), 6.22 (dd, J = 4.5, 9.9 Hz, 1 H), 5.08-5.03 (m, 1 H), 4.49† or * (s, 1 H), 4.45† or * (s, 1 H), 3.95-3.91 (m, 2 H), 3.91* or † (s, 3 H), 3.90* or † (s, 3 H), 3.88 (s, 3 H), 3.67 (dd, J = 9.9, 14.1 Hz, 1 H), 3.35-3.28 (m, 1 H), 2.88-2.56 (m, 4 H), 2.51† or * (s, 3 H), 2.45† or * (s, 3 H), 1.90-1.54 (m, 4 H). † and * refer to different isomers (arbitrarily assigned). NH not visible. LCMS (Method 2): [MH+] = 714 at 3.22 min |
| 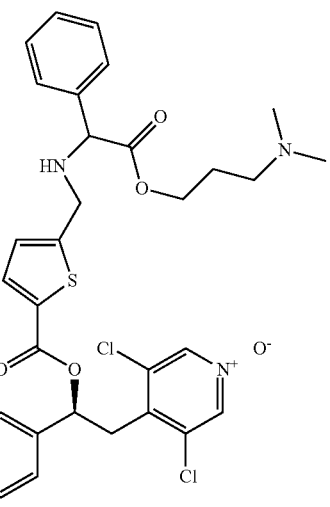<br>[(1S)-2-(3,5-dichloro-1-oxido-pyridin-1-ium-4-yl)-1-(3,4-dimethoxyphenyl)ethyl] 5-[[[2-[3-(dimethylamino)propoxy]-2-oxo-1-phenyl-ethyl]amino]methyl]thiophene-2-carboxylate | Example 90 | Intermediate 3 and Intermediate 116 | $^1$H NMR (400 MHz, CDCl$_3$): δ 8.14† or * (s, 2 H), 8.13† or * (s, 2 H), 7.64 (d, J = 3.8 Hz, 1 H), 7.38-7.35 (m, 5 H), 7.00-6.96 (m, 2 H), 6.89-6.83 (m, 2 H), 6.24-6.20 (m, 1 H), 4.42 (d, J = 2.8 Hz, 1 H), 4.23-4.09 (m, 2 H), 3.93 (d, J = 5.4 Hz, 2 H), 3.90† or * (s, 3 H), 3.90† or * (s, 3 H), 3.88 (s, 3 H), 3.66 (dd, J = 10.0, 13.8 Hz, 1 H), 3.31 (ddd, J = 2.7, 4.4, 13.9 Hz, 1 H), 2.18-2.15 (m, 2 H), 2.14 (s, 6 H), 1.75-1.69 (m, 2 H), † and * refer to different isomers (arbitrarily assigned), NH not observed. LCMS (Method 1): [MH+] = 702 at 2.53 min. |

Example 91

Epimeric mixture 2 of [2-(3,5-dichloro-1-oxido-pyridin-1-ium-4-yl)-1-(3-ethoxy-4-methoxy-phenyl)ethyl]5-[[[2-oxo-1-phenyl-2-[(3R)-quinuclidin-3-yl]oxy-ethyl]amino]methyl]thiophene-2-carboxylate

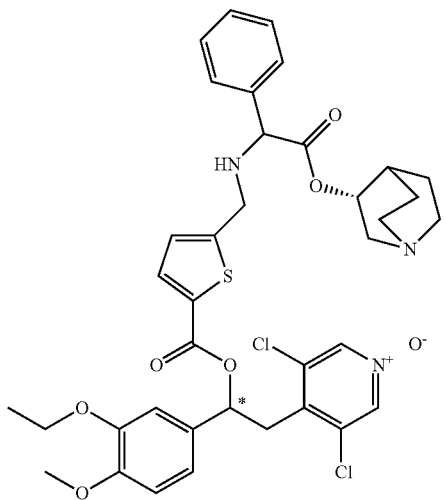

To a solution of [(3R)-quinuclidin-3-yl]2-amino-2-phenylacetate bis hydrochloride salt (273 mg, 0.82 mmol) in ethanol (10 mL) was added the single enantiomer 2 of [2-(3,5-dichloro-1-oxido-pyridin-1-ium-4-yl)-1-(3-ethoxy-4-methoxy-phenyl)ethyl] 5-formylthiophene-2-carboxylate (Intermediate 75, 135 mg, 0.27 mmol) and acetic acid (40 μL, 0.68 mmol). The resulting mixture was stirred at room temperature for 16 h. Sodium cyanoborohydride (45 mg, 0.68 mmol) was added and the reaction mixture was stirred at room temperature for a further 24 h. The solvent was removed by evaporation under reduced pressure and the residue was partitioned between 1 M aqueous hydrochloric acid (3 mL) and ethyl acetate (3 mL). The layers were separated and the aqueous phase was extracted with ethyl acetate (2×3 mL). The aqueous phase was basified with saturated aqueous sodium bicarbonate solution and then extracted with ethyl acetate (2×3 mL). The combined organic fractions were extracted with 1 M aqueous hydrochloric acid (2 mL). Brine (2 mL) was added and the aqueous layer was extracted with chloroform (5 mL and 2 mL). The combined organic fractions were washed with saturated aqueous sodium bicarbonate solution (2 mL), passed through a hydrophobic frit and the solvent was removed by evaporation under reduced pressure. Purification by preparative HPLC gave the title compound as an off-white solid (50 mg, 25%).

$^1$H NMR (400 MHz, CDCl$_3$): δ 8.13 (s, 2H), 7.64 (d, J=3.8 Hz, 1H), 7.38-6.96 (m, 5H), 7.00-6.96 (m, 2H), 6.89-6.83 (m, 2H), 6.21 (dd, J=4.4, 9.7 Hz, 1H), 4.84-4.79 (m, 1H), 4.44 (s, 1H), 4.16-4.07 (m, 2H), 3.96 (s, 2H), 3.86 (s, 3H), 3.66 (dd, J=9.9, 13.9 Hz, 1'-1), 3.34-3.27 (m, 1H), 3.17-3.10 (m, 1H), 2.80-2.69 (m, 3H), 2.51-2.49 (m, 1H), 2.40-2.35 (m, 1H), 2.08-2.00 (m, 1H), 1.69-1.64 (m, 3H), 1.48-1.46 (m, 3H), 1.28-1.26 (m, 2H). LCMS (Method 1): [MH+]=740 at 2.66 min.

The following compounds were synthesized via a similar method as mixture of diastereoisomers.

| Structure | Example number | Precursor | Analytical Data |
|---|---|---|---|
| Epimeric mixture 1 of [2-(3,5-dichloro-1-oxido-pyridin-1-ium-4-yl)-1-(3-ethoxy-4-methoxy-phenyl)ethyl] 5-[[[2-oxo-1-phenyl-2-[(3R)-quinuclidin-3-yl]oxy-ethyl]amino]methyl]thiophene-2-carboxylate | Example 92 | Intermediate 74 and Intermediate 111 | $^1$H NMR (400 MHz, CDCl$_3$): δ 8.13 (s, 2 H), 7.64 (d, J = 3.8 Hz, 1 H), 7.37-7.30 (m, 5 H), 7.00-6.96 (m, 2 H), 6.88-6.83 (m, 2 H), 6.21 (dd, J = 4.4, 9.7 Hz, 1 H), 4.86-4.78 (m, 1 H), 4.44 (d, J = 2.8 Hz, 1 H), 4.15-4.08 (m, 2 H), 3.94 (s, 2 H), 3.86 (s, 3 H), 3.65 (dd, J = 9.9, 13.1 Hz, 1 H), 3.32-3.30 (m, 1 H), 3.23-3.08 (m, 1 H), 2.75-2.65 (m, 4 H), 2.56-2.47 (m, 1 H), 2.33-2.32 (m, 1 H), 2.01-1.98 (m, 1 H), 1.88-1.56 (m, 2 H), 1.51-1.49 (m, 3 H), 1.36-1.15 (m, 2 H). LCMS (Method 1): [MH+] = 740 at 2.66 min. |

Example 93

[(1S)-2-(3,5-dichloro-1-oxido-pyridin-1-ium-4-yl)-1-(3,4-dimethoxyphenyl)ethyl]5-[[[2-[(8-methyl-8-azabicyclo[3.2.1]octan-3-yl)oxy]-2-oxo-1-phenyl-ethyl]amino]methyl]thiophene-2-carboxylate

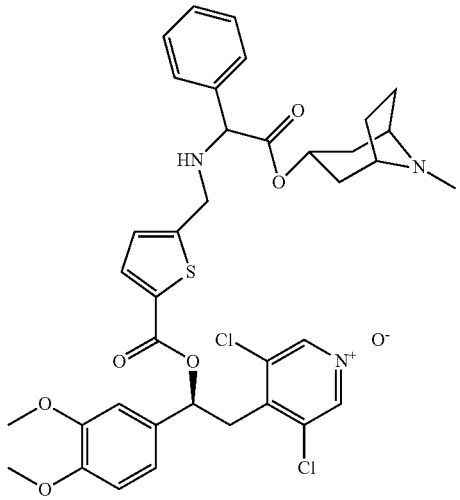

A mixture of [(1S)-2-(3,5-dichloro-1-oxido-pyridin-1-ium-4-yl)-1-(3,4-dimethoxyphenyl)ethyl]5-formylthiophene-2-carboxylate (0.17 g, 0.35 mmol), (8-methyl-8-azabicyclo[3.2.1]octan-3-yl) 2-amino-2-phenyl-acetate (0.14 g, 0.53 mmol) and acetic acid (40 µL, 0.71 mmol) in dichloromethane (8 mL) was stirred at room temperature for 20 h. Sodium triacetoxyborohydride was added and the reaction mixture was stirred at room temperature for a further 24 h. The mixture was diluted with dichloromethane (10 mL) and washed with saturated sodium bicarbonate solution (2×10 mL) and saturated sodium chloride solution (10 mL). The organic layer was separated and filtered through a phase separator and the solvent was removed by evaporation under reduced pressure. Purification by preparative HPLC gave the title compound (mixture of diastereoisomers) as a pale yellow solid (72 mg, 28%).

$^1$H NMR (400 MHz, CDCl$_3$): δ 8.14*$^{or\,\dagger}$ (s, 2H), 8.15*$^{or\,\dagger}$ (s, 2H), 7.64 (d, J=3.8 Hz, 1H), 7.34 (d, J=3.3 Hz, 5H), 7.02-6.96 (m, 2H), 6.88-6.84 (m, 2H), 6.22 (dd, J=9.6, 4.4 Hz, 1H), 5.03-4.99 (m, 1H), 4.37 (d, J=2.3 Hz, 1H), 3.97-3.91 (m, 2H), 3.90*$^{or\,\dagger}$ (s, 3H), 3.90*$^{or\,\dagger}$ (s, 3H), 3.88 (s, 3H), 3.67 (dd, J=13.9, 9.7 Hz, 1H), 3.31 (d, J=14.0 Hz, 1H), 3.16 (d, J=22.9 Hz, 2H), 2.27 (s, 3H), 2.01 (s, 2H), 1.85-1.54 (m, 6H). NH not visible.

LCMS (Method 1): [MH+]=740 at 2.62 min.

The following compounds were synthesized via a similar method as mixture of diastereoisomers.

| Structure | Example number | Precursor | Analytical Data |
|---|---|---|---|
| [(1S)-2-(3,5-dichloro-1-oxido-pyridin-1-ium-4-yl)-1-(3,4-dimethoxyphenyl)ethyl] 5-[[[1-(2-fluorophenyl)-2-[(3R)-1-methylpyrrolidin-3-yl]oxy-2-oxo-ethyl]amino]methyl]thiophene-2-carboxylate | Example 94 | Intermediate 3 and Intermediate 117 | $^1$H NMR (400 MHz, CDCl$_3$): δ δ 8.14 (s, 2 H), 7.64 (d, J = 3.8 Hz, 1 H), 7.35-7.26 (m, 2 H), 7.17-7.07 (m, 2 H), 7.00-6.97 (m, 2 H), 6.90-6.84 (m, 2 H), 6.22 (dd, J = 9.7, 4.5 Hz, 1 H), 5.26-5.18 (m, 1 H), 4.72 (s, 1 H), 3.95 (s, 2 H), 3.91 (s, 3 H), 3.88*$^{or\,\dagger}$ (s, 3 H), 3.87*$^{or\,\dagger}$ (s, 3H), 3.69-3.63 (m, 1 H), 3.35-3.27 (m, 1 H), 2.80-2.60 (m, 3 H), 2.45-2.10 (m, 2 H), 2.32*$^{or\,\dagger}$ (s, 3 H), 2.27*$^{or\,\dagger}$ (s, 3 H) 1.86-1.60 (m, 2 H). LCMS (Method 1): [MH+] = 718 at 2.65 min. |

| Structure | Example number | Precursor | Analytical Data |
|---|---|---|---|
| 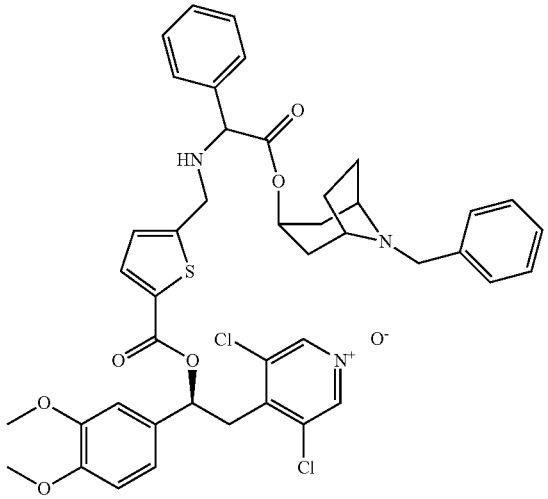<br>[(1S)-2-(3,5-dichloro-1-oxido-pyridin-1-ium-4-yl)-1-(3,4-dimethoxyphenyl)ethyl] 5-[[[2-[(8-benzyl-8-azabicyclo[3.2.1]octan-3-yl)oxy]-2-oxo-1-phenyl-ethyl]amino]methyl]thiophene-2-carboxylate | Example 95 | Intermediate 3 and Intermediate 122 | $^1$H NMR (400 MHz, CDCl$_3$): δ 8.13 (s, 2 H), 7.64 (d, J = 3.8 Hz, 1 H), 7.40-7.26 (m, 10 H), 7.02-6.96 (m, 2 H), 6.90-6.84 (m, 2 H), 6.24-6.19 (m, 1 H), 5.04 (s, 1 H), 4.37 (s, 1 H), 3.94-3.84 (m, 8 H), 3.70-3.62 (m, 1 H), 3.42 (s, 2 H), 3.35-3.27 (m, 1 H), 3.06 (s, 1 H), 2.93 (s, 1 H), 2.65-2.50 (m, 1 H), 2.15-2.04 (m, 1 H), 2.05-1.95 (m, 1 H), 1.90-1.80 (m, 1 H), 1.72-1.60 (m, 3 H), 1.40 (d, J = 15.0 Hz, 1 H), 1.12-1.05 (m, 1 H). LCMS (Method 1): [MH+] = 816 at 2.77 min. |
| 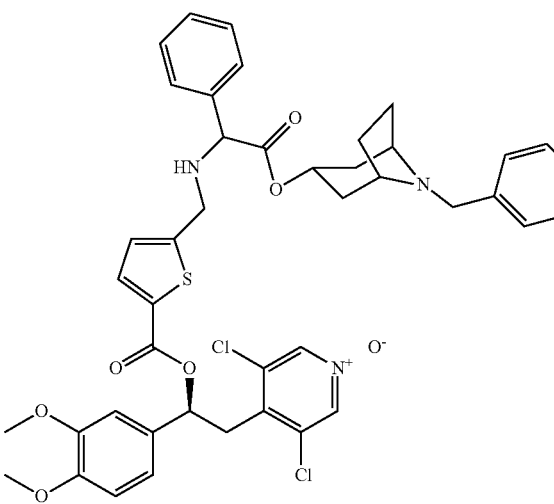<br>[(1S)-2-(3,5-dichloro-1-oxido-pyridin-1-ium-4-yl)-1-(3,4-dimethoxyphenyl)ethyl] 5-[[[2-[[(1R,5R)-8-benzyl-8-azabicyclo[3.2.1]octan-3-yl]oxy]-2-oxo-1-phenyl-ethyl]amino]methyl]thiophene-2-carboxylate | Example 96 | Intermediate 3 and Intermediate 123 | $^1$H NMR (400 MHz, CDCl$_3$): δ 8.14* $^{or †}$ (s, 2 H), 8.13* $^{or †}$ (s, 2 H), 7.64 (d, J = 3.8 Hz, 1 H), 7.39-7.22 (m, 10 H), 7.02-6.96 (m, 2 H), 6.89-6.82 (m, 2 H), 6.25-6.19 (m, 1 H), 5.12-5.04 (m, 1 H), 4.38 (s, 1 H), 3.97-3.91 (m, 2 H), 3.90* $^{or †}$ (s, 3 H), 3.90* $^{or †}$ (s, 3 H), 3.88* $^{or †}$ (s, 3 H), 3.88* $^{or †}$ (s, 3 H) 3.66 (dd, J = 13.9, 9.8 Hz, 1 H), 3.55 (s, 2 H), 3.37-3.18 (m, 3 H), 2.52 (s, 1 H), 2.01 (s, 2 H), 1.88-1.53 (m, 6 H). * and † refer to different isomers. LCMS (Method 1): [MH+] = 816 at 2.77 min. |

-continued

| Structure | Example number | Precursor | Analytical Data |
|---|---|---|---|
| 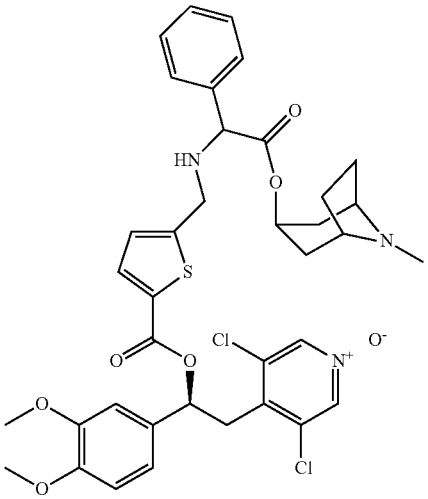<br>[(1S)-2-(3,5-dichloro-1-oxido-pyridin-1-ium-4-yl)-1-(3,4-dimethoxyphenyl)ethyl] 5-[[[2-[[(1R,5R)-8-methyl-8-azabicyclo[3.2.1]octan-3-yl]oxy]-2-oxo-1-phenyl-ethyl]amino]methyl]thiophene-2-carboxylate | Example 97 | Intermediate 3 and Intermediate 124 | $^1$H NMR (400 MHz, CDCl$_3$): δ 8.13 (s, 2 H), 7.64 (d, J = 3.8 Hz, 1 H), 7.37-7.32 (m, 5 H), 7.01-6.96 (m, 2 H), 6.88-6.83 (m, 2 H), 6.26-6.20 (m, 1 H), 5.01 (s, 1 H), 4.37 (s, 1 H), 3.95-3.85 (m, 8 H), 3.70-3.63 (m, 1 H), 3.34-3.28 (m, 1 H), 3.01 (s, 1 H), 2.88 (s, 1 H), 2.70 (s, 1 H), 2.19 (s, 3 H), 2.10 (d, J = 15.7 Hz, 1 H), 2.01 (s, 1 H), 1.90-1.80 (m, 1 H), 1.70-1.57 (m, 3 H), 1.41 (d, J = 15.2 Hz, 1 H), 1.04 (d, J = 9.7 Hz, 1 H). LCMS (Method 1): [MH+] = 740 at 2.57 min. |
| 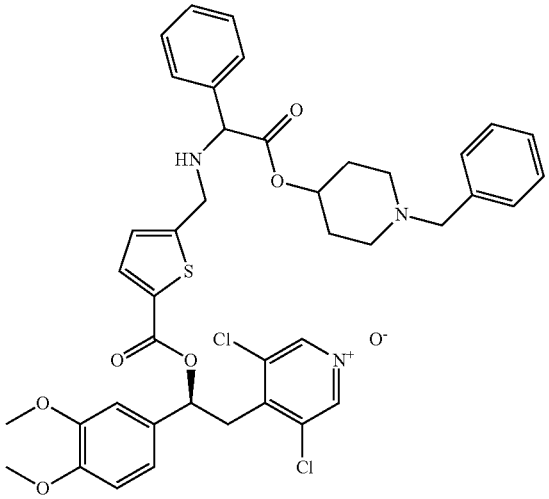<br>[(1S)-2-(3,5-dichloro-1-oxido-pyridin-1-ium-4-yl)-1-(3,4-dimethoxyphenyl)ethyl] 5-[[[2-[(1-benzyl-4-piperidyl)oxy]-2-oxo-1-phenyl-ethyl]amino]methyl]thiophene-2-carboxylate | Example 98 | Intermediate 3 and Intermediate 126 | $^1$H NMR (400 MHz, CDCl$_3$): δ 8.14* $^{or†}$ (s, 2 H), 8.13* $^{or†}$ (s, 2 H), 7.64 (d, J = 3.8 Hz, 1 H), 7.41-7.22 (m, 10 H), 7.02-6.96 (m, 2 H), 6.89-6.83 (m, 2 H), 6.24-6.19 (m, 1 H), 4.88-4.79 (m, 1 H), 4.44-4.38 (m, 1 H), 3.94-3.85 (m, 8 H), 3.66 (dd, J = 13.9, 9.8 Hz, 1 H), 3.42 (s, 2 H), 3.34-3.28 (m, 1 H), 2.63-2.51 (m, 2 H), 2.40-2.35 (m, 1 H), 2.30-2.20 (m, 1 H), 2.19-2.12 (m, 1 H), 1.90-1.80 (m, 1 H), 1.79-1.60 (m, 2 H), 1.62-1.44 (m, 1 H), * and † refer to different isomers. LCMS (Method 1): [MH+] = 790 at 2.76 min. |

| Structure | Example number | Precursor | Analytical Data |
|---|---|---|---|
| 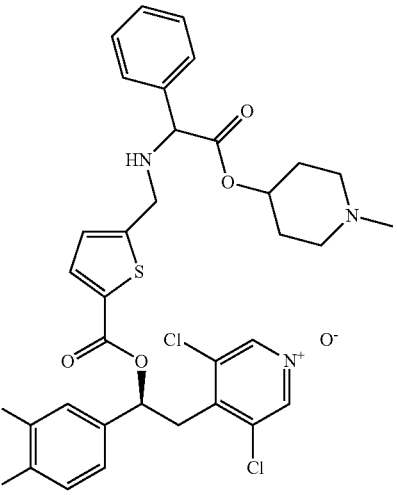<br>[(1S)-2-(3,5-dichloro-1-oxido-pyridin-1-ium-4-yl)-1-(3,4-dimethoxyphenyl)ethyl] 5-[[[2-[(1-methyl-4-piperidyl)oxy]-2-oxo-1-phenyl-ethyl]amino]methyl]thiophene-2-carboxylate | Example 99 | Intermediate 3 and Intermediate 127 | $^1$H NMR (400 MHz, CDCl$_3$): δ 8.14* $^{or\,†}$ (s, 2 H), 8.13* $^{or\,†}$ (s, 2 H), 7.64 (d, J = 3.8 Hz, 1 H), 7.37-7.30 (m, 5 H), 7.02-6.96 (m, 2 H), 6.91-6.83 (m, 2 H), 6.25-6.19 (m, 1 H), 4.88-4.77 (m, 1 H), 4.42 (d, J = 3.7 Hz, 1 H), 3.97-3.85 (m, 8 H), 3.67 (dd, J = 14.1, 9.7 Hz, 1 H), 3.34-3.27 (m, 1 H), 2.60-2.40 (m, 2 H), 2.30-2.15 (m, 2 H), 2.21 (s, 3 H), 1.92-1.80 (m, 2 H), 1.75-1.45 (m, 3 H), * and † refer to different isomers. LCMS (Method 2): [MH+] = 714 at 3.3 min. |

Example 100

[(1S)-2-(3,5-dichloro-1-oxido-pyridin-1-ium-4-yl)-1-(3,4-dimethoxyphenyl)ethyl]5-[[[1-(o-tolyl)-2-oxo-2-[(3R)-quinuclidin-3-yl]oxy-ethyl]amino]methyl]thiophene-2-carboxylate

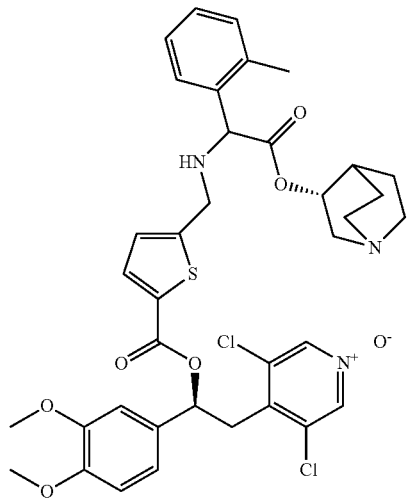

To a solution of [(2R)-quinuclidin-2-yl]2-(tert-butoxycarbonylamino)-2-(o-tolyl)acetate (240 mg, 0.64 mmol) in ethyl acetate (6 mL) was added 4N HCl/dioxane (6 mL) and the resultant solution was stirred at room temperature for 18 h. The solvent was removed in vacuo. The crude material (220 mg, 0.63 mmol) was dissolved in ethanol (20 mL) and [(1S)-2-(3,5-dichloro-1-oxido-pyridin-1-ium-4-yl)-1-(3,4-dimethoxyphenyl)ethyl]5-formylthiophene-2-carboxylate (305 mg, 0.63 mmol) was added followed by acetic acid (74 µL, 1.26 mmol) and triethylamine (351 µL, 2.52 mmol). The resultant solution was stirred at room temperature for 20 minutes then sodium cyanoborohydride (79 mg, 1.26 mmol) was added. The solution was stirred at room temperature for a further 18 h. The solvent was removed in vacuo and the residue was taken up in water (20 mL) and ethyl acetate (20 mL). The layers were separated and the aqueous phase was extracted with ethyl acetate (2×20 mL). The combined organic phases were extracted with 0.2 N aqueous hydrochloric acid (40 mL) and water (40 mL). The aqueous extracts were combined and sodium chloride (6 g) was added. The mixture was extracted with chloroform (3×30 mL) and the combined organic extracts were passed through a hydrophobic fit and the solvent was removed in vacuo. Purification of the crude material by preparative HPLC afforded the title compound (28 mg, 6% in two steps) as an off white solid.

$^1$H NMR (400 MHz, DMSO): δ 8.60$^{†\,or*}$ (s, 2H), 8.59$^{†\,or*}$ (s, 2H), 7.73 (dd, J=1.0, 3.8 Hz, 1H), 7.47-7.41 (m, 1H), 7.28-7.23 (m, 3H), 7.07-7.04 (m, 2H), 7.03 (s, 2H), 6.19 (dd, J=4.3, 9.9 Hz, 1H), 4.81-4.73 (m, 1H), 4.69 (d, J=6.3 Hz, 1H), 4.00-3.85 (m, 2 H), 3.82 (s, 3H), 3.80$^{†\,or*}$ (s, 3H), 3.79$^{†\,or*}$ (s, 3H), 3.66-3.60 (m, 2H), 3.20-3.12$^{†\,or*}$ (m, 1H), 3.11-3.03$^{†\,or*}$ (m, 1H), 2.74-2.60 (m, 4H), 2.36-2.34 (m, 3H), 2.26-2.19 (m, 1H), 1.96-1.92$^{†\,or*}$ (m, 1H), 1.80-1.76$^{†\,or*}$ (m, 1H), 1.66-1.45 (m, 3H), 1.35-1.15 (m, 2H). † and * refer to different isomers (arbitrarily assigned). LCMS (Method 1): [MH+]= 740 at 2.64 min.

The following compounds were synthesized via a similar method as mixture of diastereoisomers.

| Structure | Example number | Precursor | Analytical Data |
|---|---|---|---|
| [(1S)-2-(3,5-dichloro-1-oxido-pyridin-1-ium-4-yl)-1-(3,4-dimethoxyphenyl)ethyl] 5-[[[3-oxo-1-phenyl-3-[(3R)-quinuclidin-3-yl]oxy-propyl]amino]methyl]thiophene-2-carboxylate | Example 101 | Intermediate 3 and Intermediate 106 | $^1$H NMR (400 MHz, DMSO): δ 8.61† or * (s, 2 H), 8.60† or * (s, 2 H), 7.71 (d, J = 3.7 Hz, 1 H), 7.41-7.38 (m, 4 H), 7.34-7.28 (m, 1 H), 7.07 (s, 1 H), 7.03 (s, 2 H), 6.98 (d, J = 4.1 Hz, 1 H), 6.19 (dd, J = 4.3, 9.5 Hz, 1 H), 4.67-4.61 (m, 1 H), 4.07-4.01 (m, 1 H), 3.83 (s, 3 H), 3.80 (s, 3 H), 3.75 (s, 1 H), 3.68-3.59 (m, 2 H), 3.50-3.47 (m, 1H), 3.39-3.32 (m, 1 H), 3.12-3.00 (m, 1 H), 2.84-2.75 (m, 1 H), 2.73-2.60 (m, 5 H), 2.48-2.37† or * (m, 1 H), 2.32-2.26† or * (m, 1 H), 1.92-1.88† or * (m, 1 H), 1.75-1.71† or * (m, 1 H), 1.68-1.40 (m, 3 H), 1.34-1.16 (m, 1 H), † and * refer to different isomers (arbitrarily assigned). LCMS (Method 2): [MH+] = 740 at 3.67 min. |
| [(1S)-2-(3,5-dichloro-1-oxido-pyridin-1-ium-4-yl)-1-(3,4-dimethoxyphenyl)ethyl] 5-[[[1-(2-fluorophenyl)-3-oxo-3-[(3R)-quinuclidin-3-yl]oxy-propyl]amino]methyl]thiophene-2-carboxylate | Example 102 | Intermediate 3 and Intermediate 109 | $^1$H NMR (400 MHz, DMSO): δ 8.61† or * (s, 2 H), 8.60† or * (s, 2 H), 7.71 (d, J = 3.7 Hz, 1 H), 7.61 (tt, J = 1.9, 7.8 Hz, 1 H), 7.40-7.33 (m, 1 H), 7.30-7.25 (m, 1 H), 7.24-7.17 (m, 1 H), 7.08-6.98 (m, 4 H), 6.19 (dd, J = 4.4, 9.5 Hz, 1 H), 4.68-4.62 (m, 1 H), 4.44-4.38 (m, 1 H), 3.83† or * (s, 3H), 3.83† or * (s, 3 H), 3.87-3.81 (m, 1H), 3.80† or * (s, 3 H), 3.80† or * (s, 3 H), 3.69-3.59 (m, 2 H), 3.47-3.44 (m, 1 H), 3.39-3.32 (m, 1 H), 3.11-3.02 (m, 1 H), 2.82-2.59 (m, 6 H), 2.45-2.38† or * (m, 1 H), 2.37-2.30† or * (m, 1 H), 1.92-1.88† or * (m, 1 H), 1.74-1.70† or * (m, 1 H), 1.67-1.38 (m, 3 H), 1.33-1.16 (m, 1 H), † and * refer to different isomers (arbitrarily assigned). LCMS (Method 2): [MH+] = 758 at 3.68 min. |

| Structure | Example number | Precursor | Analytical Data |
|---|---|---|---|
| 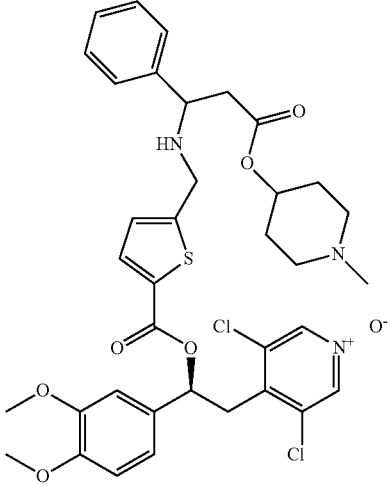 [(1S)-2-(3,5-dichloro-1-oxido-pyridin-1-ium-4-yl)-1-(3,4-dimethoxyphenyl)ethyl] 5-[[[3-[(1-methyl-4-piperidyl)oxy]-3-oxo-1-phenyl-propyl]amino]methyl]thiophene-2-carboxylate | Example 103 | Intermediate 3 and Intermediate 107 | $^1$H NMR (400 MHz, CD$_3$CN): δ 8.20 (s, 2 H), 7.68 (d, J = 4.1 Hz, 1 H), 7.39-7.35 (m, 4 H), 7.33-7.28 (m, 1 H), 7.07-7.02 (m, 2 H), 6.97-6.94 (m, 1 H), 6.89 (d, J = 4.1 Hz, 1 H), 6.19 (dd, J = 5.0, 9.3 Hz, 1 H), 4.70-4.62 (m, 1 H), 4.09 (dd, J = 6.1, 8.0 Hz, 1 H), 3.84 (s, 3 H), 3.83 (s, 3 H), 3.81-3.64 (m, 3 H), 3.35 (dd, J = 5.8, 14.3 Hz, 1 H), 2.73*$^{or\,\dagger}$ (dd, J = 2.7, 7.6 Hz, 1 H), 2.69 (dd, J = 2.6, 8.1 Hz, 1 H), 2.61 (dd, J = 1.6, 6.5 Hz, 1 H), 2.58*$^{or\,\dagger}$ (dd, J = 1.7, 6.4 Hz, 1 H), 2.54-2.41 (m, 3 H), 1.84-1.76 (m, 2 H), 1.75-1.67 (m, 2 H), 1.63-1.45 (m, 3 H), 1.37-1.28*$^{or\,\dagger}$ (m, 1 H), 1.23-1.06*$^{or\,\dagger}$ (m, 1 H), * and † refer to different isomers (arbitrarily assigned). LCMS (Method 1): [MH+] = 728 at 2.35 min. |
| 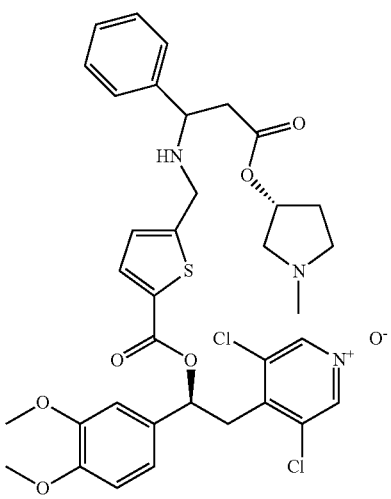 [(1S)-2-(3,5-dichloro-1-oxido-pyridin-1-ium-4-yl)-1-(3,4-dimethoxyphenyl)ethyl] 5-[[[3-[(3R)-1-methylpyrrolidin-3-yl]oxy-3-oxo-1-phenyl-propyl]amino]methyl]thiophene-2-carboxylate | Example 104 | Intermediate 3 and Intermediate 108 | $^1$H NMR (400 MHz, CD$_3$CN): δ 8.17 (s, 2 H), 7.65 (d, J = 3.9 Hz, 1 H), 7.36-7.25 (m, 5 H), 7.05-6.85 (m, 4 H), 6.18-6.14 (m, 1 H), 5.06-4.99 (m, 1 H), 4.07-4.02 (m, 1 H), 3.81 (s, 3 H), 3.78 (s, 3 H), 3.77-3.61 (m, 3 H), 3.31 (dd, J = 5.3, 14.1 Hz, 1 H), 2.71-2.47 (m, 6 H), 2.22 (s, 3 H), 2.12-2.04 (m, 2 H), 1.71-1.63$^{\dagger\,or\,*}$ (m, 1 H), 1.61-1.52$^{\dagger\,or\,*}$ (m, 1 H), * and † refer to different diastereomers (arbitrarily assigned). LCMS (Method 2): [MH+] = 714 at 2.93 min. |

Example 105

[(1S)-2-(3,5-dichloro-1-oxido-pyridin-1-ium-4-yl)-1-(3,4-dimethoxyphenyl)ethyl]5-[[ethyl-[2-oxo-1-phenyl-2-[(3R)-quinuclidin-3-yl]oxy-ethyl]amino]methyl]thiophene-2-carboxylate

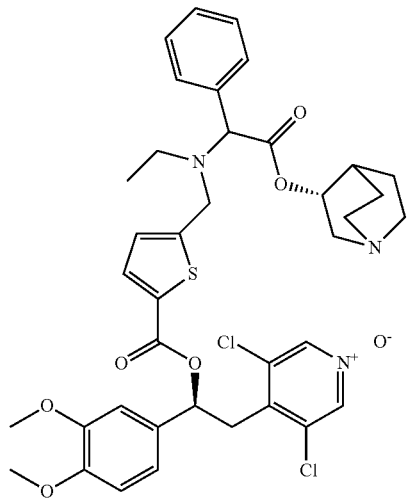

A suspension of [(1S)-2-(3,5-dichloro-1-oxido-pyridin-1-ium-4-yl)-1-(3,4-dimethoxyphenyl)ethyl]5-[[[2-oxo-1-phenyl-2-[(3R)-quinuclidin-3-yl]oxy-ethyl]amino]methyl]thiophene-2-carboxylate (Example 42, 100 mg, 0.12 mmol) in trifluoroethanol (0.5 mL) was heated at 40 C for 5 min. Acetaldehyde (11 µL, 0.19 mmol) was added followed by acetic acid (7 µL, 0.12 mmol) and the reaction mixture was heated at 40° C. for 18 h. Sodium triacetoxyborohydride (52 mg, 0.25 mmol) was added and the mixture was heated at 40° C. for 2 h. The solvent was evaporated in vacuo and the residue was partitioned between ethyl acetate (1 mL) and water (1 mL). 0.2N aqueous HCl was added to adjust pH=1. The acidic aqueous phase was washed with ethyl acetate (3×1 mL), sodium chloride (1 g) was added to the aqueous phase that was extracted with chloroform (3×1 mL), the combined chloroform extracts were filtered through a phase separator and the solvent was removed in vacuo. The combined ethyl acetate washes were extracted with 0.2N HCl (1 mL), water (1 mL). The aqueous phases were combined, saturated with solid sodium chloride and extracted with chloroform (3×1 mL). The crude product from both extractions was combined and purification by preparative HPLC gave the title compound as an off-white solid (23 mg, 24%).

$^1$H NMR (400 MHz, DMSO): δ 8.62*$^{or}$ † (s, 2H), 8.61*$^{or}$ † (s, 2H), 7.70 (d, J=3.8 Hz, 1 H), 7.51-7.36 (m, 5H), 7.08-7.05 (m, 2H), 7.03 (s, 2H), 6.17 (ddd, J=2.2, 4.4, 9.8 Hz, 1H), 4.88 (dd, J=3.8, 7.8 Hz, 1H), 4.75 (d, J=8.3 Hz, 1H), 4.03 (dd, J=5.2, 16.0 Hz, 1H), 3.88 (d, J=16.2 Hz, 1H), 3.83*$^{or}$ † (s, 3H), 3.83*$^{or}$ † (s, 3H), 3.80 (s, 3H), 3.68-3.60 (m, 1H), 3.37-3.30 (m, 1H), 3.26-3.14 (m, 1H), 2.75-2.58 (m, 6H), 2.50-2.46 (m, 1H), 2.04-1.97*$^{or}$ † (m, 1H), 1.97-1.89*$^{or}$ † (m, 1H), 1.71-1.54 (m, 3H), 1.40-1.28 (m, 1H), 1.09-1.02 (m, 3H), † and * refer to different isomers (arbitrarily assigned). LCMS (Method 1): [MH+]=754 at 2.87 min.

Example 106

[(3R)-quinuclidin-3-yl]2-[[5-[(1S)-2-(3,5-dichloro-1-oxido-pyridin-1-ium-4-yl)-1-(3,4-dimethoxyphenyl)ethoxy]carbonyl-2-thienyl]methyl]-3,4-dihydro-1H-isoquinoline-1-carboxylate

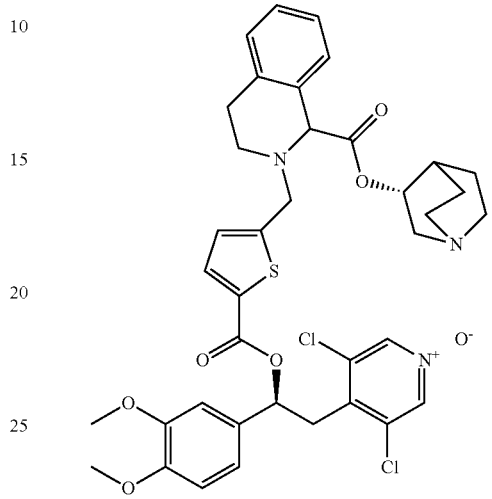

o a solution of O2-tert-butyl O1-[(3R)-quinuclidin-3-yl] 3,4-dihydro-1H-isoquinoline-1,2-dicarboxylate (440 mg, 1.14 mmol) in ethyl acetate (1.42 mL) was added 4N HCl/dioxane (1.42 mL, 5.70 mmol) and the resultant solution was stirred at room temperature for 18 h. The solvent was removed in vacuo to give a white solid. The crude material (200 mg, 0.56 mmol) was dissolved in acetonitrile (5 mL) and [(1S)-2-(3,5-dichloro-1-oxido-pyridin-1-ium-4-yl)-1-(3,4-dimethoxyphenyl)ethyl]5-formylthiophene-2-carboxylate (270 mg, 0.56 mmol) was added followed by acetic acid (67 µL, 1.12 mmol). The resultant solution was stirred at room temperature for 18 h. The solvent was removed in vacuo and the residue azeotroped with toluene. The residue was rediluted with acetonitrile (5 mL) and sodium triacetoxyborohydride (237 mg, 1.12 mmol) was added and the resultant solution was stirred at room temperature for 18 h. The solvent was removed in vacuo and the residue was taken up in water (20 mL) and ethyl acetate (20 mL). The layers were separated and the aqueous phase was extracted with ethyl acetate (2×20 mL). The combined organic phases were extracted with 0.2 N aqueous hydrochloric acid (40 mL) and water (40 mL). The aqueous extracts were combined and sodium chloride (6 g) was added. The mixture was extracted with chloroform (3×30 mL) and the combined organic extracts were passed through a hydrophobic fit and the solvent was removed in vacuo. Purification of the crude material by preparative HPLC afforded the title compound (77 mg, 18%) as a pale yellow solid.

$^1$H NMR (400 MHz, DMSO): δ 8.59† $^{or}$* (s, 2H), 8.58† $^{or}$* (s, 2H), 7.76 (dd, J=1.7, 3.8 Hz, 1H), 7.32-7.22 (m, 4H), 7.16 (t, J=3.3 Hz, 1H), 7.07-7.05 (m, 1H), 7.02 (s, 2H), 6.21-6.15 (m, 1H), 4.82-4.75 (m, 1H), 4.67 (d, J=8.6 Hz, 1H), 4.14 (d, J=10.2 Hz, 2H), 3.82 (s, 3H), 3.80 (s, 3H), 3.63 (dd, J=9.5, 14.2 Hz, 1H), 3.34 (dd, J=5.6, 14.5 Hz, 1H), 3.22-3.09 (m, 1H), 2.99-2.86 (m, 2H), 2.84-2.64 (m, 6H), 2.50-2.37 (m, 1H), 1.95-1.90 (m, 1H), 1.71-1.59 (m, 2H), 1.56-1.48 (m, 1H), 1.40-1.29 (m, 1H), † and * refer to different isomers (arbitrarily assigned). LCMS (Method 2): [MH+]=752 at 3.97 min.

Example 107
[(3R)-quinuclidin-3-yl]2-[2-[5-[2-[(1S)-2-(3,5-dichloro-1-oxido-pyridin-1-ium-4-yl)-1-(3,4-dimethoxyphenyl)ethoxy]-2-oxo-ethyl]-2-thienyl]ethylamino]-2-phenyl-acetate
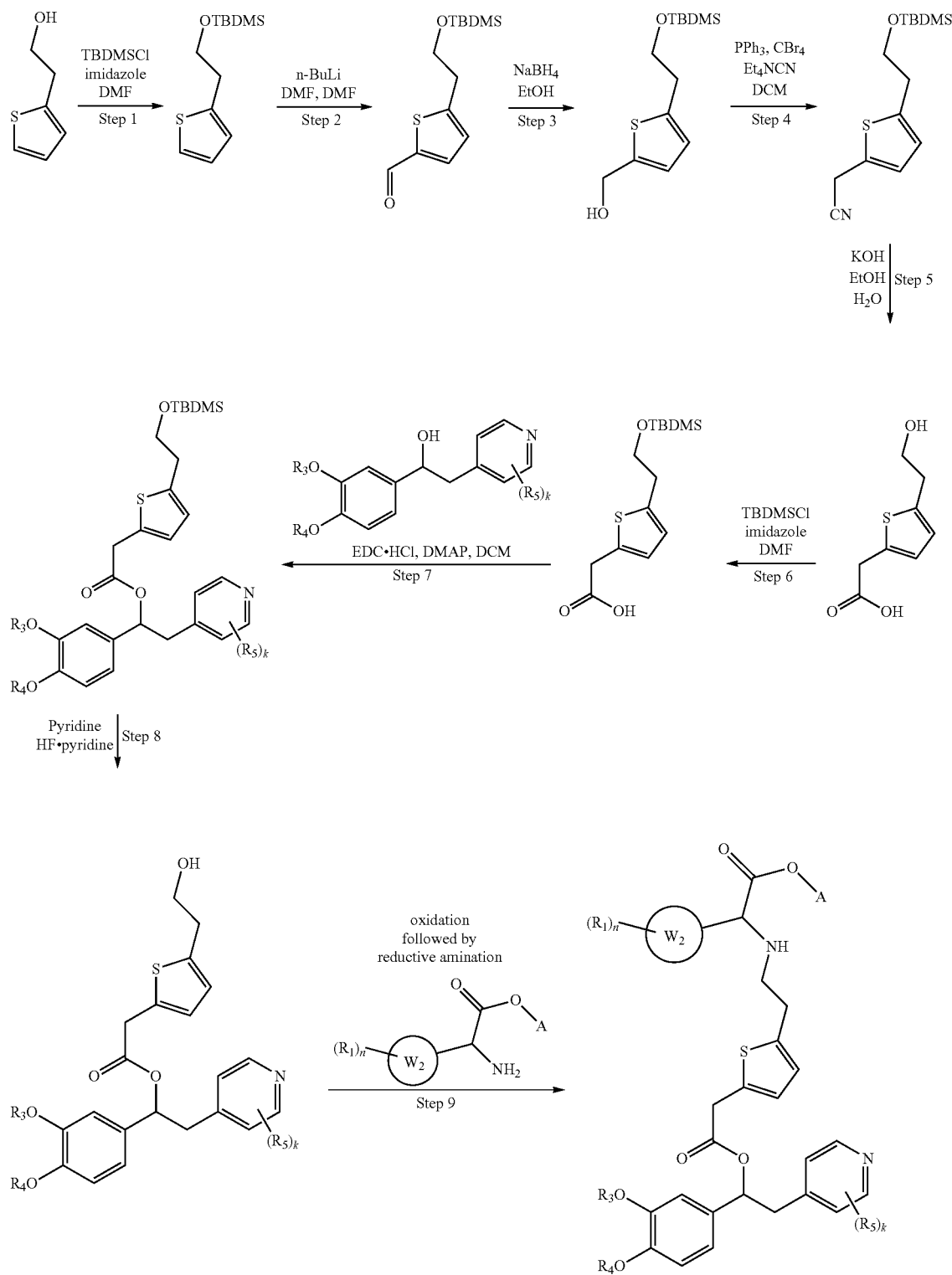

Step 1: Preparation of tert-butyl-dimethyl-[2-(2-thienyl)ethoxy]silane

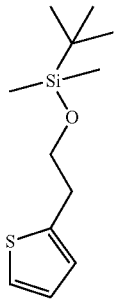

Tert-butyldimethylsilyl chloride (15.5 g, 103 mmol) was added portionwise to a solution of 2-(2-thienyl)ethanol (11.0 g, 85.9 mmol) and imidazole (7.0 g, 103 mmol) in N,N-dimethylformamide (35 mL). The resultant solution was stirred at room temperature for 18 h. The reaction mixture was partitioned between ethyl acetate (30 mL) and water (30 mL) and the organic phases washed with water (3×50 mL). The organic phase was dried over sodium sulfate, filtered and concentrated in vacuo. The residue was purified by silica gel chromatography, eluting with 1-4% ethyl acetate in iso-hexane to give the title compound as a colourless oil (20 g, 96%).

LCMS (Method 2): [MH+]=243 at 4.95 min

Step 2: Preparation of 5-[2-[tert-butyl(dimethyl)silyl]oxyethyl]thiophene-2-carbaldehyde

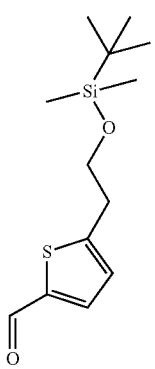

To a solution of tert-butyl-dimethyl-[2-(2-thienyl)ethoxy] (16.0 g, 66.1 mmol) in tetrahydrofuran (250 mL) was added n-butyl lithium (2.5 M in hexanes, 30 mL) dropwise at −78° C. The reaction mixture was allowed to warm to 0° C. and stirred for 1 h. The reaction mixture was then cooled to −78° C. and N,N-dimethylformamide was added over 10 minutes. The mixture was allowed to warm to room temperature and stirred for 18 h. The reaction mixture was partitioned between ethyl acetate (100 mL) and water (100 mL) and the organic phases washed with water (3×100 mL). The organic phase was dried over sodium sulfate, filtered and concentrated in vacuo to give the title compound as a yellow oil (17.8 g, quantitative yield).

LCMS (Method 2): [MH+]=271 at 4.60 min.

Step 3: Preparation of [5-[2-[tert-butyl(dimethyl)silyl]oxyethyl]-2-thienyl]methanol

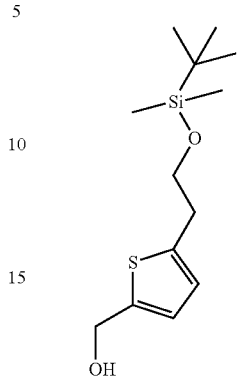

To a solution of 5-[2-[tert-butyl(dimethyl)silyl]oxyethyl]thiophene-2-carbaldehyde (17.8 g, 66.1 mmol) in ethanol (180 mL) at 0° C. was added sodium borohydride (2.5 g, 66.1 mmol). The resulting solution was stirred at 0° C. for 1.5 h. The reaction solution was concentrated in vacuo and partitioned between ethyl acetate (30 mL) and brine (30 mL). The organic phase was over sodium sulphate, filtered and concentrated in vacuo to give the title compound as a yellow oil (17.5 g, 97%) which was used in the next step without further purification.

$^1$H NMR (400 MHz, CDCl$_3$): δ 6.79 (d, J=3.3 Hz, 1H), 6.65 (d, J=3.5 Hz, 1H), 4.72 (d, J=6.1 Hz, 2H), 3.78 (t, J=6.7 Hz, 2H), 2.95 (t, J=6.7 Hz, 2H), 1.59 (t, J=6.1 Hz, 1H), 0.86 (s, 9H), 0.00 (s, 6H).

Step 4: Preparation of 2-[5-[2-[tert-butyl(dimethyl)silyl]oxyethyl]-2-thienyl]acetonitrile

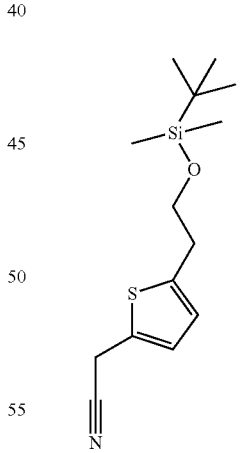

To a solution of [5-[2-[tert-butyl(dimethyl)silyl]oxyethyl]-2-thienyl]methanol (5.47 g, 20.1 mmol) in dichloromethane (10 mL) was added triphenylphosphine (6.52 g, 24.9 mmol) and tetrabromomethane (7.86 g, 23.7 mmol) in one portion at 0° C. The resulting solution was stirred at room temperature for 1 h. The reaction mixture was cooled to 0° C. and tetraethylammonium cyanide (4.48 g, 28.7 mmol) was added. The mixture was diluted with dichloromethane (5 mL) and stirred at room temperature for 40 minutes. The reaction mixture was partitioned between dichloromethane (30 mL) and brine (30 mL). The organic phase was passed through a hydrophobic frit and concentrated in vacuo. The residue was purified by silica gel chromatography, eluting with 0-6% ethyl acetate in iso-hexane to give the title compound as a yellow oil (3.8 g, 67%).

LCMS (Method 2): [MH+]=282 at 4.63 min.

Step 5: Preparation of 2-[5-(2-hydroxyethyl)-2-thienyl]acetic acid

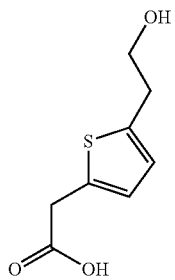 [SMILES: O=C(O)Cc1ccc(CCO)s1]

A solution of 2-[5-[2-[tert-butyl(dimethyl)silyl]oxyethyl]-2-thienyl]acetonitrile (3.0 g, 10.7 mmol) in ethanol (30 mL) was added to a stirred solution of potassium hydroxide (1.2 g, 21.4 mmol) in water (30 mL). The resultant mixture was stirred at 100° C. for 4 h. The reaction mixture was concentrated in vacuo and the residue partitioned between ethyl acetate (30 mL) and brine (30 mL). The aqueous layer was cooled with ice and acidified with concentrated HCl until pH 1 was reached. The aqueous solution was then extracted with ethyl acetate (3×30 mL). The combine organic phases were washed with brine (30 mL), dried over magnesium sulfate, filtered and concentrated in vacuo to give the title compound as a yellow solid (1.35 g, 68%) which was used in the next step without further purification.

LCMS (Method 1): [MH+]=187 at 2.49 min.

Step 6: Preparation of 2-[5-[2-[tert-butyl(dimethyl)silyl]oxyethyl]-2-thienyl]acetic acid

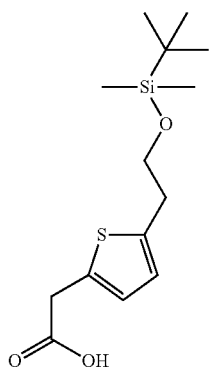 [SMILES: CC(C)(C)[Si](C)(C)OCCc1ccc(CC(=O)O)s1]

To a solution of 2-[5-(2-hydroxyethyl)-2-thienyl]acetic acid (1.35 g, 7.26 mmol) and imidazole (1.04 g, 15.25) in N,N-dimethylformamide (18 mL) was added tert-butyldimethylsilyl chloride (2.29 g, 15.25 mmol) over 20 minutes. The resultant solution was stirred at room temperature for one hour. Tetrahydrofuran (18 mL) was then added and reaction solution cooled to 0° C. A solution of potassium carbonate (1.04 g, 7.6 mmol) in water (18 mL) was added and the solution stirred for 20 minutes. The reaction solution was then partitioned between ethyl acetate and brine. The organic phases were combined, dried over magnesium sulfate, filtered and concentrated in vacuo. The residue was purified by silica gel chromatography, eluting with 0-50% ethyl acetate in iso-hexane to give the title compound as a yellow oil (500 mg, 23%).

LCMS (Method 2): [MH+]=301 at 2.97 min.

Step 7: Preparation of [(1S)-2-(3,5-dichloro-1-oxido-pyridin-1-ium-4-yl)-1-(3,4-dimethoxyphenyl)ethyl] 2-[5-[2-[tert-butyl(dimethyl)silyl]oxyethyl]-2-thienyl]acetate

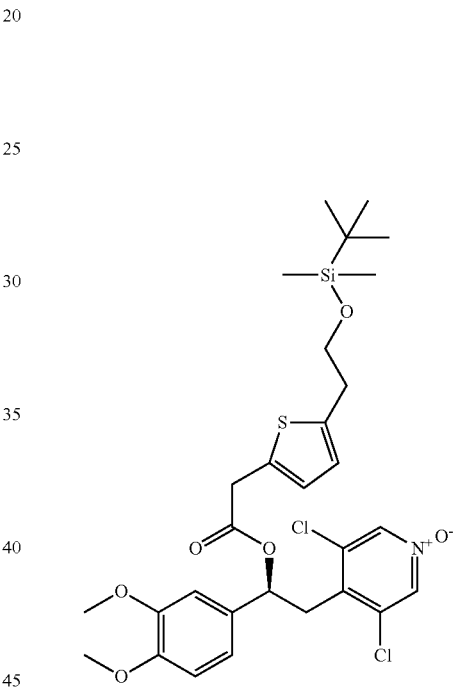

To a solution of 2-[5-(2-hydroxyethyl)-2-thienyl]acetic acid (500 mg, 1.67 mmol) in dichloromethane (20 mL) was added 4-(dimethylamino)-pyridine (102 mg, 0.84 mmol), (S)-3,5-dichloro-4-(2-(3,4-dimethoxyphenyl)-2-hydroxyethyl)pyridine 1-oxide (687 mg, 2.00 mmol) and N-(3-dimethylaminopropyl)-N'-ethylcarbodiimide hydrochloride (640 mg, 3.34 mmol). The resultant solution was stirred at room temperature for 18 h. The reaction mixture was washed with saturated aqueous sodium bicarbonate, the organic phase passed through a hydrophobic frit and concentrated in vacuo. The residue was purified by silica gel chromatography, eluting with 0-100% ethyl acetate in iso-hexane to give the title compound as a yellow oil (800 mg, 76%).

LCMS (Method 1): [MH+]=626 at 4.70 min.

Step 8: Preparation of [(1S)-2-(3,5-dichloro-1-oxido-pyridin-1-ium-4-yl)-1-(3,4-dimethoxyphenyl)ethyl] 2-[5-(2-hydroxyethyl)-2-thienyl]acetate

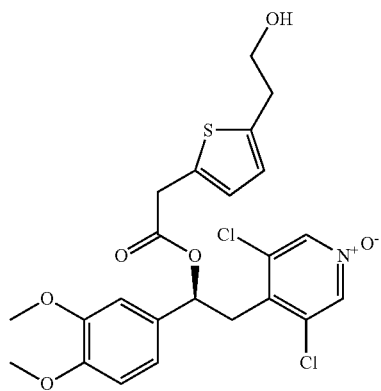

To a solution of [(1S))-2-(3,5-dichloro-1-oxido-pyridin-1-ium-4-yl)-1-(3,4-dimethoxyphenyl)ethyl]2-[5-[2-[tert-butyl(dimethyl)silyl]oxyethyl]-2-thienyl]acetate (780 mg, 1.25 mmol) in pyridine (10 mL) was added HF.pyridine (70%) (1.7 mL) and the resultant solution was stirred at room temperature for 4 h. The reaction solution was cooled to 0° C. and quenched by the dropwise addition of saturated aqueous sodium bicarbonate. The solution was extracted with ethyl acetate (3×10 mL). The organic phases were combined, passed through a hydrophobic fit and concentrated in vacuo to give the title compound as a yellow solid (520 mg, 81%) which was used in the next step without further purification.

LCMS (Method 2): [MH+]=512 at 2.59 min

Step 9: Preparation of [(3R)-quinuclidin-3-yl]2-[2-[5-[2-[(1S)-2-(3,5-dichloro-1-oxido-pyridin-1-ium-4-yl)-1-(3,4-dimethoxyphenyl)ethoxy]-2-oxo-ethyl]-2-thienyl]ethylamino]-2-phenyl-acetate (Example 107)

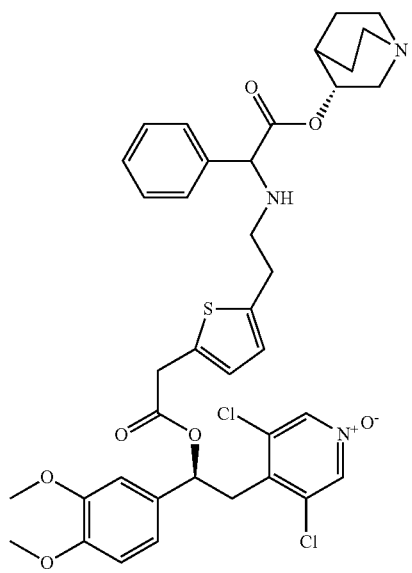

To a solution of [(1S)-2-(3,5-dichloro-1-oxido-pyridin-1-ium-4-yl)-1-(3,4-dimethoxyphenyl)ethyl]2-[5-(2-hydroxyethyl)-2-thienyl]acetate (80 mg, 0.16 mmol) in dichloromethane (2 mL) at −78° C. was added Dess-Martin periodinane (81 mg, 0.19 mmol). The reaction solution was stirred at room temperature for 30 minutes. The reaction solution was washed with saturated aqueous sodium thiosulfate (5 mL) followed by saturated aqueous sodium bicarbonate (5 mL). The organic phase was passed through a hydrophobic fit and concentrated in vacuo to give [(1S)-2-(3,5-dichloro-1-oxido-pyridin-1-ium-4-yl)-1-(3,4-dimethoxyphenyl)ethyl]2-[5-(2-oxoethyl)-2-thienyl]acetate as a brown solid (76 mg, 94%) which was used in the next step without further purification. To a solution of the crude residue (199 mg, 0.39 mmol) in ethanol (20 mL) was added [(3R)-quinuclidin-3-yl]2-amino-2-phenyl-acetate hydrochloride salt (260 mg, 0.78 mmol), triethylamine (219 μL, 1.56 mmol) and acetic acid (102 μL, 0.78 mmol). The resultant solution was stirred at room temperature for 20 minutes. Sodium borohydride (49 mg, 0.78 mmol) was then added and the resultant solution was stirred at room temperature for 18 h. The solvent was removed in vacuo and the residue taken up in water (20 mL) and ethyl acetate (20 mL). The layers were separated and the aqueous phase was extracted with ethyl acetate (2×20 mL). The combined organic phases were extracted with 0.2 N aqueous hydrochloric acid (40 mL) and water (40 mL). The aqueous extracts were combined and sodium chloride (6 g) was added. The mixture was extracted with chloroform (3×30 mL) and the combined organic extracts were passed through a hydrophobic fit and the solvent was removed in vacuo. Purification of the crude material by preparative HPLC afforded the title compound (42 mg, 14%) as an off-white solid.

$^1$H NMR (400 MHz, CD$_3$CN): δ 8.18 (s, 2H), 7.43-7.31 (m, 5H), 6.94 (d, J=1.6 Hz, 1H), 6.92 (d, J=1.6 Hz, 2H), 6.68 (s, 2H), 6.01 (dd, J=4.9, 9.7 Hz, 1H), 4.79-4.72 (m, 1H), 4.45 (d, J=2.6 Hz, 1H), 3.81 (s, 3H), 3.79 (s, 3H), 3.74 (s, 2H), 3.53 (dd, J=9.7, 14.0 Hz, 1H), 3.23 (dd, J=4.7, 14.0 Hz, 1H), 3.17-3.10$^{† or *}$ (m, 1H), 3.09-3.02$^{† or *}$ (m, 1H), 2.97-2.91 (m, 2H), 2.86-2.79 (m, 1H), 2.75-2.55 (m, 6H), 1.81-1.77 (m, 1H), 1.70-1.46 (m, 3H), 1.42-1.17 (m, 2H). † and * refer to different isomers (arbitrarily assigned).

LCMS (Method 1): [MH+]=754 at 2.39 min.

Example 108
[(1S)-2-(3,5-dichloro-1-oxido-pyridin-1-ium-4-yl)-1-(3,4-dimethoxyphenyl)ethyl]5-[2-[[2-oxo-1-phenyl-2-[(3R)-quinuclidin-3-yl]oxy-ethyl]amino]ethyl]thiophene-2-carboxylate
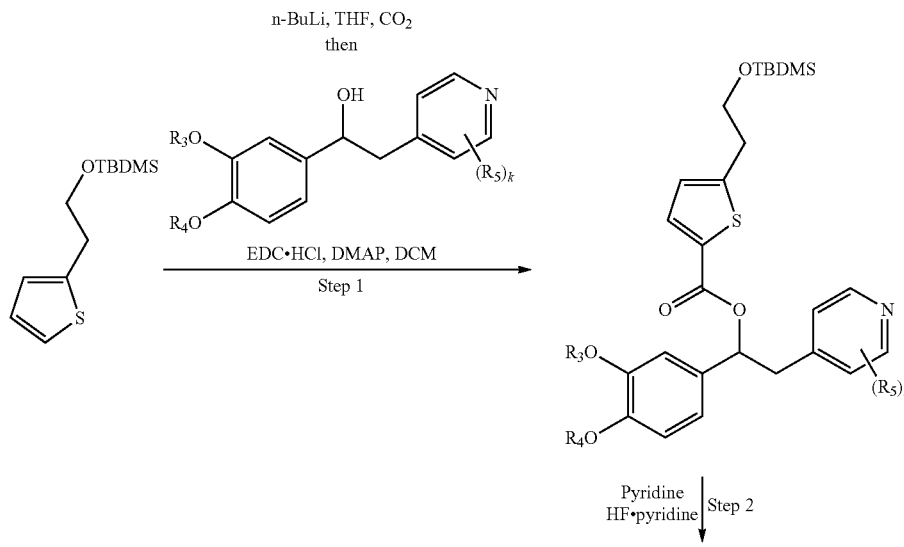
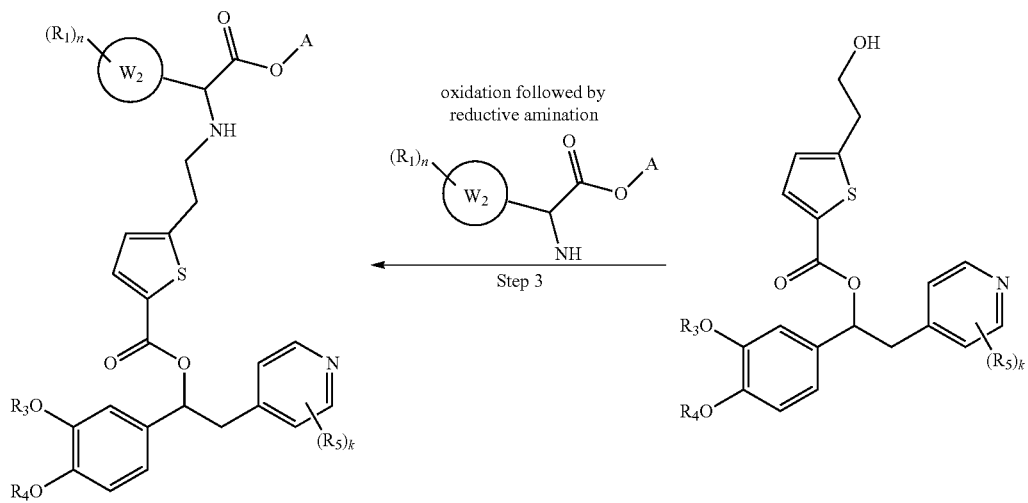

Step 1: Preparation of [(1S)-2-(3,5-dichloro-1-oxido-pyridin-1-ium-4-yl)-1-(3,4-dimethoxyphenyl)ethyl] 5-[2-[tert-butyl(dimethyl)silyl]oxyethyl]thiophene-2-carboxylate

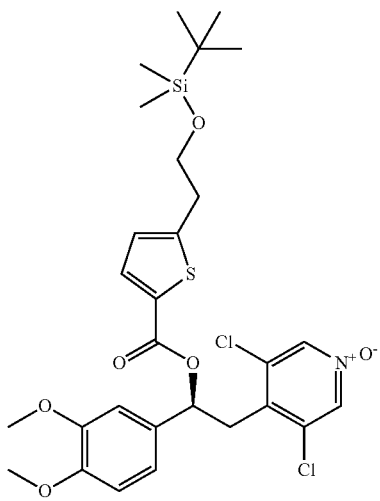

To a solution of tert-butyl-dimethyl-[2-(2-thienyl)ethoxy]silane synthesized as described in example 107 step 1 (485 mg, 2 mmol) in tetrahydrofuran (7.5 mL) at −78° C. was added n-butyl lithium (0.92 mL, 2.5 M in hexanes, 2.3 mmol) dropwise. The mixture was allowed to warm to 0° C. and allowed to stir at 0° C. for 1 h. The mixture was cooled to −78° C. and then gaseous $CO_2$ was bubbled through the mixture for 30 minutes. The mixture was quenched by the addition of saturated aqueous ammonium chloride solution (15 mL), and allowed to warm to room temperature. The mixture was extracted with ethyl acetate (3×15 mL) and the combined organic fractions were passed through a hydrophobic fit and the solvent was removed by evaporation under reduced pressure. The residue was taken up in dichloromethane (4 mL) and (1S)-2-(3,5-dichloro-1-oxido-pyridin-1-ium-4-yl)-1-(3,4-dimethoxyphenyl)ethanol I-1/A (585 mg, 1.7 mmol), 4-dimethylaminopyridine (110 mg, 0.9 mmol) and N-(3-dimethylaminopropyl)-N'-ethylcarbodiimide hydrochloride (658 mg, 3.4 mmol) were added. The mixture was stirred at room temperature for 18 h and saturated aqueous sodium bicarbonate solution (10 mL) and dichloromethane (10 mL) were added. The layers were separated, and the organic phase was passed through a hydrophobic fit and the solvent was removed by evaporation under reduced pressure. The crude material was purified by silica gel column chromatography, eluting with 0-100% dichloromethane/10% methanol in dichloromethane, to afford the title compound (710 mg, 68%) as a brown oil.

$^1$H NMR (400 MHz, $CDCl_3$): δ 8.13 (s, 2H), 7.63 (d, J=3.8 Hz, 1H), 7.01-6.96 (m, 2H), 6.86-6.81 (m, 2H), 6.23 (dd, J=4.5, 10.1 Hz, 1H), 3.90 (s, 3H), 3.88 (s, 3H), 3.83 (t, J=6.8 Hz, 2H), 3.66 (dd, J=9.7, 14.0 Hz, 1H), 3.31 (dd, J=5.1, 13.6 Hz, 1H), 3.02 (t, J=6.3 Hz, 2H), 0.90 (s, 9H), 0.03 (s, 6H). LCMS (Method 2): [MH+]=612 at 4.19 min.

Step 2: Preparation of [(1S)-2-(3,5-dichloro-1-oxido-pyridin-1-ium-4-yl)-1-(3,4-dimethoxyphenyl)ethyl] 5-(2-hydroxyethyl)thiophene-2-carboxylate

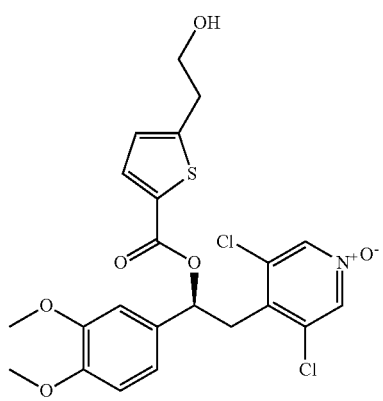

To a solution of [(1S)-2-(3,5-dichloro-1-oxido-pyridin-1-ium-4-yl)-1-(3,4-dimethoxyphenyl)ethyl]5-[2-[tert-butyl(dimethyl)silyl]oxyethyl]thiophene-2-carboxylate (400 mg, 0.65 mmol) in pyridine (6 mL) was added HF.pyridine (0.88 ml) dropwise and the mixture was allowed to stir at room temperature for 3 h. The mixture was cooled to 0° C. and quenched with saturated aqueous sodium bicarbonate solution (10 mL). The mixture was extracted with ethyl acetate (3×30 mL) and the combined organic fractions were passed through a hydrophobic fit and the solvent was removed by evaporation under reduced pressure. The crude material was purified by silica gel column chromatography, eluting with 0-100% ethyl acetate/10% methanol in ethyl acetate, to afford the title compound (323 mg, quantitative yield) as a white solid.

$^1$H NMR (400 MHz, $CDCl_3$): δ 8.14 (s, 2H), 7.64 (d, J=3.8 Hz, 1H), 7.02-6.96 (m, 2H), 6.87-6.84 (m, 2H), 6.21 (dd, J=4.7, 9.7 Hz, 1H), 3.90 (s, 3H), 3.90-3.84 (m, 2H), 3.88 (s, 3H), 3.67 (dd, J=9.9, 13.9 Hz, 1H), 3.31 (dd, J=4.9, 14.3 Hz,

1H), 3.07 (t, J=6.3 Hz, 2H), 2.43 (t, J=5.1 Hz, 1H). LCMS (Method 1): [MH+]=498 at 3.24 min.

Step 3: Preparation of [(1S)-2-(3,5-dichloro-1-oxido-pyridin-1-ium-4-yl)-1-(3,4-dimethoxyphenyl)ethyl] 5-[2-[[2-oxo-1-phenyl-2-[(3R)-quinuclidin-3-yl]oxy-ethyl]amino]ethyl]thiophene-2-carboxylate
(Example 108)

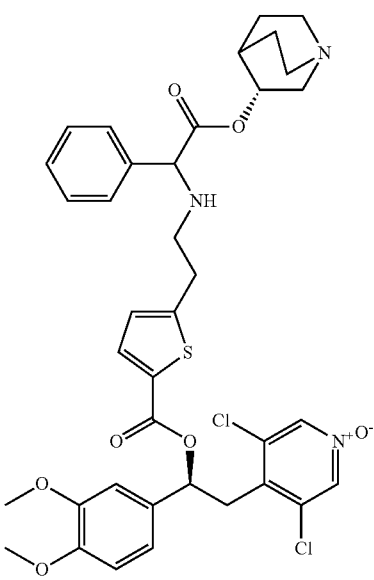

To a mixture of [(1S)-2-(3,5-dichloro-1-oxido-pyridin-1-ium-4-yl)-1-(3,4-dimethoxyphenyl)ethyl]5-(2-hydroxy-ethyl)thiophene-2-carboxylate (100 mg, 0.2 mmol) in dichloromethane (2 mL) at −78° C. was added Dess-Martin periodinane (102 mg, 0.24 mmol) and the mixture was allowed to warm to room temperature. The mixture was stirred at room temperature for 30 min. and then quenched with saturated aqueous sodium thiosulfate solution (5 mL) and then saturated aqueous sodium carbonate solution (5 mL). The mixture was extracted with dichloromethane (3×10 mL) and the organic phases were passed through a hydrophobic frit and the solvent was removed by evaporation under reduced pressure. The residue was taken up in ethanol (8 mL) and [(3R)-quinuclidin-3-yl]2-amino-2-phenyl-acetate hydrochloride salt I-111 (154 mg, 0.44 mmol) was added followed by triethylamine (0.12 ml, 0.81 mmol) and acetic acid (0.025 mL, 0.44 mmol). Sodium cyanoborohydride (94 mg, 0.44 mmol) was added and the mixture was stirred at room temperature for 66 h. The solvent was removed by evaporation under reduced pressure and the residue was partitioned between 1 N aqueous hydrochloric acid (3 mL) and ethyl acetate (3 mL). The layers were separated and the aqueous phase was extracted with ethyl acetate (2×3 mL). The aqueous phase was basified with saturated aqueous sodium bicarbonate solution and then extracted with ethyl acetate (2×3 mL). The combined organic fractions were extracted with 1 N aqueous hydrochloric acid (2 mL). Brine (2 mL) was added and the aqueous layer was extracted with chloroform (5 mL and 2 mL). The combined organic fractions were washed with saturated aqueous sodium bicarbonate solution (2 mL), passed through a hydrophobic frit and the solvent was removed by evaporation under reduced pressure. Purification by preparative HPLC gave the title compound as an off-white solid (26 mg, 18% over two steps).

$^1$H NMR (400 MHz, CD$_3$CN): δ 8.18 (s, 2H), 7.67 (d, J=3.5 Hz, 1H), 7.43-7.30 (m, 5H), 7.07-7.01 (m, 2H), 6.97-6.90 (m, 2H), 6.17 (dd, J=4.3, 9.6 Hz, 1H), 4.78-4.71 (m, 1H), 4.45*$^{or}$$^†$ (s, 1H), 4.44*$^{or}$$^†$ (s, 1H), 3.83 (s, 3H), 3.82 (s, 3H), 3.66 (dd, J=9.6, 14.1 Hz, 1H), 3.33 (dd, J=4.5, 14.1 Hz, 1H), 3.16-3.04 (m, 1H), 3.02 (t, J=6.4 Hz, 2H), 2.93-2.85 (m, 1H), 2.82-2.73 (m, 1H), 2.71-2.23 (m, 5H), 1.93-1.74 (m, 1H), 1.68-1.25 (m, 3H), 1.22-1.13 (m, 1H), * and † refer to different isomers, NH not observed. LCMS (Method 1): [MH+]=740 at 2.40 min.

Example 47 and Example 48

Single diastereoisomers of [(1S)-2-(3,5-dichloro-1-oxido-pyridin-1-ium-4-yl)-1-(3,4-dimethoxyphenyl)ethyl]5-[[[1-(3-fluorophenyl)-2-oxo-2-[(3R)-quinuclidin-3-yl]oxy-ethyl]amino]methyl]thiophene-2-carboxylate (diastereoisomers 1 and 2)

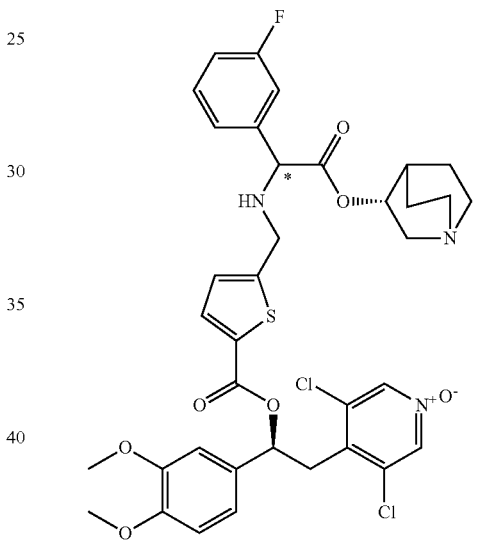

Purification of the 1:1 mixture of diastereoisomers of Example 37 by chiral preparative SFC afforded the single diastereoisomers.

Title compound (example 47, single diastereoisomer 1) was obtained as white solid (50.4 mg, 13%).

$^1$H NMR (400 MHz, DMSO-d$_6$): δ 8.52-8.48 (m, 2H), 7.62 (d, J=3.78 Hz, 1H), 7.37-7.30 (m, 1H), 7.26-7.18 (m, 2H), 7.08 (td, J=8.58, 2.57 Hz, 1H), 6.95 (d, J=3.00 Hz, 2H), 6.91 (s, 2H), 6.07 (dd, J=9.63, 4.42 Hz, 1H), 4.66-4.61 (m, 1H), 4.43 (d, J=9.34 Hz, 1H), 3.82 (d, J=5.96 Hz, 2H), 3.70 (s, 3H), 3.69 (s, 3H), 3.63 (dt, J=9.40, 6.14 Hz, 1H), 3.51 (dd, J=14.20, 9.68 Hz, 1H), 3.40-3.25 (m, 1H), 2.99 (dd, J=14.62, 8.24 Hz, 1H), 2.63-2.46 (m, 5H), 1.68 (d, J=4.12 Hz, 1H), 1.56-1.12 (m, 4H). LCMS (Method 1): [MH+]=744 at 2.70 min. Chiral Analysis (Method 23) at 10.82 min.

Title compound (Example 48, single diastereoisomer 2) was obtained as white solid (58.2 mg, 16%).

$^1$H NMR (400 MHz, DMSO-d$_6$): δ 8.48 (s, 2H), 7.61 (d, J=3.79 Hz, 1H), 7.39-7.32 (m, 1H), 7.27-7.17 (m, 2H), 7.09 (td, J=8.59, 2.55 Hz, 1H), 6.99-6.87 (m, 4H), 6.07 (dd, J=9.69, 4.30 Hz, 1H), 4.62-4.57 (m, 1H), 4.42 (d, J=9.38 Hz, 1H), 3.88-3.76 (m, 2H), 3.72-3.59 (m, 7H), 3.51 (dd, J=14.20, 9.72 Hz, 1H), 3.21 (d, J=4.97 Hz, 1H), 2.92 (dd, J=14.71, 8.14 Hz, 1H), 2.55-2.45 (m, 2H), 2.38-2.27 (m, 1H), 2.09 (d, J=14.65 Hz, 1H), 1.79 (s, 1H), 1.54-1.42 (m, 2H), 1.22-1.07 (m, 1H), 0.97 (d, J=6.10 Hz, 1H). NH not visible.
Chiral Analysis (Method 23) at 12.48 min.

Compounds reported in the table herebelow were made according to the analogous procedures as that described for the preparation of Example 47 and Example 48. Chiral preparative SFC or chiral preparative HPLC afforded the single diastereoisomers.

| Compound | Example number | Precursor | Analytical Data |
|---|---|---|---|
| Single diastereoisomer of [(1S)-2-(3,5-dichloro-1-oxido-pyridin-1-ium-4-yl)-1-(3,4-dimethoxyphenyl)ethyl] 5-[[(2-oxo-1-phenyl-2-quinuclidin-3-yloxy-ethyl)amino]methyl]thiophene-2-carboxylate | Example 49 | Example 42 | $^1$H NMR (400 MHz, DMSO): δ 8.56 (s, 2 H), 7.69 (d, J = 3.78 Hz, 1 H), 7.44-7.27 (m, 5 H), 7.04-6.96 (m, 4 H), 6.14 (dd, J = 9.62, 4.40 Hz, 1 H), 4.72-4.67 (m, 1 H), 4.43 (d, J = 9.25 Hz, 1 H), 3.88 (d, J = 5.70 Hz, 2 H), 3.76 (d, J = 5.87 Hz, 6 H), 3.63-3.53 (m, 2 H), 3.06 (dd, J = 14.61, 8.26 Hz, 1 H), 2.59 (t, J = 10.90 Hz, 5 H), 2.45 (s, 1 H), 1.73 (s, 1 H), 1.61-1.13 (m, 4 H). LCMS (Method 1): [MH+] = 728 at 2.63 min. Chiral analysis (Method 24) at 13.8 min. |
| Single diastereoisomer of [(1S)-2-(3,5-dichloro-1-oxido-pyridin-1-ium-4-yl)-1-(3,4-dimethoxyphenyl)ethyl] 5-[[(2-oxo-1-phenyl-2-quinuclidin-3-yloxy-ethyl)amino]methyl]thiophene-2-carboxylate | Example 50 | Example 42 | $^1$H NMR (400 MHz, DMSO-d$_6$): δ 8.55 (s, 2 H), 7.68 (d, J = 3.78 Hz, 1 H), 7.45-7.29 (m, 5 H), 7.05-6.95 (m, 4 H), 6.14 (dd, J = 9.59, 4.29 Hz, 1 H), 4.67 (d, J = 7.13 Hz, 1 H), 4.43 (d, J = 9.21 Hz, 1 H), 3.89 (t, J = 5.31 Hz, 2 H), 3.77 (d, J = 8.16 Hz, 6 H), 3.59 (t, J = 11.05 Hz, 2 H), 3.00-2.93 (m, 1 H), 2.57 (s, 4 H), 2.36 (d, J = 20.05 Hz, 1 H), 2.15 (d, J = 14.66 Hz, 1 H), 1.86 (s, 1 H), 1.60-1.50 (m, 2 H), 1.44 (s, 1 H), 1.24 (s, 1 H). LCMS (Method 1): [MH+] = 726 at 2.66 min. Chiral analysis (Method 24) at 15.81 min. |

-continued

| Compound | Example number | Precursor | Analytical Data |
|---|---|---|---|
| 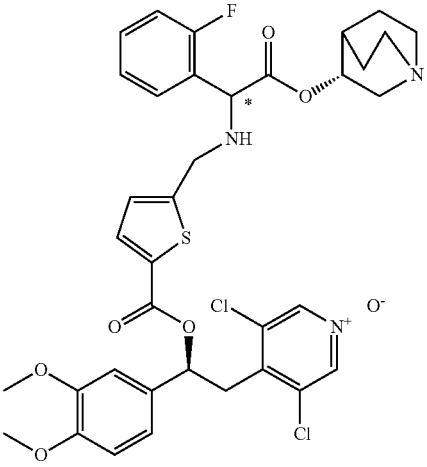<br>Single diastereoisomer of [(1S)-2-(3,5-dichloro-1-oxido-pyridin-1-ium-4-yl)-1-(3,4-dimethoxyphenyl)ethyl] 5-[[[1-(2-fluorophenyl)-2-oxo-2-[(3R)-quinuclidin-3-yl]oxy-ethyl]amino]methyl]thiophene-2-carboxylate | Example 51 | Example 38 | $^1$H NMR (400 MHz, DMSO) δ 8.55 (s, 2 H), 7.69 (d, J = 3.8 Hz, 1 H), 7.56-7.50 (m, 1 H), 7.41-7.34 (m, 1 H), 7.26-7.18 (m, 2 H), 7.04-6.96 (m, 4 H), 6.14 (dd, J = 9.6, 4.4 Hz, 1 H), 4.77-4.67 (m, 2 H), 3.94 (d, J = 5.1 Hz, 2 H), 3.77 (s, 3 H), 3.76 (s, 3 H), 3.67-3.53 (m, 2 H), 3.30 (dd, J = 14.1, 4.4 Hz, 1 H), 3.09 (dd, J = 14.8, 8.4 Hz, 1 H), 2.70-2.44 (m, 5 H), 1.77-1.71 (m, 1 H), 1.59-1.38 (m, 2 H), 1.31-1.09 (m, 2 H). LCMS (Method 1): [MH+] = 744 at 2.68 min. Chiral analysis (Method 21) at 17.65 min |
| 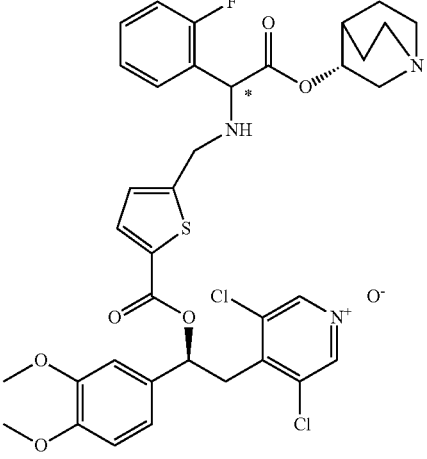<br>Single diastereoisomer of [(1S)-2-(3,5-dichloro-1-oxido-pyridin-1-ium-4-yl)-1-(3,4-dimethoxyphenyl)ethyl] 5-[[[1-(2-fluorophenyl)-2-oxo-2-[(3R)-quinuclidin-3-yl]oxy-ethyl]amino]methyl]thiophene-2-carboxylate | Example 52 | Example 38 | $^1$H NMR (400 MHz, DMSO): δ 8.55 (s, 2 H), 7.68 (d, J = 3.8 Hz, 1 H), 7.57-7.51 (m, 1 H), 7.42-7.35 (m, 1 H), 7.28-7.19 (m, 2 H), 7.04-6.96 (m, 4 H), 6.14 (dd, J = 9.6, 4.3 Hz, 1 H), 4.72-4.66 (m, 2 H), 3.94 (d, J = 5.6 Hz, 2 H), 3.77 (s, 3 H), 3.76 (s, 3 H), 3.67-3.53 (m, 2 H), 3.30 (dd, J = 14.3, 4.5 Hz, 1 H), 3.01 (dd, J = 14.8, 8.1 Hz, 1 H), 2.69-2.44 (m, 3 H), 2.38-2.27 (m, 1 H), 2.20-2.12 (m, 1 H), 1.89-1.82 (m, 1 H), 1.60-1.39 (m, 3 H), 1.28-1.14 (m, 1 H). LCMS (Method 1): [MH+] = 744 at 2.67 min. Chiral analysis (Method 21) at 15.61 min. |

| Compound | Example number | Precursor | Analytical Data |
|---|---|---|---|
| Single diastereoisomer of [(1S)-1-[3-(cyclopropylmethoxy)-4-(difluoromethoxy)phenyl]-2-(3,5-dichloro-1-oxido-pyridin-1-ium-4-yl)ethyl] 5-[[[1-(2-fluorophenyl)-2-oxo-2-[(3R)-quinuclidin-3-yl]oxy-ethyl]amino]methyl]thiophene-2-carboxylate | Example 53 | Example 40 | $^1$H NMR (400 MHz, DMSO): δ 8.55 (s, 2 H), 7.70 (d, J = 3.8 Hz, 1 H), 7.55-7.50 (m, 1 H), 7.40-7.34 (m, 1 H), 7.28-7.16 (m, 4 H), 7.08-7.01 (m, 2 H), 7.07 (t, J = 74.7 Hz, 1 H), 6.14 (dd, J = 9.5, 4.4 Hz, 1 H), 4.75-4.67 (m, 2 H), 3.95-3.89 (m, 4 H), 3.60 (dd, J = 14.1, 9.7 Hz, 1 H), 3.36 (dd, J = 14.2, 4.3 Hz, 1 H), 3.06 (ddd, J = 14.8, 8.4, 2.0 Hz, 1 H), 2.69-2.32 (m, 5 H), 1.76-1.69 (m, 1 H), 1.57-1.06 (m, 5 H), 0.59-0.53 (m, 2 H), 0.37-0.32 (m, 2 H). NH not visible. LCMS (Method 1): [MH+] = 820 at 3.02 min. Chiral analysis (Method 11) at 8.36 min |
| Single diastereoisomer of [(1S)-1-[3-(cyclopropylmethoxy)-4-(difluoromethoxy)phenyl]-2-(3,5-dichloro-1-oxido-pyridin-1-ium-4-yl)ethyl] 5-[[[1-(2-fluorophenyl)-2-oxo-2-[(3R)-quinuclidin-3-yl]oxy-ethyl]amino]methyl]thiophene-2-carboxylate | Example 54 | Example 40 | $^1$H NMR (400 MHz, DMSO): δ 8.55 (s, 2 H), 7.70 (d, J = 3.8 Hz, 1 H), 7.53 (td, J = 7.5, 1.7 Hz, 1 H), 7.42-7.35 (m, 1 H), 7.27-7.16 (m, 4 H), 7.08-7.00 (m, 2 H), 7.07 (t, J = 74.6 Hz, 1 H), 6.14 (dd, J = 9.5, 4.3 Hz, 1 H), 4.71-4.66 (m, 2 H), 3.96-3.90 (m, 4 H), 3.65 (dd, J = 14.2, 9.7 Hz, 1 H), 3.39 (dd, J = 14.2, 4.1 Hz, 1 H), 3.00 (ddd, J = 14.8, 8.0, 2.3 Hz, 1 H), 2.69-2.26 (m, 4 H), 2.19-2.12 (m, 1 H), 1.89-1.84 (m, 1 H), 1.60-1.15 (m, 5 H), 0.59-0.53 (m, 2 H), 0.37-0.31 (m, 2 H). NH not visible. LCMS (Method 1): [MH+] = 820 at 3.01 min. Chiral analysis (Method 11) at 6.78 min |

| Compound | Example number | Precursor | Analytical Data |
|---|---|---|---|
| Single diastereoisomer of [(1S)-1-[3-(cyclopropylmethoxy)-4-(difluoromethoxy)phenyl]-2-(3,5-dichloro-1-oxido-pyridin-1-ium-4-yl)ethyl] 5-[[[2-oxo-1-phenyl-2-[(3R)-quinuclidin-3-yl]oxy-ethyl]amino]methyl]thiophene-2-carboxylate | Example 55 | Example 41 | ¹H NMR (400 MHz, DMSO): δ 8.55 (s, 2 H), 7.70 (d, J = 3.8 Hz, 1 H), 7.45-7.17 (m, 7 H), 7.08-7.01 (m, 2 H), 7.07 (t, J = 74.6 Hz, 1 H), 6.14 (dd, J = 9.5, 4.3 Hz, 1 H), 4.70-4.65 (m, 1 H), 4.44-4.41 (m, 1 H), 3.95-3.86 (m, 4 H), 3.57 (dd, J = 16.2, 9.7 Hz, 1 H), 3.31 (dd, J = 14.2, 4.2 Hz, 1 H), 3.03-2.94 (m, 1 H), 2.70-2.32 (m, 4 H), 2.19-2.13 (m, 1 H), 1.90-1.84 (m, 1 H), 1.62-1.15 (m, 5 H), 0.57-0.55 (m, 2 H), 0.36-0.34 (m, 2 H). NH not visible. LCMS (Method 1): [MH+] = 802 at 2.94 min. Chiral analysis (Method 25) at 6.64 min |
| Single diastereoisomer of [(1S)-1-[3-(cyclopropylmethoxy)-4-(difluoromethoxy)phenyl]-2-(3,5-dichloro-1-oxido-pyridin-1-ium-4-yl)ethyl] 5-[[[2-oxo-1-phenyl-2-[(3R)-quinuclidin-3-yl]oxy-ethyl]amino]methyl]thiophene-2-carboxylate | Example 56 | Example 41 | ¹H NMR (400 MHz, DMSO): δ 8.56 (s, 2 H), 7.71 (d, J = 3.8 Hz, 1 H), 7.44-7.16 (m, 7 H), 7.09-7.00 (m, 2 H), 7.07 (t, J = 74.6 Hz, 1 H), 6.14 (dd, J = 9.3, 4.2 Hz, 1 H), 4.74-4.65 (m, 1 H), 4.43 (d, J = 9.3 Hz, 1 H), 3.92 (d, J = 6.9 Hz, 2 H), 3.90-3.85 (m, 2 H), 3.57 (dd, J = 14.1, 9.7 Hz, 1 H), 3.32 (dd, J = 14.1, 4.1 Hz, 1 H), 3.09-3.02 (m, 1 H), 2.69-2.32 (m, 5 H), 1.75-1.70 (m, 1 H), 1.56-1.07 (m, 5 H), 0.59-0.53 (m, 2 H), 0.37-0.32 (m, 2 H). NH not visible. LCMS (Method 1): [MH+] = 802 at 2.94 min. Chiral analysis (Method 25) at 8.22 min. |

| Compound | Example number | Precursor | Analytical Data |
|---|---|---|---|
| 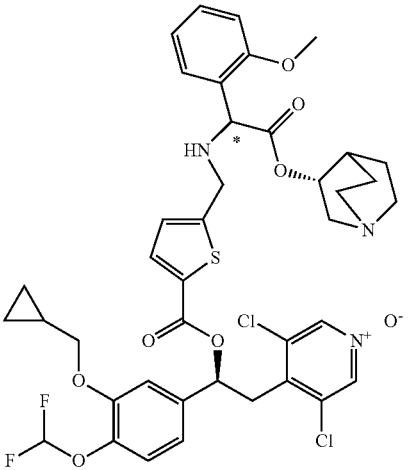<br>Single diastereoisomer of [(1S)-1-[3-(cyclopropylmethoxy)-4-(difluoromethoxy)phenyl]-2-(3,5-dichloro-1-oxido-pyridin-1-ium-4-yl)ethyl] 5-[[[1-(2-methoxyphenyl)-2-oxo-2-[(3R)-quinuclidin-3-yl]oxy-ethyl]amino]methyl]thiophene-2-carboxylate formate salt | Example 57 | Example 39 | $^1$H NMR (400 MHz, DMSO): δ 8.55 (s, 2 H), 8.22 (s, 1 H), 7.70 (d, J = 3.8 Hz, 1 H), 7.38-7.15 (m, 4 H), 7.08-6.92 (m, 4 H), 7.07 (t, J = 74.8 Hz, 1 H), 6.14 (dd, J = 9.4, 4.4 Hz, 1 H), 4.73-4.68 (m, 1 H), 4.65 (s, 1 H), 3.95-3.89 (m, 4 H), 3.73 (s, 3 H), 3.56 (dd, J = 14.7, 9.7 Hz, 1 H), 3.40-2.84 (m, 3 H), 2.70-2.31 (m, 5 H), 1.78-1.00 (m, 5 H), 0.59-0.53 (m, 2 H), 0.37-0.32 (m, 2 H). LCMS (Method 1): [MH+] = 832 at 2.80 min. Chiral analysis (Method 29) at 13.23 min. |
| 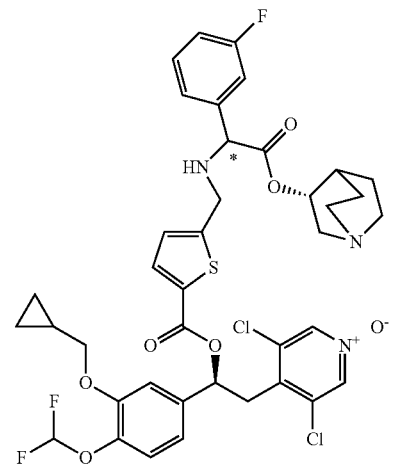<br>Single diastereoisomer of [(1S)-1-[3-(cyclopropylmethoxy)-4-(difluoromethoxy)phenyl]-2-(3,5-dichloro-1-oxido-pyridin-1-ium-4-yl)ethyl] 5-[[[1-(3-fluorophenyl)-2-oxo-2-[(3R)-quinuclidin-3-yl]oxy-ethyl]amino]methyl]thiophene-2-carboxylate | Example 58 | Example 43 | $^1$H NMR (400 MHz, DMSO): 8.56 (s, 2 H), 7.70 (d, J = 3.8 Hz, 1 H), 7.45-7.37 (m, 1 H), 7.32-7.11 (m, 5 H), 7.08-7.01 (m, 2 H), 7.07 (t, J = 74.6 Hz, 1 H), 6.14 (dd, J = 9.5, 4.4 Hz, 1 H), 4.73-4.68 (m, 1 H), 4.50 (d, J = 9.1 Hz, 1 H), 3.95-3.85 (m, 5 H), 3.73-2.43 (m, 7 H), 1.78-0.80 (m, 6 H), 0.59-0.53 (m, 2 H), 0.37-0.33 (m, 2 H). NH not visible. LCMS (Method 1): [MH+] = 820 at 3.03 min. Chiral analysis (Method 29) at 8.69 min |

| Compound | Example number | Precursor | Analytical Data |
|---|---|---|---|
| Single diastereoisomers of [(1S)-2-(3,5-dichloro-1-oxido-pyridin-1-ium-4-yl)-1-(3,4-dimethoxyphenyl)ethyl] 5-[[[1-(2-fluorophenyl)-2-[(1-methyl-4-piperidyl)oxy]-2-oxo-ethyl]amino]methyl]thiophene-2-carboxylate | Example 109 | Example 45 | $^1$H NMR (400 MHz, CD$_3$CN): δ 8.19 (s, 2 H), 7.69 (d, J = 3.5 Hz, 1 H), 7.47-7.35 (m, 2 H), 7.24-7.20 (m, 1 H), 7.18-7.12 (m, 1 H), 7.07-7.00 (m, 2 H), 6.98-6.93 (m, 2 H), 6.18 (dd, J = 4.5, 9.6 Hz, 1 H), 4.84-4.78 (m, 1 H), 4.69 (s, 1 H), 3.99 (d, J = 4.0 Hz, 2 H), 3.83 (s, 3 H), 3.82 (s, 3 H), 3.67 (dd, J = 9.6, 14.1 Hz, 1 H), 3.34 (dd, J = 4.7, 14.3 Hz, 1 H), 2.47-2.42 (m, 2 H), 2.36-2.21 (m, 3 H), 2.15 (s, 3 H), 1.88-1.83 (m, 1 H), 1.78-1.61 (m, 2 H), 1.55-1.46 (m, 1 H). LCMS (Method 1): [MH+] = 732 at 2.63 min. Chiral analysis (Method 13) at 3.05 min. |
| Single diastereoisomers of [(1S)-2-(3,5-dichloro-1-oxido-pyridin-1-ium-4-yl)-1-(3,4-dimethoxyphenyl)ethyl] 5-[[[1-(2-fluorophenyl)-2-[(1-methyl-4-piperidyl)oxy]-2-oxo-ethyl]amino]methyl]thiophene-2-carboxylate | Example 110 | Example 45 | $^1$H NMR (400 MHz, CD$_3$CN): δ 8.18 (s, 2 H), 7.69 (d, J = 3.8 Hz, 1 H), 7.47-7.34 (m, 2 H), 7.23 (dd, J = 7.5, 7.5 Hz, 1 H), 7.16 (dd, J = 9.5, 9.5 Hz, 1 H), 7.07-7.01 (m, 2 H), 6.98-6.93 (m, 2 H), 6.17 (dd, J = 4.5, 9.6 Hz, 1 H), 4.85-4.78 (m, 1 H), 4.69 (s, 1 H), 3.99 (d, J = 6.8 Hz, 2 H), 3.83 (s, 3 H), 3.82 (s, 3 H), 3.67 (dd, J = 9.6, 14.1 Hz, 1 H), 3.34 (dd, J = 4.5, 14.1 Hz, 1 H), 2.46-2.45 (m, 1 H), 2.37-2.18 (m, 4 H), 2.16 (s, 3 H), 1.90-1.83 (m, 1 H), 1.81-1.60 (m, 2 H), 1.56-1.46 (m, 1 H). LCMS (Method 1): [MH+] = 732 at 2.63 min. Chiral analysis (Method 13) at 3.99 min. |

-continued

| Compound | Example number | Precursor | Analytical Data |
|---|---|---|---|
| Single diastereoisomer of [(1S)-2-(3,5-dichloro-1-oxido-pyridin-1-ium-4-yl)-1-(3,4-dimethoxyphenyl)ethyl] 5-[[[2-[(3R)-1-methylpyrrolidin-3-yl]oxy-2-oxo-1-phenyl-ethyl]amino]methyl]thiophene-2-carboxylate | Example 111 | Example 87 | $^1$H NMR (400 MHz, CDCl$_3$): δ 8.14 (s, 2 H), 7.64 (d, J = 3.8 Hz, 1 H), 7.37-7.29 (m, 5 H), 7.00-6.97 (m, 2 H), 6.87-6.84 (m, 2 H), 6.22 (dd, J = 4.4, 10.0 Hz, 1 H), 5.24-5.21 (m, 1 H), 4.43 (s, 1 H), 3.91-3.90 (m, 2 H), 3.89 (s, 3 H), 3.87 (s, 3 H), 3.66 (dd, J = 10.0, 14.0 Hz, 1 H), 3.31 (dd, J = 4.4, 14.0 Hz, 1 H), 2.69-2.67 (m, 3 H), 2.29 (s, 3 H), 2.27-2.25 (m, 1 H), 2.19-2.14 (m, 1 H), 1.69-1.58 (m, 2 H). LCMS (Method 1): [MH+] = 700 at 2.59 min. Chiral analysis (Method 9) at 11.66 min. |
| Single diastereoisomer of [(1S)-2-(3,5-dichloro-1-oxido-pyridin-1-ium-4-yl)-1-(3,4-dimethoxyphenyl)ethyl] 5-[[[2-[(3R)-1-methylpyrrolidin-3-yl]oxy-2-oxo-1-phenyl-ethyl]amino]methyl]thiophene-2-carboxylate | Example 112 | Example 87 | $^1$H NMR (400 MHz, CDCl$_3$): δ 8.13 (s, 2 H), 7.64 (d, J = 3.8 Hz, 1 H), 7.37-7.29 (m, 5 H), 7.01-6.96 (m, 2 H), 6.86-6.84 (m, 2 H), 6.22 (dd, J = 4.4, 9.7 Hz, 1 H), 5.23-5.17 (m, 1 H), 4.43 (s, 1 H), 3.91-3.90 (m, 2 H), 3.89 (s, 3 H), 3.87 (s, 3 H), 3.67 (dd, J = 9.9, 13.9 Hz, 1 H), 3.31 (dd, J = 4.5, 13.9 Hz, 1 H), 2.77-2.70 (m, 1 H), 2.64-2.62 (m, 1 H), 2.48 (dd, J = 2.1, 11.0 Hz, 1 H), 2.34-2.29 (m, 2 H), 2.28 (s, 3 H), 1.86-1.80 (m, 2 H). LCMS (Method 1): [MH+] = 700 at 2.56 min. Chiral analysis (Method 9) at 13.61 min. |

| Compound | Example number | Precursor | Analytical Data |
|---|---|---|---|
| single diastereoisomer 1 of epimeric mixture 1 of [1-[3-(cyclopentoxy)-4-methoxy-phenyl]-2-(3,5-dichloro-1-oxido-pyridin-1-ium-4-yl)ethyl] 5-[[[2-oxo-1-phenyl-2-[(3R)-quinuclidin-3-yl]oxy-ethyl]amino]methyl]thiophene-2-carboxylate | Example 113 | Example 71 | $^1$H NMR (400 MHz, CD$_3$CN): δ 8.20 (s, 2 H), 7.69 (d, J = 3.5 Hz, 1 H), 7.43-7.34 (m, 5 H), 7.02-6.91 (m, 4 H), 6.15 (dd, J = 4.8, 9.3 Hz, 1 H), 4.83-4.75 (m, 2 H), 4.45 (s, 1 H), 3.96-3.94 (m, 2 H), 3.79 (s, 3 H), 3.65 (dd, J = 9.3, 14.1 Hz, 1 H), 3.34 (dd, J = 4.8, 14.1 Hz, 1 H), 3.16-3.08 (m, 1 H), 2.73-2.54 (m, 5 H), 1.98-1.84 (m, 3 H), 1.83-1.68 (m, 5 H), 1.67-1.57 (m, 3 H), 1.53-1.36 (m, 2 H), 1.30-1.18 (m, 1 H). LCMS (Method 1): [MH+] = 780 at 2.83 min. Chiral analysis (Method 15) at 5.64 min. |
| single diastereoisomer 2 of epimeric mixture 1 of [1-[3-(cyclopentoxy)-4-methoxy-phenyl]-2-(3,5-dichloro-1-oxido-pyridin-1-ium-4-yl)ethyl] 5-[[[2-oxo-1-phenyl-2-[(3R)-quinuclidin-3-yl]oxy-ethyl]amino]methyl]thiophene-2-carboxylate | Example 114 | Example 71 | $^1$H NMR (400 MHz, CD$_3$CN): δ 8.18 (s, 2 H), 7.69 (d, J = 3.8 Hz, 1 H), 7.44-7.35 (m, 5 H), 7.00-6.91 (m, 4 H), 6.15 (dd, J = 4.9, 9.3 Hz, 1 H), 4.84-4.76 (m, 2 H), 4.46 (s, 1 H), 3.99-3.96 (m, 2 H), 3.80 (s, 3 H), 3.64 (dd, J = 9.3, 14.1 Hz, 1 H), 3.35 (dd, J = 4.9, 14.0 Hz, 1 H), 3.10-3.08 (m, 1 H), 2.74-2.61 (m, 3 H), 2.55-2.46 (m, 1 H), 2.37-2.34 (m, 1 H), 1.99-1.81 (m, 4 H), 1.80-1.60 (m, 9 H), 1.42-1.29 (m, 1 H). LCMS (Method 1): [MH+] = 780 at 2.84 min. Chiral analysis (Method 15) at 6.83 min. |

-continued

| Compound | Example number | Precursor | Analytical Data |
|---|---|---|---|
| Single diasteroisomer of [(1S)-2-(3,5-dichloro-1-oxido-pyridin-1-ium-4-yl)-1-(3,4-dimethoxyphenyl)ethyl] 5-[[methyl-[2-oxo-1-phenyl-2-[(3R)-quinuclidin-3-yl]oxy-ethyl]amino]methyl]thiophene-2-carboxylate | Example 115 | Example 81 | $^1$H NMR (400 MHz, CD$_3$CN): δ 8.19 (s, 2 H), 7.68 (d, J = 3.8 Hz, 1 H), 7.50 (d, J = 6.8 Hz, 2 H), 7.46-7.37 (m, 3 H), 7.08-7.02 (m, 2 H), 6.97-6.94 (m, 2 H), 6.18 (dd, J = 4.5, 9.6 Hz, 1 H), 4.88-4.83 (m, 1 H), 4.46 (s, 1 H), 3.91 (d, J = 15.2 Hz, 1 H), 3.84 (s, 3 H), 3.84-3.78 (m, 4 H), 3.68 (dd, J = 9.7, 14.0 Hz, 1 H), 3.35 (dd, J = 4.5, 14.1 Hz, 1 H), 3.19 (dd, J = 8.3, 14.7 Hz, 1 H), 2.79-2.64 (m, 4 H), 2.64-2.55 (m, 1 H), 2.30 (s, 3H), 1.94-1.88 (m, 1 H), 1.70-1.50 (m, 3 H), 1.37-1.29 (m, 1 H). LCMS (Method 1): [MH+] = 740 at 2.79 min. Chiral analysis (Method 15) at 3.08 min. |
| Single diasteroisomer of [(1S)-2-(3,5-dichloro-1-oxido-pyridin-1-ium-4-yl)-1-(3,4-dimethoxyphenyl)ethyl] 5-[[methyl-[2-oxo-1-phenyl-2-[(3R)-quinuclidin-3-yl]oxy-ethyl]amino]methyl]thiophene-2-carboxylate | Example 116 | Example 81 | $^1$H NMR (400 MHz, CD$_3$CN): δ 8.19 (s, 2 H), 7.67 (d, J = 3.8 Hz, 1 H), 7.51 (d, J = 7.8 Hz, 2 H), 7.46-7.38 (m, 3 H), 7.08-7.01 (m, 2 H), 6.97-6.93 (m, 2 H), 6.18 (dd, J = 4.5, 9.6 Hz, 1 H), 4.86-4.81 (m, 1 H), 4.44 (s, 1 H), 3.90-3.85 (m, 4 H), 3.83-3.77 (m, 4 H), 3.68 (dd, J = 9.9, 14.1 Hz, 1 H), 3.35 (dd, J = 4.5, 13.9 Hz, 1 H), 3.12 (ddd, J = 2.1, 8.2, 14.5 Hz, 1 H), 2.75-2.60 (m, 4 H), 2.46 (d, J = 14.4 Hz, 1 H), 2.30 (s, 3 H), 1.94-1.88 (m, 1 H), 1.76-1.50 (m, 3 H), 1.41-1.29 (m, 1 H). LCMS (Method 1): [MH+] = 740 at 2.8 min. Chiral analysis (Method 15) at 2.27 min. |

-continued

| Compound | Example number | Precursor | Analytical Data |
|---|---|---|---|
| single diastereoisomer 1 of epimeric mixture 2 of [1-[3-(cyclopentoxy)-4-methoxy-phenyl]-2-(3,5-dichloro-1-oxido-pyridin-1-ium-4-yl)ethyl] 5-[[[2-oxo-1-phenyl-2-[(3R)-quinuclidin-3-yl]oxy-ethyl]amino]methyl]thiophene-2-carboxylate | Example 117 | Example 72 | $^1$H NMR (400 MHz, CD$_3$CN): δ 8.18 (s, 2 H), 7.69 (dd, J = 4.3, 4.3 Hz, 1 H), 7.44-7.34 (m, 5 H), 7.00-6.91 (m, 4 H), 6.15 (dd, J = 4.9, 9.2 Hz, 1 H), 4.85-4.76 (m, 2 H), 4.46 (s, 1 H), 3.99-3.95 (m, 2 H), 3.80 (s, 3 H), 3.68-3.59 (m, 1 H), 3.35 (dd, J = 4.8, 14.1 Hz, 1 H), 3.17-3.09 (m, 1 H), 2.73-2.55 (m, 5 H), 1.98-1.94 (m, 3 H), 1.81-1.70 (m, 5 H), 1.67-1.57 (m, 3 H), 1.51-1.45 (m, 2 H), 1.26-1.16 (m, 1 H). LCMS (Method 1): [MH+] = 780 at 2.84 min. Chiral analysis (Method 15) at 2.57 min. |
| single diastereoisomer 2 of epimeric mixture 2 of [1-[3-(cyclopentoxy)-4-methoxy-phenyl]-2-(3,5-dichloro-1-oxido-pyridin-1-ium-4-yl)ethyl] 5-[[[2-oxo-1-phenyl-2-[(3R)-quinuclidin-3-yl]oxy-ethyl]amino]methyl]thiophene-2-carboxylate | Example 118 | Example 72 | $^1$H NMR (400 MHz, CD$_3$CN): δ 8.18 (s, 2 H), 7.69 (d, J = 3.8 Hz, 1 H), 7.44-7.41 (m, 5 H), 7.02-6.92 (m, 4 H), 6.16 (dd, J = 4.8, 9.3 Hz, 1 H), 4.90-4.79 (m, 2 H), 4.48 (s, 1 H), 4.04-3.93 (m, 2 H), 3.80 (s, 3 H), 3.64 (dd, J = 9.3, 14.1 Hz, 1 H), 3.34 (dd, J = 4.8, 14.1 Hz, 1 H), 3.24-3.16 (m, 1 H), 2.86-2.76 (m, 3 H), 2.74-2.47 (m, 2 H), 1.98-1.94 (m, 3 H), 1.80-1.70 (m, 5 H), 1.65-1.58 (m, 4 H), 1.51-1.41 (m, 1 H), 1.29-1.16 (m, 1 H). LCMS (Method 1): [MH+] = 780 at 2.85 min. Chiral analysis (Method 15) at 3.49 min. |

| Compound | Example number | Precursor | Analytical Data |
|---|---|---|---|
| Single diastereoisomer of [(3R)-quinuclidin-3-yl] 2-[[5-[(1S)-2-(3,5-dichloro-1-oxido-pyridin-1-ium-4-yl)-1-(3,4-dimethoxyphenyl)ethoxy]carbonyl-2-thienyl]methyl]-3,4-dihydro-1H-isoquinoline-1-carboxylate | Example 119 | Example 106 | $^1$H NMR (400 MHz, CDCl$_3$): δ 8.13 (s, 2 H), 7.66 (d, J = 3.5 Hz, 1 H), 7.22-7.14 (m, 4 H), 7.00-6.93 (m, 3 H), 6.84 (d, J = 8.3 Hz, 1 H), 6.22 (dd, J = 4.5, 9.6 Hz, 1 H), 4.87-4.82 (m, 1 H), 4.62 (s, 1 H), 4.14-4.02 (m, 2 H), 3.88 (s, 3 H), 3.87 (s, 3 H), 3.65 (dd, J = 9.9, 13.9 Hz, 1 H), 3.53-3.45 (m, 1 H), 3.33-3.22 (m, 2 H), 3.01-2.74 (m, 7 H), 2.73-2.65 (m, 1 H), 2.00-1.99 (m, 1 H), 1.78-1.64 (m, 1 H), 1.59-1.50 (m, 1 H), 1.44-1.35 (m, 1 H), 1.27-1.24 (m, 1 H). LCMS (Method 2): [MH+] = 752 at 3.39 min. Chiral analysis (Method 20) at 8.25 min. |
| Single diastereoisomer of [(3R)-quinuclidin-3-yl] 2-[[5-[(1S)-2-(3,5-dichloro-1-oxido-pyridin-1-ium-4-yl)-1-(3,4-dimethoxyphenyl)ethoxy]carbonyl-2-thienyl]methyl]-3,4-dihydro-1H-isoquinoline-1-carboxylate | Example 120 | Example 106 | $^1$H NMR (400 MHz, CDCl$_3$): δ 8.11 (s, 2 H), 7.65 (d, J = 3.8 Hz, 1 H), 7.24-7.16 (m, 4 H), 7.00-6.92 (m, 3 H), 6.85 (d, J = 8.1 Hz, 1 H), 6.22 (dd, J = 4.5, 9.9 Hz, 1 H), 4.88-4.83 (m, 1 H), 4.63 (s, 1 H), 4.13-4.00 (m, 2 H), 3.88 (s, 3 H), 3.87 (s, 3 H), 3.65 (dd, J = 9.6, 13.9 Hz, 1 H), 3.55-3.47 (m, 1 H), 3.33-3.18 (m, 2 H), 3.00-2.74 (m, 7 H), 2.63 (d, J = 14.9 Hz, 1 H), 2.05-1.99 (m, 1 H), 1.75-1.67 (m, 1 H), 1.57-1.55 (m, 1 H), 1.42-1.38 (m, 1 H), 1.29-1.26 (m, 1 H). LCMS (Method 2): [MH+] = 752 at 3.35 min. Chiral analysis (Method 20) at 10.70 min. |

| Compound | Example number | Precursor | Analytical Data |
|---|---|---|---|
| 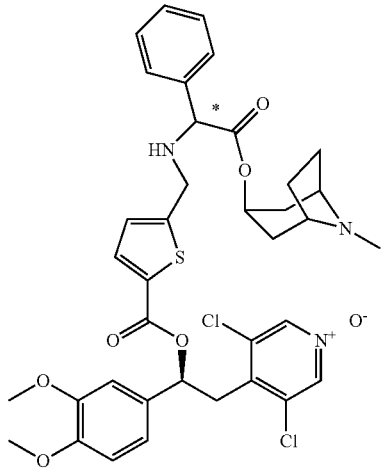<br>Single diasteroisomer of [(1S)-2-(3,5-dichloro-1-oxido-pyridin-1-ium-4-yl)-1-(3,4-dimethoxyphenyl)ethyl] 5-[[[2-[[(1R,5R)-8-methyl-8-azabicyclo[3.2.1]octan-3-yl]oxy]-2-oxo-1-phenyl-ethyl]amino]methyl]thiophene-2-carboxylate | Example 121 | Example 97 | $^1$H NMR (400 MHz, CDCl$_3$): δ 8.13 (s, 2 H), 7.64 (d, J = 3.8 Hz, 1 H), 7.38-7.36 (m, 5 H), 7.02-6.96 (m, 2 H), 6.88-6.84 (m, 2 H), 6.22 (dd, J = 4.3, 9.9 Hz, 1 H), 5.00 (dd, J = 5.4, 5.4 Hz, 1 H), 4.36 (s, 1 H), 3.93-3.87 (m, 8 H), 3.67 (dd, J = 10.0, 14.0 Hz, 1 H), 3.31 (dd, J = 4.5, 13.9 Hz, 1 H), 3.03-3.00 (m, 1 H), 2.90-2.88 (m, 1 H), 2.62 (d, J = 70.9 Hz, 1 H), 2.19 (s, 3 H), 2.14-1.98 (m, 2 H), 1.86-1.81 (m, 1 H), 1.60-1.70 (m, 3 H), 1.42 (d, J = 15.2 Hz, 1 H), 1.1-1.0 (m, 1 H). LCMS (Method 1): [MH+] = 740 at 2.57 min. Chiral analysis (Method 10) at 9.50 min. |
| 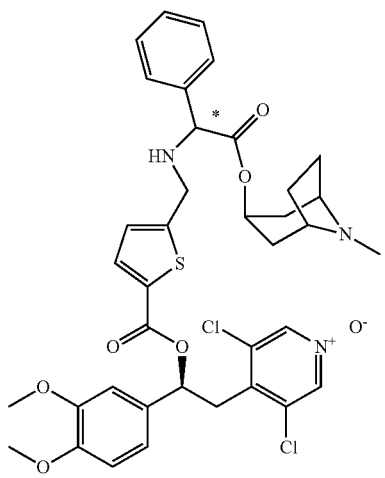<br>Single diasteroisomer of [(1S)-2-(3,5-dichloro-1-oxido-pyridin-1-ium-4-yl)-1-(3,4-dimethoxyphenyl)ethyl] 5-[[[2-[[(1R,5R)-8-methyl-8-azabicyclo[3.2.1]octan-3-yl]oxy]-2-oxo-1-phenyl-ethyl]amino]methyl]thiophene-2-carboxylate | Example 122 | Example 97 | $^1$H NMR (400 MHz, CDCl$_3$): δ 8.14 (s, 2 H), 7.65 (d, J = 3.8 Hz, 1 H), 7.39-7.35 (m, 5 H), 6.99 (d, J = 8.3 Hz, 2 H), 6.88-6.83 (m, 2 H), 6.23 (dd, J = 4.7, 9.7 Hz, 1 H), 5.01 (dd, J = 5.2, 5.2 Hz, 1 H), 4.38 (s, 1 H), 3.93-3.88 (m, 8 H), 3.67 (dd, J = 9.9, 13.9 Hz, 1 H), 3.31 (dd, J = 4.7, 14.0 Hz, 1 H), 3.07-3.05 (m, 1 H), 2.92 (d, J = 3.0 Hz, 1 H), 2.21 (s, 3 H), 2.20-2.00 (m, 2 H), 1.86-1.70 (m, 4 H), 1.44 (d, J = 14.9 Hz, 1 H), 1.06-1.04 (m, 1H), NH not visible. LCMS (Method 1): [MH+] = 740 at 2.55 min. Chiral analysis (Method 10) at 11.81 min. |

| Compound | Example number | Precursor | Analytical Data |
|---|---|---|---|
| Single diastereoisomer of [(1S)-2-(3,5-dichloro-1-oxido-pyridin-1-ium-4-yl)-1-[4-(difluoromethoxy)-3-isopropoxy-phenyl]ethyl] 5-[[[2-oxo-1-phenyl-2-[(3R)-quinuclidin-3-yl]oxy-ethyl]amino]methyl]thiophene-2-carboxylate | Example 123 | Example 75 | $^1$HNMR (400 MHz, DMSO): δ 8.57 (s, 2 H), 7.71 (d, J = 3.8 Hz, 1 H), 7.45-7.30 (m, 5 H), 7.23-7.19 (m, 2 H), 7.06-7.01 (m, 2 H), 7.04 (t, J = 74.3 Hz, 1 H), 6.13 (dd, J = 4.5, 9.3 Hz, 1 H), 4.70-4.62 (m, 2 H), 4.42 (d, J = 9.1 Hz, 1 H), 3.89 (dd, J = 5.3, 5.3 Hz, 2 H), 3.64-3.52 (m, 2 H), 3.35-3.25 (m, 1H), 3.03-2.94 (m, 1 H), 2.60-2.53 (m, 4 H), 2.39-2.33 (m, 1 H), 2.14 (d, J = 14.7 Hz, 1 H), 1.87 (d, J = 2.8 Hz, 1 H), 1.60-1.39 (m, 3 H), 1.26 (dd, J = 6.1, 20.7 Hz, 6 H). LCMS (Method 2): [MH+] = 790 at 3.63 min. Chiral analysis (Method 11) at 5.44 min. |
| Single diastereoisomer of [(1S)-2-(3,5-dichloro-1-oxido-pyridin-1-ium-4-yl)-1-[4-(difluoromethoxy)-3-isopropoxy-phenyl]ethyl] 5-[[[2-oxo-1-phenyl-2-[(3R)-quinuclidin-3-yl]oxy-ethyl]amino]methyl]thiophene-2-carboxylate | Example 124 | Example 75 | $^1$H NMR (400 MHz, DMSO): δ 8.57 (s, 2 H), 7.71 (d, J = 3.8 Hz, 1 H), 7.44-7.31 (m, 5 H), 7.23-7.19 (m, 2 H), 7.06-7.02 (m, 2 H), 7.03 (t, J = 73.8 Hz, 1 H), 6.13 (dd, J = 4.5, 9.3 Hz, 1 H), 4.73-4.62 (m, 2 H), 4.43 (d, J = 8.8 Hz, 1 H), 3.89 (s, 2 H), 3.60-3.52 (m, 2 H), 3.36-3.25 (m, 1 H), 3.10-3.04 (m, 1 H), 2.68-2.53 (m, 5 H), 2.45 (s, 1 H), 1.76-1.72 (m, 1 H), 1.56-1.38 (m, 2 H), 1.26 (dd, J = 6.1, 22.0 Hz, 6 H), 1.15-1.09 (m, 1 H). LCMS (Method 2): [MH+] = 790 at 3.68 min. Chiral analysis (Method 11) at 6.77 min |

-continued

| Compound | Example number | Precursor | Analytical Data |
|---|---|---|---|
| 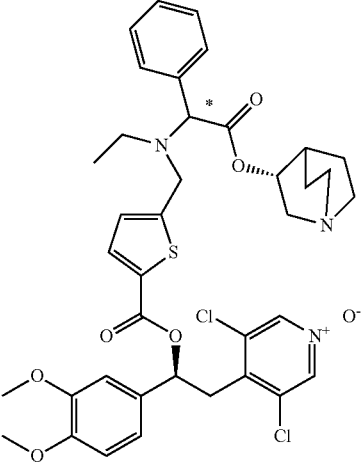<br>Single diastereoisomer of [(1S)-2-(3,5-dichloro-1-oxido-pyridin-1-ium-4-yl)-1-(3,4-dimethoxyphenyl)ethyl] 5-[[ethyl-[2-oxo-1-phenyl-2-[(3R)-quinuclidin-3-yl]oxy-ethyl]amino]methyl]thiophene-2-carboxylate; formic acid | Example 125 | Example 105 | $^1$H NMR (400 MHz, CD$_3$CN): δ 8.20 (s, 1 H), 8.16 (s, 2 H), 7.63 (d, J = 3.8 Hz, 1 H), 7.46 (d, J = 7.3 Hz, 2 H), 7.42-7.33 (m, 3 H), 7.06-7.00 (m, 2 H), 6.96-6.91 (m, 2 H), 6.16 (dd, J = 4.4, 9.7 Hz, 1 H), 4.96-4.93 (m, 1 H), 4.72 (s, 1 H), 4.05-3.85 (m, 2 H), 3.82 (s, 3 H), 3.80 (s, 3 H), 3.70-3.63 (m, 1 H), 3.36-3.21 (m, 2 H), 2.95-2.89 (m, 2 H), 2.79-2.59 (m, 5 H), 2.13-2.05 (m, 1 H), 1.79-1.71 (m, 2 H), 1.67-1.62 (m, 1 H), 1.48-1.43 (m, 1 H), 1.05 (t, J = 7.2 Hz, 3 H). LCMS (Method 1): [MH+] = 754 at 2.88 min. Chiral analysis (Method 19) at 8.01 min |
| 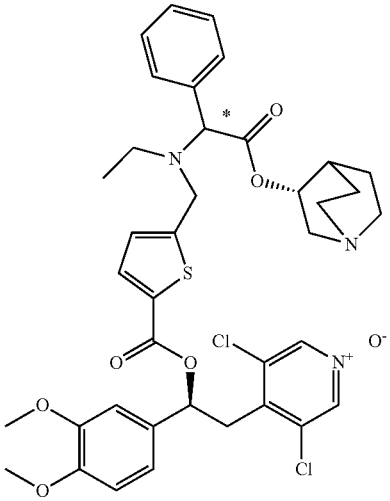<br>Single diastereoisomer of [(1S)-2-(3,5-dichloro-1-oxido-pyridin-1-ium-4-yl)-1-(3,4-dimethoxyphenyl)ethyl] 5-[[ethyl-[2-oxo-1-phenyl-2-[(3R)-quinuclidin-3-yl]oxy-ethyl]amino]methyl]thiophene-2-carboxylate | Example 126 | Example 105 | $^1$H NMR (400 MHz, CD$_3$CN): δ 8.19 (s, 2 H), 7.65 (d, J = 3.8 Hz, 1 H), 7.48 (d, J = 7.1 Hz, 2 H), 7.44-7.35 (m, 3 H), 7.08-7.01 (m, 2 H), 6.97-6.93 (m, 2 H), 6.17 (dd, J = 4.5, 9.6 Hz, 1 H), 4.92-4.88 (m, 1 H), 4.74 (s, 1 H), 4.09-3.88 (m, 2 H), 3.84 (s, 3 H), 3.83 (s, 3 H), 3.68 (dd, J = 9.6, 14.1 Hz, 1 H), 3.34 (dd, J = 4.5, 14.1 Hz, 1 H), 3.23 (dd, J = 8.2, 14.5 Hz, 1 H), 2.81-2.61 (m, 8 H), 1.72-1.52 (m, 3 H), 1.39-1.29 (m, 1 H), 1.08 (dd, J = 7.1, 7.1 Hz, 3 H). LCMS (Method 1): [MH+] = 754 at 2.87 min. Chiral analysis (Method 19) at 12.12 min |

-continued

| Compound | Example number | Precursor | Analytical Data |
|---|---|---|---|
| Single diastereoisomer of [(1S)-2-(3,5-dichloro-1-oxido-pyridin-1-ium-4-yl)-1-(3,4-dimethoxyphenyl)ethyl] 5-[[[2-[2-(dimethylamino)ethoxy]-2-oxo-1-phenyl-ethyl]amino]methyl]thiophene-2-carboxylate | Example 127 | Example 79 | $^1$H NMR (400 MHz, CD$_3$CN): δ 8.19 (s, 2 H), 7.70 (d, J = 3.5 Hz, 1 H), 7.42-7.36 (m, 5 H), 7.08-7.01 (m, 2 H), 6.98-6.93 (m, 2 H), 6.18 (dd, J = 4.5, 9.6 Hz, 1 H), 4.44 (s, 1 H), 4.23-4.14 (m, 2 H), 4.01-3.90 (m, 2 H), 3.84 (s, 3 H), 3.82 (s, 3 H), 3.67 (dd, J = 9.7, 14.0 Hz, 1 H), 3.35 (dd, J = 4.5, 14.1 Hz, 1 H), 2.47 (t, J = 5.7 Hz, 2 H), 2.15 (s, 6 H), NH not visible. LCMS (Method 1): [MH+] = 688 at 2.55 min. Chiral analysis (Method 19) at 10.27 min |
| Single diastereoisomer of [(1S)-2-(3,5-dichloro-1-oxido-pyridin-1-ium-4-yl)-1-(3,4-dimethoxyphenyl)ethyl] 5-[[[2-[2-(dimethylamino)ethoxy]-2-oxo-1-phenyl-ethyl]amino]methyl]thiophene-2-carboxylate | Example 128 | Example 79 | $^1$H NMR (400 MHz, CD$_3$CN): δ 8.18 (s, 2 H), 7.69 (d, J = 3.7 Hz, 1 H), 7.42-7.39 (m, 5 H), 7.07-7.01 (m, 2 H), 6.97-6.93 (m, 2 H), 6.21-6.15 (m, 1 H), 4.43 (s, 1 H), 4.23-4.14 (m, 2 H), 3.96 (dd, J = 15.2, 29.6 Hz, 2 H), 3.83 (s, 3 H), 3.82 (s, 3 H), 3.72-3.63 (m, 1 H), 3.34 (d, J = 26.1 Hz, 1 H), 2.47 (t, J = 5.6 Hz, 2 H), 2.15 (s, 6 H), NH not observed. LCMS (Method 1): [MH+] = 688 at 2.56 min. Chiral analysis (Method 19) at 12.21 min |

| Compound | Example number | Precursor | Analytical Data |
|---|---|---|---|
| Single diastereoisomer of [(1S)-2-(3,5-dichloro-1-oxido-pyridin-1-ium-4-yl)-1-(3,4-dimethoxyphenyl)ethyl] 5-[[[1-(2-fluorophenyl)-2-[(3R)-1-methylpyrrolidin-3-yl]oxy-2-oxo-ethyl]amino]methyl]thiophene-2-carboxylate | Example 129 | Example 94 | $^1$H NMR (400 MHz, CDCl$_3$): δ 8.14 (s, 2 H), 7.64 (d, J = 3.8 Hz, 1 H), 7.37-7.27 (m, 2 H), 7.17-7.12 (m, 1 H), 7.10-7.04 (m, 1 H), 7.01-6.96 (m, 2 H), 6.90-6.83 (m, 2 H), 6.22 (dd, J = 4.5, 9.6 Hz, 1 H), 5.26-5.20 (m, 1 H), 4.72 (s, 1 H), 3.94 (d, J = 2.8 Hz, 2 H), 3.90 (s, 3 H), 3.88 (s, 3 H), 3.66 (dd, J = 9.6, 13.9 Hz, 1 H), 3.31 (dd, J = 4.5, 13.9 Hz, 1 H), 2.77-2.61 (m, 3 H), 2.32 (s, 3 H), 2.31-2.27 (m, 1 H), 2.22-2.13 (m, 1 H), 1.70-1.61 (m, 2 H). LCMS (Method 1): [MH+] = 718 at 2.64 min. Chiral analysis (Method 12) at 6.75 min. |
| Single diastereoisomer of [(1S)-2-(3,5-dichloro-1-oxido-pyridin-1-ium-4-yl)-1-(3,4-dimethoxyphenyl)ethyl] 5-[[[1-(2-fluorophenyl)-2-[(3R)-1-methylpyrrolidin-3-yl]oxy-2-oxo-ethyl]amino]methyl]thiophene-2-carboxylate | Example 130 | Example 94 | $^1$H NMR (400 MHz, CDCl$_3$): δ 8.14 (s, 2 H), 7.63 (d, J = 3.8 Hz, 1 H), 7.38-7.28 (m, 2 H), 7.17-7.06 (m, 2 H), 7.01-6.97 (m, 2 H), 6.90-6.83 (m, 2 H), 6.22 (dd, J = 4.5, 9.6 Hz, 1 H), 5.24-5.18 (m, 1 H), 4.71 (s, 1 H), 3.95 (d, J = 4.0 Hz, 2 H), 3.90 (s, 3 H), 3.87 (s, 3 H), 3.66 (dd, J = 9.9, 13.9 Hz, 1 H), 3.31 (dd, J = 4.5, 13.9 Hz, 1 H), 2.71-2.63 (m, 2 H), 2.27-2.26 (m, 6 H), 1.87-1.79 (m, 1 H), NH not visible. LCMS (Method 1): [MH+] = 718 at 2.68 min. Chiral analysis (Method 12) at 8.59 min. |

-continued

| Compound | Example number | Precursor | Analytical Data |
|---|---|---|---|
| Single diastereoisomer of [(1S)-2-(3,5-dichloro-1-oxido-pyridin-1-ium-4-yl)-1-(3,4-dimethoxyphenyl)ethyl] 5-[[[2-[[(3R)-1-methyl-3-piperidyl]oxy]-2-oxo-1-phenyl-ethyl]amino]methyl]thiophene-2-carboxylate | Example 131 | Example 89 | $^1$H NMR (400 MHz, CD$_3$CN): δ 8.19 (s, 2 H), 7.69 (d, J = 3.8 Hz, 1 H), 7.41-7.36 (m, 5 H), 7.07-7.02 (m, 2 H), 6.97-6.93 (m, 2 H), 6.18 (dd, J = 4.5, 9.6 Hz, 1 H), 4.87-4.80 (m, 1 H), 4.41 (s, 1 H), 3.97-3.90 (m, 2 H), 3.83 (s, 3 H), 3.82 (s, 3 H), 3.67 (dd, J = 9.6, 14.1 Hz, 1 H), 3.34 (dd, J = 4.5, 14.1 Hz, 1 H), 2.65 (dd, J = 1.8, 10.9 Hz, 1 H), 2.45-2.25 (m, 3 H), 2.00 (s, 3H), 1.70-1.59 (m, 2 H), 1.52-1.44 (m, 1 H), 1.32-1.25 (m, 2 H). LCMS (Method 2): [MH+] = 714 at 3.26 min. Chiral analysis (Method 19) at 8.14 min. |
| Single diastereoisomer of [(1S)-2-(3,5-dichloro-1-oxido-pyridin-1-ium-4-yl)-1-(3,4-dimethoxyphenyl)ethyl] 5-[[[2-[[(3R)-1-methyl-3-piperidyl]oxy]-2-oxo-1-phenyl-ethyl]amino]methyl]thiophene-2-carboxylate | Example 132 | Example 89 | $^1$H NMR (400 MHz, CD$_3$CN): δ 8.18 (s, 2 H), 7.70 (d, J = 3.8 Hz, 1 H), 7.42-7.39 (m, 4 H), 7.39-7.35 (m, 1 H), 7.07-7.02 (m, 2 H), 6.98-6.93 (m, 2 H), 6.18 (dd, J = 4.4, 9.7 Hz, 1 H), 4.84-4.77 (m, 1 H), 4.41 (s, 1 H), 3.96 (q, J = 15.2 Hz, 2 H), 3.84 (s, 3 H), 3.82 (s, 3 H), 3.68 (dd, J = 9.7, 14.3 Hz, 1 H), 3.34 (dd, J = 4.5, 14.1 Hz, 1 H), 2.59-2.54 (m, 1 H), 2.47-2.41 (m, 1 H), 2.25-2.10 (m, 4H), 1.80 (dd, J = 2.4, 4.9 Hz, 2 H), 1.78-1.69 (m, 2 H), 1.59-1.48 (m, 1 H), 1.43-1.33 (m, 1 H). LCMS (Method 2): [MH+] = 714 at 3.23 min. Chiral analysis (Method 19) at 10.12 min. |

| Compound | Example number | Precursor | Analytical Data |
|---|---|---|---|
| Single diastereoisomer of [(1S)-2-(3,5-dichloro-1-oxido-pyridin-1-ium-4-yl)-1-(3,4-dimethoxyphenyl)ethyl] 5-[[[2-[3-(dimethylamino)propoxy]-2-oxo-1-phenyl-ethyl]amino]methyl]thiophene-2-carboxylate | Example 133 | Example 90 | $^1$H NMR (400 MHz, CD$_3$CN): δ 8.19 (s, 2 H), 7.69 (d, J = 3.8 Hz, 1 H), 7.40 (d, J = 4.3 Hz, 4 H), 7.39-7.34 (m, 1 H), 7.07-7.02 (m, 2 H), 6.97-6.93 (m, 2 H), 6.18 (dd, J = 4.5, 9.6 Hz, 1 H), 4.43 (s, 1 H), 4.13 (q, J = 6.1 Hz, 2 H), 3.96-3.89 (m, 2 H), 3.83 (s, 3 H), 3.82 (s, 3 H), 3.67 (dd, J = 9.6, 14.1 Hz, 1 H), 3.34 (dd, J = 4.7, 14.0 Hz, 1 H), 2.70 (br s, 1 H) 2.13 (d, J = 7.1 Hz, 2 H), 2.08 (s, 6 H), 1.72-1.64 (m, 2 H). LCMS (Method 2): [MH+] = 702 at 2.72 min. Chiral analysis (Method 14) at 2.45 min. |
| Single diastereoisomer of [(1S)-2-(3,5-dichloro-1-oxido-pyridin-1-ium-4-yl)-1-(3,4-dimethoxyphenyl)ethyl] 5-[[[2-[3-(dimethylamino)propoxy]-2-oxo-1-phenyl-ethyl]amino]methyl]thiophene-2-carboxylate | Example 134 | Example 90 | $^1$H NMR (400 MHz, CD$_3$CN): δ 8.18 (s, 2 H), 7.69 (d, J = 3.8 Hz, 1 H), 7.40 (d, J = 4.3 Hz, 5 H), 7.07-7.01 (m, 2 H), 6.96-6.93 (m, 2 H), 6.18 (dd, J = 4.4, 9.7 Hz, 1 H), 4.43 (s, 1 H), 4.15-4.08 (m, 2 H), 4.00-3.87 (m, 2 H), 3.83 (s, 3 H), 3.82 (s, 3 H), 3.67 (dd, J = 9.6, 14.1 Hz, 1 H), 3.34 (dd, J = 4.5, 14.1 Hz, 1 H), 2.93-2.92 (m, 1 H), 2.14 (dd, J = 7.1, 7.1 Hz, 2 H), 2.08 (s, 6 H), 1.72-1.64 (m, 2 H). LCMS (Method 1): [MH+] = 702 at 2.52 min. Chiral analysis (Method 14) at 3.21 min. |

-continued

| Compound | Example number | Precursor | Analytical Data |
|---|---|---|---|
| Single diastereoisomer of [(1S)-2-(3,5-dichloro-1-oxido-pyridin-1-ium-4-yl)-1-(3,4-dimethoxyphenyl)ethyl] 5-[[[2-oxo-1-phenyl-2-[(3R)-quinuclidin-3-yl]oxy-ethyl]amino]methyl]thiophene-3-carboxylate | Example 135 | Example 76 | $^1$H NMR (400 MHz, CD$_3$CN): δ 8.19 (s, 2 H), 8.14 (d, J = 1.3 Hz, 1 H), 7.42-7.35 (m, 5 H), 7.30 (d, J = 1.0 Hz, 1 H), 7.08-7.02 (m, 2 H), 6.95 (d, J = 8.1 Hz, 1 H), 6.17 (dd, J = 4.5, 9.6 Hz, 1 H), 4.78-4.74 (m, 1 H), 4.44 (s, 1 H), 3.94 (d, J = 14.7 Hz, 1 H), 3.90 (d, J = 14.7 Hz, 1 H), 3.84 (s, 3 H), 3.82 (s, 3 H), 3.67 (dd, J = 9.6, 14.1 Hz, 1 H), 3.34 (dd, J = 4.5, 14.1 Hz, 1 H), 3.16-3.08 (m, 1 H), 2.71-2.60 (m, 4 H), 2.55 (td, J = 2.6, 15.0 Hz, 1 H), 1.81-1.76 (m, 1 H), 1.64-1.55 (m, 1 H), 1.53-1.35 (m, 2 H), 1.25-1.15 (m, 1 H), NH not visible. LCMS (Method 1): [MH+] = 726 at 2.54 min. Chiral analysis (Method 8) at 4.92 min. |
| Single diastereoisomer of [(1S)-2-(3,5-dichloro-1-oxido-pyridin-1-ium-4-yl)-1-(3,4-dimethoxyphenyl)ethyl] 5-[[[2-oxo-1-phenyl-2-[(3R)-quinuclidin-3-yl]oxy-ethyl]amino]methyl]thiophene-3-carboxylate | Example 136 | Example 76 | $^1$H NMR (400 MHz, CD$_3$CN): δ 8.19 (s, 2 H), 8.15 (d, J = 1.5 Hz, 1 H), 7.43-7.40 (m, 5 H), 7.29 (d, J = 1.3 Hz, 1 H), 7.07 (d, J = 2.0 Hz, 1 H), 7.03 (dd, J = 2.0, 8.2 Hz, 1 H), 6.94 (d, J = 8.3 Hz, 1 H), 6.17 (dd, J = 4.7, 9.5 Hz, 1 H), 4.75-4.71 (m, 1 H), 4.44 (s, 1 H), 3.95 (d, J = 14.5 Hz, 1 H), 3.91 (d, J = 14.7 Hz, 1 H), 3.84 (s, 3 H), 3.82 (s, 3 H), 3.67 (dd, J = 9.7, 14.0 Hz, 1 H), 3.34 (dd, J = 4.5, 14.1 Hz, 1 H), 3.09-3.01 (m, 1 H), 2.69-2.60 (m, 3 H), 2.53-2.45 (m, 1 H), 2.28 (d, J = 14.3 Hz, 1 H), 1.92-1.89 (m, 1 H), 1.68-1.58 (m, 2 H), 1.53-1.44 (m, 1 H), 1.35-1.27 (m, 1 H), NH not visible. LCMS (Method 1): [MH+] = 726 at 2.5 min. Chiral analysis (Method 8) at 10.49 min. |

-continued

| Compound | Example number | Precursor | Analytical Data |
|---|---|---|---|
| Single diastereoisomer of [(1S)-2-(3,5-dichloro-1-oxido-pyridin-1-ium-4-yl)-1-(3,4-dimethoxyphenyl)ethyl] 4-[[[2-oxo-1-phenyl-2-[(3R)-quinuclidin-3-yl]oxy-ethyl]amino]methyl]thiophene-2-carboxylate | Example 137 | Example 78 | $^1$H NMR (400 MHz, CD$_3$CN): δ 8.19 (s, 2 H), 7.77 (d, J = 1.5 Hz, 1 H), 7.51 (d, J = 1.3 Hz, 1 H), 7.44-7.32 (m, 5 H), 7.07 (d, J = 1.9 Hz, 1 H), 7.04 (dd, J = 1.9, 8.4 Hz, 1 H), 6.95 (d, J = 8.3 Hz, 1 H), 6.18 (dd, J = 4.4, 9.7 Hz, 1 H), 4.74-4.70 (m, 1 H), 4.38 (s, 1 H), 3.83 (s, 3 H), 3.82 (s, 3 H), 3.73 (s, 2 H), 3.68 (dd, J = 9.6, 14.1 Hz, 1 H), 3.34 (dd, J = 4.5, 14.1 Hz, 1 H), 3.14-3.06 (m, 1 H), 2.71-2.57 (m, 4 H), 2.56-2.49 (m, 1 H), 1.79-1.74 (m, 1 H), 1.61-1.53 (m, 1 H), 1.51-1.35 (m, 2 H), 1.24-1.15 (m, 1 H), NH not visible. LCMS (Method 1): [MH+] = 726 at 2.37 min. Chiral analysis (Method 15) at 3.18 min. |
| Single diastereoisomer of [(1S)-2-(3,5-dichloro-1-oxido-pyridin-1-ium-4-yl)-1-(3,4-dimethoxyphenyl)ethyl] 4-[[[2-oxo-1-phenyl-2-[(3R)-quinuclidin-3-yl]oxy-ethyl]amino]methyl]thiophene-2-carboxylate | Example 138 | Example 78 | $^1$H NMR (400 MHz, CD$_3$CN): δ 8.19 (s, 2 H), 7.77 (d, J = 1.3 Hz, 1 H), 7.51 (d, J = 1.3 Hz, 1 H), 7.45-7.34 (m, 5 H), 7.06 (d, J = 2.1 Hz, 1 H), 7.03 (dd, J = 2.3, 8.3 Hz, 1 H), 6.95 (d, J = 8.3 Hz, 1 H), 6.18 (dd, J = 4.5, 9.6 Hz, 1 H), 4.76-4.72 (m, 1 H), 4.40 (s, 1 H), 3.83 (s, 3 H), 3.82 (s, 3 H), 3.74 (s, 2 H), 3.68 (dd, J = 9.7, 14.0 Hz, 1 H), 3.34 (dd, J = 4.5, 14.1 Hz, 1 H), 3.07 (ddd, J = 2.7, 9.8, 12.9 Hz, 1 H), 2.75-2.57 (m, 3 H), 2.55-2.45 (m, 1 H), 2.31 (d, J = 14.7 Hz, 1 H), 1.95-1.90 (m, 1 H), 1.69-1.60 (m, 2 H), 1.55-1.46 (m, 1 H), 1.38-1.28 (m, 1 H), NH not visible. LCMS (Method 1): [MH+] = 726 at 2.39 min. Chiral analysis (Method 15) at 4.07 min. |

| Compound | Example number | Precursor | Analytical Data |
|---|---|---|---|
| Single diastereoisomer of [(1S)-2-(3,5-dichloro-1-oxido-pyridin-1-ium-4-yl)-1-(3,4-dimethoxyphenyl)ethyl] 5-[[[1-(2-fluorophenyl)-2-oxo-2-[(3R)-quinuclidin-3-yl]oxy-ethyl]amino]methyl]thiophene-3-carboxylate | Example 139 | Example 77 | $^1$H NMR (400 MHz, CD$_3$CN): δ 8.15 (s, 2 H), 8.11 (d, J = 1.3 Hz, 1 H), 7.42 (dt, J = 1.8, 7.6 Hz, 1 H), 7.38-7.30 (m, 1 H), 7.28 (d, J = 0.6 Hz, 1 H), 7.19 (dt, J = 1.2, 7.6 Hz, 1 H), 7.14-7.08 (m, 1 H), 7.04 (d, J = 1.8 Hz, 1 H), 7.00 (dd, J = 2.1, 8.3 Hz, 1 H), 6.92 (d, J = 8.3 Hz, 1 H), 6.14 (dd, J = 4.5, 9.6 Hz, 1 H), 4.79-4.73 (m, 1 H), 4.69 (s, 1 H), 3.93 (s, 2 H), 3.81 (s, 3 H), 3.79 (s, 3 H), 3.64 (dd, J = 9.6, 14.1 Hz, 1 H), 3.30 (dd, J = 4.5, 14.1 Hz. 1 H), 3.10 (ddd, J = 1.8, 8.3, 14.7 Hz, 1 H), 2.72-2.58 (m, 4 H), 2.54 (d, J = 15.3 Hz, 1 H), 2.59-2.31 (m, 1 H), 1.78-1.74 (m, 1 H), 1.61-1.53 (m, 1 H), 1.51-1.40 (m, 1 H), 1.35-1.27 (m, 1 H), 1.22-1.12 (m, 1 H). LCMS (Method 1): [MH+] = 744 at 2.64 min. Chiral analysis (Method 8) at 3.89 min. |
| Single diastereoisomer of [(1S)-2-(3,5-dichloro-1-oxido-pyridin-1-ium-4-yl)-1-(3,4-dimethoxyphenyl)ethyl] 5-[[[1-(2-fluorophenyl)-2-oxo-2-[(3R)-quinuclidin-3-yl]oxy-ethyl]amino]methyl]thiophene-3-carboxylate | Example 140 | Example 77 | $^1$H NMR (400 MHz, CD$_3$CN): δ 8.18 (s, 2 H), 8.13 (d, J = 1.3 Hz, 1 H), 7.45 (dt, J = 1.7, 7.5 Hz, 1 H), 7.41-7.34 (m, 1 H), 7.29 (s, 1 H), 7.23 (dt, J = 1.1, 7.6 Hz, 1 H), 7.19-7.12 (m, 1 H), 7.06 (d, J = 1.2 Hz, 1 H), 7.03 (dd, J = 1.9, 8.3 Hz, 1 H), 6.94 (d, J = 8.1 Hz, 1 H), 6.17 (dd, J = 4.5, 9.6 Hz, 1 H), 4.79-4.73 (m, 1 H), 4.72 (s, 1 H), 4.01-3.91 (m, 2 H), 3.84 (s, 3 H), 3.82 (s, 3 H), 3.66 (dd, J = 9.7, 14.0 Hz, 1 H), 3.33 (dd, J = 4.5, 14.1 Hz, 1 H), 3.12-3.03 (m, 1 H), 2.74-2.59 (m, 3 H), 2.49-2.38 (m, 1 H), 2.31 (d, J = 14.7 Hz, 1 H), 1.93-1.88 (m, 1 H), 1.68-1.45 (m, 3 H), 1.35-1.23 (m, 1 H), NH not visible. LCMS (Method 1): [MH+] = 744 at 2.63 min. Chiral analysis (Method 8) at 7.91 min. |

| Compound | Example number | Precursor | Analytical Data |
|---|---|---|---|
| Single diastereoisomer of [(1S)-2-(3,5-dichloro-1-oxido-pyridin-1-ium-4-yl)-1-(3,4-dimethoxyphenyl)ethyl] 5-[[[2-[(3S)-1-methylpyrrolidin-3-yl]oxy-2-oxo-1-phenyl-ethyl]amino]methyl]thiophene-2-carboxylate | Example 141 | Example 82 | $^1$H NMR (400 MHz, DMSO): δ 8.62 (s, 2 H), 7.74 (d, J = 3.8 Hz, 1 H), 7.44-7.41 (m, 5 H), 7.08-7.05 (m, 2 H), 7.04-7.02 (m, 2 H), 6.19 (dd, J = 4.3, 9.6 Hz, 1 H), 5.13 (dd, J = 6.7, 6.7 Hz, 1 H), 4.43 (d, J = 9.3 Hz, 1 H), 3.97-3.85 (m, 2 H), 3.82 (s, 3 H), 3.80 (s, 3 H), 3.67-3.56 (m, 2 H), 3.35 (dd, J = 4.2, 14.1 Hz, 1 H), 2.74-2.68 (m, 2 H), 2.43-2.37 (m, 2 H), 2.28-2.18 (m, 1 H), 2.25 (s, 3 H), 1.78-1.73 (m, 1 H). LCMS (Method 1): [MH+] = 700 at 2.56 min. Chiral analysis (Method 15) at 1.49 min. |
| Single diastereoisomer of [(1S)-2-(3,5-dichloro-1-oxido-pyridin-1-ium-4-yl)-1-(3,4-dimethoxyphenyl)ethyl] 5-[[[2-[(3S)-1-methylpyrrolidin-3-yl]oxy-2-oxo-1-phenyl-ethyl]amino]methyl]thiophene-2-carboxylate | Example 142 | Example 82 | $^1$H NMR (400 MHz, DMSO): δ 8.62 (s, 2 H), 7.74 (d, J = 3.8 Hz, 1 H), 7.45-7.42 (m, 4 H), 7.42-7.36 (m, 1 H), 7.08-7.06 (m, 2 H), 7.04-7.00 (m, 2 H), 6.19 (dd, J = 4.3, 9.9 Hz, 1 H), 5.17-5.10 (m, 1 H), 4.42 (d, J = 9.3 Hz, 1 H), 3.97-3.85 (m, 2 H), 3.82 (s, 3 H), 3.80 (s, 3 H), 3.67-3.56 (m, 2 H), 3.34 (dd, J = 4.3, 14.1 Hz, 1 H), 2.75-2.60 (m, 3 H), 2.36-2.23 (m, 1 H), 2.30 (s, 3 H), 2.21-2.10 (m, 1 H), 1.56-1.47 (m, 1 H). LCMS (Method 1): [MH+] = 700 at 2.59 min. Chiral analysis (Method 15) at 1.90 min. |

-continued

| Compound | Example number | Precursor | Analytical Data |
|---|---|---|---|
| Single diastereoisomer of [(1S)-2-(3,5-dichloro-1-oxido-pyridin-1-ium-4-yl)-1-(3,4-dimethoxyphenyl)ethyl] 5-[[[1-(3-hydroxyphenyl)-2-oxo-2-[(3R)-quinuclidin-3-yl]oxy-ethyl]amino]methyl]thiophene-2-carboxylate | Example 143 | Example 83 | $^1$H NMR (400 MHz, DMSO): δ 9.52 (s, 1 H), 8.62 (s, 2 H), 7.74 (d, J = 3.8 Hz, 1 H), 7.21 (dd, J = 8.0, 8.0 Hz, 1 H), 7.07 (d, J = 3.8 Hz, 2 H), 7.03 (s, 2 H), 6.89-6.86 (m, 2 H), 6.76 (dd, J = 1.5, 8.1 Hz, 1 H), 6.19 (dd, J = 4.4, 9.7 Hz, 1 H), 4.74-4.72 (m, 1 H), 4.36 (d, J = 9.4 Hz, 1 H), 3.92 (s, 2 H), 3.82 (s, 3 H), 3.80 (s, 3 H), 3.64 (dd, J = 9.7, 14.1 Hz, 1 H), 3.58-3.51 (m, 1 H), 3.35 (dd, J = 4.7, 14.3 Hz, 1 H), 3.10-3.03 (m, 1 H), 2.69-2.59 (m, 3 H), 2.56-2.43 (m, 1 H), 2.26 (d, J = 14.4 Hz, 1 H), 1.97-1.93 (m, 1 H), 1.69-1.58 (m, 2 H), 1.53-1.48 (m, 1 H), 1.34-1.28 (m, 1 H). LCMS (Method 1): [MH+] = 742 at 2.77 min. Chiral analysis (Method 7) at 6.37 min. |
| Single diastereoisomer of [(1S)-2-(3,5-dichloro-1-oxido-pyridin-1-ium-4-yl)-1-(3,4-dimethoxyphenyl)ethyl] 5-[[[1-(3-hydroxyphenyl)-2-oxo-2-[(3R)-quinuclidin-3-yl]oxy-ethyl]amino]methyl]thiophene-2-carboxylate | Example 144 | Example 83 | $^1$H NMR (400 MHz, DMSO): δ 9.51 (s, 1 H), 8.62 (s, 2 H), 7.74 (d, J = 3.8 Hz, 1 H), 7.19 (dd, J = 8.1, 8.1 Hz, 1 H), 7.07 (d, J = 3.5 Hz, 2 H), 7.03 (s, 2 H), 6.86 (d, J = 7.3 Hz, 2 H), 6.75 (dd, J = 1.4, 8.0 Hz, 1 H), 6.19 (dd, J = 4.4, 9.7 Hz, 1 H), 4.77-4.72 (m, 1 H), 4.41 (d, J = 3.8 Hz, 1 H), 4.36 (d, J = 6.9 Hz, 1 H), 3.91-3.89 (m, 2 H), 3.82 (s, 3 H), 3.80 (s, 3 H), 3.63 (dd, J = 9.7, 14.0 Hz, 1 H), 3.34 (dd, J = 4.2, 14.1 Hz, 1 H), 3.13 (dd, J = 8.2, 14.3 Hz, 1 H), 2.71-2.49 (m, 5 H), 1.83-1.79 (m, 1 H), 1.62-1.54 (m, 1 H), 1.52-1.38 (m, 2 H), 1.26-1.19 (m, 1 H). LCMS (Method 1): [MH+] = 742 at 2.75 min. Chiral analysis (Method 7) at 7.55 min. |

| Compound | Example number | Precursor | Analytical Data |
|---|---|---|---|
| Single diastereomer of [(1S)-2-(3,5-dichloro-1-oxido-pyridin-1-ium-4-yl)-1-(3,4-dimethoxyphenyl)ethyl] 5-[[[2-[(1-methyl-4-piperidyl)oxy]-2-oxo-1-phenyl-ethyl]amino]methyl]thiophene-2-carboxylate | Example 145 | Example 99 | $^1$H NMR (400 MHz, CD$_3$CN): δ 8.19 (s, 2 H), 7.69 (d, J = 3.8 Hz, 1 H), 7.43-7.32 (m, 5 H), 7.08-7.01 (m, 2 H), 6.97-6.92 (m, 2 H), 6.18 (dd, J = 4.5, 9.6 Hz, 1 H), 4.81-4.73 (m, 1 H), 4.42 (s, 1 H), 3.95 (dd, J = 15.0, 22.4 Hz, 2 H), 3.83 (s, 3 H), 3.82 (s, 3 H), 3.67 (dd, J = 9.6, 14.1 Hz, 1 H), 3.34 (dd, J = 4.5, 14.1 Hz, 1 H), 2.53-2.08 (m, 4 H), 2.15 (s, 3 H), 1.90-1.81 (m, 1 H), 1.77-1.59 (m, 2 H), 1.55-1.44 (m, 1 H), NH not observed. LCMS (Method 2): [MH+] = 714 at 3.34 min. Chiral analysis (Method 15) at 1.68 min. |
| Single diastereomer of [(1S)-2-(3,5-dichloro-1-oxido-pyridin-1-ium-4-yl)-1-(3,4-dimethoxyphenyl)ethyl] 5-[[[2-[(1-methyl-4-piperidyl)oxy]-2-oxo-1-phenyl-ethyl]amino]methyl]thiophene-2-carboxylate | Example 146 | Example 99 | $^1$H NMR (400 MHz, CD$_3$CN): δ 8.18 (s, 2 H), 7.69 (d, J = 4.3 Hz, 1 H), 7.44-7.32 (m, 5 H), 7.07-7.01 (m, 2 H), 6.97-6.91 (m, 2 H), 6.18 (dd, J = 4.4, 9.7 Hz, 1 H), 4.81-4.73 (m, 1 H), 4.41 (s, 1 H), 3.95 (dd, J = 14.9, 25.1 Hz, 2 H), 3.83 (s, 3 H), 3.82 (s, 3 H), 3.67 (dd, J = 9.6, 14.1 Hz, 1 H), 3.33 (dd, J = 4.5, 14.1 Hz, 1 H), 2.56-2.11 (m, 4 H), 2.16 (s, 3 H), 1.89-1.81 (m, 1 H), 1.77-1.59 (m, 2 H), 1.55-1.45 (m, 1 H), NH not observed. LCMS (Method 2): [MH+] = 714 at 3.61 min. Chiral analysis (Method 15) at 2.50 min. |

| Compound | Example number | Precursor | Analytical Data |
|---|---|---|---|
| Single diastereomer of [(1R)-2-(3,5-dichloro-1-oxido-pyridin-1-ium-4-yl)-1-(3,4-dimethoxyphenyl)ethyl] 5-[[[2-oxo-1-phenyl-2-[(3R)-quinuclidin-3-yl]oxy-ethyl]amino]methyl]thiophene-2-carboxylate | Example 147 | Example 70 | $^1$H NMR (400 MHz, DMSO): δ 8.63 (s, 2 H), 7.75 (d, J = 3.8 Hz, 1 H), 7.51-7.36 (m, 5 H), 7.09-7.02 (m, 4 H), 6.20 (dd, J = 4.2, 9.7 Hz, 1 H), 4.75-4.71 (m, 1 H), 4.50 (d, J = 9.3 Hz, 1 H), 3.97-3.92 (m, 2 H), 3.83 (s, 3 H), 3.82 (s, 3 H), 3.69 (dd, J = 10.1, 14.1 Hz, 1 H), 3.40 (dd, J = 4.2, 14.3 Hz, 1 H), 3.08-3.00 (m, 1 H), 2.72-2.38 (m, 4 H), 2.20 (d, J = 14.4 Hz, 1 H), 1.95-1.91 (m, 1 H), 1.68-1.55 (m, 2 H), 1.55-1.44 (m, 1 H), 1.35-1.24 (m, 1 H), NH not observed. LCMS (Method 2): [MH+] = 726 at 3.07 min. Chiral analysis (Method 18) at 3.72 min. |
| Single diastereomer of [(1R)-2-(3,5-dichloro-1-oxido-pyridin-1-ium-4-yl)-1-(3,4-dimethoxyphenyl)ethyl] 5-[[[2-oxo-1-phenyl-2-[(3R)-quinuclidin-3-yl]oxy-ethyl]amino]methyl]thiophene-2-carboxylate | Example 148 | Example 70 | $^1$H NMR (400 MHz, DMSO): δ 8.62 (s, 2 H), 7.74 (d, J = 3.8 Hz, 1 H), 7.51-7.33 (m, 5 H), 7.10-7.02 (m, 4 H), 6.19 (dd, J = 4.3, 9.6 Hz, 1 H), 4.77-4.71 (m, 1 H), 4.47 (d, J = 9.3 Hz, 1 H), 3.93 (dd, J = 4.9, 4.9 Hz, 2 H), 3.82 (s, 3 H), 3.81 (s, 3 H), 3.69 (dd, J = 9.9, 14.4 Hz, 1 H), 3.40 (dd, J = 4.2, 14.3 Hz, 1 H), 3.14-3.06 (m, 1 H), 2.70-2.47 (m, 5 H), 1.80-1.75 (m, 1 H), 1.61-1.42 (m, 2 H), 1.41-1.28 (m, 1 H), 1.22-1.11 (m, 1 H), NH not observed. LCMS (Method 2): [MH+] = 726 at 3.11 min. Chiral analysis (Method 18) at 4.28 min. |

-continued

| Compound | Example number | Precursor | Analytical Data |
|---|---|---|---|
| Single diastereomer of [(1S)-2-(3,5-dichloro-1-oxido-pyridin-1-ium-4-yl)-1-(3,4-dimethoxyphenyl)ethyl] 5-[2-[[2-oxo-1-phenyl-2-[(3R)-quinuclidin-3-yl]oxy-ethyl]amino]ethyl]thiophene-2-carboxylate | Example 149 | Example 108 | $^1$H NMR (400 MHz, CD$_3$CN): δ 8.21 (s, 2 H), 7.68 (d, J = 3.5 Hz, 1 H), 7.43-7.31 (m, 5 H), 7.07-7.01 (m, 2 H), 6.97-6.91 (m, 2 H), 6.17 (dd, J = 4.4, 8.8 Hz, 1 H), 4.77-4.72 (m, 1 H), 4.45 (s, 1 H), 3.83 (s, 3 H), 3.82 (s, 3 H), 3.67 (dd, J = 9.3, 14.6 Hz, 1 H), 3.34 (dd, J = 4.4, 14.6 Hz, 1 H), 3.08-2.56 (m, 8 H), 2.51-2.41 (m, 1 H), 2.30 (td, J = 2.3, 14.6 Hz, 1 H), 1.94-1.89 (m, 1 H), 1.68-1.23 (m, 4 H), NH not observed. LCMS (Method 1): [MH+] = 740 at 2.41 min. Chiral analysis (Method 6) at 10.52 min. |
| Single diastereomer of [(1S)-2-(3,5-dichloro-1-oxido-pyridin-1-ium-4-yl)-1-(3,4-dimethoxyphenyl)ethyl] 5-[2-[[2-oxo-1-phenyl-2-[(3R)-quinuclidin-3-yl]oxy-ethyl]amino]ethyl]thiophene-2-carboxylate | Example 150 | Example 108 | $^1$H NMR (400 MHz, CD$_3$CN): δ 8.18 (s, 2 H), 7.68 (d, J = 3.8 Hz, 1 H), 7.43-7.31 (m, 5 H), 7.07-7.01 (m, 2 H), 6.97-6.91 (m, 2 H), 6.17 (dd, J = 4.7, 9.5 Hz, 1 H), 4.78-4.73 (m, 1 H), 4.44 (s, 1 H), 3.83 (s, 3 H), 3.82 (s, 3 H), 3.67 (dd, J = 9.6, 14.1 Hz, 1 H), 3.34 (dd, J = 4.4, 14.2 Hz, 1 H), 3.15-3.09 (m, 1 H), 3.02 (t, J = 6.3 Hz, 2 H), 2.93-2.59 (m, 6 H), 2.54 (td, J = 3.1, 15.2 Hz, 1 H), 1.82-1.74 (m, 1 H), 1.63-1.11 (m, 4 H), NH not observed. LCMS (Method 1): [MH+] = 740 at 2.41 min. Chiral analysis (Method 6) at 11.25 min. |

| Compound | Example number | Precursor | Analytical Data |
|---|---|---|---|
| Single diastereomer of [(1S)-2-(3,5-dichloro-1-oxido-pyridin-1-ium-4-yl)-1-(3,4-dimethoxyphenyl)ethyl] 5-[[[1-(o-tolyl)-2-oxo-2-[(3R)-quinuclidin-3-yl]oxy-ethyl]amino]methyl]thiophene-2-carboxylate | Example 151 | Example 100 | ¹H NMR (400 MHz, DMSO): δ 8.58 (s, 2 H), 7.73 (d, J = 3.8 Hz, 1 H), 7.45-7.41 (m, 1 H), 7.26-7.23 (m, 3 H), 7.07-7.02 (m, 4 H), 6.19 (dd, J = 4.5, 9.6 Hz, 1 H), 4.79-4.73 (m, 1 H), 4.69 (s, 1 H), 3.93 (s, 2 H), 3.82 (s, 3 H), 3.80 (s, 3 H), 3.62 (dd, J = 10.1, 14.4 Hz, 2 H), 3.35 (dd, J = 4.5, 14.0 Hz, 2 H), 3.17-3.09 (m, 1 H), 2.70-2.60 (m, 4 H), 2.34 (s, 3 H), 1.78-1.74 (m, 1 H), 1.61-1.52 (m, 1 H), 1.51-1.43 (m, 1 H), 1.25-1.13 (m, 2 H). LCMS (Method 1): [MH+] = 740 at 2.63 min. Chiral analysis (Method 19) at 13.59 min. |
| Single diastereomer of [(1S)-2-(3,5-dichloro-1-oxido-pyridin-1-ium-4-yl)-1-(3,4-dimethoxyphenyl)ethyl] 5-[[[1-(o-tolyl)-2-oxo-2-[(3R)-quinuclidin-3-yl]oxy-ethyl]amino]methyl]thiophene-2-carboxylate | Example 152 | Example 100 | ¹H NMR (400 MHz, DMSO): δ 8.60 (s, 2 H), 7.73 (d, J = 3.9 Hz, 1 H), 7.46-7.42 (m, 1 H), 7.28-7.25 (m, 3 H), 7.08-7.02 (m, 4 H), 6.19 (dd, J = 4.4, 9.6 Hz, 1 H), 4.77-4.72 (m, 1 H), 4.67 (s, 1 H), 3.94 (s, 2 H), 3.82 (s, 3 H), 3.80 (s, 3 H), 3.63 (dd, J = 10.3, 14.0 Hz, 2 H), 3.36-3.32 (m, 2 H), 3.09-3.01 (m, 1 H), 2.70-2.60 (m, 3 H), 2.36 (s, 3 H), 2.20 (d, J = 16.5 Hz, 1 H), 1.94-1.91 (m, 1 H), 1.64-1.55 (m, 1 H), 1.54-1.44 (m, 1 H), 1.33-1.26 (m, 2 H). LCMS (Method 1): [MH+] = 740 at 2.64 min. Chiral analysis (Method 19) at 19.32 min. |

| Compound | Example number | Precursor | Analytical Data |
|---|---|---|---|
| 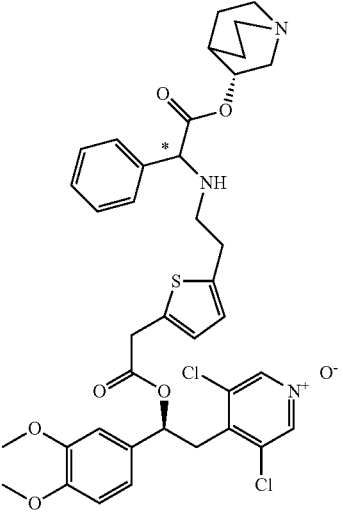<br>Single diastereomer of [(3R)-quinuclidin-3-yl] 2-[2-[5-[2-[(1S)-2-(3,5-dichloro-1-oxido-pyridin-1-ium-4-yl)-1-(3,4-dimethoxyphenyl)ethoxy]-2-oxo-ethyl]-2-thienyl]ethylamino]-2-phenyl-acetate | Example 153 | Example 107 | $^1$H NMR (400 MHz, DMSO): δ 8.55 (s, 2 H), 7.46-7.31 (m, 5 H), 6.99-6.90 (m, 3 H), 6.71 (dd, J = 3.5, 6.8 Hz, 2 H), 6.02 (dd, J = 4.9, 8.7 Hz, 1 H), 4.77-4.72 (m, 1 H), 4.50 (s, 1 H), 3.83 (d, J = 10.1 Hz, 2 H), 3.79 (s, 3 H), 3.77 (s, 3 H), 3.49 (dd, J = 9.3, 13.6 Hz, 1 H), 3.43-3.41 (m, 2 H), 3.26 (dd, J = 4.6, 14.4 Hz, 1 H), 3.16-3.08 (m, 1 H), 2.93 (t, J = 7.1 Hz, 2 H), 2.80-2.53 (m, 6 H), 1.79-1.75 (m, 1 H), 1.62-1.43 (m, 2 H), 1.39-1.28 (m, 1 H), 1.22-1.14 (m, 1 H). LCMS (Method 1): [MH+] = 754 at 2.41 min. Chiral analysis (Method 19) at 16.18 min. |
| 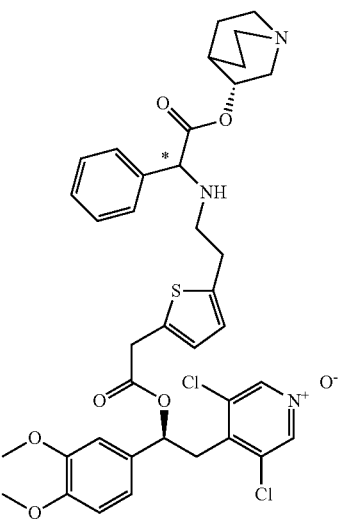<br>Single diastereomer of [(3R)-quinuclidin-3-yl] 2-[2-[5-[2-[(1S)-2-(3,5-dichloro-1-oxido-pyridin-1-ium-4-yl)-1-(3,4-dimethoxyphenyl)ethoxy]-2-oxo-ethyl]-2-thienyl]ethylamino]-2-phenyl-acetate | Example 154 | Example 107 | $^1$H NMR (400 MHz, DMSO): δ 8.56 (s, 2 H), 7.49-7.34 (m, 5 H), 7.00-6.92 (m, 3 H), 6.74-6.71 (m, 2 H), 6.03 (dd, J = 5.7, 9.4 Hz, 1 H), 4.81-4.76 (m, 1 H), 4.53 (s, 1 H), 3.84 (d, J = 8.4 Hz, 2 H), 3.81 (s, 3 H), 3.78 (s, 3 H), 3.49 (dd, J = 10.2, 14.1 Hz, 1 H), 3.27 (dd, J = 5.6, 13.9 Hz, 1 H), 3.19-3.10 (m, 1 H), 2.94 (t, J = 7.2 Hz, 2 H), 2.82-2.64 (m, 7 H), 2.35-2.28 (m, 1 H), 2.01-1.97 (m, 1 H), 1.72-1.51 (m, 3 H), 1.42-1.33 (m, 1 H). LCMS (Method 1): [MH+] = 754 at 2.4 min. Chiral analysis (Method 19) at 13.10 min. |

-continued

| Compound | Example number | Precursor | Analytical Data |
|---|---|---|---|
| Single diastereomer of [(3R)-quinuclidin-3-yl] 2-[[5-[2-[(1S)-2-(3,5-dichloro-1-oxido-pyridin-1-ium-4-yl)-1-(3,4-dimethoxyphenyl)ethoxy]-2-oxo-ethyl]-2-thienyl]methylamino]-2-phenyl-acetate | Example 155 | Example 84 | $^1$H NMR (400 MHz, CD$_3$CN): δ 8.13 (s, 2 H), 7.47-7.33 (m, 5 H), 6.97-6.90 (m, 3 H), 6.75-6.69 (m, 2 H), 6.04 (dd, J = 3.6, 10.0 Hz, 1 H), 4.81-4.76 (m, 1 H), 4.47 (s, 1 H), 3.85 (s, 2 H), 3.81 (s, 3 H), 3.80 (s, 3 H), 3.75 (s, 2 H), 3.53 (dd, J = 9.9, 13.7 Hz, 1 H), 3.24 (dd, J = 5.1, 13.4 Hz, 1 H), 3.19-3.11 (m, 1 H), 2.75-2.57 (m, 6 H), 1.84-1.79 (m, 1 H), 1.66-1.57 (m, 1 H), 1.55-1.48 (m, 1 H), 1.47-1.39 (m, 1 H), 1.28-1.17 (m, 1 H). LCMS (Method 2): [MH+] = 740 at 3.06 min. Chiral analysis (Method 21) at 10.69 min. |
| Single diastereomer of [(1S)-2-(3,5-dichloro-1-oxido-pyridin-1-ium-4-yl)-1-(3,4-dimethoxyphenyl)ethyl] 5-[[[3-oxo-1-phenyl-3-[(3R)-quinuclidin-3-yl]oxy-propyl]amino]methyl]thiophene-2-carboxylate | Example 156 | Example 101 | $^1$H NMR (400 MHz, DMSO): δ 8.62 (s, 2 H), 7.72 (d, J = 3.8 Hz, 1 H), 7.42-7.39 (m, 4 H), 7.35-7.29 (m, 1 H), 7.08-6.98 (m, 4 H), 6.20 (dd, J = 4.0, 10.1 Hz, 1 H), 4.85-4.81 (m, 1 H), 4.05 (t, J = 8.4 Hz, 1 H), 3.83 (s, 3 H), 3.80 (s, 3 H), 3.79-3.73 (m, 2 H), 3.68-3.60 (m, 2 H), 3.35 (dd, J = 4.5, 14.4 Hz, 2 H), 3.08-2.90 (m, 4 H), 2.87-2.79 (m, 2 H), 2.67 (dd, J = 7.2, 14.9 Hz, 1 H), 1.96-1.90 (m, 1 H), 1.76-1.60 (m, 3 H), 1.49-1.41 (m, 1 H). LCMS (Method 1): [MH+] = 740 at 2.41 min. Chiral analysis (Method 17) at 4.26 min. |

-continued

| Compound | Example number | Precursor | Analytical Data |
|---|---|---|---|
| 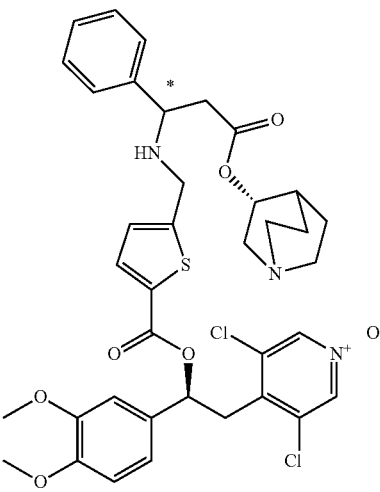<br>Single diastereomer of [(1S)-2-(3,5-dichloro-1-oxido-pyridin-1-ium-4-yl)-1-(3,4-dimethoxyphenyl)ethyl] 5-[[[3-oxo-1-phenyl-3-[(3R)-quinuclidin-3-yl]oxy-propyl]amino]methyl]thiophene-2-carboxylate | Example 157 | Example 101 | $^1$H NMR (400 MHz, DMSO): δ 8.60 (s, 2 H), 7.71 (d, J = 4.5 Hz, 1 H), 7.41-7.38 (m, 4 H), 7.34-7.29 (m, 1 H), 7.07-6.97 (m, 4 H), 6.19 (dd, J = 4.1, 9.8 Hz, 1 H), 4.66-4.61 (m, 1 H), 4.05 (t, J = 7.1 Hz, 1 H), 3.83 (s, 3 H), 3.81 (s, 3 H), 3.82-3.73 (m, 2 H), 3.68-3.59 (m, 2 H), 3.36 (dd, J = 4.3, 13.8 Hz, 2 H), 3.07-3.00 (m, 1 H), 2.79 (dd, J = 7.9, 14.3 Hz, 1 H), 2.64 (dd, J = 7.0, 14.0 Hz, 4 H), 2.32-2.25 (m, 1 H), 1.92-1.87 (m, 1 H), 1.70-1.56 (m, 2 H), 1.53-1.44 (m, 1 H), 1.34-1.25 (m, 1 H). LCMS (Method 1): [MH+] = 740 at 2.38 min. Chiral analysis (Method 17) 5.28 min. |
| 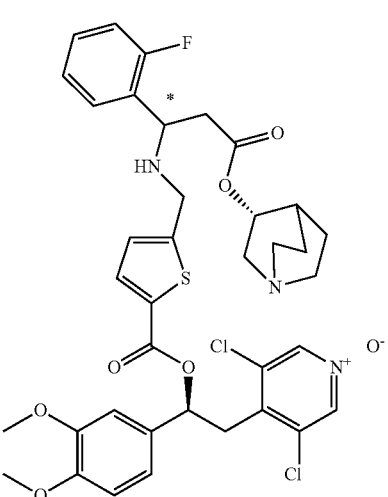<br>Single diastereomer of [(1S)-2-(3,5-dichloro-1-oxido-pyridin-1-ium-4-yl)-1-(3,4-dimethoxyphenyl)ethyl] 5-[[[1-(2-fluorophenyl)-3-oxo-3-[(3R)-quinuclidin-3-yl]oxy-propyl]amino]methyl]thiophene-2-carboxylate | Example 158 | Example 102 | $^1$H NMR (400 MHz, DMSO): δ 8.61 (s, 2 H), 7.71 (d, J = 4.8 Hz, 1 H), 7.64-7.59 (m, 1 H), 7.40-7.34 (m, 1 H), 7.30-7.26 (m, 1 H), 7.24-7.18 (m, 1 H), 7.08-6.98 (m, 4 H), 6.19 (dd, J = 4.0, 9.7 Hz, 1 H), 4.67-4.62 (m, 1 H), 4.41 (t, J = 7.3 Hz, 1 H), 3.84 (d, J = 15.5 Hz, 1 H), 3.83 (s, 3 H), 3.80 (s, 3 H), 3.68-3.59 (m, 2 H), 3.33 (d, J = 4.3 Hz, 1 H), 3.10 (dd, J = 7.4, 15.5 Hz, 2 H), 2.79 (dd, J = 8.5, 14.8 Hz, 1 H), 2.74-2.64 (m, 4 H), 2.46-2.40 (m, 1 H), 1.75-1.71 (m, 1 H), 1.61-1.40 (m, 3 H), 1.26-1.18 (m, 1 H), NH not visible. LCMS (Method 1): [MH+] = 758 at 2.5 min. Chiral analysis (Method 20) at 3.90 min. |

-continued

| Compound | Example number | Precursor | Analytical Data |
|---|---|---|---|
| Single diastereomer of [(1S)-2-(3,5-dichloro-1-oxido-pyridin-1-ium-4-yl)-1-(3,4-dimethoxyphenyl)ethyl] 5-[[[1-(2-fluorophenyl)-3-oxo-3-[(3R)-quinuclidin-3-yl]oxy-propyl]amino]methyl]thiophene-2-carboxylate | Example 159 | Example 102 | $^1$H NMR (400 MHz, DMSO): δ 8.60 (s, 2 H), 7.71 (d, J = 3.8 Hz, 1 H), 7.64-7.58 (m, 1 H), 7.40-7.33 (m, 1 H), 7.29-7.18 (m, 2 H), 7.07 (s, 1 H), 7.03 (s, 2 H), 6.99 (d, J = 3.8 Hz, 1 H), 6.19 (dd, J = 4.4, 9.7 Hz, 1 H), 4.68-4.63 (m, 1 H), 4.42 (t, J = 7.3 Hz, 1 H), 3.84 (d, J = 14.8 Hz, 1 H), 3.83 (s, 3 H), 3.81 (s, 3 H), 3.70-3.58 (m, 2 H), 3.35-3.33 (m, 1 H), 3.09-3.02 (m, 1 H), 2.82-2.58 (m, 6 H), 2.37-2.30 (m, 1 H), 1.93-1.87 (m, 1 H), 1.69-1.55 (m, 2 H), 1.54-1.45 (m, 1 H), 1.34-1.24 (m, 1 H), NH not visible. LCMS (Method 2): [MH+] = 758 at 3.17 min. Chiral analysis (Method 20) at 7.20 min. |
| Single diastereomer of [(1S)-2-(3,5-dichloro-1-oxido-pyridin-1-ium-4-yl)-1-(3,4-dimethoxyphenyl)ethyl] 5-[[[3-[(3R)-1-methylpyrrolidin-3-yl]oxy-3-oxo-1-phenyl-propyl]amino]methyl]thiophene-2-carboxylate | Example 160 | Example 104 | $^1$H NMR (400 MHz, CD$_3$CN): δ 8.01 (s, 2 H), 7.47 (d, J = 3.8 Hz, 1 H), 7.19-7.16 (m, 4 H), 7.13-7.08 (m, 1 H), 6.87-6.81 (m, 2 H), 6.75 (d, J = 8.3 Hz, 1 H), 6.69 (d, J = 3.8 Hz, 1 H), 5.98 (dd, J = 4.5, 9.6 Hz, 1 H), 4.88-4.82 (m, 1 H), 3.87 (dd, J = 6.3, 8.1 Hz, 1 H), 3.64 (s, 3 H), 3.62 (s, 3 H), 3.59-3.45 (m, 3 H), 3.15 (dd, J = 4.5, 14.1 Hz, 1 H), 2.53-2.31 (m, 6 H), 2.04 (s, 3 H), 1.93-1.89 (m, 2 H), 1.44-1.35 (m, 1 H). LCMS (Method 1): [MH+] = 714 at 2.53 min. Chiral analysis (Method 18) at 4.84 min. |

| Compound | Example number | Precursor | Analytical Data |
|---|---|---|---|
| 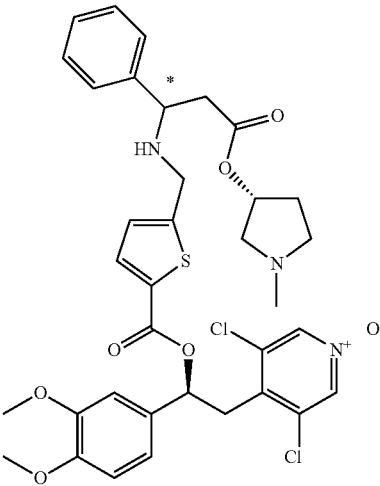<br>Single diastereomer of [(1S)-2-(3,5-dichloro-1-oxido-pyridin-1-ium-4-yl)-1-(3,4-dimethoxyphenyl)ethyl] 5-[[[3-[(3R)-1-methylpyrrolidin-3-yl]oxy-3-oxo-1-phenyl-propyl]amino]methyl]thiophene-2-carboxylate | Example 161 | Example 104 | $^1$H NMR (400 MHz, CD$_3$CN): δ 8.22 (s, 2 H), 7.68 (d, J = 3.8 Hz, 1 H), 7.39-7.36 (m, 4 H), 7.33-7.28 (m, 1 H), 7.07-7.02 (m, 2 H), 6.95 (d, J = 8.1 Hz, 1 H), 6.89 (d, J = 3.8 Hz, 1 H), 6.18 (dd, J = 4.5, 9.6 Hz, 1 H), 5.09-5.03 (m, 1 H), 4.08 (dd, J = 6.3, 8.1 Hz, 1 H), 3.84 (s, 3 H), 3.82 (s, 3 H), 3.78-3.65 (m, 3 H), 3.35 (dd, J = 4.5, 14.1 Hz, 1 H), 2.74-2.50 (m, 5 H), 2.41 (dd, J = 3.2, 10.5 Hz, 1 H), 2.28-2.22 (m, 1 H), 2.21 (s, 3 H), 2.20-2.12 (m, 1 H), 1.74-1.65 (m, 1 H). LCMS (Method 2): [MH+] = 714 at 3.3 min. Chiral analysis (Method 18) at 5.74 min. |
| 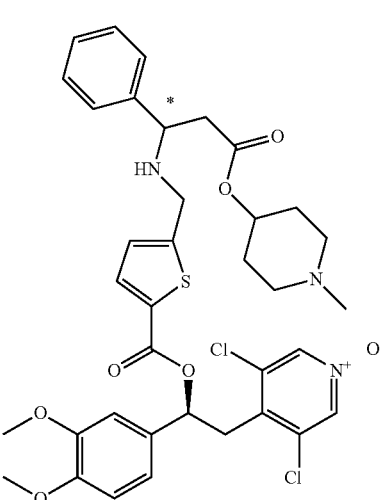<br>Single diastereomer of [(1S)-2-(3,5-dichloro-1-oxido-pyridin-1-ium-4-yl)-1-(3,4-dimethoxyphenyl)ethyl] 5-[[[3-[(1-methyl-4-piperidyl)oxy]-3-oxo-1-phenyl-propyl]amino]methyl]thiophene-2-carboxylate | Example 162 | Example 103 | $^1$H NMR (400 MHz, CD$_3$CN): δ 8.20 (s, 2 H), 7.68 (d, J = 3.8 Hz, 1 H), 7.39-7.37 (m, 4 H), 7.34-7.28 (m, 1 H), 7.07-7.02 (m, 2 H), 6.95 (d, J = 8.1 Hz, 1 H), 6.89 (d, J = 3.8 Hz, 1 H), 6.19 (dd, J = 4.7, 9.5 Hz, 1 H), 4.70-4.62 (m, 1 H), 4.09 (dd, J = 6.4, 8.0 Hz, 1 H), 3.84 (s, 3 H), 3.82 (s, 3 H), 3.79-3.64 (m, 4 H), 3.35 (dd, J = 4.5, 14.1 Hz, 1 H), 2.71 (dd, J = 8.1, 14.7 Hz, 1 H), 2.60 (dd, J = 6.1, 14.7 Hz, 1 H), 2.56-2.49 (m, 1 H), 2.49-2.41 (m, 1 H), 2.16 (s, 3 H), 2.14-2.06 (m, 2 H), 1.84-1.69 (m, 2 H), 1.63-1.44 (m, 2 H). LCMS (Method 1): [MH+] = 728 at 2.52 min. Chiral analysis (Method 13) at 3.24 min. |

| Compound | Example number | Precursor | Analytical Data |
|---|---|---|---|
| 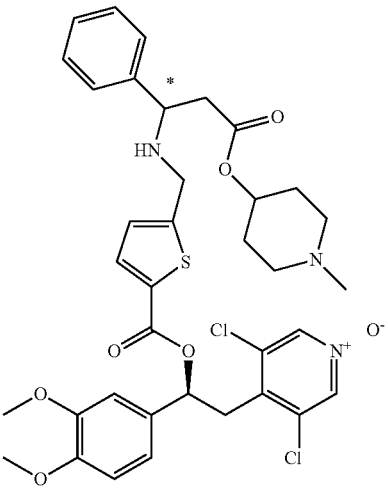<br>Single diastereomer of [(1S)-2-(3,5-dichloro-1-oxido-pyridin-1-ium-4-yl)-1-(3,4-dimethoxyphenyl)ethyl] 5-[[[3-[(1-methyl-4-piperidyl)oxy]-3-oxo-1-phenyl-propyl]amino]methyl]thiophene-2-carboxylate | Example 163 | Example 103 | $^1$H NMR (400 MHz, CD$_3$CN): δ 8.17 (s, 2 H), 7.65 (d, J = 3.8 Hz, 1 H), 7.37-7.32 (m, 4 H), 7.30-7.24 (m, 1 H), 7.05-6.98 (m, 2 H), 6.92 (d, J = 8.1 Hz, 1 H), 6.86 (d, J = 3.8 Hz, 1 H), 6.15 (dd, J = 4.4, 9.5 Hz, 1 H), 4.68-4.59 (m, 1 H), 4.06 (dd, J = 6.6, 7.8 Hz, 1 H), 3.82 (s, 3 H), 3.80 (s, 3 H), 3.78-3.60 (m, 4 H), 3.31 (dd, J = 4.5, 14.1 Hz, 1 H), 2.68 (dd, J = 8.0, 14.8 Hz, 1 H), 2.57 (dd, J = 6.4, 14.8 Hz, 1 H), 2.50-2.46 (m, 1 H), 2.41-2.40 (m, 1 H), 2.12 (s, 3 H), 2.09-2.04 (m, 2 H), 1.80-1.66 (m, 2 H), 1.61-1.41 (m, 2 H). LCMS (Method 1): [MH+] = 728 at 2.48 min. Chiral analysis (Method 13) at 3.90 min |

Pharmacological Activity of the Compounds of the Present Invention.

In Vitro Determination of PDE4 Inhibitory Activity.

In vitro determination of PDE4 inhibitory activity for compounds of the invention may be determined according to one of the protocols herebelow reported.

PDE4B2 HTRF Assay.

PDE4B2 activity is detected using the LANCE Ultra cAMP homogeneous time resolved fluorescence resonance energy transfer (TR-FRET) assay from Perkin Elmer. The assay is based on the competition between the europium (Eu) chelate-labeled cAMP tracer and sample cAMP for binding sites on cAMP-specific monoclonal antibodies (mAb) labelled with the ULight™ dye. The assay is carried out in 384-well low volume plates in a volume of 10 µl. Human recombinant PDE4B2 (80 pM) is incubated for 2 h with 3 nM cAMP in buffer containing 1×HBSS, 5 mM HEPES, 3 mM MgCl$_2$, 0.1% BSA, pH 7.4 with or without test compounds. The enzymatic reactions are efficiently stopped by the addition of 500 µM IBMX present in the combined Stop/Detection buffer containing europium (Eu) chelate-labeled cAMP tracer and cAMP-specific monoclonal antibodies (mAb) labelled with the ULight™ dye. Samples are then further incubated for 1 h before plates are read at ex 340 nm and em at 665 nm and 615 nm on an EnVision reader. IC$_{50}$ values are determined from competition curves using a non-linear curve fitting program.

PDE4 Cell Free Assay Protocol.

PDE4 activity is determined in U937 human monocytic supernatants cells lysate. Cells are cultured, harvested and supernatant fraction prepared essentially as described in Torphy T J et al J. Pharmacol. Exp. Ther. 1992; 263:1195-1205, which is incorporated herein by reference in its entirety. U937 cells are grown at 37° C., 5% CO$_2$ in RPMI 1640 with GlutaMAXT™-I medium supplemented with 10% fetal bovine serum and 100 µg/mL Pen-strep (Gibco). Cells are harvested and washed twice by centrifugation (150×g, 8 min) in cold PBS. Washed cells are re-suspended in cold Krebs-Ringer-Henseleit buffer at a final concentration 20×10$^6$ cells/mL and sonicated. After centrifugation at 15000×g for 20 min, the supernatants are pooled, divided in aliquots and stored at −80° C.

PDE4 activity is determined in cells supernatants by assaying cAMP disappearance from the incubation mixtures.

The concentration of the test compounds ranges between $10^{-12}$ M and $10^{-6}$ M. Reactions are stopped by enzyme heat inactivation (2.5 minutes at 100° C.) and residual cAMP content is determined using the 'LANCE cAMP Assay' from PerkinElmer following the provider instructions.

The results, expressed as mean±standard deviation of the molar concentration of the test compound producing 50% inhibition of cAMP disappearance (IC$_{50}$). Percentage of inhibition of PDE4 activity is calculated, assuming cAMP disappearance in the absence of inhibitors as 100% and cAMP disappearance in heat inactivated samples as 0%.

Representative compounds of the invention, when tested in one of the above reported protocols, displayed an IC$_{50}$ lower than 100 nM.

In Vitro Determination of M3 Antagonism.

In vitro determination of M3 antagonism for compounds of the invention may be determined according to one of the protocols herebelow reported:

M3 Receptor Radioligand Binding Assay.

Human M$_3$ receptor membranes (15 µg/well) from Perkin Elmer are incubated with 0.52 nM Scopolamine Methyl Chloride, [N-methyl-3H] with or without test compounds, or a saturating concentration of Atropine (5 µM) for the determination of non-specific binding. The assay is carried out in 96-well polypropylene plates in a volume of 250 μl. The assay buffer used is 50 mM Tris-HCl, 154 mM NaCl (pH 7.4). The final assay concentration of DMSO is 0.5% (v/v). The plates are sealed and incubated for 2 h at room temperature on an orbital shaker (slow speed). Membranes are harvested onto 96-well unifilter GF/C filter plates pre-treated with 0.5% polyethyleneimine (v/v), using a filter manifold, washed four times with 200 μl of assay buffer. The plates are dried before addition of 50 μl of microscint-0, sealed then read in a Trilux Microbeta scintillation counter. $IC_{50}$ values are determined from competition curves using a non-linear curve fitting program. $K_i$ values are calculated from $IC_{50}$ values by the Cheng and Prusoff equation.

M3 Binding Assay.

CHO-K1 clone cells expressing the human M3-receptor (Swissprot P20309) were harvested in $Ca^{++}/Mg^{++}$ free phosphate-buffered saline and collected by centrifugation at 1500 rpm for 3 min. The pellets were resuspended in ice cold buffer A (15 mM Tris-HCl pH 7.4, 2 mM $MgCl_2$, 0.3 mM EDTA, 1 mM EGTA) and homogenized by a PBI politron (setting 5 for 15 s). The crude membrane fraction was collected by two consecutive centrifugation steps at 40000 g for 20 min at 4° C., separated by a washing step in buffer A. The pellets obtained were finally resuspended in buffer B (75 mM Tris HCl pH 7.4, 12.5 mM $MgCl_2$, 0.3 mM EDTA, 1 mM EGTA, 250 mM sucrose), and aliquots were stored at −80° C.

The day of experiment, frozen membranes were resuspended in buffer C (50 mM Tris-HCl pH 7.4, 2.5 mM $MgCl_2$, 1 mM EDTA). The non selective muscarinic radioligand [$^3$H]-N-methyl scopolamine (*Mol. Pharmacol.* 45:899-907, which is incorporated herein by reference in its entirety) was used to label the M3 binding sites. Binding experiments were performed in duplicate (ten point concentrations curves) in 96 well plates at radioligand concentration of 0.1-0.3 nM. The non specific binding was determined in the presence of cold N-methyl scopolamine 10 μM. Samples (final volume 0.75 mL) were incubated at room temperature for 90 min. The reaction was terminated by rapid filtration through GF/B Unifilter plates and two washes (0.75 mL) with cold buffer C using a Packard Filtermate Harvester. Radioactivity on the filters was measured by a microplate scintillation counter TriCarb 2500 (PerkinElmer).

Representative compounds of the invention, when tested in one of the above reported protocols, displayed an $IC_{50}$ lower than 100 nM.

Representative compounds of the invention displayed an $IC_{50}$ lower than 100 nM in both PDE4 cell free and M3 binding assays.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:
1. A compound of formula (I):

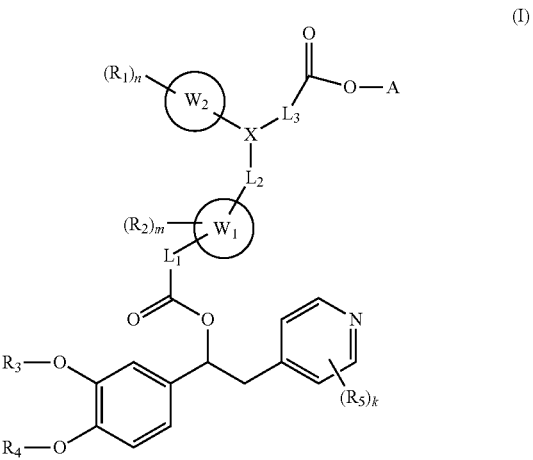

wherein
each $R_1$ is hydrogen, halogen, $(C_1$-$C_4)$ alkyl, $(C_1$-$C_4)$ alkoxy, $(C_1$-$C_4)$ haloalkyl, hydroxy, —$SO_2NR_6R_7$, —CN, —$NR_8SO_2R_9$, —$NR_6R_7$, —$CONR_6R_7$, or —$NR_8COR_9$, wherein said $(C_1$-$C_4)$ alkyl is optionally substituted by one or more groups selected from $(C_3$-$C_7)$ cycloalkyl, hydroxyl, and —$NR_6R_7$ and wherein said $(C_1$-$C_4)$ alkoxy is optionally substituted by one or more halogen atoms or $(C_3$-$C_7)$ cycloalkyl groups, wherein
$R_6$ is hydrogen or $(C_1$-$C_6)$ alkyl;
$R_7$ is hydrogen or $(C_1$-$C_6)$ alkyl;
$R_8$ is hydrogen or $(C_1$-$C_6)$ alkyl;
$R_9$ is hydrogen or $(C_1$-$C_6)$ alkyl;
n is an integer ranging from 1 to 3;
each $R_2$ is hydrogen, halogen, $(C_1$-$C_4)$ alkyl, $(C_1$-$C_4)$ alkoxy, $(C_1$-$C_4)$haloalkyl, hydroxy, —$SO_2NR_{10}R_{11}$, —CN, or —$NR_{12}SO_2R_{13}$, wherein said $(C_1$-$C_4)$ alkyl and said $(C_1$-$C_4)$ alkoxy are optionally substituted by one or more $(C_3$-$C_7)$ cycloalkyl groups, wherein
$R_{10}$ is hydrogen or $(C_1$-$C_6)$ alkyl;
$R_{11}$ is hydrogen or $(C_1$-$C_6)$ alkyl;
$R_{12}$ is hydrogen or $(C_1$-$C_6)$ alkyl;
$R_{13}$ is hydrogen or $(C_1$-$C_6)$ alkyl;
m is an integer ranging from 1 to 3;
$R_3$ and $R_4$ are different or the same and are each independently:
H;
$(C_3$-$C_7)$ cycloalkylcarbonyl;
$(C_1$-$C_6)$ alkyl, optionally substituted by one or more substituents selected from $(C_3$-$C_7)$ cycloalkyl or $(C_5$-$C_7)$ cycloalkenyl;
$(C_1$-$C_6)$ haloalkyl;
$(C_3$-$C_7)$ cycloalkyl;
$(C_5$-$C_7)$ cycloalkenyl;
$(C_2$-$C_6)$ alkenyl; or
$(C_2$-$C_6)$ alkynyl;
or $R_3$ and $R_4$, together with the interconnecting atoms, form a 2,2-difluoro-1,3-dioxolane ring of formula (r) fused to the phenyl moiety which bears groups —$OR_3$ and —$OR_4$, wherein asterisks indicate carbon atoms shared with such phenyl ring:

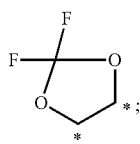

(r)

each $R_5$, whenever present, is independently CN, $NO_2$, $CF_3$, or a halogen atom;
k is 0 or an integer ranging from 1 to 3;
$L_1$ is:
   a bond,
   —$(CH2)_p$—,
   [3]-$(CH_2)_p$—O-[4]
   [3]-$(CH_2)_p$—$NR_{10}$—$(CH_2)_t$-[4]
   [3]-$(CH_2)_p$—OC(O)-[4]
   [3]-$(CH_2)_p$—$NR_{10}$C(O)-[4]
   [3]-$(CH_2)_p$—$NR_{10}$S($O_2$)-[4] or
   [3]-$(CH_2)_p$—S($O_2$)—N($R_{10}$)-[4]
wherein [3] and [4] represent, respectively, the point of attachment of group $L_1$ to the carbonyl group and to the ring $W_1$ and wherein
   $R_{10}$ is as described above,
   p is an integer ranging from 1 to 4 and
   t is an integer ranging from 1 to 4;
$W_1$ is a divalent ($C_5$-$C_6$) heteroarylene group;
$W_2$ is aryl or heteroaryl;
$L_2$ is —$(CH_2)_q$— wherein q is 1 or 2;
$L_3$ is a bond or —$(CH_2)_s$— wherein s is 1 or 2;
X is N or [1]-N($R_{19}$)—CH<[2] wherein [1] represents the point of attachment of group X to $L_2$ and [2] represents the point of attachment of group X to the group $W_2$ and to the group $L_3$-C(O)OA and wherein $R_{19}$ is hydrogen, ($C_1$-$C_6$) alkyl, or benzyl or, when $W_2$ is a phenyl ring, $R_{19}$ is optionally a ($C_1$-$C_6$) alkylene connected to $W_2$ in ortho position with respect to X, so as to form with $W_2$ and together with the interconnecting atoms a condensed ring as per formula (t) wherein "∼∼" indicate a point of attachment to the rest of the molecule:

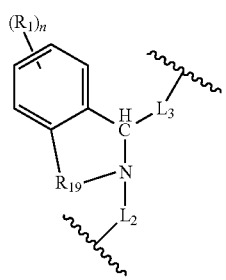

(t)

A is:
   a group-$(CH_2)_s$—$NR_{16}R_{17}$ wherein s is an integer ranging from 1 to 4 and $R_{16}$ and $R_{17}$ are independently hydrogen or ($C_1$-$C_4$) alkyl; or
   a saturated monocyclic, bicyclic or tricyclic heterocyclic ring system containing one N heteroatom or $NR_{18}$ group wherein $R_{18}$ is ($C_1$-$C_4$) alkyl or benzyl;
an N-oxides on the pyridine ring, or a pharmaceutically acceptable salt thereof.

2. A compound, N-oxide, or pharmaceutically acceptable salt according to claim 1, which is represented by formula (IB):

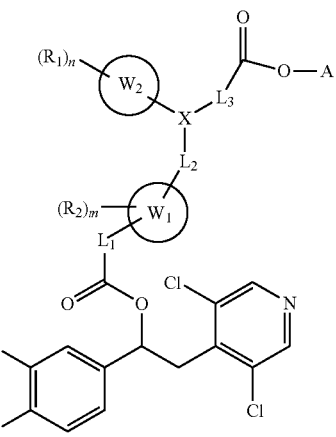

(IB)

an N-oxide on the pyridine ring, or a pharmaceutically acceptable salt thereof.

3. An N-oxide or pharmaceutically acceptable salt according to claim 1, which is represented by formula (IA):

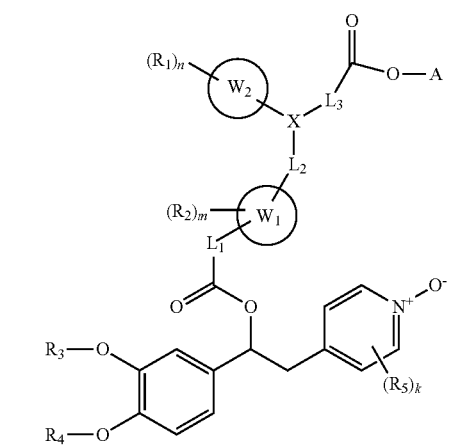

(IA)

or a pharmaceutically acceptable salt thereof.

4. A compound, N-oxide, or pharmaceutically acceptable salt according to claim 1, wherein
   $R_4$ is ($C_1$-$C_6$) haloalkyl or ($C_1$-$C_6$) alkyl, and
   $R_3$ is ($C_3$-$C_7$) cycloalkyl or ($C_1$-$C_6$) alkyl which is optionally substituted by ($C_3$-$C_7$) cycloalkyl.

5. A compound, N-oxide, or pharmaceutically acceptable salt according to claim 1, which is represented by formula (ID):

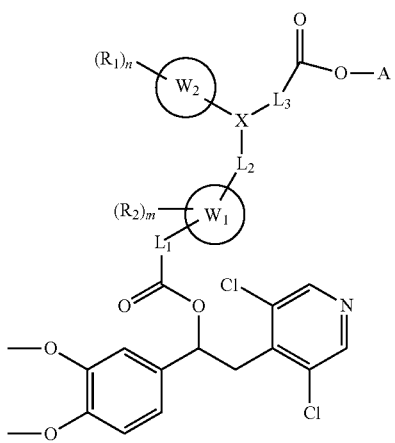

an N-oxide on the pyridine ring, or s pharmaceutically acceptable salt thereof.

6. A compound, N-oxide, or pharmaceutically acceptable salt according to claim 1, which is represented by formula (I)' wherein the absolute configuration of carbon (1) is that shown hereinbelow

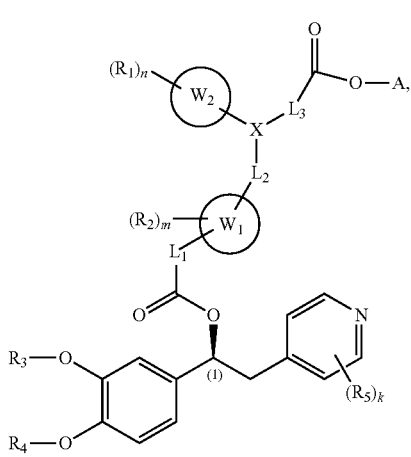

an N-oxide on the pyridine ring, or a pharmaceutically acceptable salt thereof.

7. A compound, N-oxide, or pharmaceutically acceptable salt according to claim 1, which is a compound selected from the group consisting of:
[(1S)-2-(3,5-dichloro-1-oxido-pyridin-1-ium-4-yl)-1-(3,4-dimethoxyphenyl)ethyl]5-[(2-fluoro-N-[(3R)-quinuclidin-3-yl]oxycarbonyl-anilino)methyl]thiophene-2-carboxylate;
[(1S)-2-(3,5-dichloro-1-oxido-pyridin-1-ium-4-yl)-1-(3,4-dimethoxyphenyl)ethyl]5-[(2-fluoro-N-[(3S)-quinuclidin-3-yl]oxycarbonyl-anilino)methyl]thiophene-2-carboxylate;
[(1S)-2-(3,5-dichloro-1-oxido-pyridin-1-ium-4-yl)-1-(3,4-dimethoxyphenyl)ethyl]5-[[2-fluoro-N-[[(1R,5S)-8-methyl-8-azabicyclo[3.2.1]octan-3-yl]oxycarbonyl]anilino]methyl]thiophene-2-carboxylate;
[(1S)-2-(3,5-dichloro-1-oxido-pyridin-1-ium-4-yl)-1-(3,4-dimethoxyphenyl)ethyl]5-[[2-fluoro-N-[(1-methyl-4-piperidyl)oxycarbonyl]anilino]methyl]thiophene-2-carboxylate;
[(1S)-2-(3,5-dichloro-1-oxido-pyridin-1-ium-4-yl)-1-(3,4-dimethoxyphenyl)ethyl]5-[(2-hydroxy-N-[(3R)-quinuclidin-3-yl]oxycarbonyl-anilino)methyl]thiophene-2-carboxylate;
[(1S)-2-(3,5-dichloro-1-oxido-pyridin-1-ium-4-yl)-1-[4-(difluoromethoxy)-3-(trideuteriomethoxy)phenyl]ethyl]5-[(2-fluoro-N-[(3R)-quinuclidin-3-yl]oxycarbonyl-anilino)methyl]thiophene-2-carboxylate;
[(1S)-2-(3,5-dichloro-1-oxido-pyridin-1-ium-4-yl)-1-[4-(difluoromethoxy)-3-ethoxy-phenyl]ethyl]5-[(2-fluoro-N-[(3R)-quinuclidin-3-yl]oxycarbonyl-anilino)methyl]thiophene-2-carboxylate;
[(1S)-2-(3,5-dichloro-1-oxido-pyridin-1-ium-4-yl)-1-[4-(difluoromethoxy)-3-methoxy-phenyl]ethyl]5-[(2-fluoro-N-[(3R)-quinuclidin-3-yl]oxycarbonyl-anilino)methyl]thiophene-2-carboxylate;
[(1S)-2-(3,5-dichloro-1-oxido-pyridin-1-ium-4-yl)-1-(3,4-dimethoxyphenyl)ethyl]5-[[3-pyridyl-[(3R)-quinuclidin-3-yl]oxycarbonyl-amino]methyl]thiophene-2-carboxylate;
[(1S)-2-(3,5-dichloro-1-oxido-pyridin-1-ium-4-yl)-1-(3,4-dimethoxyphenyl)ethyl]5-[[2-pyridyl-[(3R)-quinuclidin-3-yl]oxycarbonyl-amino]methyl]thiophene-2-carboxylate;
[1-[3-(cyclopropylmethoxy)-4-methoxy-phenyl]-2-(3,5-dichloro-1-oxido-pyridin-1-ium-4-yl)ethyl]5-[(2-fluoro-N-[(3R)-quinuclidin-3-yl]oxycarbonyl-anilino)methyl]thiophene-2-carboxylate;
[(1S)-1-[3-(cyclopropylmethoxy)-4-(difluoromethoxy)phenyl]-2-(3,5-dichloro-1-oxido-pyridin-1-ium-4-yl)ethyl]5-[[2-pyridyl-[(3R)-quinuclidin-3-yl]oxycarbonyl-amino]methyl]thiophene-2-carboxylate;
[(1S)-1-[3-(cyclopropylmethoxy)-4-(difluoromethoxy)phenyl]-2-(3,5-dichloro-1-oxido-pyridin-1-ium-4-yl)ethyl]5-[[3-pyridyl-[(3R)-quinuclidin-3-yl]oxycarbonyl-amino]methyl]thiophene-2-carboxylate;
[(1S)-1-[3-(cyclopropylmethoxy)-4-(difluoromethoxy)phenyl]-2-(3,5-dichloro-1-oxido-pyridin-1-ium-4-yl)ethyl]5-[(2-fluoro-N-[(3R)-quinuclidin-3-yl]oxycarbonyl-anilino)methyl]thiophene-2-carboxylate;
[(1S)-2-(3,5-dichloro-1-oxido-pyridin-1-ium-4-yl)-1-(3,4-dimethoxyphenyl)ethyl]5-[(2-methoxy-N-[(3R)-quinuclidin-3-yl]oxycarbonyl-anilino)methyl]thiophene-2-carboxylate;
[(1S)-2-(3,5-dichloro-1-oxido-pyridin-1-ium-4-yl)-1-(3,4-dimethoxyphenyl)ethyl]5-[[[(3R)-quinuclidin-3-yl]oxycarbonyl-thiazol-2-yl-amino]methyl]thiophene-2-carboxylate;
[(1S)-2-(3,5-dichloro-1-oxido-pyridin-1-ium-4-yl)-1-[4-(difluoromethoxy)-3-isopropoxy-phenyl]ethyl]5-[(2-fluoro-N-[(3R)-quinuclidin-3-yl]oxycarbonyl-anilino)methyl]thiophene-2-carboxylate;
[(1S)-1-[3-(cyclopropylmethoxy)-4-(difluoromethoxy)phenyl]-2-(3,5-dichloro-1-oxido-pyridin-1-ium-4-yl)ethyl]5-[[[(3R)-quinuclidin-3-yl]oxycarbonyl-thiazol-2-yl-amino]methyl]thiophene-2-carboxylate;
[(1S)-2-(3,5-dichloro-1-oxido-pyridin-1-ium-4-yl)-1-(3,4-dimethoxyphenyl)ethyl]5-[[(2-methoxy-3-pyridyl)-[(3R)-quinuclidin-3-yl]oxycarbonyl-amino]methyl]thiophene-2-carboxylate;

[(1S)-2-(3,5-dichloro-1-oxido-pyridin-1-ium-4-yl)-1-(3,4-dimethoxyphenyl)ethyl]5-[(3-cyano-N-[(3R)-quinuclidin-3-yl]oxycarbonyl-anilino)methyl]thiophene-2-carboxylate;

[(1S)-2-(3,5-dichloro-1-oxido-pyridin-1-ium-4-yl)-1-(3,4-dimethoxyphenyl)ethyl]5-[(3-fluoro-N-[(3R)-quinuclidin-3-yl]oxycarbonyl-anilino)methyl]thiophene-2-carboxylate;

[(1S)-2-(3,5-dichloro-1-oxido-pyridin-1-ium-4-yl)-1-(3,4-dimethoxyphenyl)ethyl]5-[(N-[(3R)-quinuclidin-3-yl]oxycarbonylanilino)methyl]thiophene-2-carboxylate;

[(1S)-2-(3,5-dichloro-1-oxido-pyridin-1-ium-4-yl)-1-(3,4-dimethoxyphenyl)ethyl]5-[[3-(difluoromethyl)-N-[(3R)-quinuclidin-3-yl]oxycarbonyl-anilino]methyl]thiophene-2-carboxylate;

[(1S)-2-(3,5-dichloro-1-oxido-pyridin-1-ium-4-yl)-1-(3,4-dimethoxyphenyl)ethyl]5-[(3-hydroxy-N-[(3R)-quinuclidin-3-yl]oxycarbonyl-anilino)methyl]thiophene-2-carboxylate;

[(1S)-1-[3-(cyclopropylmethoxy)-4-(difluoromethoxy)phenyl]-2-(3,5-dichloro-1-oxido-pyridin-1-ium-4-yl)ethyl]5-[(3-hydroxy-N-[(3R)-quinuclidin-3-yl]oxycarbonyl-anilino)methyl]thiophene-2-carboxylate;

[(1S)-2-(3,5-dichloro-1-oxido-pyridin-1-ium-4-yl)-1-(3,4-dimethoxyphenyl)ethyl]5-[(2-fluoro-N-[(3R)-1-methylpyrrolidin-3-yl]oxycarbonyl-anilino)methyl]thiophene-2-carboxylate;

[(1S)-2-(3,5-dichloro-1-oxido-pyridin-1-ium-4-yl)-1-(3,4-dimethoxyphenyl)ethyl]-4-[(2-fluoro-N-[(3R)-quinuclidin-3-yl]oxycarbonyl-anilino)methyl]thiophene-2-carboxylate;

[(1S)-2-(3,5-dichloro-1-oxido-pyridin-1-ium-4-yl)-1-[4-(difluoromethoxy)-3-methoxy-phenyl]ethyl]5-[[2-pyridyl-[(3R)-quinuclidin-3-yl]oxycarbonyl-amino]methyl]thiophene-2-carboxylate;

[(1S)-2-(3,5-dichloro-1-oxido-pyridin-1-ium-4-yl)-1-[4-(difluoromethoxy)-3-isopropoxy-phenyl]ethyl]5-[[2-pyridyl-[(3R)-quinuclidin-3-yl]oxycarbonyl-amino]methyl]thiophene-2-carboxylate;

[(1S)-2-(3,5-dichloro-1-oxido-pyridin-1-ium-4-yl)-1-[4-(difluoromethoxy)-3-isopropoxy-phenyl]ethyl]5-[(2-fluoro-N-[(3R)-quinuclidin-3-yl]oxycarbonyl-anilino)methyl]-thiophene-3-carboxylate;

[(1S)-2-(3,5-dichloro-1-oxido-pyridin-1-ium-4-yl)-1-[4-(difluoromethoxy)-3-isopropoxy-phenyl]ethyl]4-[(2-fluoro-N-[(3R)-quinuclidin-3-yl]oxycarbonyl-anilino)methyl]thiophene-2-carboxylate;

[(1S)-2-(3,5-dichloro-1-oxido-pyridin-1-ium-4-yl)-1-(3,4-dimethoxyphenyl)ethyl]5-[(2-fluoro-N-[(3R)-quinuclidin-3-yl]oxycarbonyl-anilino)methyl]thiophene-3-carboxylate;

[(1S)-2-(3,5-dichloro-1-oxido-pyridin-1-ium-4-yl)-1-(3,4-dimethoxyphenyl)ethyl]6-[(N-[(3R)-quinuclidin-3-yl]oxycarbonylanilino)methyl]pyridine-3-carboxylate;

[(1S)-2-(3,5-dichloro-1-oxido-pyridin-1-ium-4-yl)-1-(3,4-dimethoxyphenyl)ethyl]5-[(N-[(3R)-quinuclidin-3-yl]oxycarbonylanilino)methyl]-furan-2-carboxylate;

[(1S)-2-(3,5-dichloro-1-oxido-pyridin-1-ium-4-yl)-1-(3,4-dimethoxyphenyl)ethyl]6-[(N-[(3R)-quinuclidin-3-yl]oxycarbonylanilino)methyl]pyridine-2-carboxylate;

[(1S)-2-(3,5-dichloro-1-oxido-pyridin-1-ium-4-yl)-1-(3,4-dimethoxyphenyl)ethyl]2-[(N-[(3R)-quinuclidin-3-yl]oxycarbonylanilino)methyl]oxazole-4-carboxylate;

[(1S)-2-(3,5-dichloro-1-oxido-pyridin-1-ium-4-yl)-1-(3,4-dimethoxyphenyl)ethyl]5-[[[1-(3-fluorophenyl)-2-oxo-2-[(3R)-quinuclidin-3-yl]oxy-ethyl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[[1-(2-fluorophenyl)-2-oxo-2-[(3R)-quinuclidin-3-yl]oxy-ethyl]amino]methyl]thiophene-2-carboxylate;

[(1S)-1-[3-(cyclopropylmethoxy)-4-(difluoromethoxy)phenyl]-2-(3,5-dichloro-1-oxido-pyridin-1-ium-4-yl)ethyl]5-[[[1-(2-methoxyphenyl)-2-oxo-2-[(3R)-quinuclidin-3-yl]oxy-ethyl]amino]methyl]thiophene-2-carboxylate;

[(1S)-1-[3-(cyclopropylmethoxy)-4-(difluoromethoxy)phenyl]-2-(3,5-dichloro-1-oxido-pyridin-1-ium-4-yl)ethyl]5-[[[1-(2-fluorophenyl)-2-oxo-2-[(3R)-quinuclidin-3-yl]oxy-ethyl]amino]methyl]thiophene-2-carboxylate;

[(1S)-1-[3-(cyclopropylmethoxy)-4-(difluoromethoxy)phenyl]-2-(3,5-dichloro-1-oxido-pyridin-1-ium-4-yl)ethyl]5-[[[2-oxo-1-phenyl-2-[(3R)-quinuclidin-3-yl]oxy-ethyl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[[2-oxo-1-phenyl-2-[(3R)-quinuclidin-3-yl]oxy-ethyl]amino]methyl]thiophene-2-carboxylate;

[(1S)-1-[3-(cyclopropylmethoxy)-4-(difluoromethoxy)phenyl]-2-(3,5-dichloro-1-oxido-pyridin-1-ium-4-yl)ethyl]5-[[[1-(3-fluorophenyl)-2-oxo-2-[(3R)-quinuclidin-3-yl]oxy-ethyl]amino]methyl]thiophene-2-carboxylate;

[(1S)-1-[3-(cyclopropylmethoxy)-4-(difluoromethoxy)phenyl]-2-(3,5-dichloro-1-oxido-pyridin-1-ium-4-yl)ethyl]5-[[[2-oxo-1-(3-pyridyl)-2-[(3R)-quinuclidin-3-yl]oxy-ethyl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[[1-(2-fluorophenyl)-2-[(1-methyl-4-piperidyl)oxy]-2-oxo-ethyl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[[2-[(1-benzyl-4-piperidyl)oxy]-1-(2-fluorophenyl)-2-oxo-ethyl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[[1-(3-fluorophenyl)-2-oxo-2-[(3R)-quinuclidin-3-yl]oxy-ethyl]amino]methyl]thiophene-2-carboxylate single diastereoisomer 1;

[(1S)-2-(3,5-dichloro-1-oxido-pyridin-1-ium-4-yl)-1-(3,4-dimethoxyphenyl)ethyl]5-[[[1-(3-fluorophenyl)-2-oxo-2-[(3R)-quinuclidin-3-yl]oxy-ethyl]amino]methyl]thiophene-2-carboxylate single diastereoisomer 2;

[(1S)-2-(3,5-dichloro-1-oxido-pyridin-1-ium-4-yl)-1-(3,4-dimethoxyphenyl)ethyl]5-[[[2-oxo-1-phenyl-2-[(3R)-quinuclidin-3-yl]oxy-ethyl]amino]methyl]thiophene-2-carboxylate single diastereoisomer 1;

[(1S)-2-(3,5-dichloro-1-oxido-pyridin-1-ium-4-yl)-1-(3,4-dimethoxyphenyl)ethyl]5-[[[2-oxo-1-phenyl-2-[(3R)-quinuclidin-3-yl]oxy-ethyl]amino]methyl]thiophene-2-carboxylate single diastereoisomer 2;

[(1S)-2-(3,5-dichloro-1-oxido-pyridin-1-ium-4-yl)-1-(3,4-dimethoxyphenyl)ethyl]5-[[[1-(2-fluorophenyl)-2-oxo-2-[(3R)-quinuclidin-3-yl]oxy-ethyl]amino]methyl]thiophene-2-carboxylate single diastereoisomer 1;

[(1S)-2-(3,5-dichloro-1-oxido-pyridin-1-ium-4-yl)-1-(3,4-dimethoxyphenyl)ethyl]5-[[[1-(2-fluorophenyl)-2-oxo-2-[(3R)-quinuclidin-3-yl]oxy-ethyl]amino]methyl]thiophene-2-carboxylate single diastereoisomer 2;

[(1S)-1-[3-(cyclopropylmethoxy)-4-(difluoromethoxy)phenyl]-2-(3,5-dichloro-1-oxido-pyridin-1-ium-4-yl)

ethyl]5-[[[1-(2-fluorophenyl)-2-oxo-2-[(3R)-quinuclidin-3-yl]oxy-ethyl]amino]methyl]thiophene-2-carboxylate single diastereoisomer 1;

[(1S)-1-[3-(cyclopropylmethoxy)-4-(difluoromethoxy)phenyl]-2-(3,5-dichloro-1-oxido-pyridin-1-ium-4-yl)ethyl]5-[[[1-(2-fluorophenyl)-2-oxo-2-[(3R)-quinuclidin-3-yl]oxy-ethyl]amino]methyl]thiophene-2-carboxylate single diastereoisomer 2;

[(1S)-1-[3-(cyclopropylmethoxy)-4-(difluoromethoxy)phenyl]-2-(3,5-dichloro-1-oxido-pyridin-1-ium-4-yl)ethyl]5-[[[2-oxo-1-phenyl-2-[(3R)-quinuclidin-3-yl]oxy-ethyl]amino]methyl]thiophene-2-carboxylate single diastereoisomer 1;

[(1S)-1-[3-(cyclopropylmethoxy)-4-(difluoromethoxy)phenyl]-2-(3,5-dichloro-1-oxido-pyridin-1-ium-4-yl)ethyl]5-[[[2-oxo-1-phenyl-2-[(3R)-quinuclidin-3-yl]oxy-ethyl]amino]methyl]thiophene-2-carboxylate single diastereoisomer 2;

[(1S)-1-[3-(cyclopropylmethoxy)-4-(difluoromethoxy)phenyl]-2-(3,5-dichloro-1-oxido-pyridin-1-ium-4-yl)ethyl]5-[[[1-(2-methoxyphenyl)-2-oxo-2-[(3R)-quinuclidin-3-yl]oxy-ethyl]amino]methyl]thiophene-2-carboxylate single diastereoisomer 1;

[(1S)-1-[3-(cyclopropylmethoxy)-4-(difluoromethoxy)phenyl]-2-(3,5-dichloro-1-oxido-pyridin-1-ium-4-yl)ethyl]5-[[[1-(3-fluorophenyl)-2-oxo-2-[(3R)-quinuclidin-3-yl]oxy-ethyl]amino]methyl]thiophene-2-carboxylate single diastereoisomer 1;

[(1S)-2-(3,5-dichloro-1-oxido-pyridin-1-ium-4-yl)-1-(3,4-dimethoxyphenyl)ethyl]5-[(2-fluoro-3-hydroxy-N-[(3R)-quinuclidin-3-yl]oxycarbonyl-anilino)methyl]thiophene-2-carboxylate;

[(1S)-2-(3,5-dichloro-1-oxido-pyridin-1-ium-4-yl)-1-(3,4-dimethoxyphenyl)ethyl]5-[(3-fluoro-5-hydroxy-N-[(3R)-quinuclidin-3-yl]oxycarbonyl-anilino)methyl]thiophene-2-carboxylate;

[(1S)-2-(3,5-dichloro-1-oxido-pyridin-1-ium-4-yl)-1-(3,4-dimethoxyphenyl)ethyl]5-[(3-hydroxy-2-methyl-N-[(3R)-quinuclidin-3-yl]oxycarbonyl-anilino)methyl]thiophene-2-carboxylate;

[(1S)-2-(3,5-dichloro-1-oxido-pyridin-1-ium-4-yl)-1-(3,4-dimethoxyphenyl)ethyl]5-[[2-(hydroxymethyl)-N-[(3R)-quinuclidin-3-yl]oxycarbonyl-anilino]methyl]thiophene-2-carboxylate;

[(1S)-2-(3,5-dichloro-1-oxido-pyridin-1-ium-4-yl)-1-(3,4-dimethoxyphenyl)ethyl]2-[4-[(2-fluoro-N-[(3R)-quinuclidin-3-yl]oxycarbonyl-anilino)methyl]pyrazol-1-yl]acetate;

diastereoisomer 1 of [1-[3-(cyclopropylmethoxy)-4-methoxy-phenyl]-2-(3,5-dichloro-1-oxido-pyridin-1-ium-4-yl)ethyl]5-[(2-fluoro-N-[(3R)-quinuclidin-3-yl]oxycarbonyl-anilino)methyl]thiophene-2-carboxylate;

diastereoisomer 2 of [1-[3-(cyclopropylmethoxy)-4-methoxy-phenyl]-2-(3,5-dichloro-1-oxido-pyridin-1-ium-4-yl)ethyl]5-[(2-fluoro-N-[(3R)-quinuclidin-3-yl]oxycarbonyl-anilino)methyl]thiophene-2-carboxylate;

[(1S)-2-(3,5-dichloro-1-oxido-pyridin-1-ium-4-yl)-1-(3,4-dimethoxyphenyl)ethyl]5-[(2,6-dihydroxyphenyl)-N-[(3R)-quinuclidin-3-yl]oxycarbonyl-anilino)methyl]thiophene-2-carboxylate formate salt;

[(1S)-2-(3,5-dichloro-1-oxido-pyridin-1-ium-4-yl)-1-(3,4-dimethoxyphenyl)ethyl]5-[(2-hydroxy-5-methoxyphenyl)-N-[(3R)-quinuclidin-3-yl]oxycarbonyl-anilino) methyl]thiophene-2-carboxylate;

[(1S)-2-(3,5-dichloro-1-oxido-pyridin-1-ium-4-yl)-1-(3,4-dimethoxyphenyl)ethyl]5-[(2-hydroxy-5-(trifluoromethoxy)phenyl)-N-[(3R)-quinuclidin-3-yl]oxycarbonyl-anilino)methyl]thiophene-2-carboxylate formate salt;

[(1S)-2-(3,5-dichloro-1-oxido-pyridin-1-ium-4-yl)-1-(3,4-dimethoxyphenyl)ethyl]5-[(2,3-dihydroxyphenyl)-N-[(3R)-quinuclidin-3-yl]oxycarbonyl-anilino)methyl]thiophene-2-carboxylate formate salt;

[(1R)-2-(3,5-dichloro-1-oxido-pyridin-1-ium-4-yl)-1-(3,4-dimethoxyphenyl)ethyl]5-[[[2-oxo-1-phenyl-2-[(3R)-quinuclidin-3-yl]oxy-ethyl]amino]methyl]thiophene-2-carboxylate;

Epimeric mixture 1 of [1-[3-(cyclopentoxy)-4-methoxy-phenyl]-2-(3,5-dichloro-1-oxido-pyridin-1-ium-4-yl)ethyl]5-[[[2-oxo-1-phenyl-2-[(3R)-quinuclidin-3-yl]oxy-ethyl]amino]methyl]thiophene-2-carboxylate dihydrochloride;

Epimeric mixture 2 of [1-[3-(cyclopentoxy)-4-methoxy-phenyl]-2-(3,5-dichloro-1-oxido-pyridin-1-ium-4-yl)ethyl]5-[[[2-oxo-1-phenyl-2-[(3R)-quinuclidin-3-yl]oxy-ethyl]amino]methyl]thiophene-2-carboxylate dihydrochloride;

Epimeric mixture 1 of [1-[3-(cyclopropylmethoxy)-4-methoxy-phenyl]-2-(3,5-dichloro-1-oxido-pyridin-1-ium-4-yl)ethyl]5-[[[2-oxo-1-phenyl-2-[(3R)-quinuclidin-3-yl]oxy-ethyl]amino]methyl]thiophene-2-carboxylate;

Epimeric mixture 2 of [1-[3-(cyclopropylmethoxy)-4-methoxy-phenyl]-2-(3,5-dichloro-1-oxido-pyridin-1-ium-4-yl)ethyl]5-[[[2-oxo-1-phenyl-2-[(3R)-quinuclidin-3-yl]oxy-ethyl]amino]methyl]thiophene-2-carboxylate;

[(1S)-2-(3,5-dichloro-1-oxido-pyridin-1-ium-4-yl)-1-[4-(difluoromethoxy)-3-isopropoxy-phenyl]ethyl]5-[[[2-oxo-1-phenyl-2-[(3R)-quinuclidin-3-yl]oxy-ethyl]amino]methyl]thiophene-2-carboxylate; formate salt;

[(1S)-2-(3,5-dichloro-1-oxido-pyridin-1-ium-4-yl)-1-(3,4-dimethoxyphenyl)ethyl]5-[[[2-oxo-1-phenyl-2-[(3R)-quinuclidin-3-yl]oxy-ethyl]amino]methyl]thiophene-3-carboxylate;

[(1S)-2-(3,5-dichloro-1-oxido-pyridin-1-ium-4-yl)-1-(3,4-dimethoxyphenyl)ethyl]5-[[[1-(2-fluorophenyl)-2-oxo-2-[(3R)-quinuclidin-3-yl]oxy-ethyl]amino]methyl]thiophene-3-carboxylate;

[(1S)-2-(3,5-dichloro-1-oxido-pyridin-1-ium-4-yl)-1-(3,4-dimethoxyphenyl)ethyl]4-[[[2-oxo-1-phenyl-2-[(3R)-quinuclidin-3-yl]oxy-ethyl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[[2-[2-(dimethylamino)ethoxy]-2-oxo-1-phenyl-ethyl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[[1-[3-(difluoromethyl)phenyl]-2-oxo-2-[(3R)-quinuclidin-3-yl]oxy-ethyl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[methyl-[2-oxo-1-phenyl-2-[(3R)-quinuclidin-3-yl]oxy-ethyl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[[2-[(3S)-1-methylpyrrolidin-3-yl]oxy-2-oxo-1-phenyl-ethyl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[[1-(3-hydroxyphenyl)-2-oxo-2-[(3R)-quinuclidin-3-yl]oxy-ethyl]amino]methyl]thiophene-2-carboxylate;

[(3R)-quinuclidin-3-yl]2-[[5-[2-[(1S)-2-(3,5-dichloro-1-oxido-pyridin-1-ium-4-yl)-1-(3,4-dimethoxyphenyl)ethoxy]-2-oxo-ethyl]-2-thienyl]methylamino]-2-phenyl-acetate;

[(1S)-2-(3,5-dichloro-1-oxido-pyridin-1-ium-4-yl)-1-(3,4-dimethoxyphenyl)ethyl]5-[[[1-(thiophen-2-yl)-2-oxo-2-(R)-quinuclidin-3-yloxy-ethyl]amino]methyl]thiophene-2-carboxylate;

[(1S)-2-(3,5-dichloro-1-oxido-pyridin-1-ium-4-yl)-1-[4-(difluoromethoxy)-3-methoxy-phenyl]ethyl]5-[[[2-oxo-1-phenyl-2-[(3R)-quinuclidin-3-yl]oxy-ethyl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[[2-[(3R)-1-methylpyrrolidin-3-yl]oxy-2-oxo-1-phenyl-ethyl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[[2-(1-methylazetidin-3-yl)oxy-2-oxo-1-phenyl-ethyl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[[2-[[(3R)-1-methyl-3-piperidyl]oxy]-2-oxo-1-phenyl-ethyl]amino]methyl]thiophene-2-carboxylate; formate salt;

[(1S)-2-(3,5-dichloro-1-oxido-pyridin-1-ium-4-yl)-1-(3,4-dimethoxyphenyl)ethyl]5-[[[2-[3-(dimethylamino)propoxy]-2-oxo-1-phenyl-ethyl]amino]methyl]thiophene-2-carboxylate;

Epimeric mixture 2 of [2-(3,5-dichloro-1-oxido-pyridin-1-ium-4-yl)-1-(3-ethoxy-4-methoxy-phenyl)ethyl]5-[[[2-oxo-1-phenyl-2-[(3R)-quinuclidin-3-yl]oxy-ethyl]amino]methyl]thiophene-2-carboxylate;

Epimeric mixture 1 of [2-(3,5-dichloro-1-oxido-pyridin-1-ium-4-yl)-1-(3-ethoxy-4-methoxy-phenyl)ethyl]5-[[[2-oxo-1-phenyl-2-[(3R)-quinuclidin-3-yl]oxy-ethyl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[[2-[(8-methyl-8-azabicyclo[3.2.1]octan-3-yl)oxy]-2-oxo-1-phenyl-ethyl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[[1-(2-fluorophenyl)-2-[(3R)-1-methylpyrrolidin-3-yl]oxy-2-oxo-ethyl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[[2-[(8-benzyl-8-azabicyclo[3.2.1]octan-3-yl)oxy]-2-oxo-1-phenyl-ethyl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[[2-[[(1R,5R)-8-benzyl-8-azabicyclo[3.2.1]octan-3-yl]oxy]-2-oxo-1-phenyl-ethyl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[[2-[[(1R,5R)-8-methyl-8-azabicyclo[3.2.1]octan-3-yl]oxy]-2-oxo-1-phenyl-ethyl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[[2-[(1-benzyl-4-piperidyl)oxy]-2-oxo-1-phenyl-ethyl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[[2-[(1-methyl-4-piperidyl)oxy]-2-oxo-1-phenyl-ethyl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[[1-(o-tolyl)-2-oxo-2-[(3R)-quinuclidin-3-yl]oxy-ethyl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[[3-oxo-1-phenyl-3-[(3R)-quinuclidin-3-yl]oxy-propyl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[[1-(2-fluorophenyl)-3-oxo-3-[(3R)-quinuclidin-3-yl]oxy-propyl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[[3-[(1-methyl-4-piperidyl)oxy]-3-oxo-1-phenyl-propyl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[[3-[(3R)-1-methylpyrrolidin-3-yl]oxy-3-oxo-1-phenyl-propyl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[ethyl-[2-oxo-1-phenyl-2-[(3R)-quinuclidin-3-yl]oxy-ethyl]amino]methyl]thiophene-2-carboxylate;

[(3R)-quinuclidin-3-yl]2-[[5-[(1S)-2-(3,5-dichloro-1-oxido-pyridin-1-ium-4-yl)-1-(3,4-dimethoxyphenyl)ethoxy]carbonyl-2-thienyl]methyl]-3,4-dihydro-1H-isoquinoline-1-carboxylate;

[(3R)-quinuclidin-3-yl]2-[2-[5-[2-[(1S)-2-(3,5-dichloro-1-oxido-pyridin-1-ium-4-yl)-1-(3,4-dimethoxyphenyl)ethoxy]-2-oxo-ethyl]-2-thienyl]ethylamino]-2-phenyl-acetate;

[(1S)-2-(3,5-dichloro-1-oxido-pyridin-1-ium-4-yl)-1-(3,4-dimethoxyphenyl)ethyl]5-[2-[[2-oxo-1-phenyl-2-[(3R)-quinuclidin-3-yl]oxy-ethyl]amino]ethyl]thiophene-2-carboxylate;

[(1S)-2-(3,5-dichloro-1-oxido-pyridin-1-ium-4-yl)-1-(3,4-dimethoxyphenyl)ethyl]5-[[[1-(2-fluorophenyl)-2-[(1-methyl-4-piperidyl)oxy]-2-oxo-ethyl]amino]methyl]thiophene-2-carboxylate single diastereoisomer 1;

[(1S)-2-(3,5-dichloro-1-oxido-pyridin-1-ium-4-yl)-1-(3,4-dimethoxyphenyl)ethyl]5-[[[1-(2-fluorophenyl)-2-[(1-methyl-4-piperidyl)oxy]-2-oxo-ethyl]amino]methyl]thiophene-2-carboxylate single diastereoisomer 2;

[(1S)-2-(3,5-dichloro-1-oxido-pyridin-1-ium-4-yl)-1-(3,4-dimethoxyphenyl)ethyl]5-[[[2-[(3R)-1-methylpyrrolidin-3-yl]oxy-2-oxo-1-phenyl-ethyl]amino]methyl]thiophene-2-carboxylate single diastereoisomer 1;

[(1S)-2-(3,5-dichloro-1-oxido-pyridin-1-ium-4-yl)-1-(3,4-dimethoxyphenyl)ethyl]5-[[[2-[(3R)-1-methylpyrrolidin-3-yl]oxy-2-oxo-1-phenyl-ethyl]amino]methyl]thiophene-2-carboxylate single diastereoisomer 2;

single diastereoisomer 1 of epimeric mixture 1 of [1-[3-(cyclopentoxy)-4-methoxy-phenyl]-2-(3,5-dichloro-1-oxido-pyridin-1-ium-4-yl)ethyl]5-[[[2-oxo-1-phenyl-2-[(3R)-quinuclidin-3-yl]oxy-ethyl]amino]methyl]thiophene-2-carboxylate;

single diastereoisomer 2 of epimeric mixture 1 of [1-[3-(cyclopentoxy)-4-methoxy-phenyl]-2-(3,5-dichloro-1-oxido-pyridin-1-ium-4-yl)ethyl]5-[[[2-oxo-1-phenyl-2-[(3R)-quinuclidin-3-yl]oxy-ethyl]amino]methyl]thiophene-2-carboxylate;

[(1S)-2-(3,5-dichloro-1-oxido-pyridin-1-ium-4-yl)-1-(3,4-dimethoxyphenyl)ethyl]5-[[methyl-[2-oxo-1-phenyl-2-[(3R)-quinuclidin-3-yl]oxy-ethyl]amino]methyl]thiophene-2-carboxylate single diastereoisomer 1;

[(1S)-2-(3,5-dichloro-1-oxido-pyridin-1-ium-4-yl)-1-(3,4-dimethoxyphenyl)ethyl]5-[[methyl-[2-oxo-1-phenyl-2-[(3R)-quinuclidin-3-yl]oxy-ethyl]amino]methyl]thiophene-2-carboxylate single diastereoisomer 2;

single diastereoisomer 1 of epimeric mixture 2 of [1-[3-(cyclopentoxy)-4-methoxy-phenyl]-2-(3,5-dichloro-1-oxido-pyridin-1-ium-4-yl)ethyl]5-[[[2-oxo-1-phenyl-2-[(3R)-quinuclidin-3-yl]oxy-ethyl]amino]methyl]thiophene-2-carboxylate;

single diastereoisomer 2 of epimeric mixture 2 of [1-[3-(cyclopentoxy)-4-methoxy-phenyl]-2-(3,5-dichloro-1-oxido-pyridin-1-ium-4-yl)ethyl]5-[[[2-oxo-1-phenyl-2-[(3R)-quinuclidin-3-yl]oxy-ethyl]amino]methyl]thiophene-2-carboxylate;

[(3R)-quinuclidin-3-yl]2-[[5-[(1S)-2-(3,5-dichloro-1-oxido-pyridin-1-ium-4-yl)-1-(3,4-dimethoxyphenyl)ethoxy]carbonyl-2-thienyl]methyl]-3,4-dihydro-1H-isoquinoline-1-carboxylate single diastereoisomer 1;

[(3R)-quinuclidin-3-yl]2-[[5-[(1S)-2-(3,5-dichloro-1-oxido-pyridin-1-ium-4-yl)-1-(3,4-dimethoxyphenyl)ethoxy]carbonyl-2-thienyl]methyl]-3,4-dihydro-1H-isoquinoline-1-carboxylate single diastereoisomer 2;

[(1S)-2-(3,5-dichloro-1-oxido-pyridin-1-ium-4-yl)-1-(3,4-dimethoxyphenyl)ethyl]5-[[[2-[[(1R,5R)-8-methyl-8-azabicyclo[3.2.1]octan-3-yl]oxy]-2-oxo-1-phenyl-ethyl]amino]methyl]thiophene-2-carboxylate single diastereoisomer 1;

[(1S)-2-(3,5-dichloro-1-oxido-pyridin-1-ium-4-yl)-1-(3,4-dimethoxyphenyl)ethyl]5-[[[2-[[(1R,5R)-8-methyl-8-azabicyclo[3.2.1]octan-3-yl]oxy]-2-oxo-1-phenyl-ethyl]amino]methyl]thiophene-2-carboxylate single diastereoisomer 2;

[(1S)-2-(3,5-dichloro-1-oxido-pyridin-1-ium-4-yl)-1-[4-(difluoromethoxy)-3-isopropoxy-phenyl]ethyl]5-[[[2-oxo-1-phenyl-2-[(3R)-quinuclidin-3-yl]oxy-ethyl]amino]methyl]thiophene-2-carboxylate single diastereoisomer 1;

[(1S)-2-(3,5-dichloro-1-oxido-pyridin-1-ium-4-yl)-1-[4-(difluoromethoxy)-3-isopropoxy-phenyl]ethyl]5-[[[2-oxo-1-phenyl-2-[(3R)-quinuclidin-3-yl]oxy-ethyl]amino]methyl]thiophene-2-carboxylate single diastereoisomer 2;

[(1S)-2-(3,5-dichloro-1-oxido-pyridin-1-ium-4-yl)-1-(3,4-dimethoxyphenyl)ethyl]5-[[ethyl-[2-oxo-1-phenyl-2-[(3R)-quinuclidin-3-yl]oxy-ethyl]amino]methyl]thiophene-2-carboxylate; formic acid single diastereoisomer 1;

[(1S)-2-(3,5-dichloro-1-oxido-pyridin-1-ium-4-yl)-1-(3,4-dimethoxyphenyl)ethyl]5-[[ethyl-[2-oxo-1-phenyl-2-[(3R)-quinuclidin-3-yl]oxy-ethyl]amino]methyl]thiophene-2-carboxylate single diastereoisomer 2;

[(1S)-2-(3,5-dichloro-1-oxido-pyridin-1-ium-4-yl)-1-(3,4-dimethoxyphenyl)ethyl]5-[[[2-[2-(dimethylamino)ethoxy]-2-oxo-1-phenyl-ethyl]amino]methyl]thiophene-2-carboxylate single diastereoisomer 1;

[(1S)-2-(3,5-dichloro-1-oxido-pyridin-1-ium-4-yl)-1-(3,4-dimethoxyphenyl)ethyl]5-[[[2-[2-(dimethylamino)ethoxy]-2-oxo-1-phenyl-ethyl]amino]methyl]thiophene-2-carboxylate single diastereoisomer 2;

[(1S)-2-(3,5-dichloro-1-oxido-pyridin-1-ium-4-yl)-1-(3,4-dimethoxyphenyl)ethyl]5-[[[1-(2-fluorophenyl)-2-[(3R)-1-methylpyrrolidin-3-yl]oxy-2-oxo-ethyl]amino]methyl]thiophene-2-carboxylate single diastereoisomer 1;

[(1S)-2-(3,5-dichloro-1-oxido-pyridin-1-ium-4-yl)-1-(3,4-dimethoxyphenyl)ethyl]5-[[[1-(2-fluorophenyl)-2-[(3R)-1-methylpyrrolidin-3-yl]oxy-2-oxo-ethyl]amino]methyl]thiophene-2-carboxylate single diastereoisomer 2;

[(1S)-2-(3,5-dichloro-1-oxido-pyridin-1-ium-4-yl)-1-(3,4-dimethoxyphenyl)ethyl]5-[[[2-[[(3R)-1-methyl-3-piperidyl]oxy]-2-oxo-1-phenyl-ethyl]amino]methyl]thiophene-2-carboxylate single diastereoisomer 1;

[(1S)-2-(3,5-dichloro-1-oxido-pyridin-1-ium-4-yl)-1-(3,4-dimethoxyphenyl)ethyl]5-[[[2-[[(3R)-1-methyl-3-piperidyl]oxy]-2-oxo-1-phenyl-ethyl]amino]methyl]thiophene-2-carboxylate single diastereoisomer 2;

[(1S)-2-(3,5-dichloro-1-oxido-pyridin-1-ium-4-yl)-1-(3,4-dimethoxyphenyl)ethyl]5-[[[2-[3-(dimethylamino)propoxy]-2-oxo-1-phenyl-ethyl]amino]methyl]thiophene-2-carboxylate single diastereoisomer 1;

[(1S)-2-(3,5-dichloro-1-oxido-pyridin-1-ium-4-yl)-1-(3,4-dimethoxyphenyl)ethyl]5-[[[2-[3-(dimethylamino)propoxy]-2-oxo-1-phenyl-ethyl]amino]methyl]thiophene-2-carboxylate single diastereoisomer 2;

[(1S)-2-(3,5-dichloro-1-oxido-pyridin-1-ium-4-yl)-1-(3,4-dimethoxyphenyl)ethyl]5-[[[2-oxo-1-phenyl-2-[(3R)-quinuclidin-3-yl]oxy-ethyl]amino]methyl]thiophene-3-carboxylate single diastereoisomer 1;

[(1S)-2-(3,5-dichloro-1-oxido-pyridin-1-ium-4-yl)-1-(3,4-dimethoxyphenyl)ethyl]5-[[[2-oxo-1-phenyl-2-[(3R)-quinuclidin-3-yl]oxy-ethyl]amino]methyl]thiophene-3-carboxylate single diastereoisomer 2;

[(1S)-2-(3,5-dichloro-1-oxido-pyridin-1-ium-4-yl)-1-(3,4-dimethoxyphenyl)ethyl]-4-[[[2-oxo-1-phenyl-2-[(3R)-quinuclidin-3-yl]oxy-ethyl]amino]methyl]thiophene-2-carboxylate single diastereoisomer 1;

[(1S)-2-(3,5-dichloro-1-oxido-pyridin-1-ium-4-yl)-1-(3,4-dimethoxyphenyl)ethyl]-4-[[[2-oxo-1-phenyl-2-[(3R)-quinuclidin-3-yl]oxy-ethyl]amino]methyl]thiophene-2-carboxylate single diastereoisomer 2;

[(1S)-2-(3,5-dichloro-1-oxido-pyridin-1-ium-4-yl)-1-(3,4-dimethoxyphenyl)ethyl]5-[[[1-(2-fluorophenyl)-2-oxo-2-[(3R)-quinuclidin-3-yl]oxy-ethyl]amino]methyl]thiophene-3-carboxylate single diastereoisomer 1;

[(1S)-2-(3,5-dichloro-1-oxido-pyridin-1-ium-4-yl)-1-(3,4-dimethoxyphenyl)ethyl]5-[[[1-(2-fluorophenyl)-2-oxo-2-[(3R)-quinuclidin-3-yl]oxy-ethyl]amino]methyl]thiophene-3-carboxylate single diastereoisomer 2;

[(1S)-2-(3,5-dichloro-1-oxido-pyridin-1-ium-4-yl)-1-(3,4-dimethoxyphenyl)ethyl]5-[[[2-[(3S)-1-methylpyrrolidin-3-yl]oxy-2-oxo-1-phenyl-ethyl]amino]methyl]thiophene-2-carboxylate single diastereoisomer 1;

[(1S)-2-(3,5-dichloro-1-oxido-pyridin-1-ium-4-yl)-1-(3,4-dimethoxyphenyl)ethyl]5-[[[2-[(3S)-1-methylpyrrolidin-3-yl]oxy-2-oxo-1-phenyl-ethyl]amino]methyl]thiophene-2-carboxylate single diastereoisomer 2;

[(1S)-2-(3,5-dichloro-1-oxido-pyridin-1-ium-4-yl)-1-(3,4-dimethoxyphenyl)ethyl]5-[[[1-(3-hydroxyphenyl)-2-oxo-2-[(3R)-quinuclidin-3-yl]oxy-ethyl]amino]methyl]thiophene-2-carboxylate single diastereoisomer 1;

[(1S)-2-(3,5-dichloro-1-oxido-pyridin-1-ium-4-yl)-1-(3,4-dimethoxyphenyl)ethyl]5-[[[1-(3-hydroxyphenyl)-2-oxo-2-[(3R)-quinuclidin-3-yl]oxy-ethyl]amino]methyl]thiophene-2-carboxylate single diastereoisomer 2;

[(1S)-2-(3,5-dichloro-1-oxido-pyridin-1-ium-4-yl)-1-(3,4-dimethoxyphenyl)ethyl]5-[[[2-[(1-methyl-4-piperidyl)oxy]-2-oxo-1-phenyl-ethyl]amino]methyl]thiophene-2-carboxylate single diastereomer 1;

[(1S)-2-(3,5-dichloro-1-oxido-pyridin-1-ium-4-yl)-1-(3,4-dimethoxyphenyl)ethyl]5-[[[2-[(1-methyl-4-piperidyl)oxy]-2-oxo-1-phenyl-ethyl]amino]methyl]thiophene-2-carboxylate single diastereomer;

[(1R)-2-(3,5-dichloro-1-oxido-pyridin-1-ium-4-yl)-1-(3,4-dimethoxyphenyl)ethyl]5-[[[2-oxo-1-phenyl-2-[(3R)-quinuclidin-3-yl]oxy-ethyl]amino]methyl]thiophene-2-carboxylate single diastereomer 1;

[(1R)-2-(3,5-dichloro-1-oxido-pyridin-1-ium-4-yl)-1-(3,4-dimethoxyphenyl)ethyl]5-[[[2-oxo-1-phenyl-2-[(3R)-quinuclidin-3-yl]oxy-ethyl]amino]methyl]thiophene-2-carboxylate single diastereomer 2;

[(1S)-2-(3,5-dichloro-1-oxido-pyridin-1-ium-4-yl)-1-(3,4-dimethoxyphenyl)ethyl]5-[2-[[2-oxo-1-phenyl-2-[(3R)-quinuclidin-3-yl]oxy-ethyl]amino]ethyl]thiophene-2-carboxylate single diastereomer 1;

[(1S)-2-(3,5-dichloro-1-oxido-pyridin-1-ium-4-yl)-1-(3,4-dimethoxyphenyl)ethyl]5-[2-[[2-oxo-1-phenyl-2-[(3R)-quinuclidin-3-yl]oxy-ethyl]amino]ethyl]thiophene-2-carboxylate single diastereomer 2;

[(1S)-2-(3,5-dichloro-1-oxido-pyridin-1-ium-4-yl)-1-(3,4-dimethoxyphenyl)ethyl]5-[[[1-(o-tolyl)-2-oxo-2-[(3R)-quinuclidin-3-yl]oxy-ethyl]amino]methyl]thiophene-2-carboxylate single diastereomer 1;

[(1S)-2-(3,5-dichloro-1-oxido-pyridin-1-ium-4-yl)-1-(3,4-dimethoxyphenyl)ethyl]5-[[[1-(o-tolyl)-2-oxo-2-[(3R)-quinuclidin-3-yl]oxy-ethyl]amino]methyl]thiophene-2-carboxylate single diastereomer 2;

[(3R)-quinuclidin-3-yl]2-[2-[5-[2-[(1S)-2-(3,5-dichloro-1-oxido-pyridin-1-ium-4-yl)-1-(3,4-dimethoxyphenyl)ethoxy]-2-oxo-ethyl]-2-thienyl]ethylamino]-2-phenyl-acetate single diastereomer 1;

[(3R)-quinuclidin-3-yl]2-[2-[5-[2-[(1S)-2-(3,5-dichloro-1-oxido-pyridin-1-ium-4-yl)-1-(3,4-dimethoxyphenyl)ethoxy]-2-oxo-ethyl]-2-thienyl]ethylamino]-2-phenyl-acetate single diastereomer 2;

[(3R)-quinuclidin-3-yl]2-[[5-[2-[(1S)-2-(3,5-dichloro-1-oxido-pyridin-1-ium-4-yl)-1-(3,4-dimethoxyphenyl)ethoxy]-2-oxo-ethyl]-2-thienyl]methylamino]-2-phenyl-acetate single diastereomer 1;

[(1S)-2-(3,5-dichloro-1-oxido-pyridin-1-ium-4-yl)-1-(3,4-dimethoxyphenyl)ethyl]5-[[[3-oxo-1-phenyl-3-[(3R)-quinuclidin-3-yl]oxy-propyl]amino]methyl]thiophene-2-carboxylate single diastereomer 1;

[(1S)-2-(3,5-dichloro-1-oxido-pyridin-1-ium-4-yl)-1-(3,4-dimethoxyphenyl)ethyl]5-[[[3-oxo-1-phenyl-3-[(3R)-quinuclidin-3-yl]oxy-propyl]amino]methyl]thiophene-2-carboxylate single diastereomer 2;

[(1S)-2-(3,5-dichloro-1-oxido-pyridin-1-ium-4-yl)-1-(3,4-dimethoxyphenyl)ethyl]5-[[[1-(2-fluorophenyl)-3-oxo-3-[(3R)-quinuclidin-3-yl]oxy-propyl]amino]methyl]thiophene-2-carboxylate single diastereomer 1;

[(1S)-2-(3,5-dichloro-1-oxido-pyridin-1-ium-4-yl)-1-(3,4-dimethoxyphenyl)ethyl]5-[[[1-(2-fluorophenyl)-3-oxo-3-[(3R)-quinuclidin-3-yl]oxy-propyl]amino]methyl]thiophene-2-carboxylate single diastereomer 2;

[(1S)-2-(3,5-dichloro-1-oxido-pyridin-1-ium-4-yl)-1-(3,4-dimethoxyphenyl)ethyl]5-[[[3-[(3R)-1-methylpyrrolidin-3-yl]oxy-3-oxo-1-phenyl-propyl]amino]methyl]thiophene-2-carboxylate single diastereomer 1;

[(1S)-2-(3,5-dichloro-1-oxido-pyridin-1-ium-4-yl)-1-(3,4-dimethoxyphenyl)ethyl]5-[[[3-[(3R)-1-methylpyrrolidin-3-yl]oxy-3-oxo-1-phenyl-propyl]amino]methyl]thiophene-2-carboxylate single diastereomer 2;

[(1S)-2-(3,5-dichloro-1-oxido-pyridin-1-ium-4-yl)-1-(3,4-dimethoxyphenyl)ethyl]5-[[[3-[(1-methyl-4-piperidyl)oxy]-3-oxo-1-phenyl-propyl]amino]methyl]thiophene-2-carboxylate single diastereomer 1;

[(1S)-2-(3,5-dichloro-1-oxido-pyridin-1-ium-4-yl)-1-(3,4-dimethoxyphenyl)ethyl]5-[[[3-[(1-methyl-4-piperidyl)oxy]-3-oxo-1-phenyl-propyl]amino]methyl]thiophene-2-carboxylate single diastereomer 2;

[(1S)-2-(3,5-dichloro-1-oxido-pyridin-1-ium-4-yl)-1-(3,4-dimethoxyphenyl)ethyl]5-[(2,6-dihydroxyphenyl)-N-[(3R)-quinuclidin-3-yl]oxycarbonyl-anilino)methyl]thiophene-2-carboxylate;

[(1S)-2-(3,5-dichloro-1-oxido-pyridin-1-ium-4-yl)-1-(3,4-dimethoxyphenyl)ethyl]5-[(2-hydroxy-5-(trifluoromethoxy)phenyl)-N-[(3R)-quinuclidin-3-yl]oxycarbonyl-anilino)methyl]thiophene-2-carboxylate;

[(1S)-2-(3,5-dichloro-1-oxido-pyridin-1-ium-4-yl)-1-(3,4-dimethoxyphenyl)ethyl]5-[(2,3-dihydroxyphenyl)-N-[(3R)-quinuclidin-3-yl]oxycarbonyl-anilino)methyl]thiophene-2-carboxylate;

Epimeric mixture 1 of [1-[3-(cyclopentoxy)-4-methoxyphenyl]-2-(3,5-dichloro-1-oxido-pyridin-1-ium-4-yl)ethyl]5-[[[2-oxo-1-phenyl-2-[(3R)-quinuclidin-3-yl]oxy-ethyl]amino]methyl]thiophene-2-carboxylate;

Epimeric mixture 2 of [1-[3-(cyclopentoxy)-4-methoxyphenyl]-2-(3,5-dichloro-1-oxido-pyridin-1-ium-4-yl)ethyl]5-[[[2-oxo-1-phenyl-2-[(3R)-quinuclidin-3-yl]oxy-ethyl]amino]methyl]thiophene-2-carboxylate;

[(1S)-2-(3,5-dichloro-1-oxido-pyridin-1-ium-4-yl)-1-[4-(difluoromethoxy)-3-isopropoxy-phenyl]ethyl]5-[[[2-oxo-1-phenyl-2-[(3R)-quinuclidin-3-yl]oxy-ethyl]amino]methyl]thiophene-2-carboxylate; and

[(1S)-2-(3,5-dichloro-1-oxido-pyridin-1-ium-4-yl)-1-(3,4-dimethoxyphenyl)ethyl]5-[[[2-[[(3R)-1-methyl-3-piperidyl]oxy]-2-oxo-1-phenyl-ethyl]amino]methyl]thiophene-2-carboxylate;

or a pharmaceutically acceptable salt of said compound.

8. A pharmaceutical composition, comprising a compound, N-oxide, or pharmaceutically acceptable salt according to claim 1 in admixture with one or more pharmaceutically acceptable carriers.

9. A pharmaceutical composition according to claim 8, further comprising another active ingredient.

10. A method for the treatment of a disease of the respiratory tract characterized by airway obstruction, comprising administering an effective amount of a compound, N-oxide, or pharmaceutically acceptable salt according to claim 1 to a subject in need thereof.

11. A method according to claim 10, wherein said disease of the respiratory tract is asthma or COPD.

12. A method for the treatment of a disease of the respiratory tract characterized by airway obstruction, comprising administering an effective amount of a pharmaceutical composition according to claim 8 to a subject in need thereof.

13. A method according to claim 12, wherein said disease of the respiratory tract is asthma or COPD.

14. An inhalation device, comprising a pharmaceutical composition according to claim 8.

15. A kit, comprising a pharmaceutical composition according to claim 8 and a device which is a single- or multi-dose dry powder inhaler, a metered dose inhaler, or a nebulizer.

* * * * *